US012630561B2

(12) United States Patent
Gao et al.

(10) Patent No.: US 12,630,561 B2
(45) Date of Patent: May 19, 2026

(54) TRICYCLIC DERIVATIVES INHIBITOR, PREPARATION METHOD, AND APPLICATIONS THEREOF

(71) Applicants: Jiangsu Hansoh Pharmaceutical Group Co., Ltd., Lianyungang (CN); Shanghai Hansoh Biomedical Co., Ltd., Shanghai (CN)

(72) Inventors: Peng Gao, Lianyungang (CN); Guangjun Sun, Lianyungang (CN); Shaobao Wang, Lianyungang (CN); Wenhua Xiu, Lianyungang (CN); Songliang Tan, Lianyungang (CN); Rudi Bao, Lianyungang (CN)

(73) Assignees: Jiangsu Hansoh Pharmaceutical Group Co., Ltd., Lianyungang (CN); Shanghai Hansoh Biomedical Co., Ltd., Shanghai (CN)

( * ) Notice: Subject to any disclaimer, the term of this patent is extended or adjusted under 35 U.S.C. 154(b) by 1212 days.

(21) Appl. No.: 17/059,936

(22) PCT Filed: May 28, 2019

(86) PCT No.: PCT/CN2019/088788

§ 371 (c)(1),
(2) Date: Nov. 30, 2020

(87) PCT Pub. No.: WO2019/228341

PCT Pub. Date: Dec. 5, 2019

(65) Prior Publication Data

US 2021/0221822 A1 Jul. 22, 2021

(30) Foreign Application Priority Data

May 30, 2018 (CN) ......................... 201810541998.4
Jul. 13, 2018 (CN) ......................... 201810772171.4
Sep. 28, 2018 (CN) ......................... 201811142142.6
Mar. 8, 2019 (CN) ......................... 201910176302.7

(51) Int. Cl.
*C07D 498/04* (2006.01)
*A61P 35/00* (2006.01)
*C07D 498/14* (2006.01)

(52) U.S. Cl.
CPC ............ *C07D 498/04* (2013.01); *A61P 35/00* (2018.01); *C07D 498/14* (2013.01)

(58) Field of Classification Search
CPC ...... C07D 498/04; C07D 498/14; A61P 35/00
See application file for complete search history.

(56) References Cited

U.S. PATENT DOCUMENTS 8,242,104 B2 8/2012 Blaquiere et al.
8,343,955 B2 1/2013 Blaquiere et al.
8,785,626 B2 7/2014 Blaquiere et al.
9,090,628 B2 7/2015 Heffron et al.
9,198,918 B2 12/2015 Blaquiere et al.
9,546,178 B2 1/2017 Blaquiere et al.
9,643,980 B2 5/2017 Braun et al.
9,650,393 B2 5/2017 Braun et al.
9,670,228 B2 6/2017 Blaquiere et al.
10,112,932 B2 10/2018 Braun et al.
2011/0076292 A1 3/2011 Blaquiere et al.
2012/0244149 A1 9/2012 Blaquiere et al.
2012/0245144 A1 9/2012 Heffron et al.
2013/0079331 A1 3/2013 Blaquiere et al.
2014/0058098 A1 2/2014 Blaquiere et al.
2014/0288047 A1 9/2014 Blaquiere et al.
2016/0052933 A1 2/2016 Blaquiere et al.
2017/0002022 A1 1/2017 Braun et al.
2017/0015678 A1 1/2017 Braun et al.

(Continued)

FOREIGN PATENT DOCUMENTS

CN 102762576 A 10/2012
CN 103562210 A 2/2014

(Continued)

OTHER PUBLICATIONS

"International Application No. PCT/CN2019/088788, International Search Report and Written Opinion mailed Sep. 2, 2019", (Sep. 2, 2019), 17 pgs.

(Continued)

*Primary Examiner* — Adam C Milligan
*Assistant Examiner* — William Y Lee
(74) *Attorney, Agent, or Firm* — Schwegman Lundberg & Woessner, P.A.

(57) ABSTRACT

An inhibitor containing a tricyclic derivative, a preparation method therefor and a pharmaceutical composition comprising the inhibitor, as well as a use thereof as a phosphoinositide 3 kinase (PI3K) inhibitor in the treatment of cancer and diseases or conditions mediated by or dependent on PI3K imbalance.

(I)

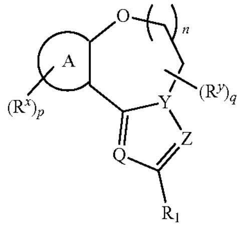

13 Claims, No Drawings

(56) References Cited

U.S. PATENT DOCUMENTS

| | | | |
|---|---|---|---|
| 2017/0081341 A1 | 3/2017 | Blaquiere et al. | |
| 2017/0210733 A1 | 7/2017 | Braun et al. | |
| 2018/0127404 A1 | 5/2018 | Braun et al. | |

FOREIGN PATENT DOCUMENTS

| | | | | |
|---|---|---|---|---|
| CN | 107873032 A | 4/2018 | | |
| CN | 107995911 A | 5/2018 | | |
| WO | WO-2010029082 A1 | 3/2010 | | |
| WO | WO-2011022439 A1 | 2/2011 | | |
| WO | WO-2017001645 A1 * | 1/2017 | ........... | A61K 31/553 |
| WO | WO-2019228341 A1 | 12/2019 | | |

OTHER PUBLICATIONS

Heffron, Timothy P., et al., "The Rational Design of Selective Benzoxazepin Inhibitors of the a-Isoform of Phosphoinositide 3-Kinase Culminating in the Identification of (S)-2-((2-(1-Isopropyl-1H-1,2,4-triazol-5-yl)-5,6-dihydrobenzo[f]imidazo[1,2-d][1,4]oxazepin-9-yl)oxy)propanamide (GDC-0326)", J Med Chem. Feb. 11, 2016;59(3):985-1002. doi: 10.1021/acs.jmedchem.5b01483. Epub Jan. 20, 2016., (Jan. 7, 2016), 985-1002.

* cited by examiner

TRICYCLIC DERIVATIVES INHIBITOR, PREPARATION METHOD, AND APPLICATIONS THEREOF

PRIORITY CLAIM TO RELATED APPLICATIONS

This application is a U.S. national stage filing under 35 U.S.C. δ 371 from International Application No. PCT/CN2019/088788, filed on 28 May 2019, and published as WO2019/228341 on 5 Dec. 2019, which claims the benefit under 35 U.S.C. 119 to Chinese Application No. 201810541998.4, filed on 30 May 2018, Chinese Application No. 201810772171.4, filed on 13 Jul. 2018, Chinese Application No. 201811142142.6, filed on 28 Sep. 2018, and Chinese Application No. 201910176302.7, filed on 8 Mar. 2019, the benefit of priority of each of which is claimed herein, and which applications and publication are hereby incorporated herein by reference in their entirety.

FIELD OF THE INVENTION

The present invention belongs to the field of drug synthesis, and in particular relates to a tricyclic derivative inhibitor, a method for preparing the same, and a use thereof.

BACKGROUND OF THE INVENTION

The phosphatidylinositol 3-kinase (PI3K) protein family is divided into four types: I, II, III and IV, and involved in the regulation of multiple cell functions such as cell growth, proliferation, differentiation, survival and glucose metabolism. The four types of PI3K proteins have different structures and functions, and the most widely studied is type I of PI3K. This type I of PI3K is further divided into four subtypes: PI3Kα, PI3Kβ, PI3Kδ and PI3Kγ. Among them, PI3Kα shows activating mutation and amplification in a variety of tumors, and is closely related to the occurrence and development of tumor. It is reported that PI3Kβ can activate platelets, and play an important role in the development of diseases such as thrombosis. PI3Kδ and PI3Kγ are mainly expressed in the blood system, and are closely related to the immune system and inflammation. PI3Kγ is also closely related to the blood pressure stability and smooth muscle contraction.

PI3Kα shows activating mutation and amplification in a variety of tumors, and is the driving factor leading to tumorigenesis. PI3Kα is a heterodimer composed of p110 catalytic subunit and p85 regulatory subunit. PI3Kα is activated by receptor tyrosine kinases (RTKs) and G protein-coupled receptors (GPCRs). After activation, it catalyzes the production of phosphatidylinositol 3 phosphate (PIP3) from phosphatidylinositol 2 phosphate (PIP2). PIP3 can further activate protein kinase B (PKB, also known as AKT) and its downstream signaling pathways. A variety of cell growth factors, such as epidermal growth factor (EGF), fibroblast growth factor (FGF), vascular endothelial growth factor (VEGF), hepatocyte growth factor (HGF) and insulin, can activate PI3Kα, thereby activating downstream cell proliferation signaling pathways. The abnormal activation of PI3Kα can lead to rapid cell proliferation, thereby causing tumorigenesis.

PI3Kα has always been an important target for tumor drug development. However, most of the compounds are broad-spectrum inhibitors of PI3Ks and can cause obvious side effects in clinical studies, which severely limit the development of PI3Ks inhibitor. Current studies have determined that most of the side effects of broad-spectrum inhibitors of PI3Ks are caused by the inhibition of PI3Kβ, PI3Kδ and PI3Kγ subtypes. PI3Kβ plays an important role in the side effects of thrombocytopenia and thrombosis. The inhibition of PI3Kδ can cause abnormalities in the immune system, and autoimmunity and virus infections such as pneumonia, hepatitis and diarrhea/enteritis are closely related to the inhibition of PI3Kδ target. PI3Kγ is closely related to blood pressure stability and smooth muscle contraction, and is the main target that causes the side effect of hypertension. Therefore, it is necessary to develop a PI3Kα inhibitor with a high activity and high selectivity, which can further improve the anti-tumor effect of PI3Kα inhibitor, and reduce or eliminate severe side effects such as various inflammation, thrombocytopenia and hypertension caused by the inhibition of other subtypes.

The PI3Kα-selective inhibitor BYL-719 developed by Novartis is currently in phase III clinical trial. The PI3Kα-selective inhibitor MLN1117 developed by Takeda has entered phase II clinical trial. The selective inhibitor GDC-0077 developed by Genentech is in phase I clinical trial.

International patent applications WO2010029082(A1) and WO2011022439(A1) disclose PI3Kα-selective inhibitor related compounds. However, subsequent studies show that the activity of these compounds in cells is not high, which affects its clinical anti-tumor effect. Therefore, there is an urgent need to develop a PI3Kα-selective inhibitor with a high activity and high selectivity. PI3Kα-selective inhibitors can be used to treat a variety of multiple tumors with PI3Kα activating mutation or amplification, and have an important clinical application value.

Studies show that the compounds of the examples of the present invention have higher activity and selectivity on PI3Kα enzyme, better activity in cells, better tumor inhibition rate in mice pharmacodynamic model, and higher safety.

SUMMARY OF THE INVENTION

The objective of the present invention is to provide a compound of formula (I), a stereoisomer thereof, or a pharmaceutically acceptable salt thereof, wherein the structure of the compound of formula (I) is as follows:

(I)

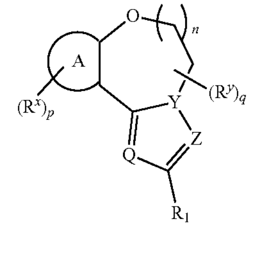

wherein:

- Q, Y and Z are each independently selected from the group consisting of N and —$CR_{aa}$;
- ring A is selected from the group consisting of cycloalkyl, heterocyclyl, aryl and heteroaryl;
- $R_1$ is selected from the group consisting of hydrogen, deuterium, alkyl, deuterated alkyl, haloalkyl, alkoxy, haloalkoxy; halogen, amino, nitro, hydroxy; cyano, alkenyl, alkynyl, cycloalkyl, heterocyclyl, oxoheterocyclyl, thioxoheterocyclyl, aryl, heteroaryl, —$(CH_2)_{n1}R_{bb}$, —$(CH_2)_{n1}OR_{bb}$, —$NR_{aa}$ $C(O)(CH_2)_{n1}OR_{bb}$, $-NR_{aa}C(S)(CH_2)_{n1}OR_{bb}$, $-(CH_2)_{n1}SR_{bb}$, $-(CH_2)_{n1}C(O)R_{bb}$, $-(CH_2)_{n1}C(O)OR_{bb}$, $-(CH_2)_{n1}S(O)_{m1}R_{bb}$, $-(CH_2)_{n1}NR_{bb}R_{cc}$, $-(CH_2)_{n1}C(O)NR_{bb}R_{cc}$, $-(CH_2)_{n1}NR_{bb}C(O)R_{cc}$ and $-(CH_2)_{n1}NR_{bb}S(O)_{m1}R_{cc}$, wherein the alkyl, deuterated alkyl, haloalkyl, alkoxy, haloalkoxy, alkenyl, alkynyl, cycloalkyl, heterocyclyl, oxoheterocyclyl, thioxoheterocyclyl, aryl and heteroaryl are each optionally further substituted by one or more substituent(s) selected from the group consisting of deuterium, substituted or unsubstituted cycloalkylalkyl, substituted or unsubstituted cycloalkylhaloalkyl, halogen, substituted or unsubstituted cycloalkylamino, oxo, thioxo, nitro, cyano, hydroxy, substituted or unsubstituted cycloalkylalkenyl, substituted or unsubstituted cycloalkylalkynyl, substituted or unsubstituted cycloalkylalkoxy, substituted or unsubstituted cycloalkylhaloalkoxy, substituted or unsubstituted cycloalkylhydroxyalkyl, substituted or unsubstituted cycloalkyl, substituted or unsubstituted heterocyclyl, substituted or unsubstituted aryl, substituted or unsubstituted heteroaryl, $-(CH_2)_{n1}R_{dd}$, $-(CH_2)_{n1}OR_{dd}$, $-(CH_2)_{n1}SR_{dd}$, $-(CH_2)_{n1}C(O)R_{dd}$, $-(CH_2)_{n1}C(O)OR_{dd}$, $-(CH_2)_{n1}S(O)_{m1}R_{dd}$, $-(CH_2)_{n1}NR_{dd}R_{ee}$, $-(CH_2)_{n1}C(O)NR_{dd}R_{ee}$, $-(CH_2)_{n1}C(O)NHR_{dd}$, $-(CH_2)_{n1}NR_{dd}C(O)R_{ee}$ and $-(CH_2)_{n1}NR_{dd}S(O)_{m1}R_{ee}$;

$R^x$ and $R^y$ are each independently selected from the group consisting of hydrogen, deuterium, alkyl, deuterated alkyl, haloalkyl, alkoxy, haloalkoxy, halogen, amino, thiol, nitro, hydroxy; cyano, alkenyl, alkynyl, cycloalkyl, heterocyclyl, aryl, heteroaryl, $-(CH_2)_{n1}R_{bb}$, $-(CH_2)_{n1}-$, $-(CH_2)_{n1}OR_{bb}$, $-(CH_2)_{n1}SR_{bb}$, $-(CH_2)_{n1}C(O)R_{bb}$, $-(CH_2)_{n1}C(O)OR_{bb}$, $-(CH_2)_{n1}S(O)_{m1}R_{bb}$, $-(CH_2)_{n1}NR_{bb}R_{cc}$, $-(CH_2)_{n1}C(O)NR_{bb}R_{cc}$, $-(CH_2)_{n1}NR_{bb}C(O)R_{cc}$ and $-(CH_2)_{n1}NR_{bb}S(O)_{m1}R_{cc}$, wherein the alkyl, deuterated alkyl, haloalkyl, alkoxy, haloalkoxy; alkenyl, alkynyl, cycloalkyl, heterocyclyl, aryl and heteroaryl are each optionally further substituted by one or more substituent(s) selected from the group consisting of deuterium, substituted or unsubstituted cycloalkylalkyl, substituted or unsubstituted cycloalkylhaloalkyl, halogen, substituted or unsubstituted cycloalkylamino, thiol, oxo, nitro, cyano, hydroxy, substituted or unsubstituted alkenyl, substituted or unsubstituted alkynyl, substituted or unsubstituted cycloalkylalkoxy, substituted or unsubstituted cycloalkylhaloalkoxy, substituted or unsubstituted cycloalkylhydroxyalkyl, substituted or unsubstituted cycloalkyl, substituted or unsubstituted heterocyclyl, substituted or unsubstituted aryl, substituted or unsubstituted heteroaryl, $-(CH_2)_{n1}R_{dd}$, $-(CH_2)_{n1}OR_{dd}$, $-(CH_2)_{n1}SR_{dd}$, $-(CH_2)_{n1}C(O)R_{dd}$, $-(CH_2)_{n1}C(O)OR_{dd}$, $-(CH_2)_{n1}S(O)_{m1}R_{dd}$, $-(CH_2)_{n1}NR_{dd}R_{ee}$, $-(CH_2)_{n1}C(O)NR_{dd}R_{ee}$, $-(CH_2)_{m1}C(O)NHR_{dd}$, $-(CH_2)_{n1}NR_{dd}C(O)R_{ee}$ and $-(CH_2)_{n1}NR_{dd}S(O)_{m1}R_{ee}$;

or, any two adjacent or non-adjacent $R^x$ are bonded to form a cycloalkyl, heterocyclyl, aryl or heteroaryl, wherein the cycloalkyl, heterocyclyl, aryl or heteroaryl is optionally further substituted by one or more substituent(s) selected from the group consisting of deuterium, substituted or unsubstituted alkyl, substituted or unsubstituted haloalkyl, halogen, substituted or unsubstituted amino, oxo, nitro, cyano, hydroxy, substituted or unsubstituted alkenyl, substituted or unsubstituted alkynyl, substituted or unsubstituted alkoxy, substituted or unsubstituted haloalkoxy, substituted or unsubstituted hydroxyalkyl, substituted or unsubstituted cycloalkyl, substituted or unsubstituted heterocyclyl, substituted or unsubstituted aryl, substituted or unsubstituted heteroaryl, $-(CH_2)_{n1}-$, $-(CH_2)_{n1}R_{bb}$, $-(CH_2)_{n1}OR_{bb}$, $-(CH_2)_{m1}SR_{bb}$, $-(CH_2)_{n1}C(O)R_{bb}$, $-(CH_2)_{n1}C(O)OR_{bb}$, $-(CH_2)_{n1}S(O)_{m1}R_{bb}$, $-(CH_2)_{n1}NR_{bb}R_{cc}$, $-(CH_2)_{n1}C(O)NR_{bb}R_{cc}$, $-(CH_2)_{n1}NR_{bb}C(O)R_{cc}$ and $-(CH_2)_{n1}NR_{bb}S(O)_{m1}R_{cc}$;

or, any two adjacent or non-adjacent $R^y$ are bonded to form a cycloalkyl, heterocyclyl, aryl or heteroaryl, wherein the cycloalkyl, heterocyclyl, aryl or heteroaryl is optionally further substituted by one or more substituent(s) selected from the group consisting of deuterium, substituted or unsubstituted alkyl, substituted or unsubstituted haloalkyl, halogen, substituted or unsubstituted amino, oxo, nitro, cyano, hydroxy, substituted or unsubstituted alkenyl, substituted or unsubstituted alkynyl, substituted or unsubstituted alkoxy, substituted or unsubstituted haloalkoxy, substituted or unsubstituted hydroxyalkyl, substituted or unsubstituted cycloalkyl, substituted or unsubstituted heterocyclyl, substituted or unsubstituted aryl, substituted or unsubstituted heteroaryl, $-(CH_2)_{n1}-$, $-(CH_2)_{n1}R_{bb}$, $-(CH_2)_{m1}OR_{bb}$, $-(CH_2)_{n1}SR_{bb}$, $-(CH_2)_{n1}C(O)R_{bb}$, $-(CH_2)_{n1}C(O)OR_{bb}$, $-(CH_2)_{n1}S(O)_{m1}R_{bb}$, $-(CH_2)_{n1}NR_{bb}R_{cc}$, $-(CH_2)_{n1}C(O)NR_{bb}R_{cc}$, $-(CH_2)_{n1}NR_{bb}C(O)R_{cc}$ and $-(CH_2)_{n1}NR_{bb}S(O)_{m1}R_{cc}$;

$R_{aa}$ is selected from the group consisting of hydrogen, deuterium, alkyl, deuterated alkyl, haloalkyl, alkoxy, hydroxyalkyl, haloalkoxy, halogen, cyano, nitro, hydroxy; amino, alkenyl, alkynyl, cycloalkyl, heterocyclyl, aryl and heteroaryl, wherein the alkyl, deuterated alkyl, haloalkyl, alkoxy, hydroxyalkyl, haloalkoxy; alkenyl, alkynyl, cycloalkyl, heterocyclyl, aryl and heteroaryl are each optionally further substituted by one or more substituent(s) selected from the group consisting of deuterium, substituted or unsubstituted alkyl, halogen, hydroxy, substituted or unsubstituted amino, oxo, nitro, cyano, substituted or unsubstituted alkenyl, substituted or unsubstituted alkynyl, substituted or unsubstituted alkoxy, substituted or unsubstituted hydroxyalkyl, substituted or unsubstituted cycloalkyl, substituted or unsubstituted heterocyclyl, substituted or unsubstituted aryl and substituted or unsubstituted heteroaryl;

$R_{bb}$, $R_{cc}$, $R_{dd}$ and $R_{ee}$ are each independently selected from the group consisting of hydrogen, deuterium, alkyl, deuterated alkyl, haloalkyl, alkoxy, hydroxyalkyl, haloalkoxy; halogen, cyano, nitro, hydroxy, amino, alkenyl, alkynyl, cycloalkyl, heterocyclyl, aryl and heteroaryl, wherein the alkyl, deuterated alkyl, haloalkyl, alkoxy, hydroxyalkyl, haloalkoxy, alkenyl, alkynyl, cycloalkyl, heterocyclyl, aryl and heteroaryl are each optionally further substituted by one or more substituent(s) selected from the group consisting of deuterium, substituted or unsubstituted alkyl, halogen, hydroxy, substituted or unsubstituted amino, oxo, nitro, cyano, substituted or unsubstituted alkenyl, substituted or unsubstituted alkynyl, substituted or unsubstituted alkoxy, substituted or unsubstituted hydroxyalkyl, substituted or unsubstituted cycloalkyl, substituted or unsubstituted heterocyclyl, substituted or unsubstituted aryl and substituted or unsubstituted heteroaryl;

n is 0, 1, 2 or 3;

p is 0, 1, 2, 3, 4, 5 or 6;

q is 0, 1, 2, 3, 4, 5 or 6;

$m_1$ is 0, 1 or 2; and $n_1$ is 0, 1, 2, 3, 4 or 5.

In a preferred embodiment, $R^x$ is —$(CH_2)_{n1}NR_{bb}C(R_{ff}R_{gg})C(O)R_{cc}$;

$R_{ff}$ and $R_{gg}$ are each independently selected from the group consisting of hydrogen, deuterium, alkyl, deuterated alkyl, haloalkyl, alkoxy, hydroxyalkyl, haloalkoxy, halogen, cyano, nitro, hydroxy, amino, alkenyl, alkynyl, cycloalkyl, heterocyclyl, aryl and heteroaryl, wherein the alkyl, deuterated alkyl, haloalkyl, alkoxy, hydroxyalkyl, haloalkoxy, alkenyl, alkynyl, cycloalkyl, heterocyclyl, aryl and heteroaryl are each optionally further substituted by one or more substituent(s) selected from the group consisting of deuterium, substituted or unsubstituted alkyl, halogen, hydroxy, substituted or unsubstituted amino, oxo, nitro, cyano, substituted or unsubstituted alkenyl, substituted or unsubstituted alkynyl, substituted or unsubstituted alkoxy, substituted or unsubstituted hydroxyalkyl, substituted or unsubstituted cycloalkyl, substituted or unsubstituted heterocyclyl, substituted or unsubstituted aryl and substituted or unsubstituted heteroaryl; and $n_1$, $R_{bb}$ and $R_{cc}$ are as defined in formula (I).

In a further preferred embodiment, when ring A is a benzene ring, $R^y$ is hydrogen, Q and Y are N, Z is —$CR_{aa}$, $R_{aa}$ is hydrogen, n is 1 and $R_1$ is

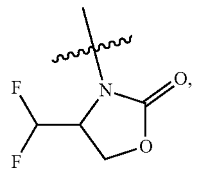

$R^x$ is not —$NHCHR_{ff}C(O)NH_2$, wherein $R_{ff}$ is $CH_3$—, cyclopropyl- or —$CH_2CH_3$;

when ring A is a benzene ring, $R^y$ is hydrogen, Q and Y are N, Z is —$CR_{aa}$, $R_{aa}$ is hydrogen, n is 1 and $R_1$ is

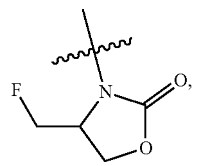

$R^x$ is not —$NCHR_{ff}C(O)NH_2$, wherein $R_{ff}$ is $CH_3$— or cyclopropyl-; and when ring A is a benzene ring, $R^y$ is hydrogen, Q and Y are N, Z is —$CR_{aa}$, $R_{aa}$ is hydrogen, n is 1 and $R_1$ is

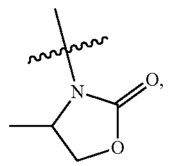 [SMILES: *N1C(=O)OCC1C]

$R^x$ is not —$NHCHR_{ff}C(O)NH_2$, wherein $R_{ff}$ is cyclopropyl- or cyclobutyl-.

In a preferred embodiment of the present invention, the compound of formula (I), the stereoisomer thereof, or the pharmaceutically acceptable salt thereof, wherein the structure of the compound is as shown in formula (II):

(II)

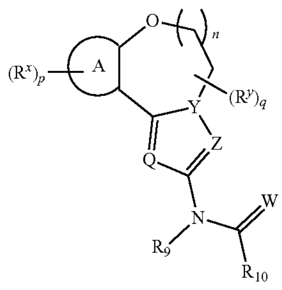

wherein:

W is selected from the group consisting of oxygen and sulfur, and preferably oxygen;

$R_9$ and $R_{10}$ are each independently selected from the group consisting of hydrogen, deuterium, alkyl, deuterated alkyl, haloalkyl, alkoxy, haloalkoxy, halogen, amino, thiol, nitro, hydroxy, cyano, alkenyl, alkynyl, cycloalkyl, halocycloalkyl, heterocyclyl, aryl, heteroaryl, —$(CH_2)_{n1}$—, —$(CH_2)_{n1}R_{bb}$, —$(CH_2)_{n1}OR_{bb}$, —$(CH_2)_{n1}SR_{bb}$, —$(CH_2)_{n1}C(O)R_{bb}$, —$(CH_2)_{n1}C(O)OR_{bb}$, —$(CH_2)_{n1}S(O)_{m1}R_{bb}$, —$(CH_2)_{n1}NR_{bb}R_{cc}$, —$(CH_2)_{n1}C(O)NR_{bb}R_{cc}$, —$(CH_2)_{n1}NR_{bb}C(O)R_{cc}$ and —$(CH_2)_{n1}NR_{bb}S(O)_{m1}R_{cc}$, wherein the alkyl, haloalkyl, cycloalkyl, heterocyclyl, aryl and heteroaryl are each optionally further substituted by one or more substituent(s) selected from the group consisting of deuterium, alkyl, haloalkyl, halogen, amino, thiol, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{dd}$, —$(CH_2)_{n1}OR_{dd}$, —$(CH_2)_{n1}SR_{dd}$, —$(CH_2)_{n1}C(O)R_{dd}$, —$(CH_2)_{n1}C(O)OR_{dd}$, —$(CH_2)_{n1}S(O)_{m1}R_{dd}$, —$(CH_2)_{n1}NR_{dd}R_{ee}$, —$(CH_2)_{n1}C(O)NR_{dd}R_{ee}$, —$(CH_2)_{n1}C(O)NHR_{dd}$, —$(CH_2)_{n1}NR_{dd}C(O)R_{ee}$ and —$(CH_2)_{n1}NR_{dd}S(O)_{m1}R_{ee}$;

or, $R_9$ and $R_{10}$ can be bonded to form a heterocyclyl or heteroaryl, wherein the heterocyclyl or heteroaryl is optionally further substituted by one or more substituent(s) selected from the group consisting of deuterium, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}$—, —$(CH_2)_{n1}R_{bb}$, —$(CH_2)_{n1}OR_{bb}$, —$(CH_2)_{n1}SR_{bb}$, —$(CH_2)_{n1}C(O)R_{bb}$, —$(CH_2)_{n1}C(O)OR_{bb}$, —$(CH_2)_{n1}S(O)_{m1}R_{bb}$, —$(CH_2)_{n1}NR_{bb}R_{cc}$, —$(CH_2)_{n1}C(O)NR_{bb}R_{cc}$, —$(CH_2)_{n1}NR_{bb}C(O)R_{cc}$ and —$(CH_2)_{n1}NR_{bb}S(O)_{m1}R_{cc}$; and ring A, H, Y, Z, $R_{23}$ to $R_{26}$, $R^x$, $R^y$, n, p, q, $m_1$ and $n_1$ are as defined in formula (II).

In a preferred embodiment of the present invention, the compound of formula (II), the stereoisomer thereof, or the pharmaceutically acceptable salt thereof, wherein the structure of the compound is shown in formula (II-A) or (II-B):

(II-A)

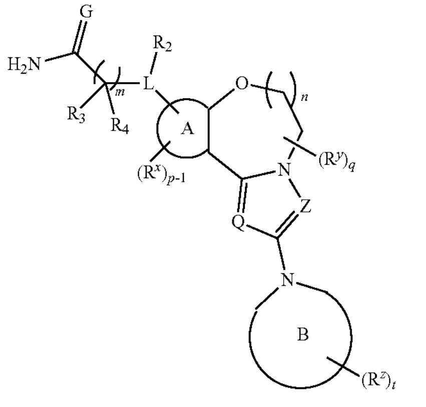

(II-B)

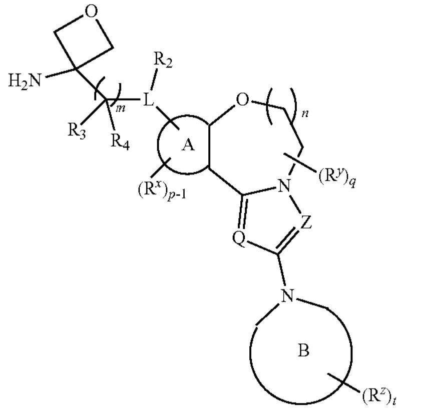

wherein:

G is selected from the group consisting of oxygen and sulfur;

L is selected from the group consisting of nitrogen, oxygen, sulfur and —$CR_{aa}$;

ring B is selected from the group consisting of heterocyclyl and heteroaryl, and preferably thioxoheterocyclyl or oxoheterocyclyl;

$R^z$ is selected from the group consisting of hydrogen, deuterium, alkyl, deuterated alkyl, haloalkyl, alkoxy, haloalkoxy, halogen, amino, thiol, nitro, hydroxy, cyano, oxo, alkenyl, alkynyl, cycloalkyl, heterocyclyl, aryl, heteroaryl, —$(CH_2)_{n1}$—, —$(CH_2)_{n1}R_{bb}$, —$(CH_2)_{n1}OR_{bb}$, —$(CH_2)_{n1}SR_{bb}$, —$(CH_2)_{n1}C(O)R_{bb}$, —$(CH_2)_{n1}C(O)OR_{bb}$, —$(CH_2)_{n1}S(O)_{m1}R_{bb}$, —$(CH_2)_{n1}NR_{bb}R_{cc}$, —$(CH_2)_{n1}C(O)NR_{bb}R_{cc}$, —$(CH_2)_{n1}NR_{bb}C(O)R_{cc}$ and —$(CH_2)_{n1}NR_{bb}S(O)_{m1}R_{ee}$, wherein the alkyl, haloalkyl, alkoxy, haloalkoxy, alkenyl, alkynyl, cycloalkyl, heterocyclyl, aryl and heteroaryl are each optionally further substituted by one or more substituent(s) selected from the group consisting of deuterium, alkyl, haloalkyl, halogen, amino, thiol, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{dd}$, —$(CH_2)_{n1}OR_{dd}$, —$(CH_2)_{n1}SR_{dd}$, —$(CH_2)_{n1}C(O)R_{dd}$, —$(CH_2)_{n1}C(O)OR_{dd}$, —$(CH_2)_{n1}S(O)_{m1}R_{dd}$, —$(CH_2)_{n1}NR_{dd}R_{ee}$, —$(CH_2)_{n1}C(O)NR_{dd}R_{ee}$, —$(CH_2)_{n1}C(O)NHR_{dd}$, —$(CH_2)_{n1}NR_{dd}C(O)R_{ee}$ and —$(CH_2)_{n1}NR_{dd}S(O)_{m1}R_{ee}$;

or, any two adjacent or non-adjacent $R^z$ can be bonded to form a cycloalkyl, heterocyclyl, aryl or heteroaryl, wherein the cycloalkyl, heterocyclyl, aryl or heteroaryl is optionally further substituted by one or more substituent(s) selected from the group consisting of deuterium, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}$—, —$(CH_2)_{n1}R_{bb}$, —$(CH_2)_{n1}OR_{bb}$, —$(CH_2)_{n1}SR_{bb}$, —$(CH_2)_{n1}C(O)R_{bb}$, —$(CH_2)_{n1}C(O)OR_{bb}$, —$(CH_2)_{n1}S(O)_{m1}R_{bb}$, —$(CH_2)_{n1}NR_{bb}R_{cc}$, —$(CH_2)_{n1}C(O)NR_{bb}R_{cc}$, —$(CH_2)_{n1}NR_{bb}C(O)R_{cc}$ and —$(CH_2)_{n1}NR_{bb}S(O)_{m1}R_{cc}$;

$R_2$ is present or absent, when L is nitrogen or —$CR_{aa}$, $R_2$ is selected from the group consisting of hydrogen, deuterium, alkyl, deuterated alkyl, haloalkyl, alkoxy, haloalkoxy; halogen, amino, thiol, nitro, hydroxy, cyano, alkenyl, alkynyl, cycloalkyl, heterocyclyl, aryl, heteroaryl, —$(CH_2)_{n1}$—, —$(CH_2)_{n1}R_{bb}$, —$(CH_2)_{n1}OR_{bb}$, —$(CH_2)_{n1}SR_{bb}$, —$(CH_2)_{n1}C(O)R_{bb}$, —$(CH_2)_{n1}C(O)OR_{bb}$, —$(CH_2)_{n1}S(O)_{m1}R_{bb}$, —$(CH_2)_{n1}NR_{bb}R_{cc}$, —$(CH_2)_{n1}C(O)NR_{bb}R_{cc}$, —$(CH_2)_{n1}NR_{bb}C(O)R_{cc}$ and —$(CH_2)_{n1}NR_{bb}S(O)_{m1}R_{cc}$;

$R_3$ and $R_4$ are each independently selected from the group consisting of hydrogen, deuterium, alkyl, deuterated alkyl, haloalkyl, alkoxy, hydroxyalkyl, haloalkoxy, halogen, amino, thiol, nitro, hydroxy, cyano, alkenyl, alkynyl, cycloalkyl, heterocyclyl, aryl, heteroaryl, —$(CH_2)_{n1}$—, —$(CH_2)_{n1}R_{bb}$, —$(CH_2)_{n1}OR_{bb}$, —$(CH_2)_{n1}SR_{bb}$, —$(CH_2)_{n1}C(O)R_{bb}$, —$(CH_2)_{n1}C(O)OR_{bb}$, —$(CH_2)_{n1}S(O)_{m1}R_{bb}$, —$(CH_2)_{n1}NR_{bb}R_{cc}$, —$(CH_2)_{n1}C(O)NR_{bb}R_{cc}$, —$(CH_2)_{n1}NR_{bb}C(O)R_{cc}$ and —$(CH_2)_{n1}NR_{bb}S(O)_{m1}R_{cc}$, wherein the alkyl, deuterated alkyl, haloalkyl, alkoxy, haloalkoxy; alkenyl, alkynyl, cycloalkyl, heterocyclyl, aryl and heteroaryl are each optionally further substituted by one or more substituent(s) selected from the group consisting of deuterium, alkyl, haloalkyl, halogen, amino, thiol, oxo, nitro, cyano, hydroxy; alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{dd}$, —$(CH_2)_{n1}OR_{dd}$, —$(CH_2)_{n1}SR_{dd}$, —$(CH_2)_{n1}C(O)R_{dd}$, —$(CH_2)_{n1}C(O)OR_{dd}$, —$(CH_2)_{n1}S(O)_{m1}R_{dd}$, —$(CH_2)_{n1}NR_{dd}R_{ee}$, —$(CH_2)_{n1}C(O)NR_{dd}R_{ee}$, —$(CH_2)_{n1}C(O)NHR_{dd}$, —$(CH_2)_{n1}NR_{dd}C(O)R_{ee}$ and —$(CH_2)_{n1}NR_{dd}S(O)_{m1}R_{ee}$;

or, any two groups of $R_2$, $R_3$, $R_4$ and $R_{aa}$ are bonded to form a cycloalkyl, heterocyclyl, aryl or heteroaryl, wherein the cycloalkyl, heterocyclyl, aryl or heteroaryl is optionally further substituted by one or more substituent(s) selected from the group consisting of deuterium, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}$—, —$(CH_2)_{n1}R_{bb}$, —$(CH_2)_{n1}OR_{bb}$, —$(CH_2)_{n1}SR_{bb}$, —$(CH_2)_{n1}C(O)R_{bb}$, —$(CH_2)_{n1}C(O)

$OR_{bb}$, $-(CH_2)_{n1}S(O)_{m1}R_{bb}$, $-(CH_2)_{n1}NR_{bb}R_{cc}$, $-(CH_2)_{n1}C(O)NR_{bb}R_{cc}$, $-(CH_2)_{n1}NR_{bb}C(O)R_{cc}$ and $-(CH_2)_{n1}NR_{bb}S(O)_{m1}R_{cc}$;

m is 0, 1, 2, 3, 4, 5 or 6;

t is 0, 1, 2, 3, 4, 5 or 6;

q is 0, 1, 2, 3, 4, 5 or 6; and ring A, Q, Y, Z, $R_{bb}$, $R_{cc}$, $R_{dd}$, $R_{ee}$, $R^x$, $R^y$, n, p, q, $m_1$ and $n_1$ are as defined in formula (I).

In a preferred embodiment of the present invention, the compound of formula (I), the stereoisomer thereof, or the pharmaceutically acceptable salt thereof, wherein the structure of the compound is shown in formula (III):

(III)

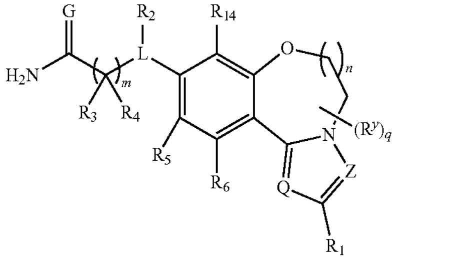

wherein:

$R_5$, $R_6$ and $R_{14}$ are each independently selected from the group consisting of hydrogen, deuterium, alkyl, deuterated alkyl, haloalkyl, alkoxy, haloalkoxy, halogen, amino, thiol, nitro, hydroxy, cyano, alkenyl, alkynyl, cycloalkyl, heterocyclyl, aryl, heteroaryl, $-(CH_2)_{n1}-$, $-(CH_2)_{n1}R_{bb}$, $-(CH_2)_{n1}OR_{bb}$, $-(CH_2)_{n1}SR_{bb}$, $-(CH_2)_{n1}C(O)R_{bb}$, $-(CH_2)_{n1}C(O)OR_{bb}$, $-(CH_2)_{n1}S(O)_{m1}R_{bb}$, $-(CH_2)_{n1}NR_{bb}R_{cc}$, $-(CH_2)_{n1}C(O)NR_{bb}R_{cc}$, $-(CH_2)_{n1}NR_{bb}C(O)R_{cc}$ and $-(CH_2)_{n1}NR_{bb}S(O)_{m1}R_{cc}$, wherein the alkyl, haloalkyl, cycloalkyl, heterocyclyl, aryl and heteroaryl are each optionally further substituted by one or more substituent(s) selected from the group consisting of deuterium, alkyl, haloalkyl, halogen, amino, thiol, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl and substituted or unsubstituted heteroaryl;

or, $R_5$ and $R_6$ are bonded to form a cycloalkyl, heterocyclyl, aryl or heteroaryl, wherein the cycloalkyl, heterocyclyl, aryl or heteroaryl is optionally further substituted by one or more substituent(s) selected from the group consisting of deuterium, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, $-(CH_2)_{n1}-$, $-(CH_2)_{n1}R_{bb}$, $-(CH_2)_{n1}OR_{bb}$, $-(CH_2)_{n1}SR_{bb}$, $-(CH_2)_{n1}C(O)R_{bb}$, $-(CH_2)_{n1}C(O)OR_{bb}$, $-(CH_2)_{n1}S(O)_{m1}R_{bb}$, $-(CH_2)_{n1}NR_{bb}R_{cc}$, $-(CH_2)_{n1}C(O)NR_{bb}R_{cc}$, $-(CH_2)_{n1}NR_{bb}C(O)R_{cc}$ and $-(CH_2)_{n1}NR_{bb}S(O)_{m1}R_{cc}$;

Q, Y, Z, $R_{bb}$, $R_{cc}$, $R_1$, $R_2$, $R^y$, n, p, q, $m_1$ and $n_1$ are as defined in formula (I); and G, m, $R_3$ and $R_4$ are as defined in formula (II-A).

In a preferred embodiment of the present invention, the compound of formula (I), the stereoisomer thereof, or the pharmaceutically acceptable salt thereof, wherein the structure of the compound is shown in formula (IV):

(IV)

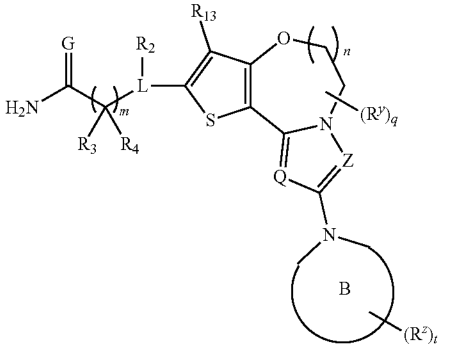

wherein:

$R_{13}$ is selected from the group consisting of hydrogen, deuterium, alkyl, deuterated alkyl, halogen, cyano, nitro, haloalkyl, hydroxy, amino, alkenyl, alkynyl, cycloalkyl, heterocyclyl, aryl and heteroaryl, wherein the alkyl, cycloalkyl, heterocyclyl, aryl and heteroaryl are each optionally further substituted by one or more substituent(s) selected from the group consisting of deuterium, alkyl, halogen, hydroxy, amino, oxo, nitro, cyano, alkenyl, alkynyl, alkoxy, hydroxyalkyl, cycloalkyl, heterocyclyl, aryl and heteroaryl, and preferably halogen, amino, nitro, cyano, alkyl, haloalkyl or cycloalkyl; and ring B, Q, Z, G, $R_2$ to $R_4$, $R^y$, $R^z$, m, n, q and t are as defined in formula (III).

In a preferred embodiment of the present invention, the compound of formula (III), the stereoisomer thereof, or the pharmaceutically acceptable salt thereof, wherein the structure of the compound is shown in formula (III-A) or (III-B):

(III-A)

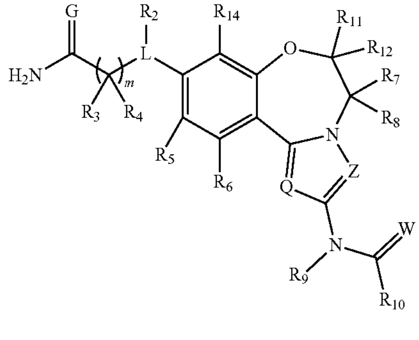

(III-B)

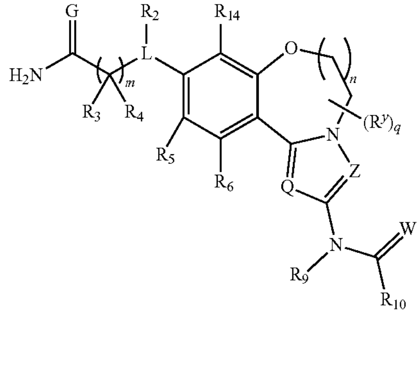

wherein:

$R_7$, $R_8$, $R_{11}$ and $R_{12}$ are each independently selected from the group consisting of hydrogen, deuterium, alkyl, deuterated alkyl, haloalkyl, alkoxy, haloalkoxy, halogen, amino, thiol, nitro, hydroxy, cyano, alkenyl, alkynyl, cycloalkyl, heterocyclyl, aryl, heteroaryl, $-(CH_2)_{n1}-$, $-(CH_2)_{n1}R_{bb}$, $-(CH_2)_{n1}OR_{bb}$, $-(CH_2)_{n1}SR_{bb}$, $-(CH_2)_{n1}C(O)R_{bb}$, $-(CH_2)_{n1}C(O)OR_{bb}$, $-(CH_2)_{n1}S(O)_{m1}R_{bb}$, $-(CH_2)_{n1}NR_{bb}R_{cc}$, $-(CH_2)_{n1}C(O)NR_{bb}R_{cc}$, $-(CH_2)_{n1}NR_{bb}C(O)R_{cc}$ and $-(CH_2)_{n1}NR_{bb}S(O)_{m1}R_{cc}$, wherein the alkyl, haloalkyl, cycloalkyl, heterocyclyl, aryl and heteroaryl are each optionally further substituted by one or more substituent(s) selected from the group consisting of deuterium, alkyl, haloalkyl, halogen, amino, thiol, oxo, nitro, cyano, hydroxy, alkenyl, alkynyl, alkoxy, haloalkoxy, hydroxyalkyl, cycloalkyl, heterocyclyl, aryl and heteroaryl;

or, any two groups of $R_7$, $R_8$, $R_{11}$ and $R_{12}$ can be bonded to form a cycloalkyl, heterocyclyl, aryl or heteroaryl, wherein the cycloalkyl, heterocyclyl, aryl or heteroaryl is optionally further substituted by one or more substituent(s) selected from the group consisting of deuterium, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl and heteroaryl;

$R_9$ and $R_{10}$ are as defined in formula (II);

Q, Z, G, $R_2$ to $R_6$, $R_{bb}$, $R_{cc}$, $R^y$, m, n, q, $m_1$ and $n_1$ are as defined in formula (III); and $R_{14}$ is as defined in formula (III-A).

In a preferred embodiment of the present invention, the compound of formula (III-A), the stereoisomer thereof, or the pharmaceutically acceptable salt thereof, wherein the structure of the compound is shown in formula (V):

(V)

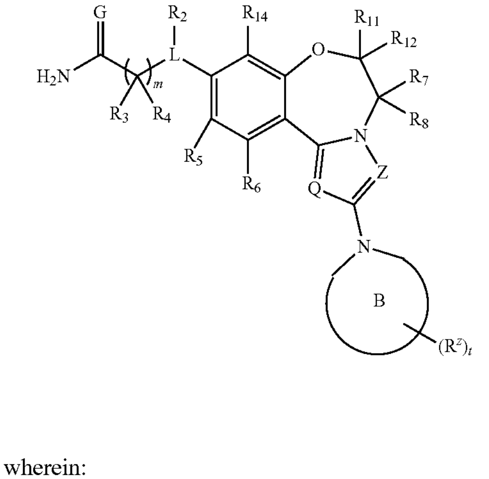

wherein:

ring B is as defined in formula (II-A); and

Q, Z, G, L, $R_2$ to $R_8$, $R_{11}$, $R_{12}$, $R_{14}$, $R^z$, m and t are as defined in formula (III-A).

In a preferred embodiment of the present invention, the compound of formula (III-A), the stereoisomer thereof, or the pharmaceutically acceptable salt thereof, wherein the structure of the compound is shown in formula (VI):

(VI)

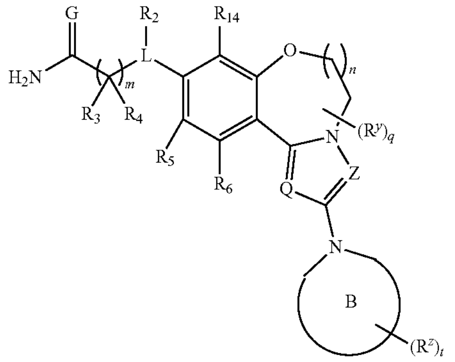

wherein:

ring B is as defined in formula (II-A); and

Q, Z, G, L, $R_2$ to $R_6$, $R_{14}$, $R^y$, $R^z$, q, m and t are as defined in formula (III-A).

In a preferred embodiment of the present invention, any one of the compound of formula (II-A), (II-B), (IV), (V) or (VI), the stereoisomer thereof, or the pharmaceutically acceptable salt thereof is characterized in that ring B is selected from the group consisting of:

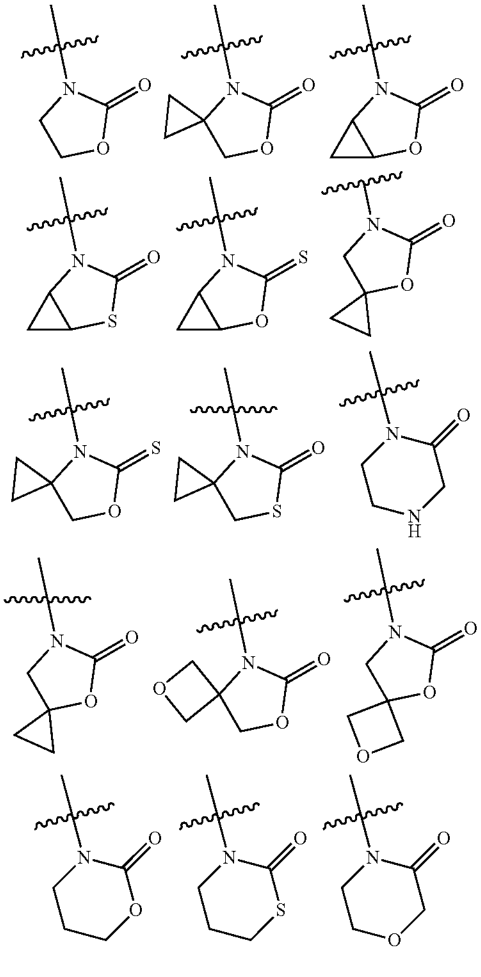

-continued

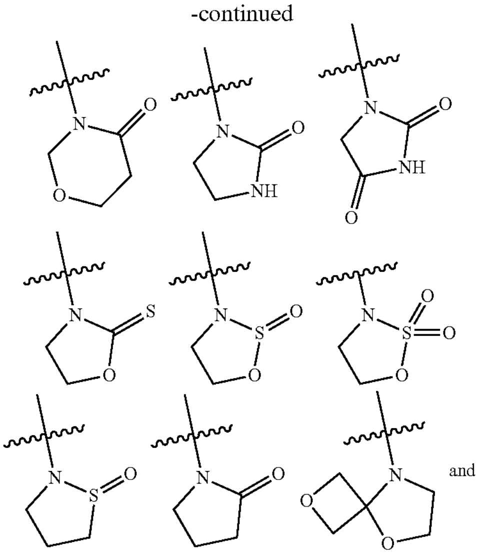

and

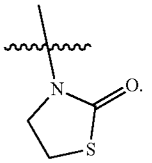

In a preferred embodiment of the present invention, the compound of formula (I), the stereoisomer thereof, or the pharmaceutically acceptable salt thereof, wherein the structure of the compound is shown in formula (VII):

(VII)

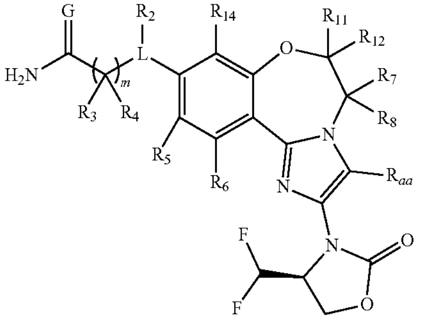

wherein:

$R_{aa}$ is selected from the group consisting of hydrogen, deuterium, alkyl, deuterated alkyl, haloalkyl, alkoxy, hydroxyalkyl, haloalkoxy, halogen, cyano, nitro, hydroxy, amino, alkenyl, alkynyl, cycloalkyl, heterocyclyl, aryl and heteroaryl, wherein the alkyl, deuterated alkyl, haloalkyl, alkoxy, hydroxyalkyl, haloalkoxy, alkenyl, alkynyl, cycloalkyl, heterocyclyl, aryl and heteroaryl are each optionally further substituted by one or more substituent(s) selected from the group consisting of deuterium, alkyl, halogen, hydroxy, amino, oxo, nitro, cyano, alkenyl, alkynyl, alkoxy, hydroxyalkyl, cycloalkyl, heterocyclyl, aryl and heteroaryl; and L, $R_2$ to $R_8$, $R_{11}$, $R_{12}$, $R_{14}$ and m are as defined in formula (V).

Preferably, when $R_{aa}$, $R_2$, $R_5$ to $R_8$, $R_{11}$, $R_{12}$ and $R_{14}$ are not hydrogen at the same time, $R_3$ and $R_4$ are as defined in formula (VII).

Further preferably, when $R_{aa}$, $R_2$, $R_5$ to $R_8$, $R_{11}$, $R_{12}$ and $R_{14}$ are hydrogen at the same time, any two groups of $R_2$, $R_3$ and $R_4$ are bonded to form a cycloalkyl, heterocyclyl, aryl or heteroaryl, wherein the cycloalkyl, heterocyclyl, aryl or heteroaryl is optionally further substituted by one or more substituent(s) selected from the group consisting of deuterium, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, $-(CH_2)_{n1}-$, $-(CH_2)_{n1}R_{bb}$, $-(CH_2)_{n1}OR_{bb}$, $-(CH_2)_{n1}SR_{bb}$, $-(CH_2)_{n1}C(O)R_{bb}$, $-(CH_2)_{n1}C(O)OR_{bb}$, $-(CH_2)_{n1}S(O)_{m1}R_{bb}$, $-(CH_2)_{n1}NR_{bb}R_{cc}$, $-(CH_2)_{n1}C(O)NR_{bb}R_{cc}$, $-(CH_2)_{n1}NR_{bb}C(O)R_{cc}$ and $-(CH_2)_{n1}NR_{bb}S(O)_{m1}R_{cc}$.

In a preferred embodiment of the present invention, the compound of formula (I), the stereoisomer thereof, or the pharmaceutically acceptable salt thereof, wherein the structure of the compound is shown in formula (VIII-A):

(VII-A)

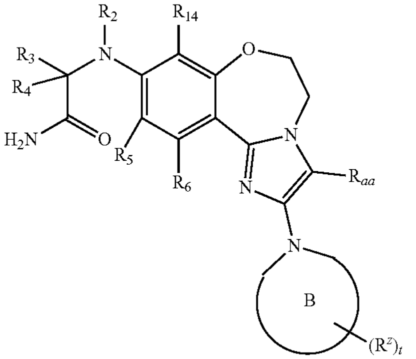

wherein:

ring B is selected from the group consisting of:

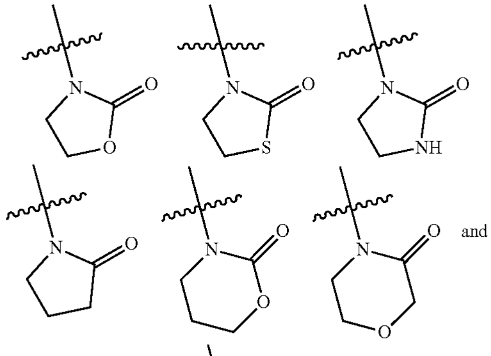

and

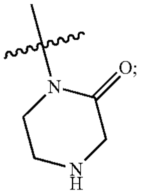

$R_2$ is selected from the group consisting of hydrogen, $C_{1-6}$ alkyl and $C_{1-6}$ haloalkyl;

$R_3$ and $R_4$ are each independently selected from the group consisting of hydrogen, $C_{1-6}$ alkyl, $C_{1-6}$ haloalkyl, $C_{1-6}$ alkoxy and $-(CH_2)_{n1}OR_{bb}$;

or, $R_3$ and $R_4$ are bonded to form a $C_{3-8}$ cycloalkyl or 3 to 8 membered heterocyclyl, and preferably oxetanyl;

or, $R_2$ and $R_3$ or $R_2$ and $R_4$ are bonded to form a 3 to 8 membered heterocyclyl, and preferably pyrrolidinyl or azetidinyl;

$R_5$, $R_6$ and $R_{14}$ are each independently selected from the group consisting of hydrogen, halogen, cyano, $C_{1-6}$ alkyl, $C_{1-6}$ alkoxy and $C_{1-6}$ haloalkyl;

$R_{aa}$ is selected from the group consisting of hydrogen, $C_{1-6}$ alkyl, halogen and cyano;

$R^z$ is selected from the group consisting of hydrogen, oxo, $C_{1-6}$ alkyl, $C_{1-6}$ haloalkyl and —$(CH_2)_{n1}R_{bb}$;

$R_{bb}$ is selected from the group consisting of hydrogen, $C_{1-6}$ alkyl, halogen and cyano; and t is 0, 1, 2 or 3.

Preferably, $R_2$ is selected from the group consisting of hydrogen, $C_{1-3}$ alkyl and $C_{1-3}$ haloalkyl, and further preferably hydrogen, methyl, ethyl or propyl;

$R_3$ and $R_4$ are each independently selected from the group consisting of hydrogen, $C_{1-3}$ alkyl, $C_{1-3}$ alkoxy and $C_{1-3}$ alkyl substituted by $C_{1-3}$ alkoxy, and further preferably hydrogen, methyl, ethyl, propyl, methoxy, ethoxy, $CH_3OCH_2$— or $CH_3CH_2OCH_2$—;

or, $R_3$ and $R_4$ are bonded to form a $C_{4-6}$ cycloalkyl or 4 to 6 membered heterocyclyl, preferably 4 to 6 membered heterocyclyl containing one oxygen or nitrogen, and more preferably oxetanyl;

$R_2$ and $R_3$ or $R_2$ and $R_4$ are bonded to form a 3 to 8 membered heterocyclyl, preferably 4 to 6 membered heterocyclyl containing nitrogen or oxygen wherein the number of heteroatoms is one or two, and more preferably tetrahydropyrrolyl, tetrahydrofuranyl, piperidinyl or azetidinyl;

$R_5$ and $R_6$ are each independently selected from the group consisting of hydrogen, halogen, cyano, $C_{1-3}$ alkyl, $C_{1-3}$ alkoxy and $C_{1-3}$ haloalkyl, and preferably hydrogen;

$R_{14}$ is selected from the group consisting of hydrogen and halogen, and preferably hydrogen, fluorine or chlorine;

$R^z$ is selected from the group consisting of hydrogen, halogen, oxo, $C_{1-3}$ alkyl, $C_{1-3}$ alkyl substituted by halogen and —$(CH_2)_{n1}R_{bb}$, preferably hydrogen, fluorine, chlorine, bromine, iodine, cyano, acetonitrilyl, propionitrilyl or $C_{1-3}$ alkyl substituted by fluorine, and further preferably fluorine, methyl, acetonitrilyl, —$CHF_2$, —$CF_2CH_3$ or $CHF_2CH_2$—;

$R_{aa}$ is selected from the group consisting of hydrogen and halogen, and preferably hydrogen;

$R_{bb}$ is cyano;

$n_1$ is 0, 1, 2 or 3; and t is 0, 1, 2 or 3.

Provided that, when $R_{aa}$ is hydrogen, ring B is

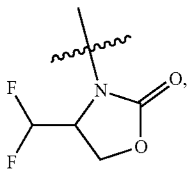

and $R_2$, $R_4$, $R_5$, $R_6$, $R_{14}$ and $R_{aa}$ are all hydrogen, $R_3$ is not —$CH(CH_3)$, cyclopropyl or $CH_3CH_2$—:

when $R_{aa}$ is hydrogen, ring B is

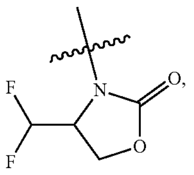 [SMILES: *N1C(=O)OCC1C(F)F]

and $R_2$, $R_3$, $R_5$, $R_6$, $R_{14}$ and $R_{aa}$ are all hydrogen, $R_4$ is not —$CH(CH_3)$, cyclopropyl or $CH_3CH_2$—;

when $R_{aa}$ is hydrogen, ring B is

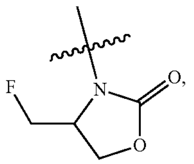

and $R_2$, $R_4$, $R_5$, $R_6$, $R_{14}$ and $R_{aa}$ are all hydrogen, $R_3$ is not —$CH_3$ or cyclopropyl;

when $R_{aa}$ is hydrogen, ring B is

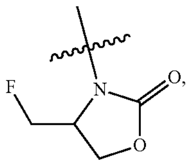 [SMILES: *N1C(=O)OCC1CF]

and $R_2$, $R_3$, $R_5$, $R_6$, $R_{14}$ and $R_{aa}$ are all hydrogen, $R_4$ is not —$CH_3$ or cyclopropyl;

when $R_{aa}$ is hydrogen, ring B is

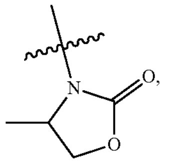 [SMILES: *N1C(=O)OCC1C]

and $R_2$, $R_4$, $R_5$, $R_6$, $R_{14}$ and $R_{aa}$ are all hydrogen, $R_3$ is not cyclopropyl or cyclobutyl; and when $R_{aa}$ is hydrogen, ring B is

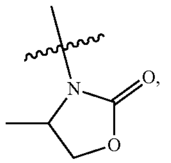 [SMILES: *N1C(=O)OCC1C]

and $R_2$, $R_3$, $R_5$, $R_6$, $R_{14}$ and $R_{aa}$ are all when $R_{aa}$ is hydrogen, ring B is hydrogen, $R_4$ is not cyclopropyl or cyclobutyl.

In a preferred embodiment of the present invention, the compound of formula (I), the stereoisomer thereof, or the pharmaceutically acceptable salt thereof, wherein the structure of the compound is shown in formula (VIII):

(VIII)

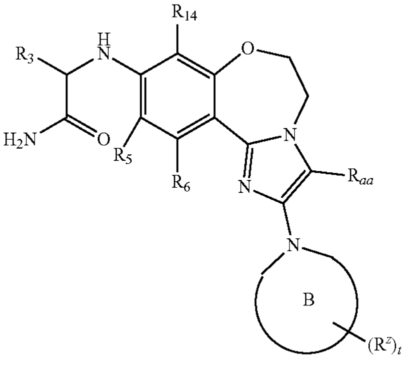

wherein: ring B, $R_3$, $R_5$, $R_6$, $R_{14}$, $R^z$, $R_{aa}$ and t are as defined in formula (III-A); and $R^z$ and t are as defined in formula (V).

In a preferred embodiment, ring B is selected from the group consisting of

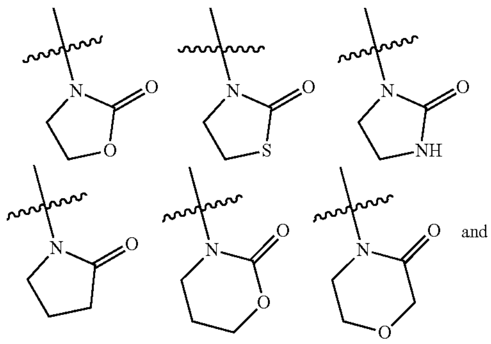

and

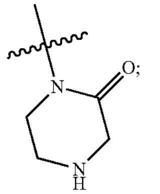

$R_2$ is selected from the group consisting of hydrogen and $C_{1-6}$ alkyl, preferably hydrogen or $C_{1-3}$ alkyl, and further preferably hydrogen, methyl, ethyl or propyl;

$R_3$ is selected from the group consisting of $C_{1-6}$ alkyl, $C_{1-6}$ alkoxy and $C_{1-6}$ alkoxy substituted by alkyl, preferably $C_{1-3}$ alkyl, $C_{1-3}$ alkoxy or $C_{1-3}$ alkyl substituted by $C_{1-3}$ alkoxy, and further preferably methyl, ethyl, propyl, methoxy, ethoxy, $CH_3OCH_2$— or $CH_3CH_2OCH_2$—;

$R_5$ and $R_6$ are each independently selected from the group consisting of hydrogen and halogen, and preferably hydrogen;

$R_{14}$ is selected from the group consisting of hydrogen and halogen, and preferably hydrogen, fluorine or chlorine; and $R^z$ is selected from the group consisting of hydrogen, halogen, cyano, $C_{1-6}$ alkyl and $C_{1-6}$ alkyl substituted by halogen, preferably hydrogen, fluorine, chlorine, bromine, iodine, cyano, acetonitrilyl, propionitrilyl or $C_{1-3}$ alkyl substituted by halogen, and further preferably fluorine, methyl, acetonitrilyl, —$CHF_2$, —$CF_2CH_3$ or $CHF_2CH_2$—.

In a preferred embodiment of the present invention, the compound of formula (I), the stereoisomer thereof, or the pharmaceutically acceptable salt thereof, wherein the structure of the compound is shown in formula (IX):

(IX)

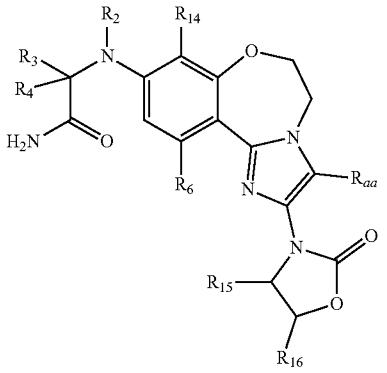

wherein:

$R_{15}$ and $R_{16}$ are each independently selected from the group consisting of hydrogen, $C_{1-6}$ alkyl, $C_{1-6}$ haloalkyl and —$(CH_2)_{n1}R_{bb}$; and $R_2$ to $R_4$, $R_6$, $R_{14}$, $R_{aa}$ and $R_{bb}$ are as defined in formula (VIII-A).

Preferably, $R_2$ is selected from the group consisting of hydrogen and $C_{1-6}$ alkyl, preferably hydrogen or $C_{1-3}$ alkyl, and further preferably hydrogen, methyl, ethyl or propyl;

$R_3$ and $R_4$ are each independently selected from the group consisting of hydrogen, $C_{1-6}$ alkyl, $C_{1-6}$ alkoxy and $C_{1-6}$ alkoxy substituted by alkyl, preferably hydrogen, $C_{1-3}$ alkyl, $C_{1-3}$ alkoxy or $C_{1-3}$ alkyl substituted by $C_{1-3}$ alkoxy, and further preferably hydrogen, methyl, ethyl, propyl, methoxy, ethoxy, $CH_3OCH_2$— or $CH_3CH_2OCH_2$—;

$R_3$ and $R_4$ are bonded to form a $C_{4-6}$ cycloalkyl or 4 to 6 membered heterocyclyl, preferably 4 to 6 membered heterocyclyl containing one oxygen or nitrogen, and more preferably oxetanyl;

$R_2$ and $R_3$ or $R_2$ and $R_4$ are bonded to form a 4 to 6 membered heterocyclyl, preferably 4 to 6 membered heterocyclyl containing nitrogen or oxygen wherein the number of heteroatoms is one or two, and more preferably tetrahydropyrrolyl, tetrahydrofuranyl, piperidinyl or azetidinyl;

$R_6$ is selected from the group consisting of hydrogen and halogen, and preferably hydrogen;

$R_{14}$ is selected from the group consisting of hydrogen and halogen, and preferably hydrogen, fluorine or chlorine;

$R_{aa}$ is selected from the group consisting of hydrogen and halogen, and preferably hydrogen; and $R_{15}$ and $R_{16}$ are each independently selected from the group consisting of hydrogen, halogen, cyano, $C_{1-6}$ alkyl and $C_{1-6}$ alkyl substituted by halogen, preferably hydrogen, fluorine, chlorine, bromine, iodine, cyano, acetonitrilyl, propionitrilyl or $C_{1-3}$ alkyl substituted by halogen, and further preferably hydrogen, fluorine, methyl, acetonitrilyl, —$CHF_2$, —$CF_2CH_3$ or $CHF_2CH_2$—.

In a preferred embodiment of the present invention, the compound of formula (I), the stereoisomer thereof, or the pharmaceutically acceptable salt thereof, wherein the structure of the compound is shown in formula (X):

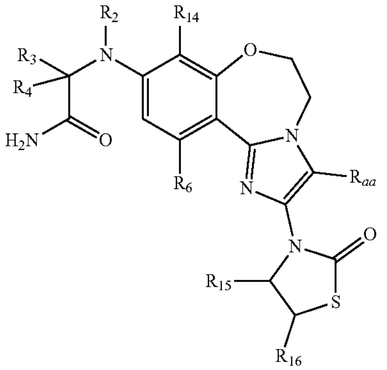

(X)

wherein:

$R_{15}$ and $R_{16}$ are each independently selected from the group consisting of hydrogen, $C_{1-6}$ alkyl, $C_{1-6}$ haloalkyl and $-(CH_2)_{n1}R_{bb}$; and $R_2$ to $R_4$, $R_6$, $R_{14}$, $R_{aa}$ and $R_{bb}$ are as defined in formula (VIII-A).

Preferably, $R_2$ is selected from the group consisting of hydrogen and $C_{1-6}$ alkyl, preferably hydrogen or $C_{1-3}$ alkyl, and further preferably hydrogen, methyl, ethyl or propyl;

$R_3$ and $R_4$ are each independently selected from the group consisting of hydrogen, $C_{1-6}$ alkyl, $C_{1-6}$ alkoxy and $C_{1-6}$ alkoxy substituted by alkyl, preferably hydrogen, $C_{1-3}$ alkyl, $C_{1-3}$ alkoxy or $C_{1-3}$ alkyl substituted by $C_{1-3}$ alkoxy, and further preferably hydrogen, methyl, ethyl, propyl, methoxy, ethoxy, $CH_3OCH_2-$ or $CH_3CH_2OCH_2-$;

$R_3$ and $R_4$ are bonded to form a $C_{4-6}$ cycloalkyl or 4 to 6 membered heterocyclyl, preferably 4 to 6 membered heterocyclyl containing one oxygen or nitrogen, and more preferably oxetanyl;

$R_2$ and $R_3$ or $R_2$ and $R_4$ are bonded to form a 4 to 6 membered heterocyclyl, preferably 4 to 6 membered heterocyclyl containing nitrogen or oxygen wherein the number of heteroatoms is one or two, and more preferably tetrahydropyrrolyl, tetrahydrofuranyl, piperidinyl or azetidinyl;

$R_3$ and $R_4$ are bonded to form a $C_{4-6}$ cycloalkyl or 4 to 6 membered heterocyclyl, preferably 4 to 6 membered heterocyclyl containing one oxygen or nitrogen, and more preferably oxetanyl;

$R_6$ is selected from the group consisting of hydrogen and halogen, and preferably hydrogen;

$R_{14}$ is selected from the group consisting of hydrogen and halogen, and preferably hydrogen, fluorine or chlorine;

$R_{aa}$ is selected from the group consisting of hydrogen and halogen, and preferably hydrogen; and $R_{15}$ and $R_{16}$ are each independently selected from the group consisting of hydrogen, halogen, cyano, $C_{1-6}$ alkyl and $C_{1-6}$ alkyl substituted by halogen, preferably hydrogen, fluorine, chlorine, bromine, iodine, cyano, acetonitrilyl, propionitrilyl or $C_{1-3}$ alkyl substituted by halogen, and further preferably hydrogen, fluorine, methyl, acetonitrilyl, $-CHF_2$, $-CF_2CH_3$ or $CHF_2CH_2-$.

In a preferred embodiment of the present invention, any one of the compound of formula (I), the stereoisomer thereof, or the pharmaceutically acceptable salt thereof, wherein $R_2$ is present or absent, when present, $R_2$ is selected from the group consisting of hydrogen, methoxy, $C_{1-6}$ alkyl and $C_{1-6}$ haloalkyl;

or, $R_2$ and $R_3$ or $R_2$ and $R_4$ are bonded to form a 3 to 8 membered heterocyclyl, and preferably pyrrolidinyl or azetidinyl;

$R_3$ and $R_4$ are each independently selected from the group consisting of hydrogen, $C_{1-6}$ alkyl, $C_{1-6}$ haloalkyl, $C_{1-6}$ alkoxy and 3 to 8 membered heterocyclyl;

or, $R_3$ and $R_4$ are bonded to form a $C_{3-8}$ cycloalkyl or 3 to 8 membered heterocyclyl, and preferably oxetanyl;

$R_5$ and $R_6$ are each independently selected from the group consisting of hydrogen, halogen, cyano, $C_{1-6}$ alkyl, $C_{1-6}$ alkoxy and $C_{1-6}$ haloalkyl;

or, $R_5$ and $R_6$ are bonded to form a $C_{3-8}$ cycloalkyl or 3 to 8 membered heterocyclyl, and preferably cyclobutanyl, cyclopentyl or 1,3-dioxolanyl;

$R_{14}$ is selected from the group consisting of hydrogen, halogen, cyano, $C_{1-6}$ alkyl, $C_{1-6}$ haloalkyl, $C_{1-6}$ alkoxy and $C_{3-8}$ cycloalkyl;

$R^y$ is selected from the group consisting of hydrogen, $C_{1-6}$ alkyl, halogen, $C_{1-6}$ alkoxy, $C_{1-6}$ haloalkyl and $-(CH_2)_{n1}-$, preferably hydrogen, $C_{1-3}$ alkyl or $C_{1-3}$ haloalkyl, and more preferably hydrogen, methyl or $-(CH_2)_{n1}-$; and $R_{aa}$ is selected from the group consisting of hydrogen, halogen, cyano, $C_{1-6}$ alkyl, $C_{1-6}$ haloalkyl, $C_{1-6}$ alkoxy and $C_{3-8}$ cycloalkyl.

In a preferred embodiment, $R_2$ is selected from the group consisting of hydrogen, $C_{1-3}$ alkyl, $C_{1-3}$ hydroxyalkyl and $C_{1-3}$ haloalkyl, and preferably methyl, ethyl, propyl, hydroxymethyl, hydroxyethyl, hydroxypropyl, halomethyl, haloethyl or halopropyl;

$R_3$ and $R_4$ are each independently selected from the group consisting of $C_{1-3}$ alkyl, $C_{1-3}$ hydroxyalkyl, $C_{1-3}$ haloalkyl and $C_{1-3}$ alkoxy, and preferably methyl, ethyl, propyl, hydroxymethyl, hydroxyethyl, hydroxypropyl, halomethyl, haloethyl, halopropyl, methoxy, ethoxy or propoxy;

$R_5$ and $R_6$ are each independently selected from the group consisting of hydrogen, $C_{1-3}$ alkyl, $C_{1-3}$ alkoxy and $C_{1-3}$ haloalkyl, and preferably methyl, ethyl, propyl, halomethyl, haloethyl, halopropyl, methoxy, ethoxy or propoxy;

$R_{14}$ is selected from the group consisting of hydrogen, $C_{1-3}$ alkyl, $C_{1-3}$ alkoxy and $C_{1-3}$ haloalkyl, and preferably methyl, ethyl, propyl, halomethyl, haloethyl, halopropyl, methoxy, ethoxy or propoxy;

$R^y$ is selected from the group consisting of hydrogen, methyl and $-(CH_2)_{n1}-$; and $R_{aa}$ is selected from the group consisting of halogen, cyano, $C_{1-3}$ alkyl, $C_{1-3}$ alkoxy and $C_{1-3}$ haloalkyl, and preferably methyl, ethyl, propyl, halomethyl, haloethyl, halopropyl, methoxy, ethoxy or propoxy.

In a preferred embodiment of the present invention, in any one of the compound of formula (I), the stereoisomer thereof, or the pharmaceutically acceptable salt thereof, wherein $R^z$ is selected from the group consisting of hydrogen, halogen, oxo, thioxo, $C_{1-6}$ alkyl, $C_{1-6}$ alkoxy, $C_{1-6}$ haloalkyl and $-(CH_2)_{n1}-$, wherein the $C_{1-6}$ alkyl, $C_{1-6}$ alkoxy and $C_{1-6}$ haloalkyl are each optionally further substituted by one or more substituent(s) selected from the group consisting of hydrogen, halogen, oxo, thioxo, $C_{1-6}$ alkyl, $C_{1-6}$ alkoxy and $C_{1-6}$ haloalkyl, $R^z$ is preferably halogen, $C_{1-6}$ alkyl, $C_{1-6}$ haloalkyl or oxo, and more preferably halogen, $C_{1-3}$ alkyl, $C_{1-3}$ haloalkyl or oxo.

The present invention also relates to a method for preparing the compound of formula (IV), the stereoisomer thereof, or the pharmaceutically acceptable salt thereof, comprising the following step of

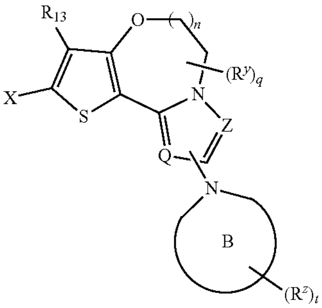
(IV-1)

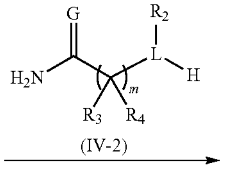
(IV-2)

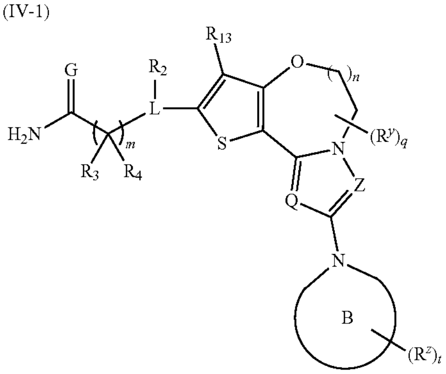
(IV)

reacting a compound of formula (IV-1) and a compound of formula (IV-2) to obtain the compound of formula (IV), the stereoisomer thereof, or the pharmaceutically acceptable salt thereof;

wherein:

X is halogen; and ring B, Q, Z, G, L, $R_2$ to $R_4$, $R^y$, $R^z$, q, m, n and t are as defined in formula (IV).

The present invention also relates to a method for preparing the compound of formula (VI), the stereoisomer thereof, or the pharmaceutically acceptable salt thereof, comprising the following step of

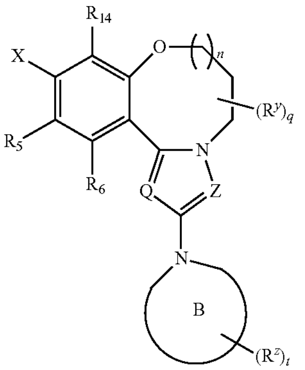
(VI-1)

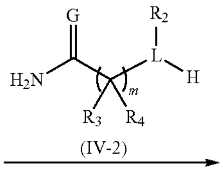
(IV-2)

-continued

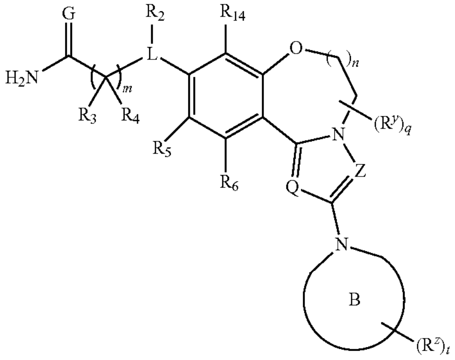
(VI)

reacting a compound of formula (VI-1) and a compound of formula (IV-2) to obtain the compound of formula (VI), the stereoisomer thereof, or the pharmaceutically acceptable salt thereof;

wherein:

X is halogen; and ring B, Q, Z, G, L, $R_2$ to $R_6$, $R_{14}$, $R^y$, $R^z$, q, m, n and t are as defined in formula (VI).

The present invention also relates to a method for preparing the compound of formula (IV), the stereoisomer thereof, or the pharmaceutically acceptable salt thereof, comprising the following steps of

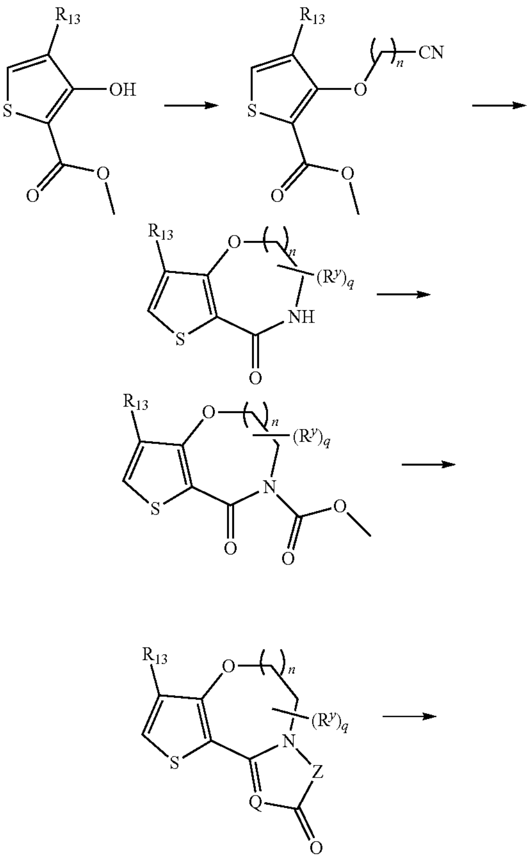

-continued

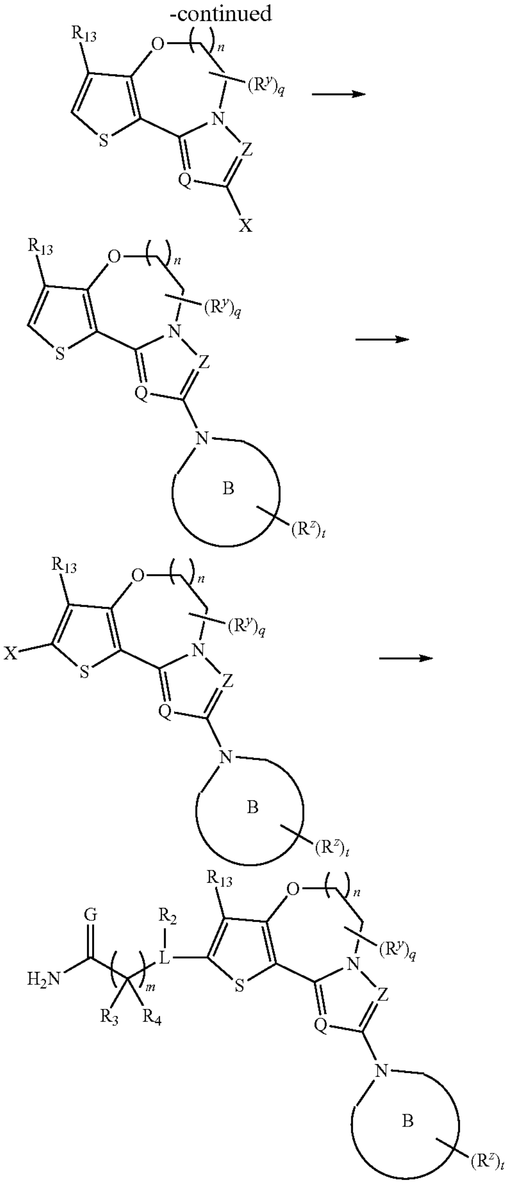

(IV)

wherein:

X is halogen; and ring B, Q, Z, G, L, $R_2$ to $R_6$, $R^y$, $R^z$, q, m, n and t are as defined in formula (VI).

The present invention also relates to a method for preparing the compound of formula (VI), the stereoisomer thereof, or the pharmaceutically acceptable salt thereof, comprising the following steps of

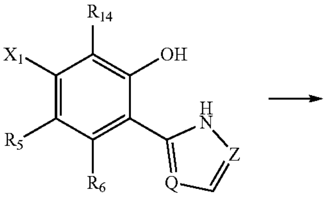

-continued

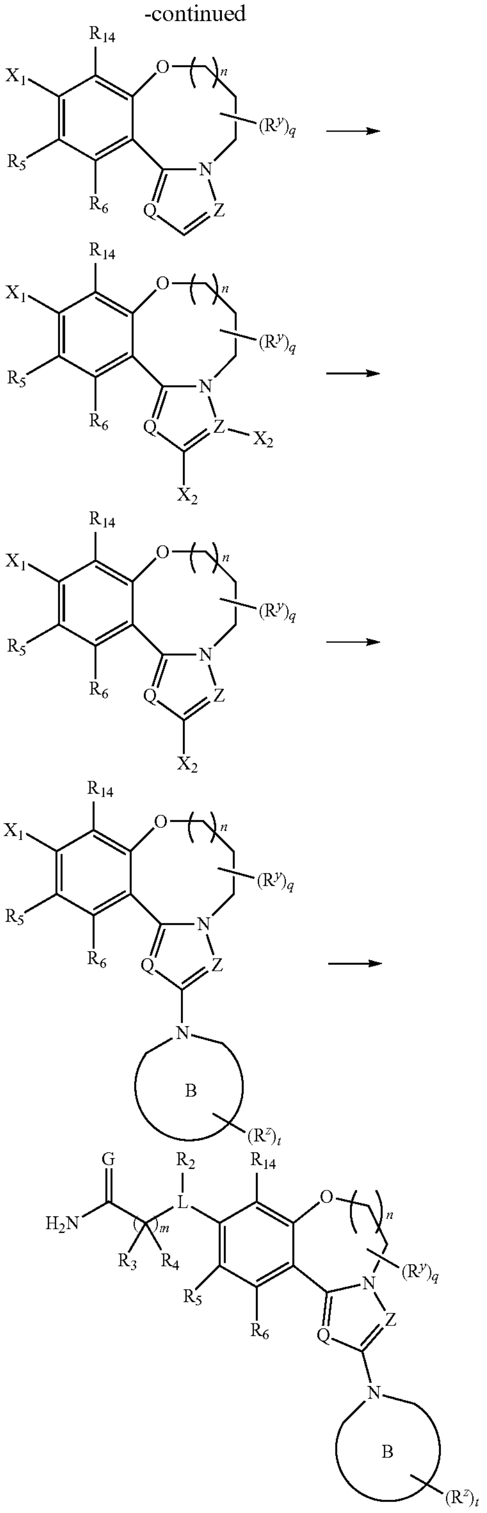

(VI)

wherein:

$X_1$ and $X_2$ are halogen; and ring B, Q, Z, G, L, $R_2$ to $R_6$, $R^y$, $R^z$, q, m, n and t are as defined in formula (VI).

The present invention also relates to a method for preparing the compound of formula (X), the stereoisomer thereof, or the pharmaceutically acceptable salt thereof, comprising the following step of

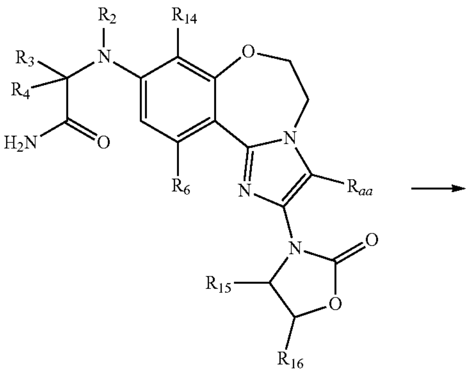

(IX)

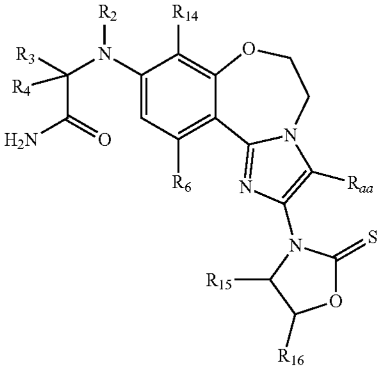

(IX-A)

reacting the compound of formula (IX) and a Lawesson's reagent to obtain the compound of formula (IX-A), the stereoisomer thereof, or the pharmaceutically acceptable salt thereof;

wherein:

$R_2$ to $R_4$, $R_6$, $R_{14}$ to $R_{16}$ and $R_{aa}$ are as defined in formula (IX).

The present invention also relates to a method for preparing the compound of formula (X), the stereoisomer thereof, or the pharmaceutically acceptable salt thereof, comprising the following step of

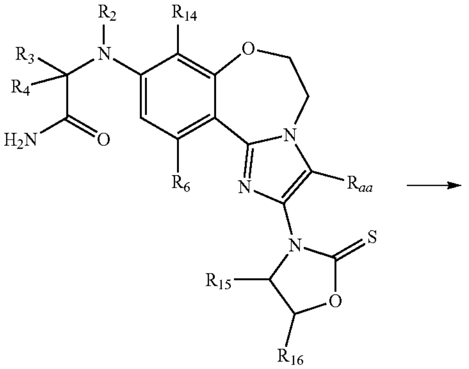

(IX-A)

-continued

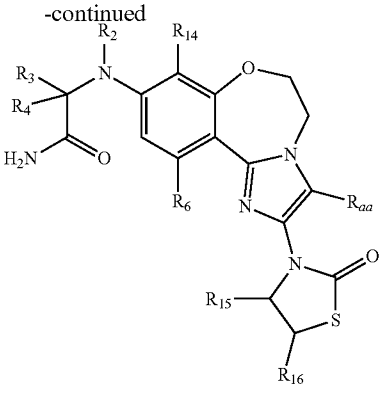

(X)

reacting the compound of formula (IX-A) with a transition metal complex and a ligand thereof to obtain the compound of formula (X), the stereoisomer thereof, or the pharmaceutically acceptable salt thereof;

wherein:

the transition metal complex and the ligand thereof are preferably dichloro(p-cymene)ruthenium(II) dimer and 2-bicyclohexylphosphino-2',6'-dimethoxybiphenyl; and $R_2$ to $R_4$, $R_6$, $R_{14}$ to $R_{16}$ and $R_{aa}$ are as defined in formula (X).

The present invention further relates to a pharmaceutical composition comprising a therapeutically effective amount of any one of the compound of formula (I), the stereoisomer thereof, or the pharmaceutically acceptable salt thereof, and one or more pharmaceutically acceptable carriers, diluents or excipients.

The present invention further relates to a use of any one of the compound of formula (I), the stereoisomer thereof, or the pharmaceutically acceptable salt thereof, or the pharmaceutical composition comprising the same in the preparation of a PI3K regulator medicament, and preferably a PI3Kα inhibitor medicament.

The present invention further relates to a use of the compound of formula (I), the stereoisomer thereof, or the pharmaceutically acceptable salt thereof, or the pharmaceutical composition comprising the same in the preparation of a medicament for treating a cancer, bone disease, inflammatory disease, immune disease, nervous system disease, metabolic disease, respiratory disease and heart disease, wherein the cancer is selected from the group consisting of breast cancer, pancreatic cancer, non-small cell lung cancer (NSCLC), thyroid cancer, seminoma, melanoma, bladder cancer, liver cancer, kidney cancer, myelodysplastic syndrome (MDS), acute myeloid leukemia (AML) and colorectal cancer.

The present invention further relates to a use of the compound of formula (I), the stereoisomer thereof, or the pharmaceutically acceptable salt thereof, or the pharmaceutical composition comprising the same in the preparation of a medicament for treating a cancer, bone disease, inflammatory disease, immune disease, nervous system disease, metabolic disease, respiratory disease and heart disease.

The present invention also relates to a method for preventing and/or treating a cancer, comprising administering to a patient a therapeutically effective amount of the compound of formula (I), the stereoisomer thereof, or the pharmaceutically acceptable salt thereof, or the pharmaceutical composition comprising the same.

The present invention also provides a method for treating a disease condition with the compound or pharmaceutical composition of the present invention, wherein the disease condition includes, but is not limited to, conditions related to PI3Kα, PI3Kβ, PI3Kδ and PI3Kγ kinase dysfunction.

The present invention also relates to a method for treating a hyperproliferative disease in a mammal, comprising administering to the mammal a therapeutically effective amount of the compound of the present invention or the pharmaceutically acceptable salt, ester, prodrug, solvate, hydrate or derivative thereof.

In some embodiments, the method involves the treatment of disease such as cancer, bone disease, inflammatory disease, immune disease, nervous system disease, metabolic disease, respiratory disease and heart disease.

In some embodiments, the method involves the treatment of cancer such as acute myeloid leukemia, myelodysplastic syndrome (MDS), thymic cancer, brain cancer, lung cancer (NSCLC and SCLC), squamous cell carcinoma, seminoma, melanoma, skin cancer, eye cancer, retinoblastoma, intraocular melanoma, oral and oropharyngeal cancer, bladder cancer, gastric cancer, stomach cancer, pancreatic cancer, bladder cancer, breast cancer, cervical cancer, head cancer, neck cancer, renal cancer, kidney cancer, liver cancer, ovarian cancer, prostate cancer, endometrial cancer, colorectal cancer, esophageal cancer, testicular cancer, gynecological cancer, thyroid cancer, CNS cancer, PNS cancer, AIDS-related cancer (such as lymphoma and Kaposi's sarcoma) and virus-induced cancer. In some embodiments, the method relates to the treatment of non-cancerous hyperproliferative disease such as skin disease (for example, psoriasis), restenosis and benign prostatic hyperplasia (for example, benign prostatic hypertrophy (BPH)). In some embodiments, the cancer is melanoma or colorectal cancer.

The treatment method provided herein comprises administering to a subject a therapeutically effective amount of the compound of the present invention. In an embodiment, the present invention provides a method for treating an inflammatory disease including autoimmune disease in a mammal. The method comprises administering to the mammal a therapeutically effective amount of the compound of the present invention or the pharmaceutically acceptable salt, ester, prodrug, solvate, hydrate or derivative thereof. The disease related to one or more types of ERK dysfunction includes, but is not limited to, acute disseminated encephalomyelitis (ADEM), Addison's disease, antiphospholipid antibody syndrome (APS), aplastic anemia, autoimmune hepatitis, celiac disease, Crohn's disease, diabetes (type 1), Good Pasteur's syndrome, Graves' disease, Guillain-Barre's syndrome (GBS), Hashimoto's disease, lupus erythematosus, multiple sclerosis, myasthenia gravis, opsoclonus myoclonus syndrome (OMS), optic neuritis, Ord's thyroiditis, pemphigus, polyarthritis, primary biliary cirrhosis, psoriasis, rheumatoid arthritis, Lytle's syndrome, Takavasu's arteritis, temporal arteritis (also known as "giant cell arteritis"), warm autoimmune hemolytic anemia, Wegener's granulomatosis, alopecia universalis, Chagas' disease, chronic fatigue syndrome, autonomic dysfunction, endometriosis, hidradenitis suppurativa, interstitial cystitis, neuromuscular rigidity, sarcoidosis, scleroderma, ulcerative colitis, vitiligo and vulvar pain. Other diseases include bone resorption disorder and thrombosis.

Definitions

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 8 carbon atoms, more preferably an alkyl having 1 to 6 carbon atoms, and most preferably an alkyl having 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2,4-dimethylhexyl, 2-ethylpentyl, 3-ethylpentyl, n-octyl, 2,3-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably; the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl group can be substituted or unsubstituted. When substituted, the substituent group(s) can be substituted at any available connection point. The substituent group(s) is preferably one or more group(s) independently selected from the group consisting of alkyl, alkenyl, alkynyl, alkoxy; alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl. The alkyl of the present invention is preferably selected from the group consisting of methyl, ethyl, isopropyl, tert-butyl, haloalkyl, deuterated alkyl, alkoxy-substituted alkyl and hydroxy-substituted alkyl.

The term "alkylene" refers to an alkyl of which a hydrogen atom is further substituted, for example, "methylene" refers to $-CH_2-$, "ethylene" refers to $-(CH_2)_2-$, "propylene" refers to $-(CH_2)_3-$, "butylene" refers to $-(CH_2)_4-$ and the like. The term "alkenyl" refers to an alkyl as defined above that consists of at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy; heterocycloalkoxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 12 carbon atoms, more preferably 3 to 8 carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring. The cycloalkyl is preferably cyclopropyl, cyclobutyl, cyclohexyl, cyclopentyl or cycloheptyl.

The term "spiro cycloalkyl" refers to a 5 to 20 membered polycyclic group with individual rings connected through one shared carbon atom (called a spiro atom), wherein the rings can contain one or more double bonds, but none of the rings has a completely conjugated π-electron system. The spiro cycloalkyl is preferably a 6 to 14 membered spiro cycloalkyl, and more preferably a 7 to 10 membered spiro cycloalkyl. According to the number of the spiro atoms shared between the rings, the spiro cycloalkyl can be divided into a mono-spiro cycloalkyl, a di-spiro cycloalkyl, or a poly-spiro cycloalkyl, and the spiro cycloalkyl is preferably a mono-spiro cycloalkyl or di-spiro cycloalkyl, and preferably more a 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

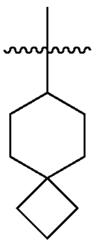
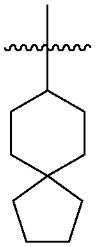
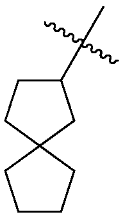
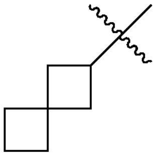
and
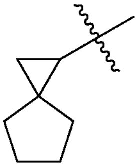
;

and also include spiro cycloalkyl in which a cycloalkyl and a heterocyclyl are connected through one spiro atom, non-limiting examples thereof include:

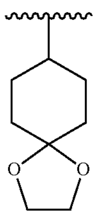
and
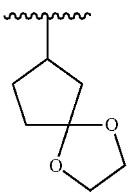
.

The term "fused cycloalkyl" refers to a 5 to 20 membered all-carbon polycyclic group, wherein each ring in the system shares an adjacent pair of carbon atoms with another ring, one or more rings can contain one or more double bonds, but none of the rings has a completely conjugated π-electron system. The fused cycloalkyl is preferably a 6 to 14 membered fused cycloalkyl, and more preferably a 7 to 10 membered fused cycloalkyl. According to the number of membered rings, the fused cycloalkyl can be divided into a bicyclic, tricyclic, tetracyclic or polycyclic fused cycloalkyl, and the fused cycloalkyl is preferably a bicyclic or tricyclic fused cycloalkyl, and more preferably a 5-membered/5-membered, or 5-membered/6-membered bicyclic fused cycloalkyl. Non-limiting examples of fused cycloalkyl include:

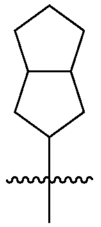
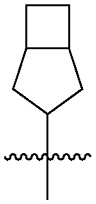
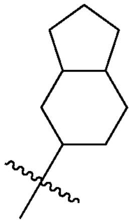
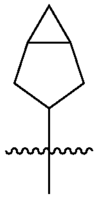
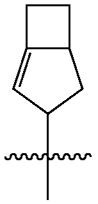
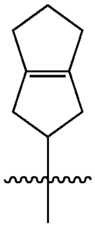
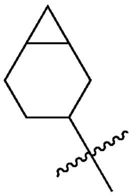
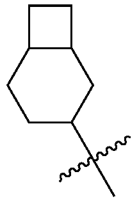
and
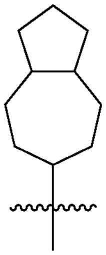
.

The term "bridged cycloalkyl" refers to a 5 to 20 membered all-carbon polycyclic group, wherein every two rings in the system share two disconnected carbon atoms, the rings can have one or more double bonds, but none of the rings has a completely conjugated π-electron system. The bridged cycloalkyl is preferably a 6 to 14 membered bridged cycloalkyl, and more preferably a 7 to 10 membered bridged cycloalkyl. According to the number of membered rings, the bridged cycloalkyl can be divided into a bicyclic, tricyclic, tetracyclic or polycyclic bridged cycloalkyl, and the bridged cycloalkyl is preferably a bicyclic, tricyclic or tetracyclic bridged cycloalkyl, and more preferably a bicyclic or tricyclic bridged cycloalkyl. Non-limiting examples of bridged cycloalkyl include:

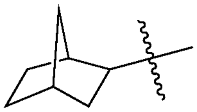
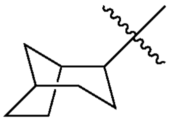
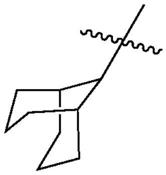
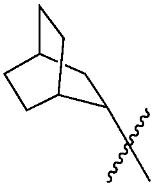
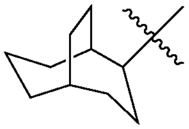
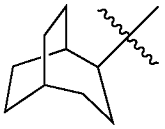

-continued

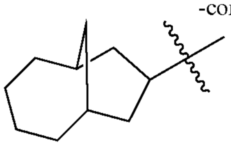

and

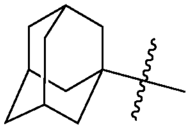

.

The cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "heterocyclyl" refers to a 3 to 20 membered saturated or partially unsaturated monocyclic or polycyclic hydrocarbon group, wherein one or more ring atoms are heteroatoms selected from the group consisting of N, O and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, 3 to 8 ring atoms; further preferably, 3 to 8 ring atoms; and most preferably 4 to 6 ring atoms. Non-limiting examples of monocyclic heterocyclyl include oxetanyl, pyrrolidinyl, pyrrolidonyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl and the like, and preferably oxetanyl, pyrrolidinyl, pyrrolidonyl, tetrahydrofuranyl, pyrazolidinyl, morpholinyl, piperazinyl and pyranyl. Polycyclic heterocyclyl includes a heterocyclyl having a spiro ring, fused ring or bridged ring. The heterocyclyl having a spiro ring, fused ring or bridged ring is optionally bonded to other group via a single bond, or further bonded to other cycloalkyl, heterocyclyl, aryl and heteroaryl via any two or more atoms on the ring.

The term "spiro heterocyclyl" refers to a 3 to 20 membered polycyclic heterocyclyl group with individual rings connected through one shared atom (called a spiro atom), wherein one or more ring atoms are heteroatoms selected from the group consisting of N, O and $S(O)_m$ (wherein m is an integer of 0 to 2), with the remaining ring atoms being carbon atoms, and the rings can contain one or more double bonds, but none of the rings has a completely conjugated π-electron system. The spiro heterocyclyl is preferably a 6 to 14 membered spiro heterocyclyl, and more preferably a 7 to 10 membered spiro heterocyclyl. According to the number of the spiro atoms shared between the rings, the spiro heterocyclyl can be divided into a mono-spiro heterocyclyl, di-spiro heterocyclyl, or poly-spiro heterocyclyl, and the spiro heterocyclyl is preferably a mono-spiro heterocyclyl or di-spiro heterocyclyl, and more preferably a 3-membered/5-membered, 4-membered/5-membered, 4-membered/6-membered, 5-membered/5-membered, or 5-membered/6-membered mono-spiro heterocyclyl. Non-limiting examples of spiro heterocyclyl include:

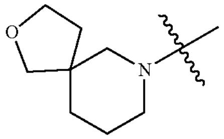
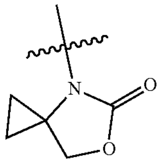
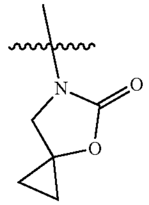
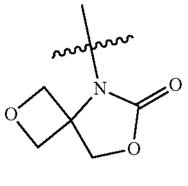
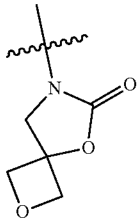
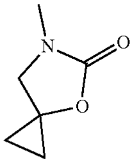
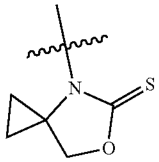
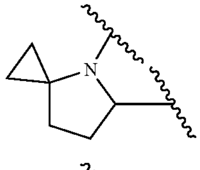
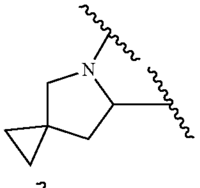
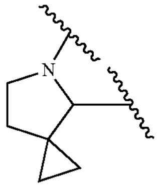
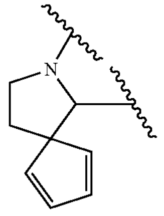
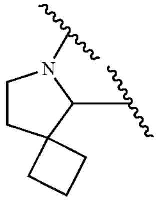
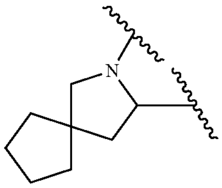
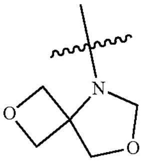
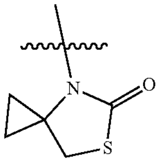
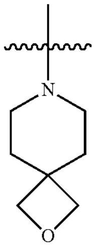
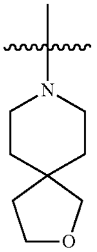
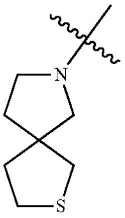
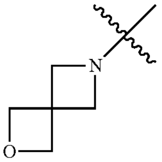

and

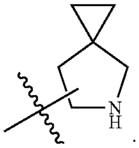

.

The term "fused heterocyclyl" refers to a 5 to 20 membered polycyclic heterocyclyl group, wherein each ring in the system shares an adjacent pair of atoms with another ring, one or more rings can contain one or more double bonds, but none of the rings has a completely conjugated-electron system, and one or more ring atoms are heteroatoms selected from the group consisting of N, O and $S(O)_m$ (wherein m is an integer of 0 to 2), with the remaining ring atoms being carbon atoms. The fused heterocyclyl is preferably a 6 to 14 membered fused heterocyclyl, and more preferably a 7 to 10 membered fused heterocyclyl. According to the number of membered rings, the fused heterocyclyl can be divided into a bicyclic, tricyclic, tetracyclic or polycyclic fused heterocyclyl, and preferably a bicyclic or tricyclic fused heterocyclyl, and more preferably a 3-membered/5-membered, 4-membered/5-membered or 5-membered/6-membered bicyclic fused heterocyclyl. Non-limiting examples of fused heterocyclyl include:

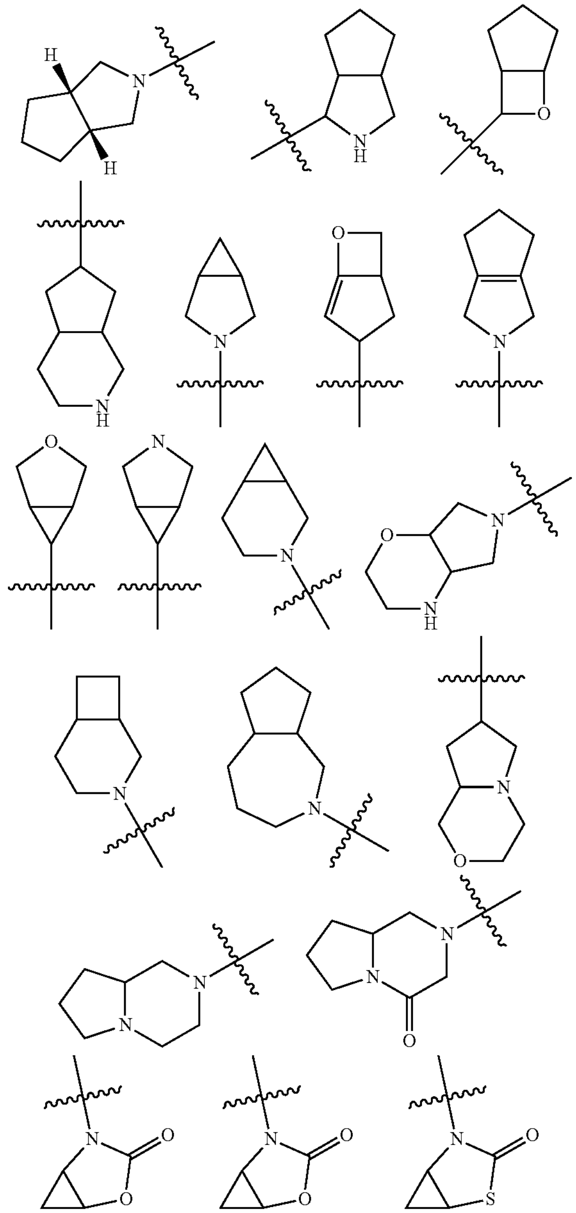

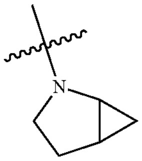

and

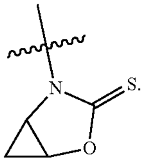

The term "bridged heterocyclyl" refers to a 5 to 14 membered polycyclic heterocyclyl group, wherein every two rings in the system share two disconnected atoms, wherein the rings can have one or more double bond(s), but none of the rings has a completely conjugated π-electron system, and one or more ring atoms are heteroatoms selected from the group consisting of N, O and $S(O)_m$ (wherein m is an integer of 0 to 2), with the remaining ring atoms being carbon atoms. The bridged heterocyclyl is preferably a 6 to 14 membered bridged heterocyclyl, and more preferably a 7 to 10 membered bridged heterocyclyl. According to the number of membered rings, the bridged heterocyclyl can be divided into a bicyclic, tricyclic, tetracyclic or polycyclic bridged heterocyclyl, and the bridged heterocyclyl is preferably a bicyclic, tricyclic or tetracyclic bridged heterocyclyl, and more preferably a bicyclic or tricyclic bridged heterocyclyl. Non-limiting examples of bridged heterocyclyl include:

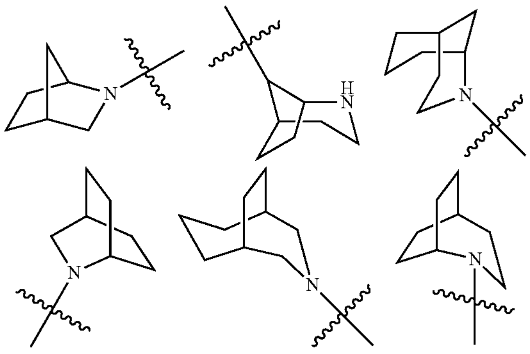

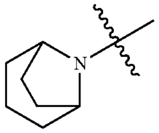

and

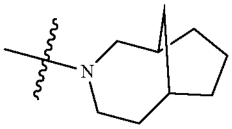

.

The heterocyclyl ring can be fused to the ring of aryl, heteroaryl or cycloalkyl, wherein the ring bound to the parent structure is heterocyclyl. Non-limiting examples thereof include:

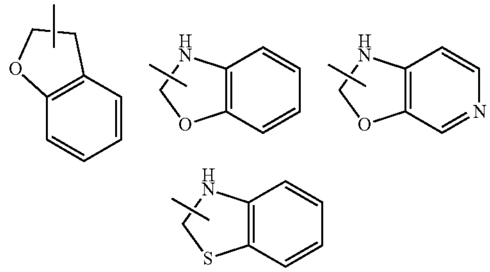

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably a 6 to 10 membered aryl, for example, phenyl and naphthyl. The aryl is more preferably phenyl. The aryl ring can be fused to the ring of heteroaryl, heterocyclyl or cycloalkyl, wherein the ring bound to the parent structure is aryl ring. Non-limiting examples thereof include:

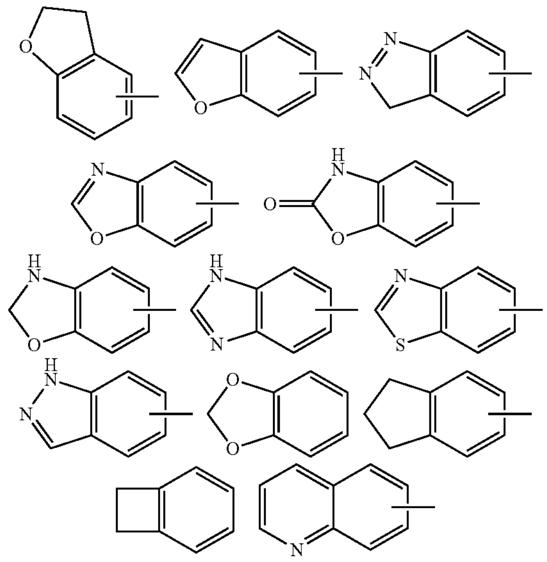

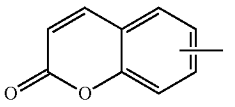

and

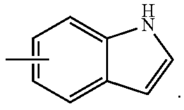

.

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term “heteroaryl” refers to a 5 to 14 membered heteroaromatic system having 1 to 4 heteroatoms selected from the group consisting of O, S and N. The heteroaryl is preferably a 5 to 10 membered heteroaryl, and more preferably a 5 or 6 membered heteroaryl, for example imidazolyl, furyl, thienyl, thiazolyl, pyrazolyl, oxazolyl, pyrrolyl, triazolyl, tetrazolyl, pyridyl, pyrimidinyl, thiadiazolyl, pyrazinyl and the like, preferably triazolyl, thienyl, imidazolyl, pyrazolyl, pyridyl, pyrimidinyl and thiazolyl, and more preferably triazolyl, pyrrolyl, thienyl, thiazolyl, pyridyl and pyrimidinyl. The heteroaryl ring can be fused to the ring of aryl, heterocyclyl or cycloalkyl, wherein the ring bound to the parent structure is heteroaryl ring. Non-limiting examples thereof include:

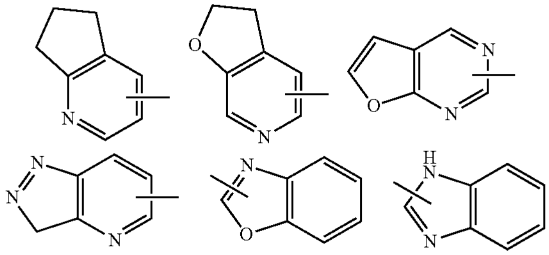

-continued

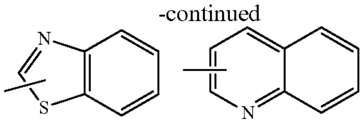

and

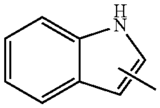

.

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term “alkoxy” refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

“Haloalkyl” refers to an alkyl group substituted by one or more halogen(s), wherein the alkyl is as defined above.

“Haloalkoxy” refers to an alkoxy group substituted by one or more halogen(s), wherein the alkoxy is as defined above.

“Hydroxyalkyl” refers to an alkyl group substituted by hydroxy(s), wherein the alkyl is as defined above.

“Alkenyl” refers to a chain alkenyl, also known as alkene group. The alkenyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy or alkoxycarbonyl.

“Alkynyl” refers to (CH≡C—). The alkynyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy or alkoxycarbonyl.

“Hydroxy” refers to an —OH group.

“Halogen” refers to fluorine, chlorine, bromine or iodine.

“Amino” refers to a $—NH_2$ group.

“Cyano” refers to a —CN group.

“Nitro” refers to a $—NO_2$ group.

“Carboxy” refers to a —C(O)OH group.

“THF” refers to tetrahydrofuran.

“EtOAc” refers to ethyl acetate.

“EA” refers to ethyl acetate.

“MeOH” refers to methanol.

“DMF” refers to N,N-dimethylformamide.

“DIPEA” refers to diisopropylethylamine.

“TFA” refers to trifluoroacetic acid.

“MeCN” refers to acetonitrile.

“DMA” refers to N,N-dimethylacetamide.

“$Et_2O$” refers to diethyl ether.

"DCE" refers to 1,2-dichloroethane.

"DIPEA" refers to N,N-diisopropylethylamine.

"NBS" refers to N-bromosuccinimide.

"NIS" refers to N-iodosuccinimide.

"Cbz-Cl" refers to benzyl chloroformate.

"$Pd_2(dba)_3$" refers to tris(dibenzylideneacetone)dipalladium.

"Dppf" refers to 1,1'-bisdiphenylphosphinoferrocene.

"HATU" refers to 2-(7-azabenzotriazol-1-yl)-N,N,N',N'-tetramethyluronium hexafluorophosphate.

"KHMDS" refers to potassium hexamethyldisilazide.

"LiHMDS" refers to lithium bis(trimethylsilyl)amide.

"MeLi" refers to methyl lithium.

"n-BuLi" refers to n-butyl lithium.

"$NaBH(OAc)_3$" refers to sodium triacetoxyborohydride.

"DCM" refers to dichloromethane.

Different expressions such as "X is selected from the group consisting of A, B or C", "X is selected from the group consisting of A, B and C", "X is A, B or C", "X is A, B and C" and the like, express the same meaning, that is, X can be any one or more of A, B and C.

The hydrogen atom of the present invention can be substituted by its isotope deuterium. Any of the hydrogen atoms in the compounds of the examples of the present invention can also be substituted by deuterium atom.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to exert biological activity.

A "pharmaceutically acceptable salt" refers to a salt of the compound of the present invention, which is safe and effective in mammals and has the desired biological activity.

DETAILED DESCRIPTION OF THE INVENTION

The present invention will be further described with reference to the following examples, but the examples should not be considered as limiting the scope of the present invention.

EXAMPLES

The structures of the compounds of the present invention were identified by nuclear magnetic resonance (NMR) and/or liquid chromatography-mass spectrometry (LC-MS). NMR shifts (8) are given in parts per million (ppm). NMR was determined by a Bruker AVANCE-400 machine. The solvents for determination were deuterated-dimethyl sulfoxide (DMSO-$d_6$), deuterated-methanol ($CD_3OD$) and deuterated-chloroform ($CDCl_3$), and the internal standard was tetramethylsilane (TMS).

Liquid chromatography-mass spectrometry (LC-MS) was determined on an Agilent 1200 Infinity Series mass spectrometer. High performance liquid chromatography (HPLC) was determined on an Agilent 1200DAD high pressure liquid chromatograph (Sunfire C18 150×4.6 mm chromatographic column), and a Waters 2695-2996 high pressure liquid chromatograph (Gimini C18 150×4.6 mm chromatographic column).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm. Yantai Huanghai 200 to 300 mesh silica gel was generally used as a carrier for column chromatography.

The raw materials used in the examples of the present invention are known and commercially available, or can be synthesized by adopting or according to known methods in the art.

Unless otherwise stated, all reactions of the present invention were carried out under continuous magnetic stirring under a dry nitrogen or argon atmosphere, the solvent was dry, and the reaction temperature was in degrees celsius.

Intermediate 1

(S)-4-(Difluoromethyl)oxazolidin-2-one

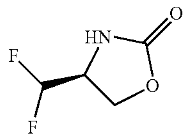

Step 1: Preparation of (R)-3-benzyl-4-(hydroxymethyl)oxazolidin-2-one

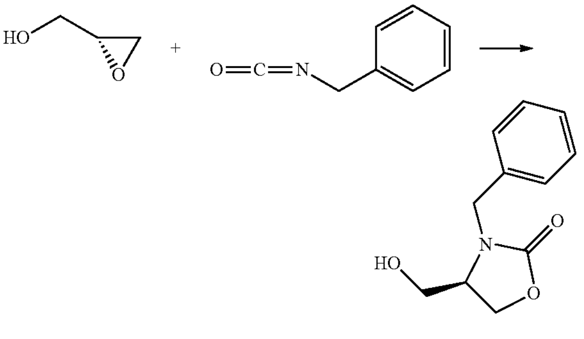

(R)-Oxiran-2-ylmethanol (3.7 g, 50.0 mmol) and (isocyanatomethyl)benzene (6.66 g, 50.0 mmol) were mixed in dichloromethane (50 mL). Under a nitrogen atmosphere, the reaction solution was warmed up to 45° C. and stirred overnight. After cooling, 100 mL of saturated aqueous sodium bicarbonate solution was added, the reaction solution was then extract with dichloromethane (100 mL×2). The organic phases were combined, washed with saturated brine, dried over anhydrous sodium sulfate and concentrated under reduced pressure. The residue was subjected to column chromatography to obtain the title compound (R)-3-benzyl-4-(hydroxymethyl)oxazolidin-2-one (4.14 g, 40%).

MS m/z (ESI): 208.2 $[M+H]^+$.

Step 2: Preparation of (S)-3-benzyl-4-(dihydroxymethyl) oxazolidin-2-one

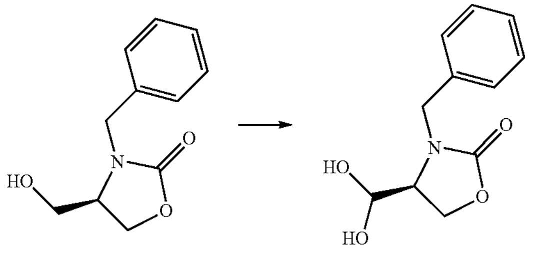 [SMILES: O=C1OC[C@@H](CO)N1Cc1ccccc1 ; O=C1OC[C@@H](C(O)O)N1Cc1ccccc1]

(R)-3-Benzyl-4-(hydroxymethyl)oxazolidin-2-one (4.14 g, 20.0 mmol) and IBX (16.8 g, 60.0 mmol) were mixed in ethyl acetate (100 mL). Under a nitrogen atmosphere, the reaction solution was stirred at 85° C. for 3 hours. The reaction solution was cooled and filtered. The filtrate was concentrated under reduced pressure to obtain the crude product(S)-3-benzyl-4-(dihydroxymethyl)oxazolidin-2-one (4.46 g), which was used directly in the next step.

MS m/z (ESI): 224.2 $[M+H]^+$.

Step 3: Preparation of (S)-3-benzyl-4-(difluoromethyl)oxazolidin-2-one

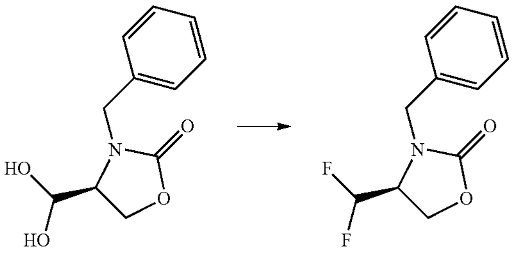 [SMILES: O=C1OC[C@@H](C(O)O)N1Cc1ccccc1 ; O=C1OC[C@@H](C(F)F)N1Cc1ccccc1]

(S)-3-Benzyl-4-(dihydroxymethyl)oxazolidin-2-one (4.46 g, 20.0 mmol) was dissolved in dichloromethane (100 mL). Under a nitrogen atmosphere, DAST (6.45 g, 40.0 mmol) was added dropwise in an ice bath, and then the reaction solution was naturally warmed up to room temperature and reacted for 3 hours. The reaction solution was slowly added dropwise to the pre-cooled saturated aqueous sodium bicarbonate solution, and then extract with dichloromethane (200 mL×2). The organic phases were combined and concentrated under reduced pressure. The residue was subjected to column chromatography to obtain the title compound (S)-3-benzyl-4-(difluoromethyl)oxazolidin-2-one (1.82 g, two-step yield 40%).

MS m/z (ESI): 228.2 $[M+H]^+$.

Step 4: Preparation of (S)-4-(difluoromethyl)oxazolidin-2-one

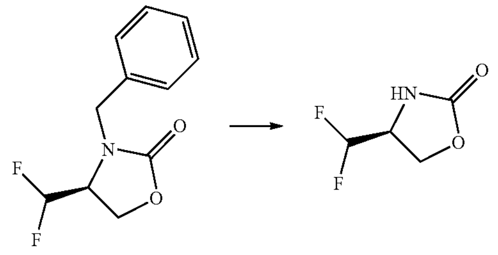 [SMILES: O=C1OC[C@@H](C(F)F)N1Cc1ccccc1 ; O=C1N[C@H](C(F)F)CO1]

(S)-3-Benzyl-4-(difluoromethyl)oxazolidin-2-one (1.82 g, 8 mmol) was dissolved in ethanol (100 mL), followed by the addition of $Pd(OH)_2/C$ (300 mg). Under a hydrogen atmosphere, the reaction solution was stirred at 70° C. overnight. The reaction solution was cooled and filtered. The filtrate was concentrated under reduced pressure to obtain the title compound (S)-4-(difluoromethyl)oxazolidin-2-one (0.88 g, 80%).

$^1H$ NMR (400 MHz, $CDCl_3$) δ 4.05-4.18 (m, 1H), 4.39-4.45 (m, 1H), 4.54 (t, J=9.3 Hz, 1H), 5.78 (td, J=55.3, 4.7 Hz, 1H), 6.07 (s, 1H);

MS m/z (ESI): 138.1 $[M+H]^+$.

Intermediate 2

9-Bromo-2-iodo-5,6-dihydrobenzo[f]imidazo[1,2-d][1,4]oxazepine

Step 1: Preparation of 5-bromo-2-(1H-imidazol-2-yl)phenol

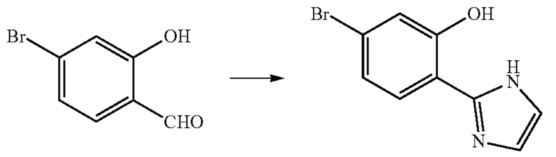 [SMILES: O=Cc1ccc(Br)cc1O ; Oc1cc(Br)ccc1-c1ncc[nH]1]

Aqueous glyoxal solution (40 wt. %, 87 g, 597 mmol) was added to a solution of 4-bromo-2-hydroxybenzaldehyde (24.0 g, 119 mmol) in methanol (250 mL). In a water bath, ammonia (28 wt. %, 121 g, 860 mmol) was slowly added dropwise to the reaction solution under stirring, the addition process lasted for 30 minutes, and the temperature of the reaction solution was controlled not to exceed 40° C. The mixture was stirred at 35° C. for two days, cooled and concentrated under reduced pressure to remove the organic solvent and obtain the crude product 5-bromo-2-(1H-imidazol-2-yl)phenol, which was used directly in the next step.

MS m/z (ESI): 239.0 $[M+H]^+$.

Step 2: Preparation of 9-bromo-5,6-dihydrobenzo[f]imidazo[1,2-d][1,4]oxazepine

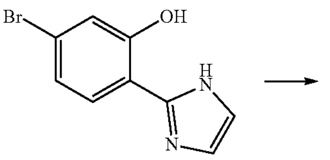

-continued

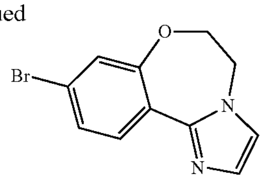

The crude product 5-bromo-2-(1H-imidazol-2-yl)phenol (about 29 g, 119 mmol), cesium carbonate (158 g, 485 mmol) and 1,2-dibromoethane (42 mL, 485 mmol) were mixed in DMF (250 mL), and the reaction solution was stirred at 85° C. overnight. The reaction solution was cooled, and diluted with a large amount of ethyl acetate. The organic phase was washed with saturated brine several times, dried over anhydrous sodium sulfate and concentrated. The residue was subjected to column chromatography to obtain the title compound 9-bromo-5,6-dihydrobenzo[f]imidazo[1,2-d][1,4]oxazepine (12.5 g, two-step yield: 38%).

MS m/z (ESI): 265.0 [M+H]+.

Step 3: Preparation of 9-bromo-2,3-diiodo-5,6-dihydrobenzo[f]imidazo[1,2-d][1,4]oxazepine

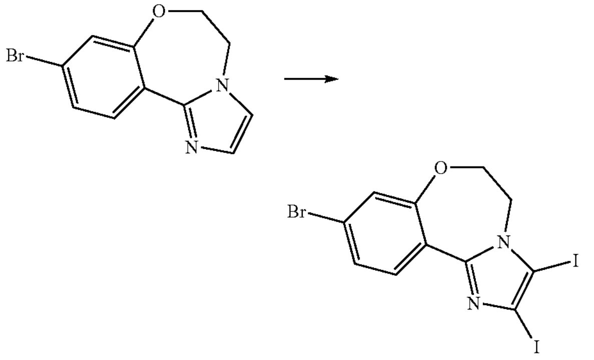

NIS (29.8 g, 132 mmol) was added in batches to a solution of 9-bromo-5,6-dihydrobenzo[f]imidazo[1,2-d][1,4]oxazepine (11.7 g, 44.1 mmol) in DMF (150 mL) at room temperature, and the reaction solution was stirred at 60° C. overnight. The reaction solution was cooled, and water was added to precipitate a solid. After filtering, the solid was dissolved in ethyl acetate. The solution was washed with 1 M aqueous NaOH solution and saturated brine successively, dried over anhydrous sodium sulfate, concentrated to obtain the title compound and 9-bromo-2,3-diiodo-5,6-dihydrobenzo[f]imidazo[1,2-d][1,4]oxazepine (22.5 g, yield: 98.7%).

MS m/z (ESI): 516.7 [M+H]+.

Step 4: Preparation of 9-bromo-2-iodo-5,6-dihydrobenzo[f]imidazo[1,2-d][1,4]oxazepine

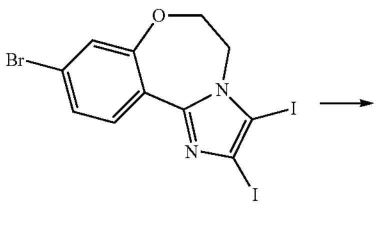

-continued

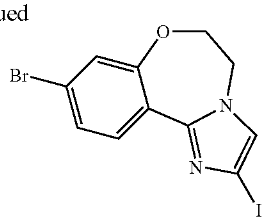

EtMgBr (1.0 M, THF solution, 60.9 mL, 60.9 mmol) was slowly added dropwise to a solution of 9-bromo-2,3-diiodo-5,6-dihydrobenzo[f]imidazo[1,2-d][1,4]oxazepine (21.0 g, 40.6 mmol) in THF (140 mL) at −20° C. After completion of the addition, the reaction solution was stirred at −15° C. for 3 hours. The reaction solution was slowly warmed up to room temperature, and saturated aqueous ammonium chloride solution was added dropwise. After stirring for 15 minutes, the reaction solution was extracted with ethyl acetate several times. The organic phases were combined, washed with saturated brine, dried over anhydrous sodium sulfate and concentrated. The residue was subjected to column chromatography to obtain the title compound 9-bromo-2-iodo-5,6-dihydrobenzo[f]imidazo[1,2-d][1,4]oxazepine (12.5 g, yield: 79%).

MS m/z (ESI): 390.9 [M+H]+.

Step 5: Preparation of (S)-3-(9-bromo-5,6-dihydrobenzo[f]imidazo[1,2-d][1,4]oxazepin-2-yl)-4-(difluorometh yl)oxazolidin-2-one

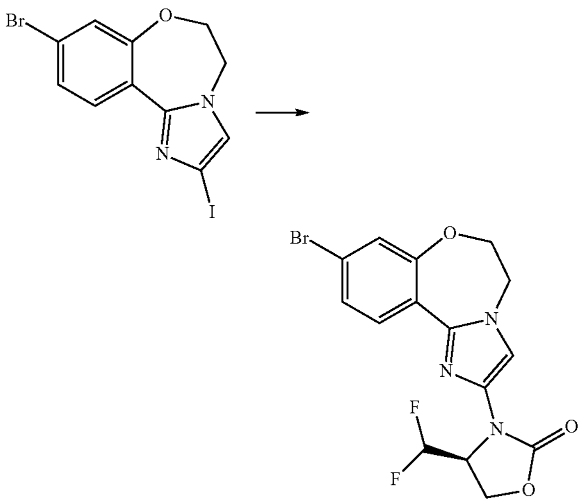

9-Bromo-2-iodo-5,6-dihydrobenzo[f]imidazo[1,2-d][1,4]oxazepine (300 mg, 0.77 mmol), (S)-4-(difluoromethyl)oxazolidin-2-one (105 mg, 0.77 mmol), (1R,2R)-$N^1$,$N^2$-dimethylcyclohexane-1,2-diamine (43 mg, 0.30 mmol), copper acetate (27 mg, 0.15 mmol) and cesium carbonate (489 mg, 1.5 mmol) were mixed in 2-methyltetrahydrofuran (6 mL). The reaction system was purged with nitrogen three times, and reacted at 78° C. for 22 hours. The reaction solution was cooled to room temperature, and 15% ammonia was added. The reaction solution was stirred for 5 minutes and extracted with EtOAc three times. The organic phases were combined, washed with saturated aqueous sodium chloride solution, dried over anhydrous sodium sulfate, and concentrated under reduced pressure to remove the organic solvent. The residue was subjected to column chromatography to obtain the title compound (S)-3-(9-bromo-5,6-dihydrobenzo[f]imidazo[1,2-d][1,4]oxazepin-2-yl)-4-(difluorometh yl)oxazolidin-2-one (186 mg, 61%).

$^1$H NMR (400 MHz, $CDCl_3$) δ 4.35-4.41 (m, 2H), 4.44-4.52 (m, 2H), 4.53-4.55 (m, 1H), 4.73-4.76 (m, 1H), 4.89-4.91 (m, 1H), 6.62-6.71 (m, 1H), 7.19-7.28 (m, 2H), 7.30 (s, 1H), 8.21 (d, J=8.6 Hz, 1H);

MS m/z (ESI): 400.1 $[M+H]^+$.

Example 1

Preparation of (S)-2-((2-((S)-4-(difluoromethyl)-2-oxooxazolidin-3-yl)-6,7-dihydro-5H-benzo[b]imidazo[2,1-d][1,5]oxazocin-10-yl)amino)propanamide

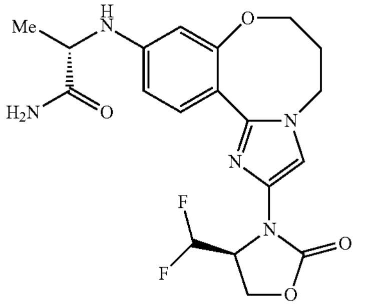 [SMILES: C[C@H](Nc1ccc2c(c1)OCCCn1cc(N3C(=O)OC[C@H]3C(F)F)nc1-2)C(N)=O]

Step 1: Preparation of 10-bromo-6,7-dihydro-5H-benzo[b]imidazo[2,1-d][1,5]oxazocine

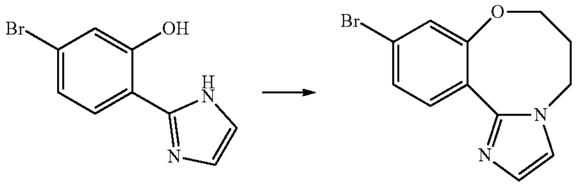 [SMILES: Oc1cc(Br)ccc1-c1ncc[nH]1 ; Brc1ccc2c(c1)OCCCn1ccnc1-2]

5-Bromo-2-(1H-imidazol-2-yl)phenol (1.0 g, 4.2 mmol), 1,3-dibromopropane (3.2 g, 15.9 mmol) and cesium carbonate (5.2 g, 15.9 mmol) were mixed in N,N-dimethylformamide (20 mL), and the reaction solution was stirred at room temperature for 1.5 hours. Water was added, and the reaction solution was stirred for 5 minutes and extracted with EtOAc three times. The organic phases were combined, dried over anhydrous sodium sulfate, and concentrated under reduced pressure. The residue was subjected to column chromatography to obtain the title compound 10-bromo-6,7-dihydro-5H-benzo[b]imidazo[2,1-d][1,5]oxazocine (1.1 g, 94%).

$^1$H NMR (400 MHz, DMSO-$d_6$) δ 1.89-1.94 (m, 2H), 4.03-4.09 (m, 4H), 7.03 (d, J=0.8 Hz, 1H), 7.28-7.33 (m, 3H), 7.95 (s, 1H);

MS m/z (ESI): 279.0 $[M+H]^+$.

Step 2: Preparation of 10-bromo-2,3-diiodo-6,7-dihydro-5H-benzo[b]imidazo[2,1-d][1,5]oxazocine

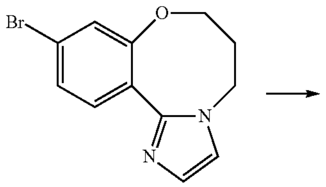

-continued

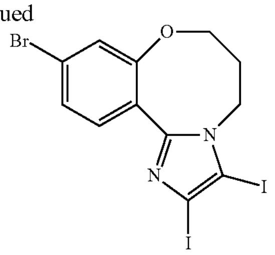

10-Bromo-6,7-dihydro-5H-benzo[b]imidazo[2,1-d][1,5]oxazocine (1.1 g, 3.96 mmol) and N-iodosuccinimide (2.5 g, 11.08 mmol) were mixed in N,N-dimethylformamide (15 mL). The reaction system was purged with nitrogen three times, and stirred at 80° C. overnight. The reaction solution was cooled to room temperature, and then ice water was added to the reaction flask. The reaction solution was stirred for 5 minutes and extracted with EtOAc three times. The organic phases were combined, dried over anhydrous sodium sulfate, and concentrated under reduced pressure. The residue was subjected to column chromatography to obtain the title compound 10-bromo-2,3-diiodo-6,7-dihydro-5H-benzo[b]imidazo[2,1-d][1,5]oxazocine (720 mg, 34%).

MS m/z (ESI): 530.8 $[M+H]^+$.

Step 3: Preparation of 10-bromo-2-iodo-6,7-dihydro-5H-benzo[b]imidazo[2,1-d][1,5]oxazocine

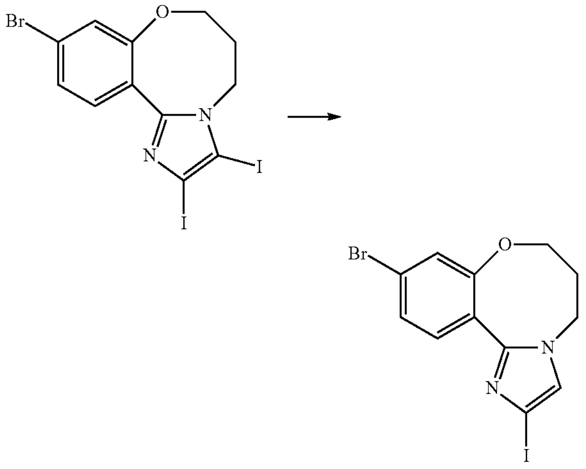

10-Bromo-2,3-diiodo-6,7-dihydro-5H-benzo[b]imidazo[2,1-d][1,5]oxazocine (500 mg, 0.94 mmol) was dissolved in tetrahydrofuran (10 mL). The reaction system was cooled to −20° C., and purged with nitrogen three times. Ethylmagnesium bromide (0.35 mL, 1.05 mmol) was added dropwise, and the reaction solution was reacted at −20° C. for 3 hours. Saturated ammonium chloride solution was added to quench the reaction, and the reaction solution was extracted with EtOAc three times. The organic phase was washed with saturated brine, dried over anhydrous sodium sulfate, and concentrated under reduced pressure. The residue was subjected to column chromatography to obtain the title compound 10-bromo-2-iodo-6,7-dihydro-5H-benzo[b]imidazo[2,1-d][1,5]oxazocine (365 mg, 96%).

$^1$H NMR (400 MHz, DMSO-$d_6$) δ 1.87-1.96 (m, 2H), 4.00-4.11 (m, 4H), 7.30-7.37 (m, 2H), 7.47-7.52 (m, 2H);

MS m/z (ESI): 404.9 $[M+H]^+$.

Step 4: Preparation of (S)-3-(10-bromo-6,7-dihydro-5H-benzo[b]imidazo[2,1-d][1,5]oxazocin-2-yl)-4-(difluor omethyl)oxazolidin-2-one

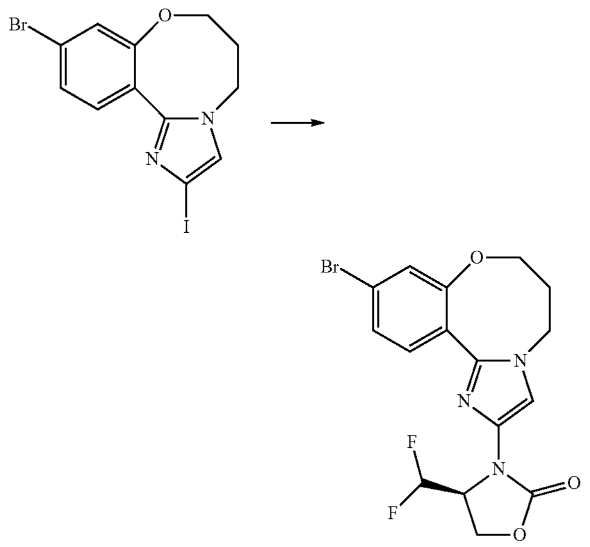

10-Bromo-2-iodo-6,7-dihydro-5H-benzo[b]imidazo[2,1-d][1,5]oxazocine (300 mg, 0.75 mmol), (S)-4-(difluoromethyl)oxazolidin-2-one (103 mg, 0.75 mmol), (1R,2R)-$N^1$, $N^2$-dimethylcyclohexane-1,2-diamine (43 mg, 0.30 mmol), cuprous iodide (29 mg, 0.15 mmol) and potassium carbonate (205 mg, 1.5 mmol) were mixed in 1,4-dioxane (6 mL). The reaction system was purged with nitrogen three times, and reacted at 100° C. for 5 hours. The reaction solution was cooled to room temperature, and 15% ammonia was added. The reaction solution was stirred for 5 minutes and extracted with EtOAc three times. The organic phases were combined, washed with saturated aqueous sodium chloride solution, dried over anhydrous sodium sulfate, and concentrated under reduced pressure. The residue was subjected to column chromatography to obtain the title compound (S)-3-(10-bromo-6,7-dihydro-5H-benzo[b]imidazo[2,1-d][1,5] oxazocin-2-yl)-4-(difluor omethyl)oxazolidin-2-one (187 mg, 60%).

MS m/z (ESI): 414.0 $[M+H]^+$.

Step 5: Preparation of (S)-2-((2-((S)-4-(difluoromethyl)-2-oxooxazolidin-3-yl)-6,7-dihydro-5H-benzo[b]imida zo[2,1-d][1,5]oxazocin-10-yl)amino)propanamide

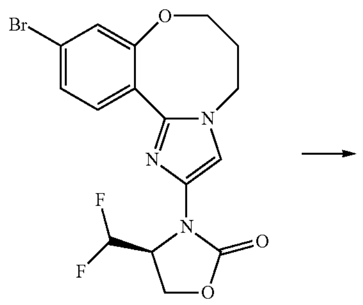

-continued

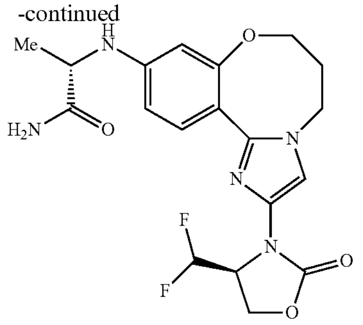

(S)-3-(10-Bromo-6,7-dihydro-5H-benzo[b]imidazo[2,1-d][1,5]oxazocin-2-yl)-4-(di fluoromethyl)oxazolidin-2-one (100 mg, 0.24 mmol), L-alanine (43 mg, 0.48 mmol), cuprous iodide (9 mg, 0.048 mmol) and potassium phosphate (103 mg, 0.48 mmol) were mixed in dimethyl sulfoxide (5 mL). The reaction system was purged with nitrogen three times, and reacted at 100° C. for 5 hours. The reaction solution was cooled to room temperature, then ammonium chloride (78 mg, 1.45 mmol) and triethylamine (367 mg, 3.63 mmol) were added, and the reaction solution was stirred for 5 minutes. O-(7-azabenzotriazol-1-yl)-N,N,N',N'-tetramethylurea hexafluorophosphate (830 mg, 2.18 mmol) was added, and the reaction solution was stirred at room temperature for 2 hours, and filtered. Saturated aqueous sodium bicarbonate solution was added to the filtrate, which was then extracted with ethyl acetate three times. The organic phases were combined, dried over anhydrous sodium sulfate, and concentrated under reduced pressure. The residue was subjected to column chromatography to obtain the title compound (S)-2-((2-((S)-4-(difluoromethyl)-2-oxooxazolidin-3-yl)-6,7-dihydro-5H-benzo[b]imida zo[2,1-d][1,5]oxazocin-10-yl)amino)propanamide (34 mg, 34%).

$^1H$ NMR (400 MHz, DMSO-$d_6$) δ 1.31 (d, J=6.9 Hz, 3H), 1.82-1.96 (m, 2H), 3.71-3.82 (m, 1H), 3.87-4.06 (m, 4H), 4.51-4.62 (m, 2H), 4.89-4.95 (m, 1H), 6.11-6.17 (m, 2H), 6.35-6.40 (m, 1H), 6.54-6.82 (m, 1H), 7.01 (s, 1H), 7.20 (s, 1H), 7.32 (d, J=8.6 Hz, 1H), 7.39 (s, 1H);

MS m/z (ESI): 422.1 $[M+H]^+$.

Example 2 and Example 3

Preparation of (S)-2-(((S)-2-((S)-4-(difluoromethyl)-2-oxooxazolidin-3-yl)-6-methyl-5,6-dihydrobenzo[f] imidazo[1,2-d][1,4]oxazepin-9-yl)amino)propanamide and (S)-2-(((R)-2-((S)-4-(difluoromethyl)-2-oxooxazolidin-3-yl)-6-methyl-5,6-dihydrobenz o[f] imidazo[1,2-d][1,4]oxazepin-9-yl)amino) propanamide

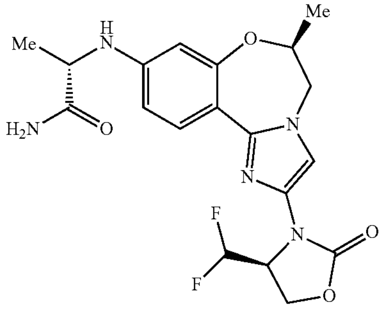

-continued

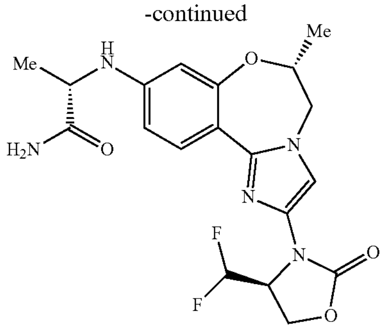

Step 1: Preparation of 2-(5-bromo-2-fluorophenyl)-1H-imidazole

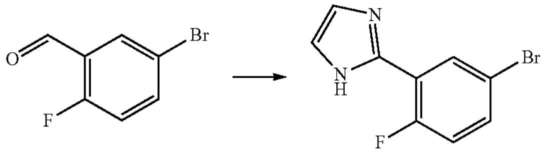 [SMILES: O=Cc1cc(Br)ccc1F ; Fc1ccc(Br)cc1-c1ncc[nH]1]

5-Bromo-2-fluorobenzaldehyde (5.0 g, 24.6 mmol) was dissolved in isopropanol/water (25 mL/25 mL) at room temperature, followed by the addition of ammonium acetate (17.6 g, 221.7 mmol) and the dropwise addition of glyoxal (4.5 mL, 221.7 mmol), and the reaction solution was stirred overnight. The reaction solution was diluted with isopropanol, filtered and concentrated under reduced pressure. Dichloromethane and water were added to the concentrate, and two phases were separated. The organic phases were combined, dried over anhydrous sodium sulfate, and concentrated under reduced pressure. The residue was subjected to column chromatography to obtain the title compound 2-(5-bromo-2-fluorophenyl)-1H-imidazole (3.3 g, 56%).

$^1$H NMR (400 MHz, DMSO-$d_6$) δ 7.18-7.27 (m, 2H), 7.33-7.38 (m, 1H), 7.56-7.60 (m, 1H), 8.10-8.16 (m, 1H);

MS m/z (ESI): 241.0 $[M+H]^+$.

Step 2: Preparation of 9-bromo-6-methyl-5,6-dihydrobenzo[f]imidazo[1,2-d][1,4]oxazepine

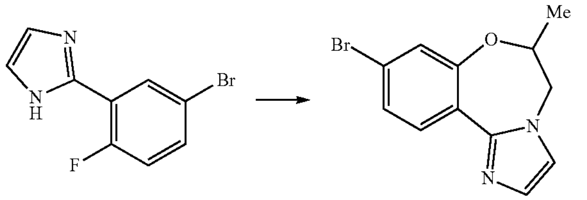 [SMILES: Fc1ccc(Br)cc1-c1ncc[nH]1 ; CC1Cn2ccnc2-c2ccc(Br)cc2O1]

2-(5-Bromo-2-fluorophenyl)-1H-imidazole (1.0 g, 4.2 mmol) was dissolved in N,N-dimethylformamide (5 mL), followed by the addition of sodium hydride (221 mg, 4.6 mmol) in an ice water bath, and the reaction solution was stirred for 10 minutes. 1,2-Propylene oxide (292 mg, 5.1 mmol) was added, and the reaction solution was warmed up to 95° C. and stirred for 6 hours. The reaction solution was cooled to room temperature, and then saturated aqueous ammonium chloride solution was added to the reaction flask. The reaction solution was extracted with dichloromethane three times. The organic phases were combined, dried over anhydrous sodium sulfate, and concentrated under reduced pressure. The residue was subjected to column chromatography to obtain the title compound 9-bromo-6-methyl-5,6-dihydrobenzo[f]imidazo[1,2-d][1,4]oxazepine (1.1 g, 94%).

$^1$H NMR (400 MHz, DMSO-$d_6$) δ 1.40 (d, J=6.4 Hz, 3H), 4.19-4.25 (m, 1H), 4.42-4.53 (m, 2H), 6.96 (d, J=8.7 Hz, 1H), 7.07 (s, 1H), 7.31 (s, 1H), 7.38-7.42 (m, 1H), 8.41 (d, J=2.5 Hz, 1H);

MS m/z (ESI): 279.0 $[M+H]^+$.

Step 3: Preparation of 9-bromo-2,3-diiodo-6-methyl-5,6-dihydrobenzo[f]imidazo[1,2-d][1,4]oxazepine

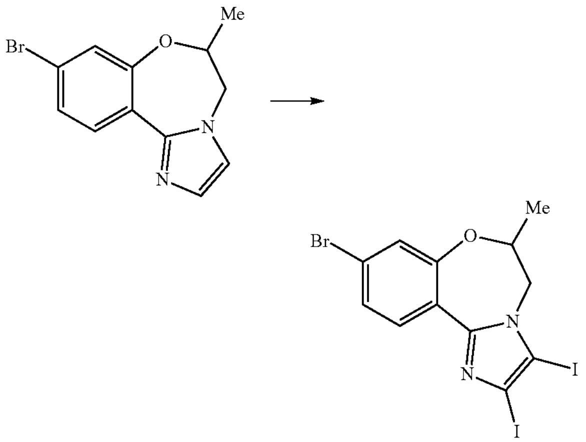

9-Bromo-2,3-diiodo-6-methyl-5,6-dihydrobenzo[f]imidazo[1,2-d][1,4]oxazepine was prepared by referring to the method of Example 1.

$^1$H NMR (400 MHz, DMSO-$d_6$) δ 1.42 (d, J=6.4 Hz, 3H), 4.14-4.20 (m, 1H), 4.31-4.36 (m, 1H), 4.44-4.56 (m, 1H), 6.99 (d, J=8.7 Hz, 1H), 7.43-7.48 (m, 1H), 8.26 (d, J=2.5 Hz, 1H);

MS m/z (ESI): 530.8 $[M+H]^+$.

Step 4: Preparation of 9-bromo-2-iodo-6-methyl-5,6-dihydrobenzo[f]imidazo[1,2-d][1,4]oxazepine

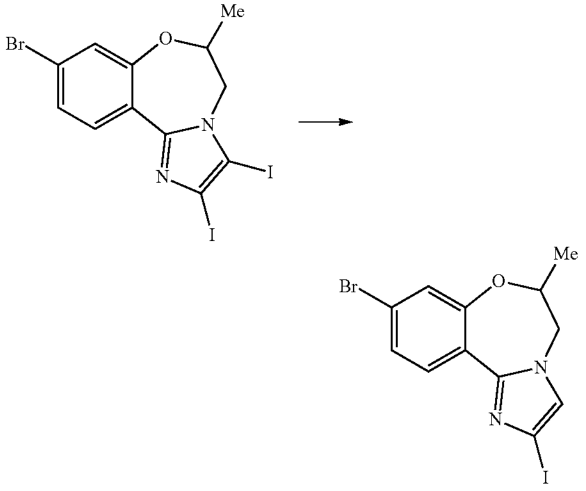

9-Bromo-2-iodo-6-methyl-5,6-dihydrobenzo[f]imidazo[1,2-d][1,4]oxazepine was prepared by referring to the method of Example 1.

MS m/z (ESI): 404.9 $[M+H]^+$.

Step 5: Preparation of (4S)-3-(9-bromo-6-methyl-5,6-dihydrobenzo[f]imidazo[1,2-d][1,4]oxazepin-2-yl)-4-(dif luoromethyl)oxazolidin-2-one

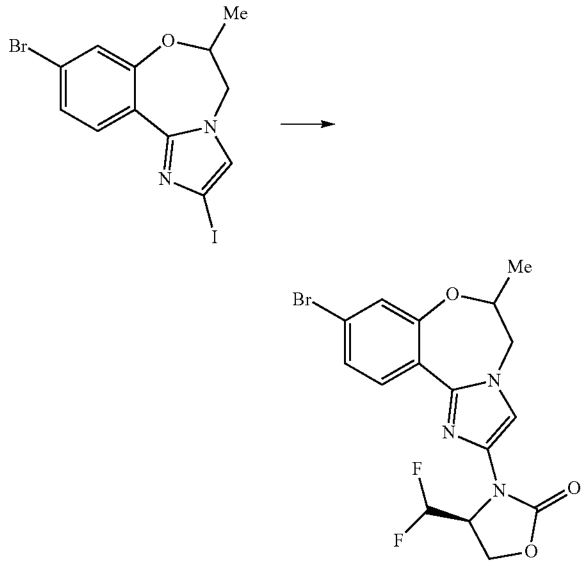

(4S)-3-(9-Bromo-6-methyl-5,6-dihydrobenzo[f]imidazo [1,2-d][1,4]oxazepin-2-yl)-4-(difluoromethyl)oxazolidin-2-one was prepared by referring to the method of Example 1.

MS m/z (ESI): 414.0 [M+H]$^+$.

Step 6: Preparation of (S)-2-(((S)-2-((S)-4-(difluoromethyl)-2-oxooxazolidin-3-yl)-6-methyl-5,6-dihydrobenzo[f]imidazo[1,2-d][1,4]oxazepin-9-yl)amino)propanamide and (S)-2-(((R)-2-((S)-4-(difluoromethyl)-2-oxooxazolidin-3-yl)-6-methyl-5,6-dihydrobenz o[f]imidazo[1,2-d][1,4]oxazepin-9-yl)amino)propanamide

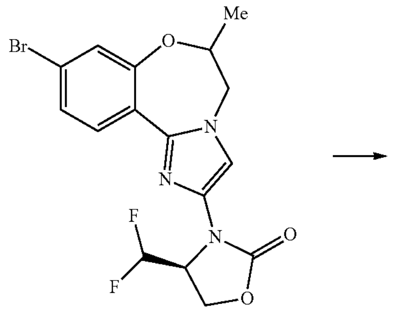

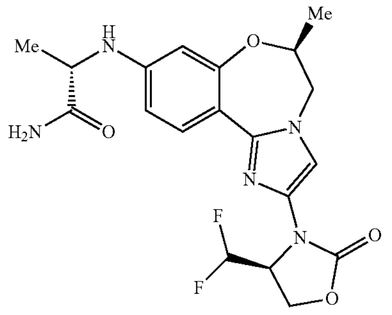

+

-continued

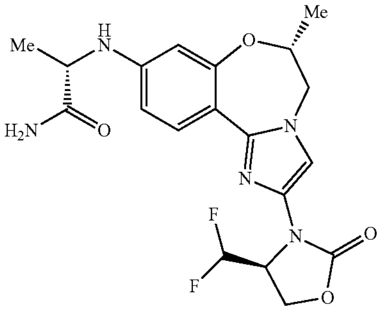

(S)-2-(((S)-2-((S)-4-(Difluoromethyl)-2-oxooxazolidin-3-yl)-6-methyl-5,6-dihydro benzo[f]imidazo[1,2-d][1,4]oxazepin-9-yl)amino)propanamide and (S)-2-(((R)-2-((S)-4-(difluoromethyl)-2-oxooxazolidin-3-yl)-6-methyl-5,6-dihydrobenz o[f]imidazo[1,2-d][1,4]oxazepin-9-yl)amino) propanamide were prepared by referring to the method of Example 1 and by chiral resolution.

The NMR and mass spectrum data of the mixed pair of epimers are as follows:

$^1$H NMR (400 MHz, DMSO-$d_6$) δ 1.24-1.41 (m, 6H), 3.65-3.77 (m, 1H), 4.01-4.13 (m, 1H), 4.35-4.41 (m, 2H), 4.55-4.65 (m, 2H), 4.91-4.97 (m, 1H), 5.69 (d, J=7.0 Hz, 1H), 6.50-6.53 (m, 1H), 6.61-6.94 (m, 1H), 6.76-6.81 (m, 1H), 6.97 (s, 1H), 7.29 (s, 1H), 7.33 (s, 2H);

MS m/z (ESI): 422.1 [M+H]$^+$.

Example 4

Preparation of (S)-2-(((R)-2-((S)-4-(difluoromethyl)-2-oxooxazolidin-3-yl)-5-methyl-5,6-dihydrobenz o[f]imidazo[1,2-d][1,4]oxazepin-9-yl)amino) propanamide

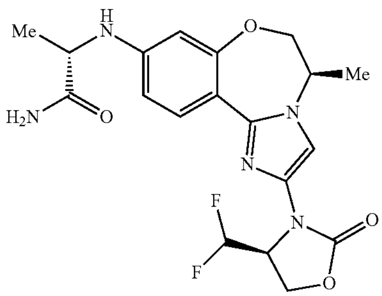 [SMILES: C[C@H](Nc1ccc2c(c1)OC[C@@H](C)n1cc(N3C(=O)OC[C@H]3C(F)F)nc1-2)C(N)=O]

(S)-2-(((R)-2-((S)-4-(Difluoromethyl)-2-oxooxazolidin-3-yl)-5-methyl-5,6-dihydro benzo[f]imidazo[1,2-d][1,4]oxazepin-9-yl)amino)propanamide was prepared by referring to the method of Example 2 and Example 3.

$^1$H NMR (400 MHz, $CD_3OD$) δ 1.47 (t, J=7.4 Hz, 6H), 3.78-3.87 (m, 1H), 4.16-4.23 (m, 1H), 4.40-4.45 (m, 1H), 4.55-4.65 (m, 3H), 4.91-4.97 (m, 1H), 6.17-6.21 (m, 1H), 6.41-6.45 (m, 1H), 6.43-6.73 (m, 1H), 7.20 (s, 1H), 8.06-8.09 (m, 1H);

MS m/z (ESI): 422.1 [M+H]$^+$.

Example 5

Preparation of (S)-2-(((S)-2-((S)-4-(difluoromethyl)-2-oxooxazolidin-3-yl)-5-methyl-5,6-dihydrobenzo[f]imidazo[1,2-d][1,4]oxazepin-9-yl)amino)propanamide

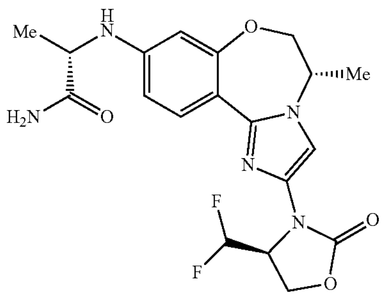 [SMILES: C[C@H](Nc1ccc2c(c1)OC[C@H](C)n1cc(N3C(=O)OC[C@H]3C(F)F)nc1-2)C(N)=O]

(S)-2-(((S)-2-((S)-4-(Difluoromethyl)-2-oxooxazolidin-3-yl)-5-methyl-5,6-dihydro benzo[f]imidazo[1,2-d][1,4]oxazepin-9-yl)amino)propanamide was prepared by referring to the method of Example 2 and Example 3.

$^1$H NMR (400 MHz, $CD_3OD$) δ 1.47 (t, J=7.4 Hz, 6H), 3.78-3.87 (m, 1H), 4.16-4.23 (m, 1H), 4.40-4.45 (m, 1H), 4.55-4.65 (m, 3H), 4.91-4.97 (m, 1H), 6.17-6.21 (m, 1H), 6.41-6.45 (m, 1H), 6.43-6.73 (m, 1H), 7.20 (s, 1H), 8.06-8.09 (m, 1H);

MS m/z (ESI): 422.1 $[M+H]^+$.

Example 6

Preparation of (S)-2-((2-((S)-4-(difluoromethyl)-2-oxooxazolidin-3-yl)-6,6-dimethyl-5,6-dihydrobenzo[f]imidazo[1,2-d][1,4]oxazepin-9-yl)amino)propanamide

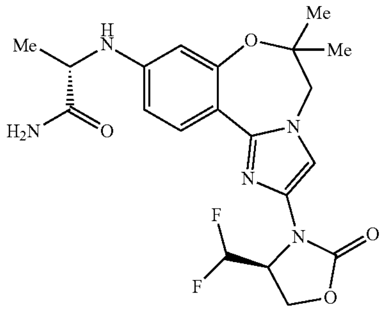 [SMILES: C[C@H](Nc1ccc2c(c1)OC(C)(C)Cn1cc(N3C(=O)OC[C@H]3C(F)F)nc1-2)C(N)=O]

(S)-2-((2-((S)-4-(Difluoromethyl)-2-oxooxazolidin-3-yl)-6,6-dimethyl-5,6-dihydro benzo[f]imidazo[1,2-d][1,4]oxazepin-9-yl)amino)propanamide was prepared by referring to the method of Example 2 and Example 3.

$^1$H NMR (400 MHz, DMSO-$d_6$) δ 1.26-1.33 (m, 9H), 3.69-3.75 (m, 1H), 3.90-3.98 (m, 2H), 4.55-4.63 (m, 2H), 4.90-5.00 (m, 1H), 5.78 (d, J=7.1 Hz, 1H), 6.54-6.58 (m, 1H), 6.78-6.83 (m, 1H), 6.55-6.86 (m, 1H), 6.94 (d, J=2.8 Hz, 1H), 6.98 (s, 1H), 7.35 (s, 1H), 7.39 (s, 1H);

MS m/z (ESI): 436.1 $[M+H]^+$.

Example 7

Preparation of (S)-2-((2-((S)-4-(difluoromethyl)-2-oxooxazolidin-3-yl)-5,5-dimethyl-5,6-dihydrobenzo[f]imidazo[1,2-d][1,4]oxazepin-9-yl)amino)propanamide

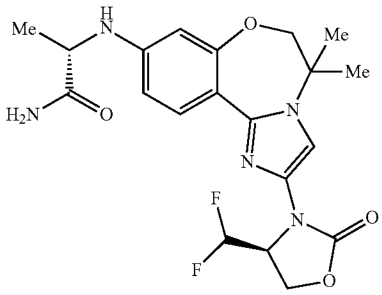 [SMILES: C[C@H](Nc1ccc2c(c1)OCC(C)(C)n1cc(N3C(=O)OC[C@H]3C(F)F)nc1-2)C(N)=O]

(S)-2-((2-((S)-4-(Difluoromethyl)-2-oxooxazolidin-3-yl)-5,5-dimethyl-5,6-dihydro benzo[f]imidazo[1,2-d][1,4]oxazepin-9-yl)amino)propanamide was prepared by referring to the method of Example 2 and Example 3.

MS m/z (ESI): 436.1 $[M+H]^+$.

Example 8

Preparation of (S)-2-((2-((S)-4-(difluoromethyl)-2-oxooxazolidin-3-yl)-5H-spiro[benzo[f]imidazo[1,2-d][1,4]oxazepine-6,1'-cyclopropan]-9-yl)amino)propanamide

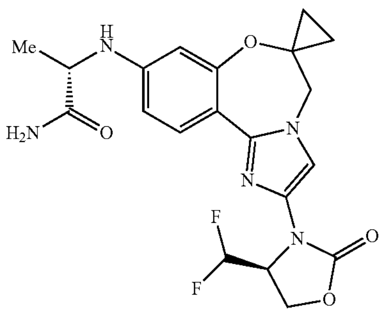 [SMILES: C[C@H](Nc1ccc2c(c1)OC1(CC1)Cn1cc(N3C(=O)OC[C@H]3C(F)F)nc1-2)C(N)=O]

(S)-2-((2-((S)-4-(Difluoromethyl)-2-oxooxazolidin-3-yl)-5H-spiro[benzo[f]imidaz o[1,2-d][1,4]oxazepine-6,1'-cyclopropan]-9-yl)amino)propanamide was prepared by referring to the method of Example 2 and Example 3.

MS m/z (ESI): 434.1 $[M+H]^+$.

Example 9

Preparation of (S)-2-((2-((S)-4-(difluoromethyl)-2-oxooxazolidin-3-yl)-6H-spiro[benzo[f]imidazo[1,2-d][1,4]oxazepine-5,1'-cyclopropan]-9-yl)amino)propanamide

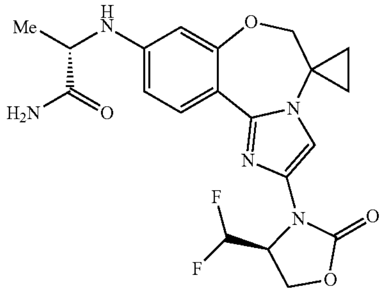 [SMILES: C[C@H](Nc1ccc2c(c1)OCC1(CC1)n1cc(N3C(=O)OC[C@H]3C(F)F)nc1-2)C(N)=O]

(S)-2-((2-((S)-4-(Difluoromethyl)-2-oxooxazolidin-3-yl)-6H-spiro[benzo[f]imidaz o[1,2-d][1,4]oxazepine-5,1'-cyclopropan]-9-yl)amino)propanamide was prepared by referring to the method of Example 2 and Example 3.

MS m/z (ESI): 434.1 $[M+H]^+$.

Example 10

Preparation of (S)-2-((2-((S)-4-(difluoromethyl)-2-oxooxazolidin-3-yl)-3-fluoro-5,6-dihydrobenzo[f]i midazo[1,2-d][1,4]oxazepin-9-yl)amino)propanamide

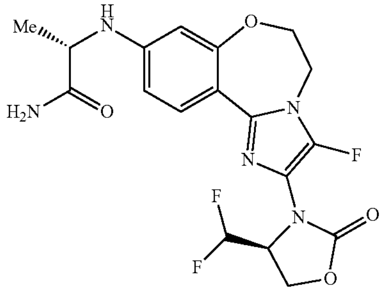 [SMILES: C[C@H](Nc1ccc2c(c1)OCCn1c-2nc(N2C(=O)OC[C@H]2C(F)F)c1F)C(N)=O]

Step 1: Preparation of 9-bromo-3-fluoro-2-iodo-5,6-dihydrobenzo[f]imidazo[1,2-d][1,4]oxazepine

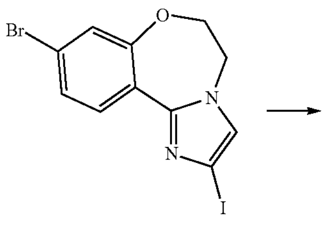

-continued

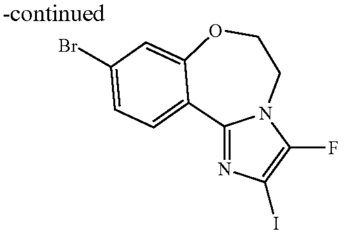

A solution of 9-bromo-2-iodo-5,6-dihydrobenzo[f]imidazo[1,2-d][1,4]oxazepine (500 mg, 1.28 mmol) in tetrahydrofuran (10 mL) was added dropwise to a solution of LDA (1.28 mL, 2.56 mmol) in tetrahydrofuran (10 mL) at −78° C. After completion of the addition, the reaction solution was stirred at −78° C. for 30 minutes. A solution of N-fluorobenzenesulfonamide (806 mg, 2.56 mmol) in tetrahydrofuran (9 mL) was added dropwise, and the reaction solution was stirred at −78° C. for 30 minutes. The reaction was quenched by saturated aqueous ammonium chloride solution, and the reaction solution was extracted with dichloromethane (100 mL×2). The organic phase was washed with saturated brine, dried over anhydrous sodium sulfate and concentrated. The residue was subjected to column chromatography to obtain the title compound 9-bromo-3-fluoro-2-iodo-5,6-dihydrobenzo[f]imidazo[1,2-d][1,4]oxazepine (150 mg, 29%).

$^1H$ NMR (400 MHz, DMSO-$d_6$) δ 4.31-4.34 (m, 2H), 4.43-4.48 (m, 2H), 7.19-7.34 (m, 2H), 8.17 (d, J=8.6 Hz, 1H);

MS m/z (ESI): 408.9 $[M+H]^+$.

Step 2: Preparation of (S)-3-(9-bromo-3-fluoro-5,6-dihydrobenzo[f]imidazo[1,2-d][1,4]oxazepin-2-yl)-4-(diflu oromethyl)oxazolidin-2-one

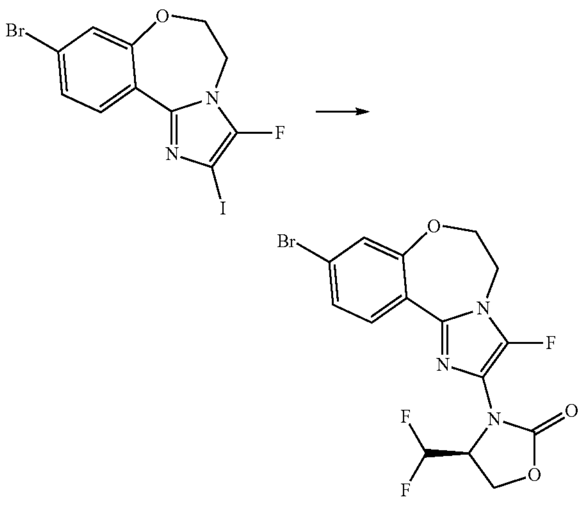

9-Bromo-3-fluoro-2-iodo-5,6-dihydrobenzo[f]imidazo[1,2-d][1,4]oxazepine (100 mg, 0.24 mmol), (S)-4-(difluoromethyl)oxazolidin-2-one (33.5 mg, 0.24 mmol), (1R,2R)-$N^1$,$N^2$-dimethylcyclohexane-1,2-diamine (35 mg, 0.24 mmol), cuprous iodide (46 mg, 0.24 mmol) and potassium phosphate (155 mg, 0.73 mmol) were mixed in dimethyl sulfoxide (10 mL), and reaction solution was reacted at 130° C. for 3 hours. The reaction solution was cooled to room temperature, and 15% ammonia was added. The reaction solution was stirred for 5 minutes and extracted with EtOAc three times. The organic phases were combined, washed with saturated sodium chloride solution, dried over anhydrous sodium sulfate, and concentrated under reduced pressure. The residue was subjected to column chromatography to obtain the title compound (S)-3-(9-bromo-3-fluoro-5,6-dihydrobenzo[f]imidazo[1,2-d][1,4]oxazepin-2-yl)-4-(diflu oromethyl)oxazolidin-2-one (21 mg, 20%).

$^1$H NMR (400 MHz, $CDCl_3$) δ 4.25-4.29 (m, 1H), 4.42-4.50 (m, 2H), 4.56-4.69 (m, 4H), 6.16-6.35 (m, 1H), 7.20-7.25 (m, 2H), 8.15 (d, J=8.4 Hz, 1H);

MS m/z (ESI): 417.9 $[M+H]^+$.

Step 3: Preparation of (2-((S)-4-(difluoromethyl)-2-oxooxazolidin-3-yl)-3-fluoro-5,6-dihydrobenzo[f]imidazo[1,2-d][1,4]oxazepin-9-yl)-L-alanine

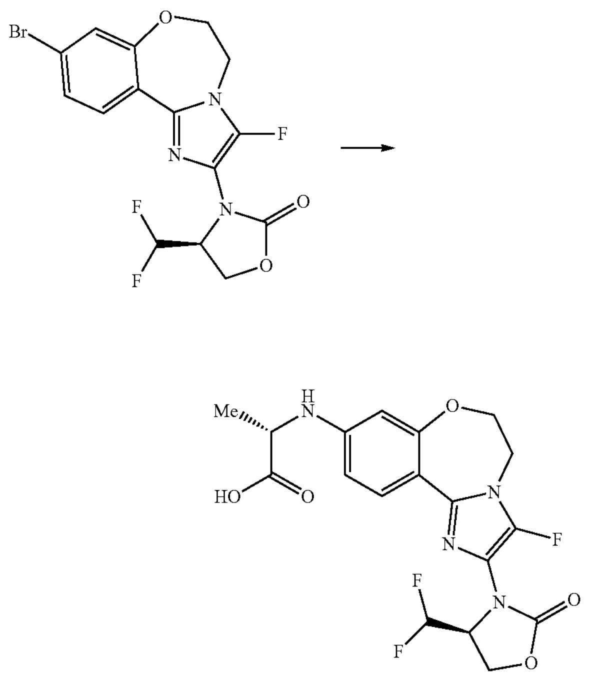 [SMILES: O=C1OC[C@@H](C(F)F)N1c1nc2n(c1F)CCOc1cc(Br)ccc1-2 ; C[C@H](Nc1ccc2c(c1)OCCn1c-2nc(N2C(=O)OC[C@H]2C(F)F)c1F)C(=O)O]

(2-((S)-4-(Difluoromethyl)-2-oxooxazolidin-3-yl)-3-fluoro-5,6-dihydrobenzo[f]imi dazo[1,2-d][1,4]oxazepin-9-yl)-L-alanine was prepared by referring to the method of Example 1.

MS m/z (ESI): 427.1 $[M+H]^+$.

Step 4: Preparation of (S)-2-((2-((S)-4-(difluoromethyl)-2-oxooxazolidin-3-yl)-3-fluoro-5,6-dihydrobenzo[f]i midazo [1,2-d][1,4]oxazepin-9-yl)amino)propanamide

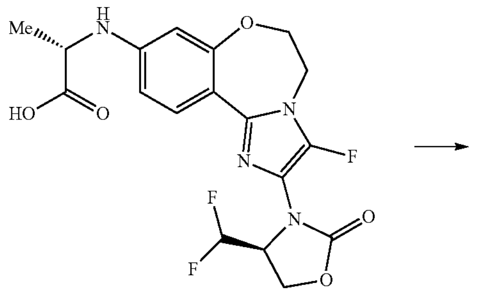

-continued

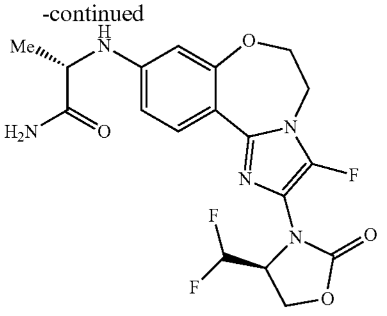

(S)-2-((2-((S)-4-(Difluoromethyl)-2-oxooxazolidin-3-yl)-3-fluoro-5,6-dihydrobenz o[f]imidazo[1,2-d][1,4]oxazepin-9-yl)amino)propanamide was prepared by referring to the method of Example 1.

$^1$H NMR (400 MHz, $CDCl_3$) δ 1.55 (d, J=7.0 Hz, 3H), 3.70-3.87 (m, 1H), 4.21 (d, J=3.6 Hz, 2H), 4.43 (d, J=5.2 Hz, 2H), 4.57-4.66 (m, 2H), 5.35 (s, 1H), 6.10-6.27 (m, 2H), 6.37-6.50 (m, 2H), 8.07 (d, J=8.6 Hz, 1H).

MS m/z (ESI): 426.1 $[M+H]^+$.

Example 11

Preparation of (S)-1-(2-((S)-4-(difluoromethyl)-2-oxooxazolidin-3-yl)-3-fluoro-5,6-dihydrobenzo[f]im idazo[1,2-d][1,4]oxazepin-9-yl)pyrrolidine-2-carboxamide

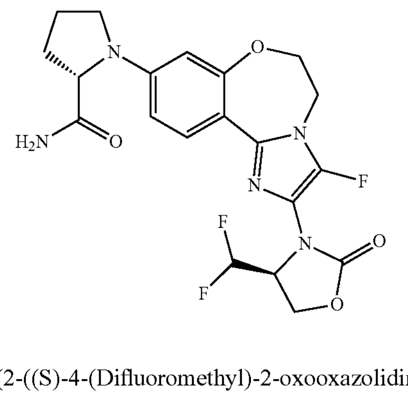

(S)-1-(2-((S)-4-(Difluoromethyl)-2-oxooxazolidin-3-yl)-3-fluoro-5,6-dihydrobenzo[f]imidazo[1,2-d][1,4]oxazepin-9-yl)pyrrolidine-2-carboxamide was prepared by referring to the method of Example 10.

MS m/z (ESI): 452.1 $[M+H]^+$.

Example 12

Preparation of (S)-2-((2-((S)-4-(difluoromethyl)-2-oxooxazolidin-3-yl)-3-fluoro-5,6-dihydrobenzo[f]imidazo[1,2-d][1,4]oxazepin-9-yl)oxy)propanamide

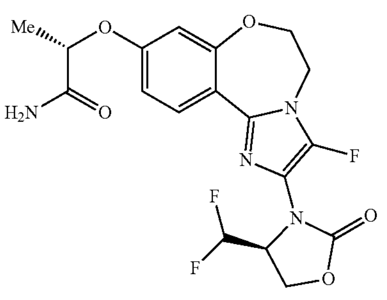 [SMILES: C[C@H](Oc1ccc2c(c1)OCCn1c-2nc(N2C(=O)OC[C@H]2C(F)F)c1F)C(N)=O]

(S)-2-((2-((S)-4-(Difluoromethyl)-2-oxooxazolidin-3-yl)-3-fluoro-5,6-dihydrobenz o[f]imidazo[1,2-d][1,4]oxazepin-9-yl)oxy)propanamide was prepared by referring to the method of Example 10.

MS m/z (ESI): 427.1 [M+H]$^+$.

Example 13

Preparation of (S)-2-((3-fluoro-2-((S)-2-oxo-4-(trifluoromethyl)oxazolidin-3-yl)-5,6-dihydrobenzo[f]imidazo[1,2-d][1,4]oxazepin-9-yl)amino)propanamide

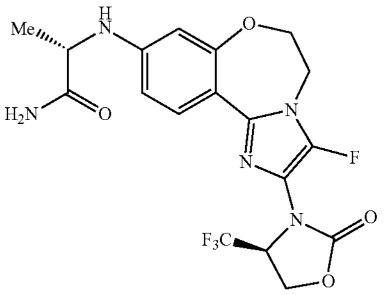 [SMILES: C[C@H](Nc1ccc2c(c1)OCCn1c-2nc(N2C(=O)OC[C@H]2C(F)(F)F)c1F)C(N)=O]

(S)-2-((3-Fluoro-2-((S)-2-oxo-4-(trifluoromethyl)oxazolidin-3-yl)-5,6-dihydrobenz o[f]imidazo[1,2-d][1,4]oxazepin-9-yl)amino)propanamide was prepared by referring to the method of Example 10.

MS m/z (ESI): 444.1 [M+H]$^+$.

Example 14

Preparation of (S)-2-((3-chloro-2-((S)-4-(difluoromethyl)-2-oxooxazolidin-3-yl)-5,6-dihydrobenzo[f]imidazo[1,2-d][1,4]oxazepin-9-yl)amino)propanamide

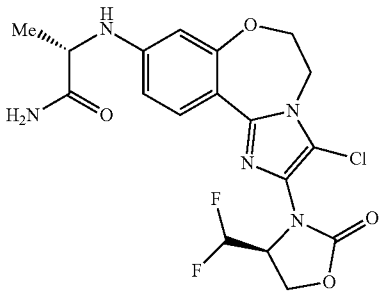

(S)-2-((3-Chloro-2-((S)-4-(difluoromethyl)-2-oxooxazolidin-3-yl)-5,6-dihydrobenz o[f]imidazo[1,2-d][1,4]oxazepin-9-yl)amino)propanamide was prepared by referring to the method of Example 10.

$^1$H NMR (400 MHz, $CD_3OD$) δ 1.46 (d, J=7.0 Hz, 3H), 3.80-3.86 (m, 1H), 4.29-4.32 (m, 2H), 4.43-4.46 (m, 2H), 4.57-4.67 (m, 3H), 6.07-6.31 (m, 2H), 6.43-6.46 (m, 1H), 7.98 (d, J=8.8 Hz, 1H);

MS m/z (ESI): 442.1 [M+H]$^+$.

Example 15

Preparation of (S)-2-((2-((S)-4-(difluoromethyl)-2-oxooxazolidin-3-yl)-3-methyl-5,6-dihydrobenzo[f]imidazo[1,2-d][1,4]oxazepin-9-yl)amino)propanamide

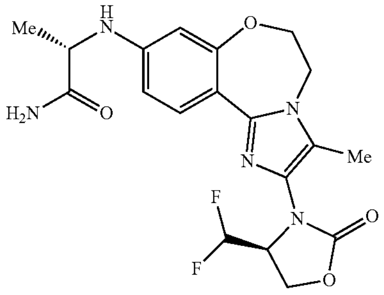

Step 1: Preparation of 5-bromo-2-(5-methyl-1H-imidazol-2-yl)phenol

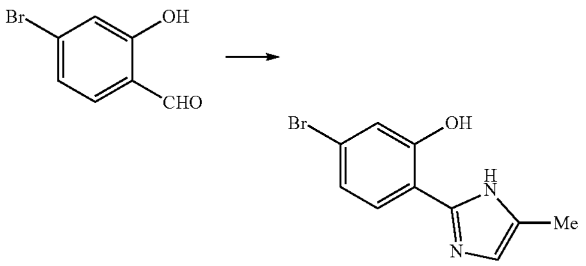

Aqueous pyruvaldehyde solution (40 wt. %, 80 mL) was added to a solution of 4-bromo-2-hydroxybenzaldehyde (5 g, 119 mmol) in methanol (100 mL). In a water bath, ammonia (28 wt. %, 40 g) was slowly added dropwise to the reaction solution under stirring, the addition process lasted for 30 minutes, and the temperature of the reaction solution was controlled not to exceed 40° C. The reaction solution was stirred at 75° C. for 2 hours, then cooled to room temperature to precipitate a solid, which was filtered to obtain the title compound 5-bromo-2-(5-methyl-1H-imidazol-2-yl)phenol (3.6 g, 57%).

MS m/z (ESI): 253.0 $[M+H]^+$.

Step 2: Preparation of 9-bromo-3-methyl-5,6-dihydrobenzo[f]imidazo[1,2-d][1,4]oxazepine

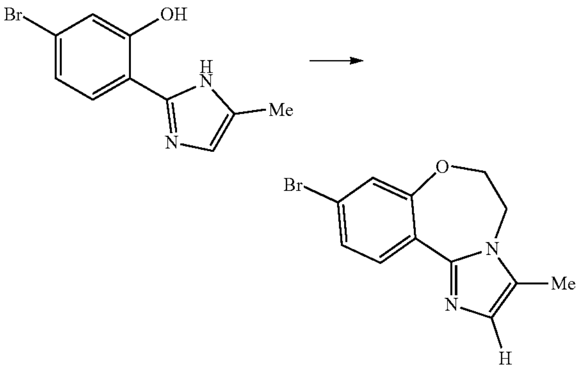

5-Bromo-2-(5-methyl-1H-imidazol-2-yl)phenol (2.5 g, 9.8 mmol), cesium carbonate (12.2 g, 37.5 mmol) and 1,2-dibromoethane (42.0 mL, 37.5 mmol) were mixed in DMF (30 mL), and the reaction solution was stirred at 85° C. overnight. The reaction solution was cooled to room temperature, and diluted with a large amount of ethyl acetate. The organic phase was washed with saturated brine several times, dried over sodium sulfate and concentrated. The residue was subjected to column chromatography to obtain the title compound 9-bromo-3-methyl-5,6-dihydrobenzo[f]imidazo[1,2-d][1,4]oxazepine (0.92 g, 33%).

$^1$H NMR (400 MHz, $CDCl_3$) δ 2.25 (s, 3H), 4.12-4.29 (m, 2H), 4.40-4.53 (m, 2H), 6.94 (s, 1H), 7.14-7.18 (m, 1H), 7.20-7.22 (m, 1H), 8.37 (d, J=8.6 Hz, 1H);

MS m/z (ESI): 279.1 $[M+H]^+$.

Step 3: Preparation of 9-bromo-2-iodo-3-methyl-5,6-dihydrobenzo[f]imidazo[1,2-d][1,4]oxazepine

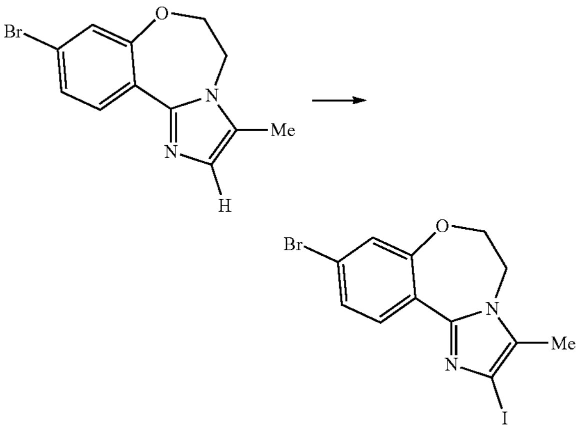

9-Bromo-2-iodo-3-methyl-5,6-dihydrobenzo[f]imidazo[1,2-d][1,4]oxazepine was prepared by referring to the method of Example 1.

MS m/z (ESI): 404.9 $[M+H]^+$.

Step 4: Preparation of (S)-3-(9-bromo-3-methyl-5,6-dihydrobenzo[f]imidazo[1,2-d][1,4]oxazepin-2-yl)-4-(difluoromethyl)oxazolidin-2-one

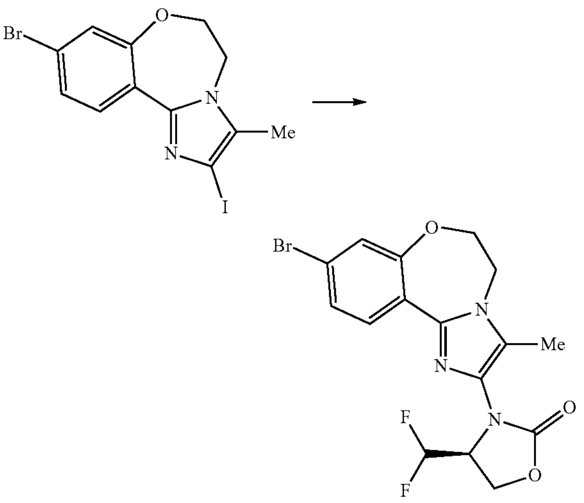

(S)-3-(9-Bromo-3-methyl-5,6-dihydrobenzo[f]imidazo[1,2-d][1,4]oxazepin-2-yl)-4-(difluoromethyl)oxazolidin-2-one was prepared by referring to the method of Example 1.

MS m/z (ESI): 414.0 $[M+H]^+$.

Step 5: Preparation of (2-((S)-4-(difluoromethyl)-2-oxooxazolidin-3-yl)-3-methyl-5,6-dihydrobenzo[f]imidazo[1,2-d][1,4]oxazepin-9-yl)-L-alanine

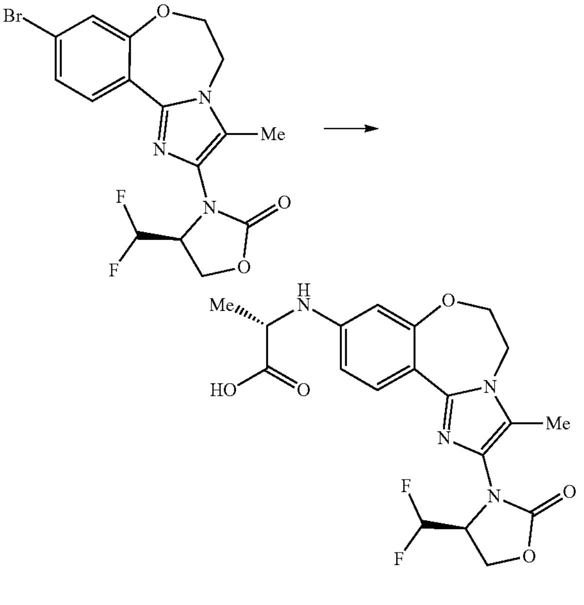

(2-((S)-4-(Difluoromethyl)-2-oxooxazolidin-3-yl)-3-methyl-5,6-dihydrobenzo[f]imidazo[1,2-d][1,4]oxazepin-9-yl)-L-alanine was prepared by referring to the method of Example 1.

MS m/z (ESI): 423.1 $[M+H]^+$.

Step 6: Preparation of (S)-2-((2-((S)-4-(difluoromethyl)-2-oxooxazolidin-3-yl)-3-methyl-5,6-dihydrobenzo[f]i midazo [1,2-d][1,4]oxazepin-9-yl)amino)propanamide

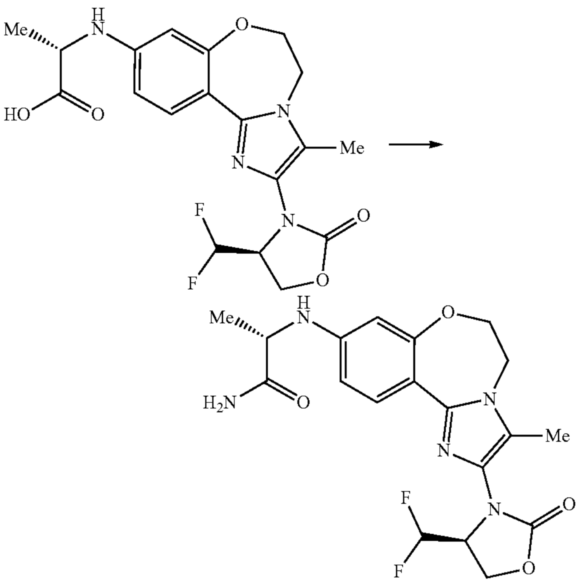

(S)-2-((2-((S)-4-(Difluoromethyl)-2-oxooxazolidin-3-yl)-3-methyl-5,6-dihydroben zo[f]imidazo[1,2-d][1,4]oxazepin-9-yl)amino)propanamide was prepared by referring to the method of Example 1.

$^1$H NMR (400 MHz, $CD_3OD$) δ 1.37 (d, J=7.0 Hz, 3H), 2.08 (s, 3H), 3.68-3.75 (m, 1H), 4.18-4.24 (m, 2H), 4.32-4.35 (m, 2H), 4.45-4.61 (m, 3H), 6.10 (m, 2H), 6.34 (d, J=8.8 Hz, 1H), 7.83 (d, J=8.8 Hz, 1H).

MS m/z (ESI): 422.2 $[M+H]^+$.

Example 16

Preparation of (S)-1-(2-((S)-4-(difluoromethyl)-2-oxooxazolidin-3-yl)-3-methyl-5,6-dihydrobenzo[f]i midazo[1,2-d][1,4]oxazepin-9-yl)pyrrolidine-2-carboxamide

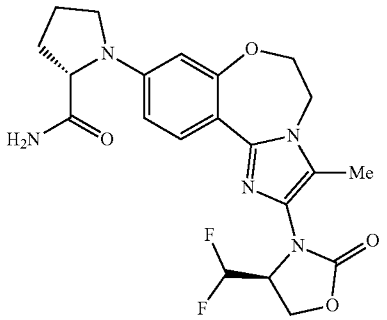 [SMILES: Cc1c(N2C(=O)OC[C@H]2C(F)F)nc2n1CCOc1cc(N3CCC[C@H]3C(N)=O)ccc1-2]

(S)-1-(2-((S)-4-(Difluoromethyl)-2-oxooxazolidin-3-yl)-3-methyl-5,6-dihydrobenz o[f]imidazo[1,2-d][1,4]oxazepin-9-yl)pyrrolidine-2-carboxamide was prepared by referring to the method of Example 15.

MS m/z (ESI): 448.2 $[M+H]^+$.

Example 17

Preparation of (S)-2-((2-((S)-4-(difluoromethyl)-2-oxooxazolidin-3-yl)-3-methyl-5,6-dihydrobenzo[f]i midazo[1,2-d][1,4]oxazepin-9-yl)oxy)propanamide

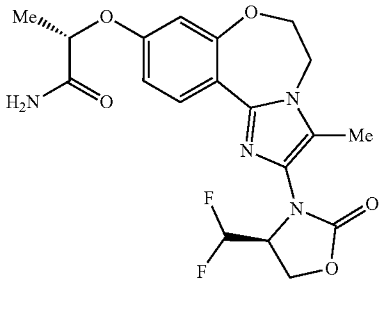 [SMILES: Cc1c(N2C(=O)OC[C@H]2C(F)F)nc2n1CCOc1cc(O[C@@H](C)C(N)=O)ccc1-2]

(S)-2-((2-((S)-4-(Difluoromethyl)-2-oxooxazolidin-3-yl)-3-methyl-5,6-dihydroben zo[f]imidazo[1,2-d][1,4]oxazepin-9-yl)oxy)propanamide was prepared by referring to the method of Example 15.

MS m/z (ESI): 423.1 $[M+H]^+$.

Example 18

Preparation of (S)-2-((3-methyl-2-((S)-2-oxo-4-(trifluoromethyl)oxazolidin-3-yl)-5,6-dihydrobenzo[f]i midazo[1,2-d][1,4]oxazepin-9-yl)amino)propanamide

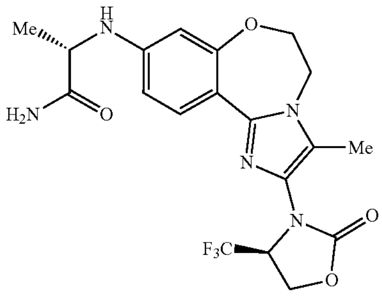 [SMILES: Cc1c(N2C(=O)OC[C@H]2C(F)(F)F)nc2n1CCOc1cc(N[C@@H](C)C(N)=O)ccc1-2]

(S)-2-((3-Methyl-2-((S)-2-oxo-4-(trifluoromethyl)oxazolidin-3-yl)-5,6-dihydroben zo[f]imidazo[1,2-d][1,4]oxazepin-9-yl)amino)propanamide was prepared by referring to the method of Example 15.

MS m/z (ESI): 440.1 $[M+H]^+$.

Example 19

Preparation of (S)-2-((2-((S)-4-(difluoromethyl)-2-oxooxazolidin-3-yl)-3-(trifluoromethyl)-5,6-dihydro benzo[f]imidazo[1,2-d][1,4]oxazepin-9-yl)amino) propanamide

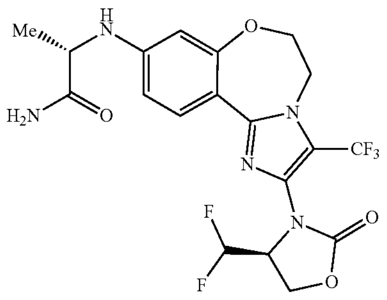

(S)-2-((2-((S)-4-(Difluoromethyl)-2-oxooxazolidin-3-yl)-3-(trifluoromethyl)-5,6-di hydrobenzo[f]imidazo[1,2-d][1,4]oxazepin-9-yl)amino)propanamide was prepared by referring to the method of Example 15.

MS m/z (ESI): 476.1 [M+H]$^+$.

Example 20

Preparation of (S)-2-((3-cyano-2-((S)-4-(difluoromethyl)-2-oxooxazolidin-3-yl)-5,6-dihydrobenzo[f]imidazo[1,2-d][1,4]oxazepin-9-yl)amino)propanamide

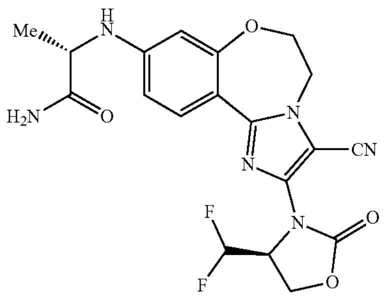 [SMILES: C[C@H](Nc1ccc2c(c1)OCCn1c-2nc(N2C(=O)OC[C@H]2C(F)F)c1C(F)(F)F)C(N)=O]

(S)-2-((3-Cyano-2-((S)-4-(difluoromethyl)-2-oxooxazolidin-3-yl)-5,6-dihydrobenz o[f]imidazo[1,2-d][1,4]oxazepin-9-yl)amino)propanamide was prepared by referring to the method of Example 15.

MS m/z (ESI): 433.1 [M+H]$^+$.

Example 21

Preparation of (S)-1-(3-cyano-2-((S)-4-(difluoromethyl)-2-oxooxazolidin-3-yl)-5,6-dihydrobenzo[f]imi dazo[1,2-d][1,4]oxazepin-9-yl)pyrrolidine-2-carboxamide

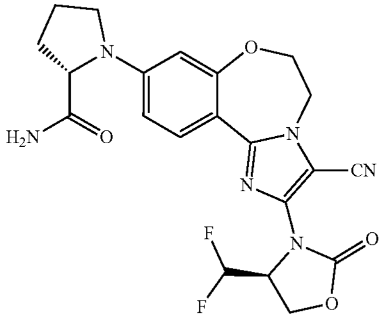 [SMILES: N#Cc1c(N2C(=O)OC[C@H]2C(F)F)nc2n1CCOc1cc(N3CCC[C@H]3C(N)=O)ccc1-2]

(S)-1-(3-Cyano-2-((S)-4-(difluoromethyl)-2-oxooxazolidin-3-yl)-5,6-dihydrobenzo[f]imidazo[1,2-d][1,4]oxazepin-9-yl)pyrrolidine-2-carboxamide was prepared by referring to the method of Example 15.

MS m/z (ESI): 459.2 [M+H]$^+$.

Example 22

Preparation of (S)-2-((3-cyano-2-((S)-2-oxo-4-(trifluoromethyl)oxazolidin-3-yl)-5,6-dihydrobenzo[f]imidazo[1,2-d][1,4]oxazepin-9-yl)amino)propanamide

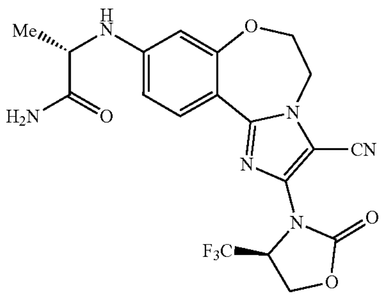 [SMILES: C[C@H](Nc1ccc2c(c1)OCCn1c-2nc(N2C(=O)OC[C@H]2C(F)(F)F)c1C#N)C(N)=O]

(S)-2-((3-Cyano-2-((S)-2-oxo-4-(trifluoromethyl)oxazolidin-3-yl)-5,6-dihydrobenz o[f]imidazo[1,2-d][1,4]oxazepin-9-yl)amino)propanamide was prepared by referring to the method of Example 15.

MS m/z (ESI): 451.1 [M+H]$^+$.

Example 23

Preparation of (S)-2-((3-cyano-2-((S)-4-(difluoromethyl)-2-oxooxazolidin-3-yl)-5,6-dihydrobenzo[f]imidazo[1,2-d][1,4]oxazepin-9-yl)oxy)propanamide

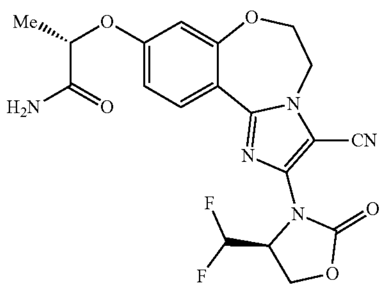 [SMILES: C[C@H](Oc1ccc2c(c1)OCCn1c-2nc(N2C(=O)OC[C@H]2C(F)F)c1C#N)C(N)=O]

(S)-2-((3-Cyano-2-((S)-4-(difluoromethyl)-2-oxooxazolidin-3-yl)-5,6-dihydrobenz o[f]imidazo[1,2-d][1,4]oxazepin-9-yl)oxy)propanamide was prepared by referring to the method of Example 15.

MS m/z (ESI): 434.1 [M+H]$^+$.

Example 24

Preparation of (S)-2-((3-cyclopropyl-2-((S)-4-(difluoromethyl)-2-oxooxazolidin-3-yl)-5,6-dihydrobenz o[f]imidazo[1,2-d][1,4]oxazepin-9-yl)amino)propanamide

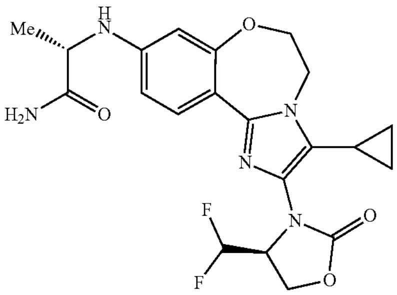 [SMILES: C[C@H](Nc1ccc2c(c1)OCCn1c-2nc(N2C(=O)OC[C@H]2C(F)F)c1C1CC1)C(N)=O]

(S)-2-((3-Cyclopropyl-2-((S)-4-(difluoromethyl)-2-oxooxazolidin-3-yl)-5,6-dihydr obenzo[f]imidazo[1,2-d][1,4]oxazepin-9-yl)amino)propanamide was prepared by referring to the method of Example 15.

MS m/z (ESI): 448.2 [M+H]$^+$.

Example 25

Preparation of (S)-2-((9-((S)-4-(difluoromethyl)-2-oxooxazolidin-3-yl)-5,6-dihydroimidazo[1,2-d]thieno[2,3-f][1,4]oxazepin-2-yl)amino)propanamide

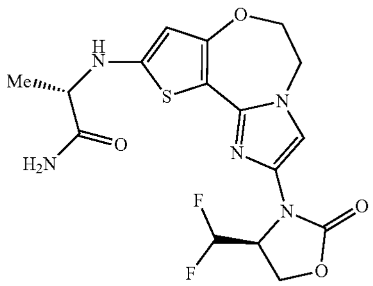 [SMILES: C[C@H](Nc1cc2c(s1)-c1nc(N3C(=O)OC[C@H]3C(F)F)cn1CCO2)C(N)=O]

Step 1: Preparation of methyl 3-(cyanomethoxy)thiophene-2-carboxylate

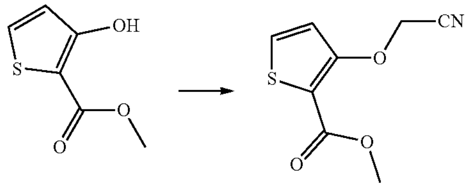

Methyl 3-hydroxythiophene-2-carboxylate (1.58 g, 10 mmol), bromoacetonitrile (2.4 g, 20 mmol) and cesium carbonate (9.77 g, 30 mmol) were added to DMF (40 mL). The reaction solution was warmed up to 60° C. and reacted for 2 hours. The reaction solution was cooled to room temperature, water (200 mL) was added, and the reaction solution was extracted with EA (200 mL×3). The organic phases were combined and washed with saturated aqueous sodium chloride solution (200 mL×3). The organic phases were collected and concentrated under reduced pressure. The residue was subjected to column chromatography to obtain the title compound methyl 3-(cyanomethoxy)thiophene-2-carboxylate (1.58 g, 80%).

Step 2: Preparation of 3,4-dihydrothieno[2,3-f][1,4]oxazepin-5 (2H)-one

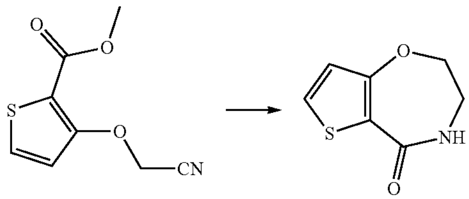

Methyl 3-(cyanomethoxy)thiophene-2-carboxylate (1.58 g, 8 mmol), Raney-Ni (400 mg) and ammonia (2 mL) were added to ethanol (100 mL). Under a hydrogen atmosphere (50 psi), the reaction solution was warmed up to reflux and reacted for 5 hours. The reaction solution was cooled to room temperature and filtered, and the filtrate was concentrated. The residue was subjected to column chromatography to obtain the title compound 3,4-dihydrothieno[2,3-f][1,4]oxazepin-5 (2H)-one (1 g, 74%).

MS m/z (ESI): 170.2 $[M+H]^+$.

Step 3 Preparation of methyl 2-(5-oxo-2,3-dihydrothieno[2,3-f][1,4]oxazepin-4 (5H)-yl)acetate

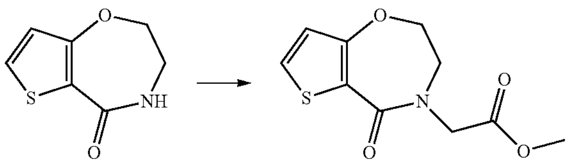 [SMILES: O=C1NCCOc2ccsc21 ; COC(=O)CN1CCOc2ccsc2C1=O]

3,4-Dihydrothieno[2,3-f][1,4]oxazepin-5 (2H)-one (1 g, 5.91 mmol), methyl bromoacetate (1.09 g, 7.09 mmol) and potassium carbonate (1.63 g, 11.8 mmol) were added to acetone (20 mL). The reaction solution was warmed up to reflux and reacted for 3 hours. The reaction solution was cooled to room temperature and concentrated. DCM and water were added to the concentrate, and two phases were separated. The organic phase was concentrated, and the residue was subjected to column chromatography to obtain the title compound methyl 2-(5-oxo-2,3-dihydrothieno[2,3-f][1,4]oxazepin-4 (5H)-yl)acetate (1.21 g, 85%).

MS m/z (ESI): 242.2 $[M+H]^+$.

Step 4: Preparation of 5,6-dihydroimidazo[1,2-d]thieno[2,3-f][1,4]oxazepin-9(8H)-one

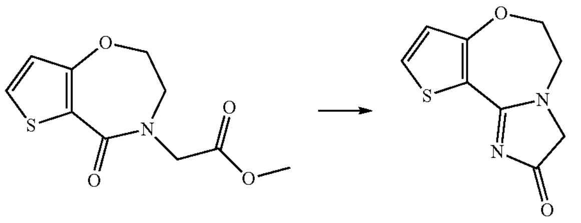 [SMILES: COC(=O)CN1CCOc2ccsc2C1=O ; O=C1CN2CCOc3ccsc3C2=N1]

Methyl 2-(5-oxo-2,3-dihydrothieno[2,3-f][1,4]oxazepin-4 (5H)-yl)acetate (1.21 g, 5.02 mmol) and ammonia (5 mL) were added to tert-amyl alcohol (25 mL). The reaction solution was warmed up to 120° C. and reacted for 5 hours in a sealed tube. The reaction solution was cooled to room temperature and concentrated. DCM and water were added to the concentrate, and two phases were separated. The organic phase was concentrated, and the residue was subjected to column chromatography to obtain the title compound 5,6-dihydroimidazo[1,2-d]thieno[2,3-f][1,4]oxazepin-9(8H)-one (521 mg, 50%).

MS m/z (ESI): 209.2 $[M+H]^+$.

Step 5: Preparation of 9-bromo-5,6-dihydroimidazo[1,2-d]thieno[2,3-f][1,4]oxazepine

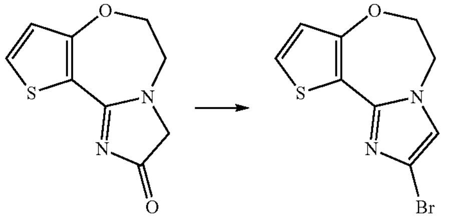 [SMILES: O=C1CN2CCOc3ccsc3C2=N1 ; Brc1cn2c(n1)-c1sccc1OCC2]

5,6-Dihydroimidazo[1,2-d]thieno[2,3-f][1,4]oxazepin-9(8H)-one (521 mg, 2.50 mmol) was dissolved in 1,2-dichloroethane (15 mL), followed by the addition of phosphorus oxybromide (2.15 g, 7.50 mmol). The reaction solution was heated to reflux and reacted overnight. The reaction solution was cooled to room temperature, and its pH was adjusted to neutral with saturated aqueous sodium bicarbonate solution. The reaction solution was extracted with DCM, and the organic phase was concentrated. The residue was subjected to column chromatography to obtain the title compound 9-bromo-5,6-dihydroimidazo[1,2-d]thieno[2,3-f][1,4]oxazepine (407 mg, 60%).

MS m/z (ESI): 271.1 $[M+H]^+$.

Step 6: Preparation of (S)-4-(difluoromethyl)-3-(5,6-dihydroimidazo[1,2-d]thieno[2,3-f][1,4]oxazepin-9-yl)ox azolidin-2-one

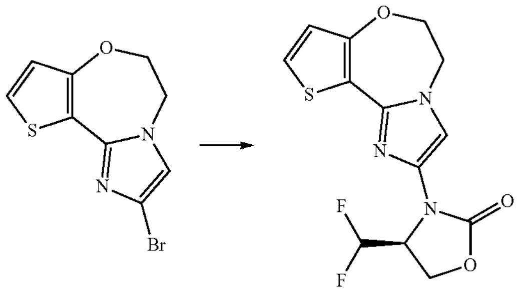 [SMILES: Brc1cn2c(n1)-c1sccc1OCC2 ; O=C1OC[C@@H](C(F)F)N1c1cn2c(n1)-c1sccc1OCC2]

(S)-4-(Difluoromethyl)-3-(5,6-dihydroimidazo[1,2-d]thieno[2,3-f][1,4]oxazepin-9-yl)oxazolidin-2-one was prepared by referring to Example 21.

MS m/z (ESI): 328.1 $[M+H]^+$.

Step 7: Preparation of (S)-4-(difluoromethyl)-3-(2-iodo-5,6-dihydroimidazo[1,2-d]thieno[2,3-f][1,4]oxazepin-9-yl)oxazolidin-2-one

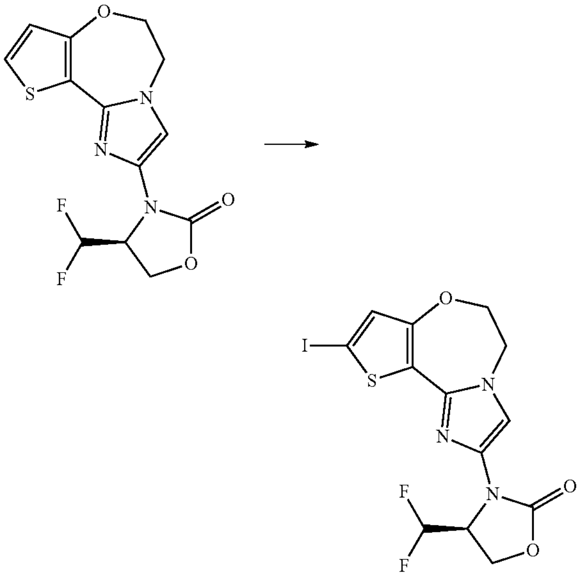

(S)-4-(Difluoromethyl)-3-(5,6-dihydroimidazo[1,2-d]thieno[2,3-f][1,4]oxazepin-9-yl)oxazolidin-2-one (327 mg, 1.0 mmol) was dissolved in dichloromethane (5 mL) and acetic acid (5 mL), followed by the addition of NIS (248 mg, 1.1 mmol). The reaction solution was reacted at room temperature overnight. The pH of the reaction solution was adjusted to neutral with saturated aqueous sodium bicarbonate solution. The reaction solution was extracted with DCM, and the organic phase was concentrated. The residue was subjected to column chromatography to obtain the title compound (S)-4-(difluoromethyl)-3-(2-iodo-5,6-dihydroimidazo[1,2-d]thieno[2,3-f][1,4]oxazepin-9-yl)oxazolidin-2-one (363 mg, 80%).

MS m/z (ESI): 454.1 [M+H]+.

Step 8: Preparation of (S)-2-((9-((S)-4-(difluoromethyl)-2-oxooxazolidin-3-yl)-5,6-dihydroimidazo[1,2-d]thie no[2,3-f][1,4]oxazepin-2-yl)amino)propanamide

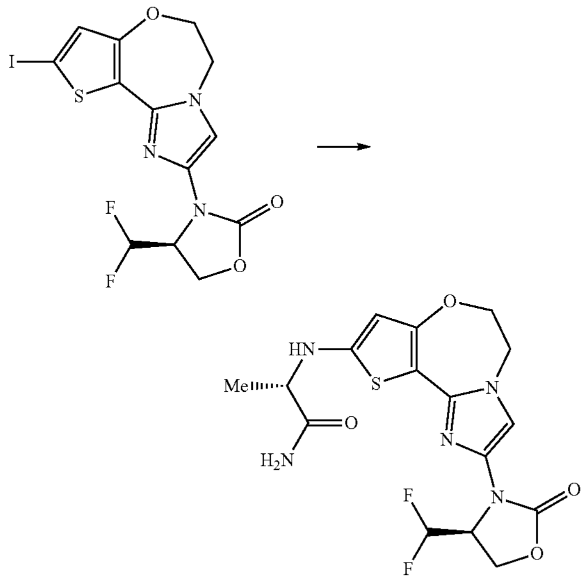

(S)-2-((9-((S)-4-(Difluoromethyl)-2-oxooxazolidin-3-yl)-5,6-dihydroimidazo[1,2-d]thieno[2,3-f][1,4]oxazepin-2-yl)amino)propanamide was prepared by referring to Example 1.

MS m/z (ESI): 414.1 [M+H]+.

Example 26

Preparation of (S)-2-((9-((S)-4-(difluoromethyl)-2-oxooxazolidin-3-yl)-3-fluoro-5,6-dihydroimidazo[1,2-d]thieno[2,3-f][1,4]oxazepin-2-yl)amino)propanamide

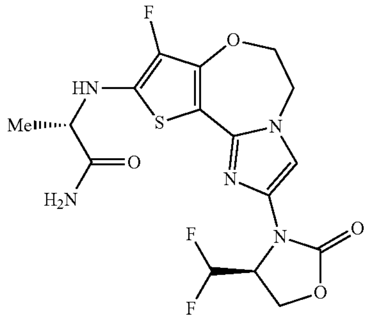 [SMILES: C[C@H](Nc1sc2c(c1F)OCCn1cc(N3C(=O)OC[C@H]3C(F)F)nc1-2)C(N)=O]

(S)-2-((9-((S)-4-(Difluoromethyl)-2-oxooxazolidin-3-yl)-3-fluoro-5,6-dihydroimid azo[1,2-d]thieno[2,3-f][1,4]oxazepin-2-yl)amino)propanamide was prepared by referring to Example 25.

MS m/z (ESI): 432.1 [M+H]+.

Example 27

Preparation of (S)-2-((9-((S)-4-(difluoromethyl)-2-oxooxazolidin-3-yl)-5,6-dihydroimidazo[1,2-d]thie no[2,3-f][1,4]oxazepin-2-yl)oxy)propanamide

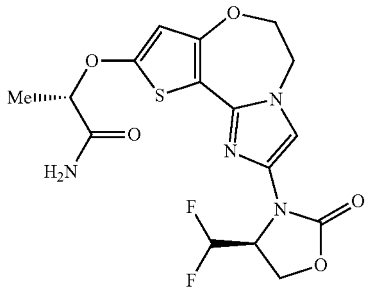 [SMILES: C[C@H](Oc1cc2c(s1)-c1nc(N3C(=O)OC[C@H]3C(F)F)cn1CCO2)C(N)=O]

(S)-2-((9-((S)-4-(Difluoromethyl)-2-oxooxazolidin-3-yl)-5,6-dihydroimidazo[1,2-d]thieno[2,3-f][1,4]oxazepin-2-yl)oxy)propanamide was prepared by referring to Example 25.

MS m/z (ESI): 415.1 [M+H]+.

Example 28

Preparation of (S)-1-(9-((S)-4-(difluoromethyl)-2-oxooxazolidin-3-yl)-5,6-dihydroimidazo[1,2-d]thien o[2,3-f][1,4]oxazepin-2-yl)pyrrolidine-2-carboxamide

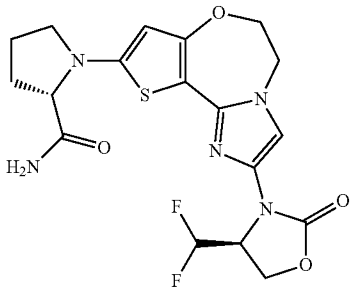 [SMILES: NC(=O)[C@@H]1CCCN1c1cc2c(s1)-c1nc(N3C(=O)OC[C@H]3C(F)F)cn1CCO2]

(S)-1-(9-((S)-4-(Difluoromethyl)-2-oxooxazolidin-3-yl)-5,6-dihydroimidazo[1,2-d]thieno[2,3-f][1,4]oxazepin-2-yl)pyrrolidine-2-carboxamide was prepared by referring to Example 25.

MS m/z (ESI): 440.1 [M+H]+.

Example 29

Preparation of (S)-2-((9-((S)-2-oxo-4-(trifluoromethyl)oxazolidin-3-yl)-5,6-dihydroimidazo[1,2-d]thieno[2,3-f][1,4]oxazepin-2-yl)amino)propanamide

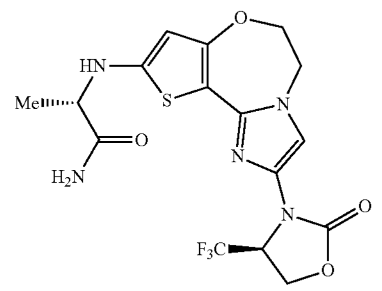 [SMILES: C[C@H](Nc1cc2c(s1)-c1nc(N3C(=O)OC[C@H]3C(F)(F)F)cn1CCO2)C(N)=O]

(S)-2-((9-((S)-2-Oxo-4-(trifluoromethyl)oxazolidin-3-yl)-5,6-dihydroimidazo[1,2-d]thieno[2,3-f][1,4]oxazepin-2-yl)amino)propanamide was prepared by referring to Example 25.

MS m/z (ESI): 432.1 $[M+H]^+$.

Example 30

Preparation of (S)-2-((2-((S)-4-(difluoromethyl)-2-oxooxazolidin-3-yl)-5,6,10,11-tetrahydrocyclobuta[5,6]benzo[1,2-f]imidazo[1,2-d][1,4]oxazepin-9-yl)amino)propanamide

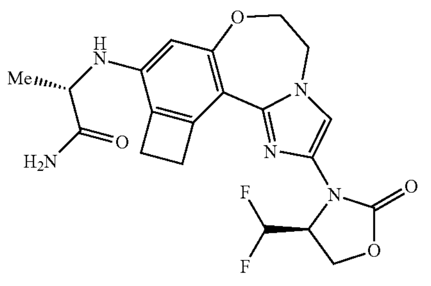 [SMILES: C[C@H](Nc1cc2c(c3c1CC3)-c1nc(N3C(=O)OC[C@H]3C(F)F)cn1CCO2)C(N)=O]

Step 1: Preparation of 1-(bicyclo[4.2.0]octa-1(6),2,4-trien-3-yl)ethan-1-one

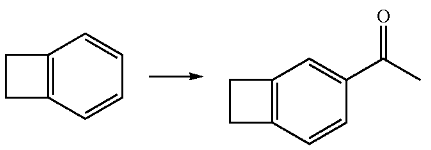

$AlCl_3$ (3.33 g, 25 mmol) was suspended in nitromethane (25 mL), followed by the dropwise addition of a solution of bicyclo[4.2.0]octa-1(6),2,4-triene (2.08 g, 20 mmol) and acetyl chloride (1.73 g, 22 mmol) in nitromethane (25 mL) in an ice bath under a $N_2$ atmosphere. The reaction solution was naturally warmed up to room temperature and reacted overnight. The reaction solution was added to 200 mL of ice water, and extracted with DCM (200 mL×2). The organic phases were combined and concentrated under reduced pressure. The residue was subjected to column chromatography to obtain the title compound 1-(bicyclo[4.2.0]octa-1(6),2,4-trien-3-yl)ethan-1-one (800 mg, 27%).

Step 2: Preparation of 1-(5-bromobicyclo[4.2.0]octa-1(6),2,4-trien-3-yl)ethan-1-one

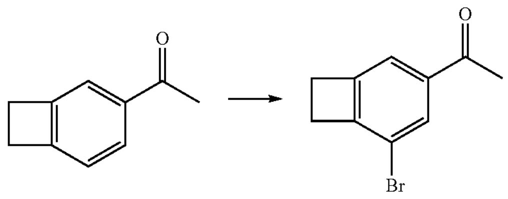

1-(Bicyclo[4.2.0]octa-1(6),2,4-trien-3-yl)ethan-1-one (731 mg, 5 mmol) was dissolved in acetic acid (20 mL). Under a $N_2$ atmosphere, bromine (878.9 mg, 5.5 mmol) was added dropwise, and the reaction solution was reacted at room temperature for 3 hours. The reaction solution was concentrated, DCM and saturated aqueous sodium bicarbonate solution were added to the concentrate, and two phases were separated. The organic phase was concentrated under reduced pressure, and the residue was subjected to column chromatography to obtain the title compound 1-(5-bromobicyclo[4.2.0]octa-1(6),2,4-trien-3-yl)ethan-1-one (900 mg, 80%).

Step 3: Preparation of 5-bromobicyclo[4.2.0]octa-1(6),2,4-trien-3-yl acetate

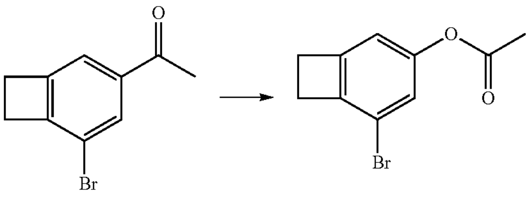

1-(5-Bromobicyclo[4.2.0]octa-1(6),2,4-trien-3-yl)ethan-1-one (900 mg, 4 mmol) and m-CPBA (75%, 2.30 g, 10 mmol) were mixed in DCM (20 mL). Under a $N_2$ atmosphere, the reaction solution was heated to reflux and reacted overnight. The reaction solution was cooled to room temperature, and filtered to remove insolubles. The reaction solution was washed with saturated aqueous sodium bicarbonate solution, and the organic phase was concentrated under reduced pressure. The residue was subjected to column chromatography to obtain the title compound 5-bromobicyclo[4.2.0]octa-1(6),2,4-trien-3-yl acetate (723 mg, 75%).

Step 4: Preparation of 5-bromobicyclo[4.2.0]octa-1(6),2,4-trien-3-ol

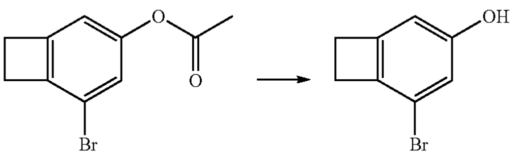

5-Bromobicyclo[4.2.0]octa-1(6),2,4-trien-3-yl acetate (723 mg, 3 mmol) was dissolved in methanol (20 mL), followed by the addition of 5 N aqueous sodium hydroxide solution (3 mL). The reaction solution was reacted at room temperature overnight. 50 mL of water was added to the reaction solution, and its pH was adjusted to 5 with 1 N hydrochloric acid. The reaction solution was extracted with DCM (50 mL×2), and the organic phases were combined and concentrated under reduced pressure. The residue was subjected to column chromatography to obtain the title compound 5-bromobicyclo[4.2.0]octa-1(6),2,4-trien-3-ol (567 mg, 95%).

Step 5: Preparation of 5-bromo-3-hydroxybicyclo[4.2.0]octa-1(6),2,4-triene-2-carbaldehyde

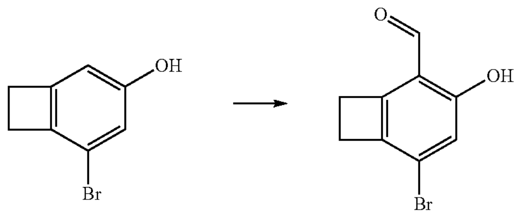 [SMILES: Oc1cc(Br)c2c(c1)CC2 ; O=Cc1c(O)cc(Br)c2c1CC2]

5-Bromobicyclo[4.2.0]octa-1(6),2,4-trien-3-ol (567.2 mg, 2.85 mmol), magnesium chloride (407 mg, 4.28 mmol) and TEA (1.15 g, 11.4 mmol) were added to acetonitrile (5 mL). The reaction solution was warmed up to 40° C. and reacted for 30 minutes. Paraformaldehyde (770 mg, 8.55 mmol) was added, and the reaction solution was reacted at 80° C. overnight. The reaction solution was cooled to room temperature, 50 mL of water was added, and the pH of the reaction solution was adjusted to 5 with 4 N hydrochloric acid. The reaction solution was extracted with DCM (50 mL×2), and the organic phases were combined and concentrated under reduced pressure. The residue was subjected to column chromatography to obtain the title compound 5-bromo-3-hydroxybicyclo[4.2.0]octa-1(6),2,4-triene-2-carbaldehyde (517.6 mg, 80%).

Step 6: Preparation of (S)-2-((2-((S)-4-(difluoromethyl)-2-oxooxazolidin-3-yl)-5,6,10,11-tetrahydrocyclobuta[5,6]benzo[1,2-f]imidazo[1,2-d][1,4]oxazepin-9-yl)amino)propanamide

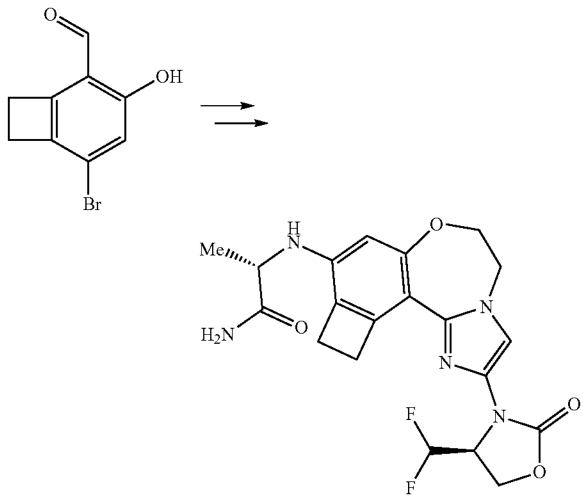

(S)-2-((2-((S)-4-(Difluoromethyl)-2-oxooxazolidin-3-yl)-5,6,10,11-tetrahydrocyclo buta[5,6]benzo[1,2-f]imidazo[1,2-d][1,4]oxazepin-9-yl)amino)propanamide was prepared by referring to Example 1.

MS m/z (ESI): 434.2 $[M+H]^+$.

Example 31

Preparation of (S)-2-((2-((S)-4-(difluoromethyl)-2-oxooxazolidin-3-yl)-5,6,10,11-tetrahydrocyclobuta[5,6]benzo[1,2-f]imidazo[1,2-d][1,4]oxazepin-9-yl)amino)-2-methoxyacetamide

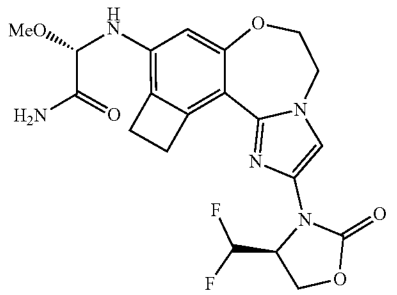 [SMILES: CO[C@H](Nc1cc2c(c3c1CC3)-c1nc(N3C(=O)OC[C@H]3C(F)F)cn1CCO2)C(N)=O]

(S)-2-((2-((S)-4-(Difluoromethyl)-2-oxooxazolidin-3-yl)-5,6,10,11-tetrahydrocyclo buta[5,6]benzo[1,2-f]imidazo[1,2-d][1,4]oxazepin-9-yl)amino)-2-methoxyacetamide was prepared by referring to Example 30.

MS m/z (ESI): 450.1 $[M+H]^+$.

Example 32

Preparation of (S)-2-((2-((S)-4-(difluoromethyl)-2-oxooxazolidin-3-yl)-5,6,11,12-tetrahydro-10H-imidazo[1,2-d]indeno[4,5-f][1,4]oxazepin-9-yl)amino)propanamide

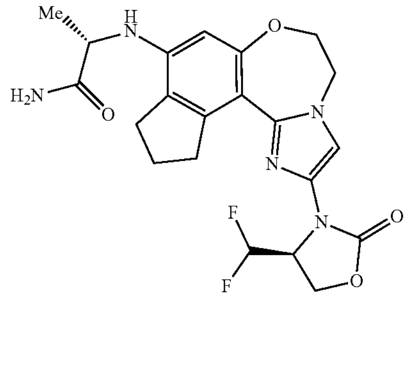 [SMILES: C[C@H](Nc1cc2c(c3c1CCC3)-c1nc(N3C(=O)OC[C@H]3C(F)F)cn1CCO2)C(N)=O]

(S)-2-((2-((S)-4-(Difluoromethyl)-2-oxooxazolidin-3-yl)-5,6,11,12-tetrahydro-10H-imidazo[1,2-d]indeno[4,5-f][1,4]oxazepin-9-yl)amino)propanamide was prepared by referring to Example 30.

MS m/z (ESI): 448.1 $[M+H]^+$.

Example 33

Preparation of (S)-2-((11-((S)-4-(difluoromethyl)-2-oxooxazolidin-3-yl)-7,8-dihydro-[1,3]dioxolo[4',5':5,6]benzo[1,2-f]imidazo[1,2-d][1,4]oxazepin-4-yl)amino)propanamide

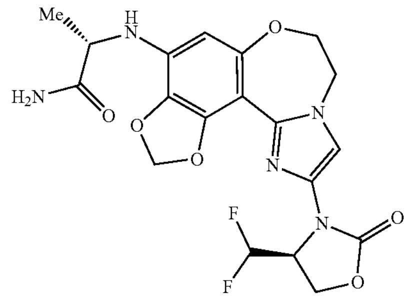

(S)-2-((11-((S)-4-(Difluoromethyl)-2-oxooxazolidin-3-yl)-7,8-dihydro-[1,3]dioxol o[4',5':5,6]benzo[1,2-f]imidazo[1,2-d][1,4]oxazepin-4-yl)amino)propanamide was prepared by referring to Example 30.

MS m/z (ESI): 452.1 $[M+H]^+$.

Example 34

Preparation of (S)-2-((2-((S)-4-(difluoromethyl)-2-oxooxazolidin-3-yl)-5,6-dihydrobenzo[f]pyrazolo[1,5-d][1,4]oxazepin-9-yl)amino)propanamide

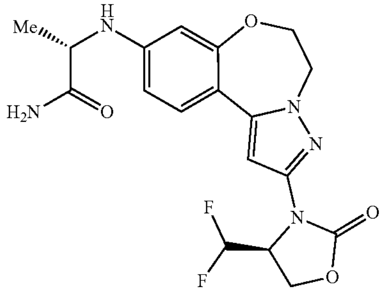 [SMILES: C[C@H](Nc1ccc2c(c1)OCCn1nc(N3C(=O)OC[C@H]3C(F)F)cc1-2)C(N)=O]

Step 1: Preparation of 1-(4-bromo-2-methoxyphenyl)ethan-1-one

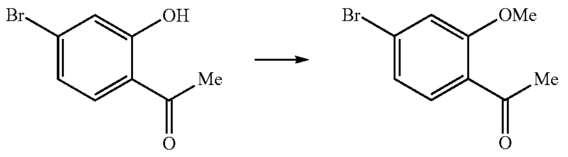 [SMILES: CC(=O)c1ccc(Br)cc1O ; COc1cc(Br)ccc1C(C)=O]

1-(4-Bromo-2-hydroxyphenyl)ethan-1-one (5.00 g, 23.3 mmol), potassium carbonate (4.82 g, 35.0 mmol) and methyl iodide (2.94 mL, 46.5 mmol) were mixed in DMF (60 mL), and the reaction solution was stirred at room temperature for 3 hours. Solid was precipitated by adding water to the reaction solution, and dried to obtain the title compound 1-(4-bromo-2-methoxyphenyl)ethan-1-one (5.3 g, 99%).

Step 2: Preparation of methyl 3-(4-bromo-2-methoxyphenyl)-3-oxopropanoate

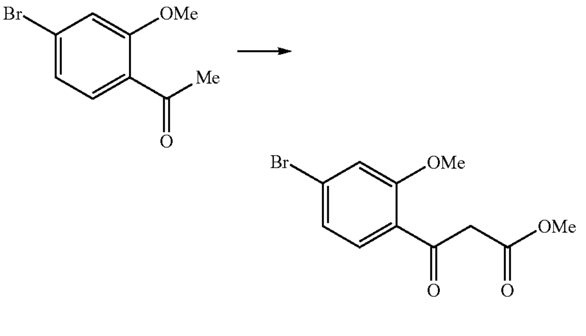

Under a nitrogen atmosphere, dimethyl carbonate (2.76 mL, 32.7 mmol) was added to a suspension of NaH (1.75 g, 43.7 mmol) in THF (40 mL). The reaction solution was warmed up to 70° C., followed by the slowly dropwise addition of a solution of 1-(4-bromo-2-methoxyphenyl)ethan-1-one (2.50 g, 10.9 mmol) in THF (10 mL). After completion of the addition, the reaction solution was stirred at 70° C. for 3 hours. The reaction solution was cooled, and 1 M HCl solution was added to make the system acidic. The reaction solution was extracted with ethyl acetate several times. The organic phases were combined, dried over anhydrous sodium sulfate and concentrated. The residue was subjected to column chromatography to obtain the title compound methyl 3-(4-bromo-2-methoxyphenyl)-3-oxopropanoate (2.2 g, 70%).

MS m/z (ESI): 227.0 $[M+H]^+$.

Step 3: Preparation of 5-(4-bromo-2-methoxyphenyl)-1,2-dihydro-3H-pyrazol-3-one

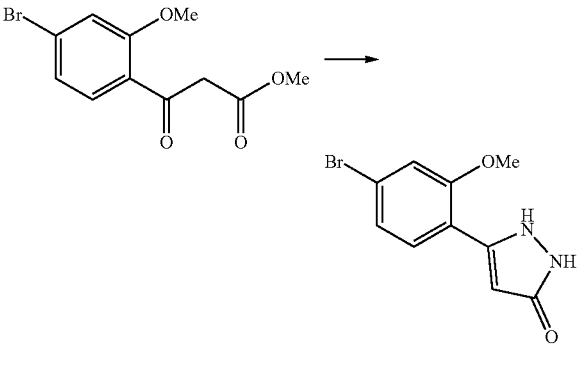

Hydrazine hydrate solution (80 wt. %, 3 mL) was added to a solution of methyl 3-(4-bromo-2-methoxyphenyl)-3-oxopropanoate (1.20 g, 4.18 mmol) in ethanol (50 mL). The reaction solution was stirred under reflux for 1 hour. The reaction solution was cooled, and water was added to precipitate a solid 5-(4-bromo-2-methoxyphenyl)-1,2-dihydro-3H-pyrazol-3-one (600 mg). The filtrate was concentrated, and the residue was subjected to column chromatography to obtain the title compound 5-(4-bromo-2-methoxyphenyl)-1,2-dihydro-3H-pyrazol-3-one (400 mg). After the two are combined, a total of 1.0 g of the title compound 5-(4-bromo-2-methoxyphenyl)-1,2-dihydro-3H-pyrazol-3-one was obtained (89%).

MS m/z (ESI): 269.0 $[M+H]^+$.

Step 4: Preparation of 5-(4-bromo-2-hydroxyphenyl)-1,2-dihydro-3H-pyrazol-3-one

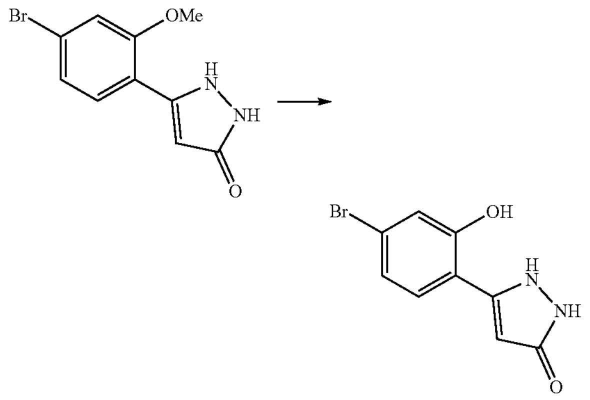

5-(4-Bromo-2-methoxyphenyl)-1,2-dihydro-3H-pyrazol-3-one (100 mg, 0.372 mmol) was mixed with a solution of $BBr_3$ in DCM (1 M, 4 mL), and the reaction solution was stirred at room temperature overnight. The reaction solution was concentrated under reduced pressure to remove the organic solvent and obtain the crude product 5-(4-bromo-2-hydroxyphenyl)-1,2-dihydro-3H-pyrazol-3-one, which was used directly in the next step.

MS m/z (ESI): 255.0 $[M+H]^+$.

Step 5: Preparation of 9-bromo-5,6-dihydrobenzo[f]pyrazolo[1,5-d][1,4]oxazepin-2 (3H)-one

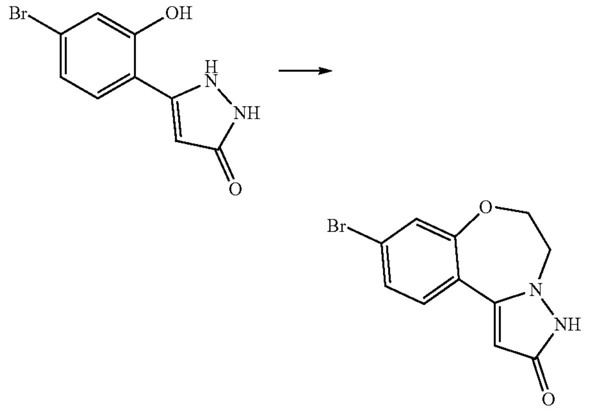

The crude product of the above step was dissolved in DMF (4 mL), followed by the successive addition of 1,2-dibromoethane (70 mg, 0.372 mmol) and potassium carbonate (515 mg, 3.72 mmol). The reaction solution was stirred at 60° C. for 1 hour, stirred at 75° C. for 1 hour, and stirred at 90° C. for 1 hour. The reaction solution was cooled, diluted with ethyl acetate, washed with saturated brine several times, dried over anhydrous sodium sulfate and concentrated. The residue was subjected to column chromatography to obtain the title compound 9-bromo-5,6-dihydrobenzo[f]pyrazolo[1,5-d][1,4]oxazepin-2 (3H)-one (44 mg, two-step yield: 42%).

MS m/z (ESI): 281.0 $[M+H]^+$.

Step 6: Preparation of 9-bromo-5,6-dihydrobenzo[f]pyrazolo[1,5-d][1,4]oxazepin-2-yl trifluoromethanesulfonate

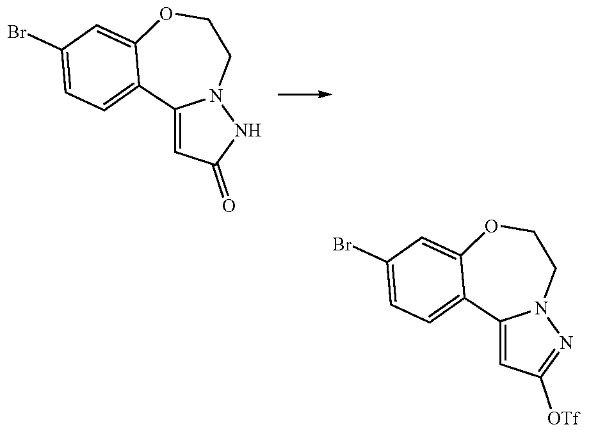

Trifluoromethanesulfonic anhydride (48 mg, 0.171 mmol) was added dropwise to a solution of 9-bromo-5,6-dihydrobenzo[f]pyrazolo[1,5-d][1,4]oxazepin-2 (3H)-one (40 mg, 0.142 mmol) in pyridine (1 mL) in an ice water bath. The reaction solution was stirred at room temperature for 2 hours. The reaction solution was concentrated under reduced pressure to remove the organic solvent. The residue was subjected to column chromatography to obtain the title compound 9-bromo-5,6-dihydrobenzo[f]pyrazolo[1,5-d][1,4]oxazepin-2-yl trifluoromethanesulfonate (42 mg, 71%).

MS m/z (ESI): 412.9 $[M+H]^+$.

Step 7: Preparation of (S)-2-((2-((S)-4-(difluoromethyl)-2-oxooxazolidin-3-yl)-5,6-dihydrobenzo[f]pyrazolo[1,5-d][1,4]oxazepin-9-yl)amino)propanamide

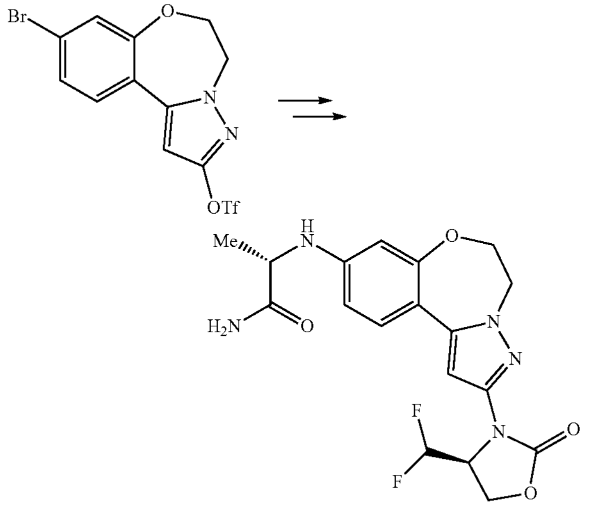

(S)-2-((2-((S)-4-(Difluoromethyl)-2-oxooxazolidin-3-yl)-5,6-dihydrobenzo[f]pyraz olo[1,5-d][1,4]oxazepin-9-yl) amino)propanamide was prepared by referring to Example 1.

MS m/z (ESI): 408.1 $[M+H]^+$.

Example 35

(S)-1-(2-((S)-4-(Difluoromethyl)-2-oxooxazolidin-3-yl)-5,6-dihydrobenzo[f]pyrazolo[1,5-d][1,4]oxazepin-9-yl)pyrrolidine-2-carboxamide

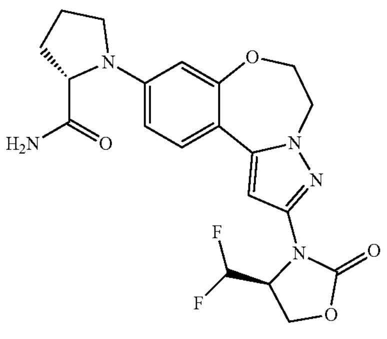 [SMILES: NC(=O)[C@@H]1CCCN1c1ccc2c(c1)OCCn1nc(N3C(=O)OC[C@H]3C(F)F)cc1-2]

(S)-1-(2-((S)-4-(Difluoromethyl)-2-oxooxazolidin-3-yl)-5,6-dihydrobenzo[f]pyraz olo[1,5-d][1,4]oxazepin-9-yl)pyrrolidine-2-carboxamide was prepared by referring to the method of Example 34.

MS m/z (ESI): 434.2 [M+H]+.

Example 36

(S)-2-((2-((S)-4-(Difluoromethyl)-2-oxooxazolidin-3-yl)-5,6-dihydrobenzo[f]pyrazolo[1,5-d][1,4]oxazepin-9-yl)oxy)propanamide

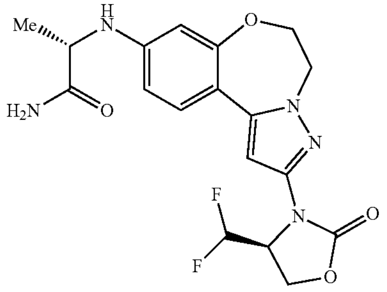 [SMILES: C[C@H](Nc1ccc2c(c1)OCCn1nc(N3C(=O)OC[C@H]3C(F)F)cc1-2)C(N)=O]

(S)-2-((2-((S)-4-(Difluoromethyl)-2-oxooxazolidin-3-yl)-5,6-dihydrobenzo[f]pyraz olo[1,5-d][1,4]oxazepin-9-yl)oxy)propanamide was prepared by referring to the method of Example 34.

MS m/z (ESI): 409.1 [M+H]+.

Example 37

(S)-2-((2-((S)-2-Oxo-4-(trifluoromethyl)oxazolidin-3-yl)-5,6-dihydrobenzo[f]pyrazolo[1,5-d][1,4]oxazepin-9-yl)amino)propanamide

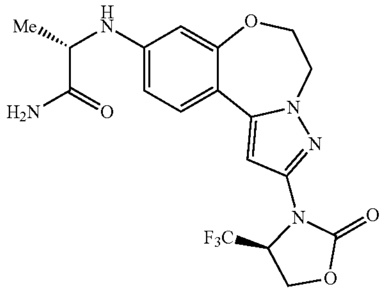 [SMILES: C[C@H](Nc1ccc2c(c1)OCCn1nc(N3C(=O)OC[C@H]3C(F)(F)F)cc1-2)C(N)=O]

(S)-2-((2-((S)-2-Oxo-4-(trifluoromethyl)oxazolidin-3-yl)-5,6-dihydrobenzo[f]pyraz olo[1,5-d][1,4]oxazepin-9-yl)amino)propanamide was prepared by referring to the method of Example 34.

MS m/z (ESI): 426.1 [M+H]+.

Example 38

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-3-methylbutanamide

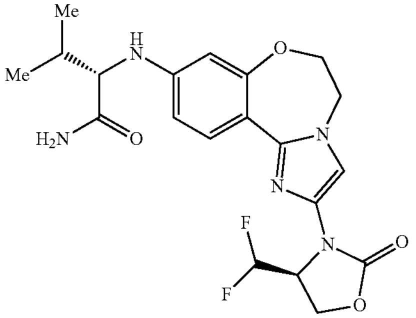 [SMILES: CC(C)[C@H](Nc1ccc2c(c1)OCCn1cc(N3C(=O)OC[C@H]3C(F)F)nc1-2)C(N)=O]

(S)-2-((2-((S)-4-(Difluoromethyl)-2-oxooxazolidin-3-yl)-5,6-dihydrobenzo[f]imida zo[1,2-d][1,4]oxazepin-9-yl)amino)-3-methylbutanamide was prepared by referring to the method of Example 1.

$^1$H NMR (400 MHz, $CD_3OD$) δ 1.09 (t, J=6.1 Hz, 6H), 2.13 (d, J=7.0 Hz, 1H), 3.60 (d, J=6.4 Hz, 1H), 4.38 (d, J=19.3 Hz, 4H), 4.68-4.60 (m, 3H), 6.27 (s, 1H), 6.43-6.78 (m, 2H), 7.17 (s, 1H), 8.06 (d, J=8.7 Hz, 1H);

MS m/z (ESI): 436.1 [M+H]+.

Example 39

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-2-methoxyacetamide

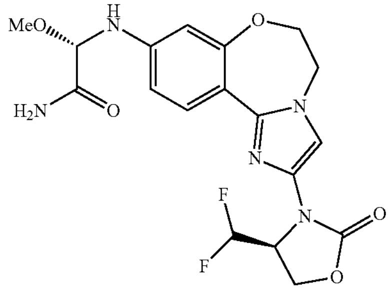 [SMILES: CO[C@H](Nc1ccc2c(c1)OCCn1cc(N3C(=O)OC[C@H]3C(F)F)nc1-2)C(N)=O]

(S)-2-((2-((S)-4-(difluoromethyl)-2-oxooxazolidin-3-yl)-5,6-dihydrobenzo[f]imida zo[1,2-d][1,4]oxazepin-9-yl)amino)-2-methoxyacetamide was prepared by referring to the method of Example 1.

MS m/z (ESI): 424.1 [M+H]+.

Example 40

Preparation of (R)-2-((2-((S)-4-(difluoromethyl)-2-oxooxazolidin-3-yl)-5,6-dihydrobenzo[f]imidazo[1,2-d][1,4]oxazepin-9-yl)amino)-3-fluoropropanamide

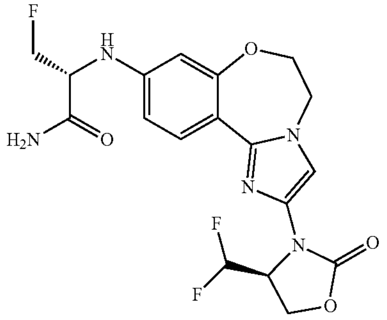 [SMILES: NC(=O)[C@H](CF)Nc1ccc2c(c1)OCCn1cc(N3C(=O)OC[C@H]3C(F)F)nc1-2]

(R)-2-((2-((S)-4-(Difluoromethyl)-2-oxooxazolidin-3-yl)-5,6-dihydrobenzo[f]imid azo[1,2-d][1,4]oxazepin-9-yl) amino)-3-fluoropropanamide was prepared by referring to the method of Example 1.

MS m/z (ESI): 426.1 $[M+H]^+$.

Example 41

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-2-(oxetan-3-yl)acetamide

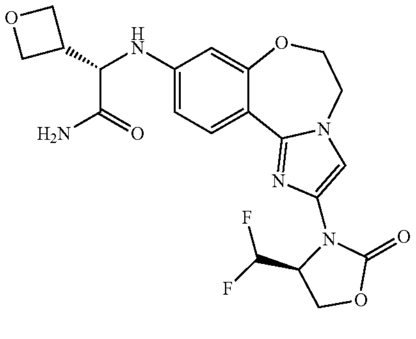 [SMILES: NC(=O)[C@@H](Nc1ccc2c(c1)OCCn1cc(N3C(=O)OC[C@H]3C(F)F)nc1-2)C1COC1]

(S)-2-((2-((S)-4-(Difluoromethyl)-2-oxooxazolidin-3-yl)-5,6-dihydrobenzo[f]imida zo[1,2-d][1,4]oxazepin-9-yl) amino)-2-(oxetan-3-yl)acetamide was prepared by referring to the method of Example 1.

$^1$H NMR (400 MHz, $CD_3OD$) δ 3.26-3.33 (m, 2H), 4.08 (d, J=9.6 Hz, 1H), 4.22-4.25 (m, 2H), 4.29-4.31 (m, 2H), 4.40-4.50 (m, 5H), 4.61-4.69 (m, 1H), 6.18 (d, J=2.2 Hz, 1H), 6.44-6.50 (m, 2H), 7.06 (s, 1H), 7.97 (d, J=8.8 Hz, 1H);

MS m/z (ESI): 450.1 $[M+H]^+$.

Example 42

Preparation of (S)-2-((2-(4-(difluoromethyl)-2-oxooxazolidin-3-yl)-5,6-dihydrobenzo[f]imidazo[1,2-d][1,4]oxazepin-9-yl)amino)-2-methylpropanamide

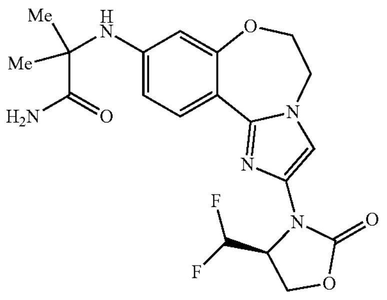 [SMILES: CC(C)(Nc1ccc2c(c1)OCCn1cc(N3C(=O)OC[C@H]3C(F)F)nc1-2)C(N)=O]

(S)-2-((2-(4-(Difluoromethyl)-2-oxooxazolidin-3-yl)-5,6-dihydrobenzo[f]imidazo[1,2-d][1,4]oxazepin-9-yl) amino)-2-methylpropanamide was prepared by referring to the method of Example 1.

$^1$H NMR (400 MHz, $CD_3OD$) δ 1.50 (s, 6H), 4.31-4.36 (m, 2H), 4.38-4.43 (m, 2H), 4.61-4.65 (m, 2H), 4.95 (d, J=10.6 Hz, 1H), 6.19 (d, J=2.2 Hz, 1H), 6.64-6.81 (m, 2H), 7.17 (s, 1H), 8.05 (d, J=8.8 Hz, 1H);

MS m/z (ESI): 422.1 $[M+H]^+$.

Example 43

Preparation of (S)-2-((2-((S)-4-(difluoromethyl)-2-oxooxazolidin-3-yl)-5,6-dihydrobenzo[f]imidazo[1,2-d][1,4]oxazepin-9-yl)(methyl)amino)propanamide

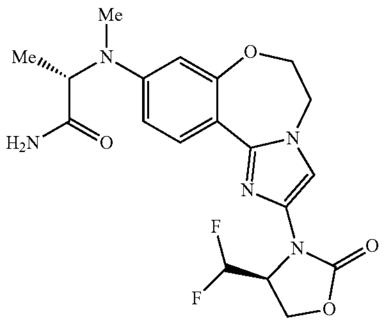 [SMILES: C[C@@H](C(N)=O)N(C)c1ccc2c(c1)OCCn1cc(N3C(=O)OC[C@H]3C(F)F)nc1-2]

(S)-2-((2-((S)-4-(Difluoromethyl)-2-oxooxazolidin-3-yl)-5,6-dihydrobenzo[f]imida zo[1,2-d][1,4]oxazepin-9-yl) (methyl)amino)propanamide was prepared by referring to the method of Example 1.

$^1$H NMR (400 MHz, $CD_3OD$): δ 1.40 (d, J=6.8 Hz, 3H), 2.90 (s, 3H), 4.37-4.64 (m, 7H), 4.96 (m, 1H), 6.41 (s, 1H), 6.46-6.74 (m, 2H), 7.16 (s, 1H), 8.13 (d, J=9.2 Hz, 1H);

MS m/z (ESI): 422.1 $[M+H]^+$.

Example 44

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)propanethioamide

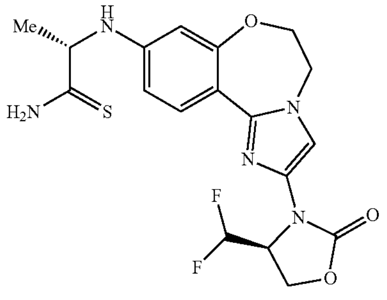 [SMILES: C[C@H](Nc1ccc2c(c1)OCCn1cc(N3C(=O)OC[C@H]3C(F)F)nc1-2)C(N)=S]

(S)-2-((2-((S)-4-(Difluoromethyl)-2-oxooxazolidin-3-yl)-5,6-dihydrobenzo[f]imida zo[1,2-d][1,4]oxazepin-9-yl) amino)propanethioamide was prepared by referring to the method of Example 1.

MS m/z (ESI): 424.1 $[M+H]^+$.

Example 45

Preparation of (S)-2-((2-((S)-4-(difluoromethyl)-2-oxooxazolidin-3-yl)-5,6-dihydrobenzo[f]imidazo[1,2-d][1,4]oxazepin-9-yl)thio)propanamide

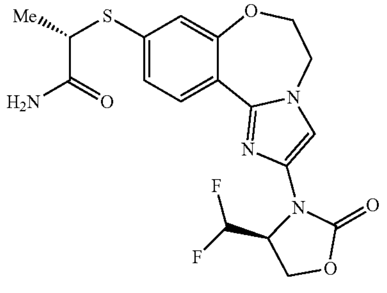 [SMILES: C[C@H](Sc1ccc2c(c1)OCCn1cc(N3C(=O)OC[C@H]3C(F)F)nc1-2)C(N)=O]

(S)-2-((2-((S)-4-(Difluoromethyl)-2-oxooxazolidin-3-yl)-5,6-dihydrobenzo[f]imida zo[1,2-d][1,4]oxazepin-9-yl)thio) propanamide was prepared by referring to the method of Example 1.

MS m/z (ESI): 425.1 $[M+H]^+$.

Example 46

Preparation of (S)-3-((2-(4-(difluoromethyl)-2-oxooxazolidin-3-yl)-5,6-dihydrobenzo[f]imidazo[1,2-d][1,4]oxazepin-9-yl)amino)oxetane-3-carboxamide

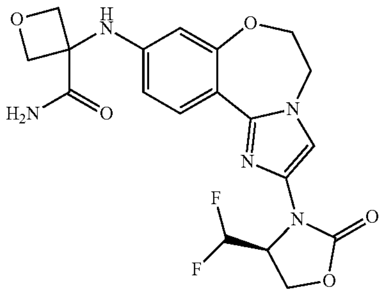 [SMILES: NC(=O)C1(Nc2ccc3c(c2)OCCn2cc(N4C(=O)OC[C@H]4C(F)F)nc2-3)COC1]

(S)-3-((2-(4-(Difluoromethyl)-2-oxooxazolidin-3-yl)-5,6-dihydrobenzo[f]imidazo[1,2-d][1,4]oxazepin-9-yl)amino) oxetane-3-carboxamide was prepared by referring to the method of Example 1.

$^1H$ NMR (400 MHz, $CD_3OD$) δ 4.35 (m, 4H), 4.63 (m, 4H), 4.90 (m, 1H), 5.10 (d, J=8.0 Hz, 2H), 5.90 (s, 1H), 6.29 (d, J=8.0 Hz, 1H), 6.59 (t, J=56 Hz, 1H), 7.16 (s, 1H), 8.10 (d, J=8.0 Hz, 1H);

MS m/z (ESI): 436.1 $[M+H]^+$.

Example 47

Preparation of (S)-3-(9-(((3-aminooxetan-3-yl)methyl)amino)-5,6-dihydrobenzo[f]imidazo[1,2-d][1,4]oxazepin-2-yl)-4-(difluoromethyl)oxazolidin-2-one

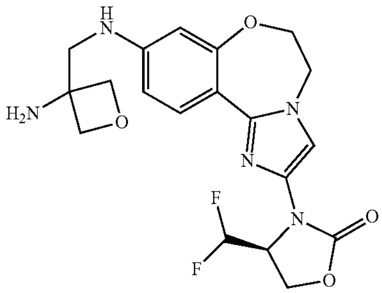 [SMILES: NC1(CNc2ccc3c(c2)OCCn2cc(N4C(=O)OC[C@H]4C(F)F)nc2-3)COC1]

(S)-3-(9-(((3-Aminooxetan-3-yl)methyl)amino)-5,6-dihydrobenzo[f]imidazo[1,2-d][1,4]oxazepin-2-yl)-4-(difluoromethyl)oxazolidin-2-one was prepared by referring to the method of Example 1.

$^1H$ NMR (400 MHz, $CD_3OD$): δ 3.35 (s, 2H), 4.24 (d, J=4.7 Hz, 2H), 4.30 (d, J=4.7 Hz, 2H), 4.41 (d, J=6.4 Hz, 2H), 4.45-4.60 (m, 5H), 6.22 (d, J=2.3 Hz, 1H), 6.27-6.71 (m, 2H), 7.05 (s, 1H), 7.94 (d, J=8.8 Hz, 1H);

MS m/z (ESI): 422.1 $[M+H]^+$.

Example 48

Preparation of (S)-1-(2-((S)-4-(difluoromethyl)-2-oxooxazolidin-3-yl)-5,6-dihydrobenzo[f]imidazo[1,2-d][1,4]oxazepin-9-yl) azetidine-2-carboxamide

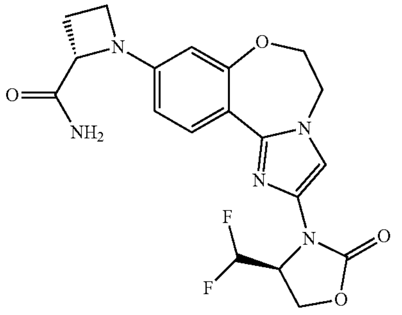 [SMILES: NC(=O)[C@@H]1CCN1c1ccc2c(c1)OCCn1cc(N3C(=O)OC[C@H]3C(F)F)nc1-2]

(S)-1-(2-((S)-4-(Difluoromethyl)-2-oxooxazolidin-3-yl)-5,6-dihydrobenzo[f]imida zo[1,2-d][1,4]oxazepin-9-yl) azetidine-2-carboxamide was prepared by referring to the method of Example 1.

$^1$H NMR (400 MHz, $CD_3OD$) δ 2.30-2.40 (m, 1H), 2.52-2.58 (m, 1H), 3.66-3.72 (m, 1H), 3.91-3.96 (m, 1H), 4.22-4.27 (m, 2H), 4.28-4.34 (m, 2H), 4.48-4.59 (m, 2H), 4.79-4.85 (m, 2H), 6.00 (d, J=2.2 Hz, 1H), 6.20-6.22 (m, 1H), 6.37-6.65 (m, 1H), 7.08 (s, 1H), 8.06 (d, J=8.7 Hz, 1H).

MS m/z (ESI): 420.1 $[M+H]^+$.

Example 49

Preparation of (S)-1-(2-(4-(difluoromethyl)-2-oxooxazolidin-3-yl)-5,6-dihydrobenzo[f]imidazo[1,2-d][1,4]oxazepin-9-yl) azetidine-3-carboxamide

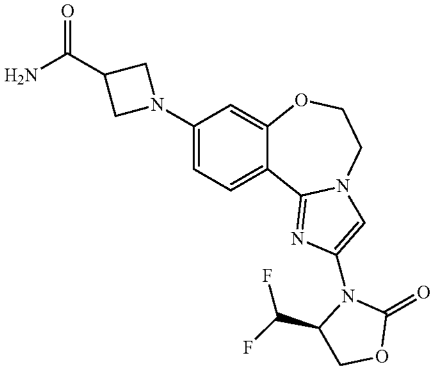 [SMILES: NC(=O)C1CN(c2ccc3c(c2)OCCn2cc(N4C(=O)OC[C@H]4C(F)F)nc2-3)C1]

(S)-1-(2-(4-(Difluoromethyl)-2-oxooxazolidin-3-yl)-5,6-dihydrobenzo[f]imidazo[1,2-d][1,4]oxazepin-9-yl) azetidine-3-carboxamide was prepared by referring to the method of Example 1.

$^1$H NMR (400 MHz, $CD_3OD$) δ 3.42-3.49 (m, 1H), 3.87 (t, J=6.7 Hz, 2H), 3.98 (t, J=7.9 Hz, 2H), 4.23-4.27 (m, 2H), 4.29-4.33 (m, 2H), 4.50-4.58 (m, 3H), 5.97 (d, J=2.2 Hz, 1H), 6.17-6.20 (m, 1H), 6.36-6.64 (m, 1H), 7.07 (s, 1H), 8.02 (d, J=8.7 Hz, 1H);

MS m/z (ESI): 420.1 $[M+H]^+$.

Example 50

Preparation of (S)-2-((2-((S)-4-(difluoromethyl)-2-thioxooxazolidin-3-yl)-5,6-dihydrobenzo[f]imidazo[1,2-d][1,4]oxazepin-9-yl)amino)propanamide

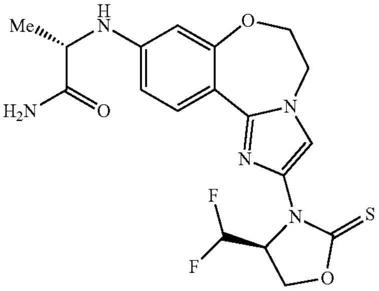

(S)-2-((2-((S)-4-(Difluoromethyl)-2-thioxooxazolidin-3-yl)-5,6-dihydrobenzo[f]im idazo[1,2-d][1,4]oxazepin-9-yl) amino)propanamide was prepared by referring to the method of Example 1.

MS m/z (ESI): 424.1 $[M+H]^+$.

Example 51

Preparation of (S)-2-((2-((R)-4-(difluoromethyl)-2-oxothiazolidin-3-yl)-5,6-dihydrobenzo[f]imidazo[1,2-d][1,4]oxazepin-9-yl)amino)propanamide

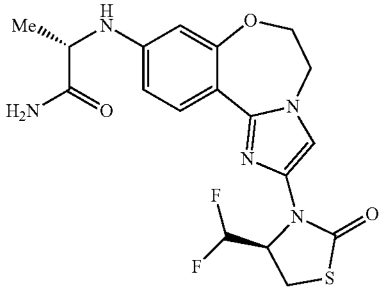

Step 1: Preparation of (S)-3-(9-bromo-5,6-dihydrobenzo[f]imidazo[1,2-d][1,4]oxazepin-2-yl)-4-(difluorometh yl)oxazolidine-2-thione

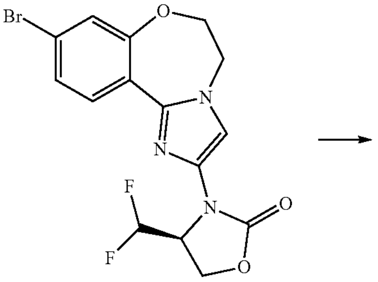

-continued

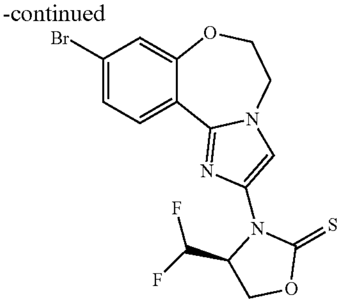

Lawesson's reagent (1.01 g, 2.5 mmol) was added to a solution of (S)-3-(10-bromo-6,7-dihydro-5H-benzo[b]imidazo[2,1-d][1,5]oxazocin-2-yl)-4-(difluor omethyl)oxazolidin-2-one (100 mg, 0.25 mmol) in toluene (10 mL). The reaction solution was reacted under microwave at 140° C. for 3 hours. The reaction solution was cooled to room temperature and filtered, and the filter cake was washed with EtOAc (20 mL). The filtrate was dried over anhydrous sodium sulfate, and concentrated under reduced pressure. The residue was subjected to column chromatography to obtain the title compound (S)-3-(9-bromo-5,6-dihydrobenzo[f]imidazo[1,2-d][1,4]oxazepin-2-yl)-4-(difluorometh yl)oxazolidine-2-thione (42 mg, 40%).

$^1$H NMR (400 MHz, DMSO-$d_6$) δ 4.43-4.52 (m, 4H), 4.79-4.86 (m, 2H), 5.24-5.35 (m, 1H), 6.57-6.85 (m, 1H), 7.23-7.38 (m, 2H), 8.10 (s, 1H), 8.26 (d, J=8.6 Hz, 1H);

MS m/z (ESI): 416.1 $[M+H]^+$.

Step 2: Preparation of (R)-3-(9-bromo-5,6-dihydrobenzo[f]imidazo[1,2-d][1,4]oxazepin-2-yl)-4-(difluorometh yl)thiazolidin-2-one

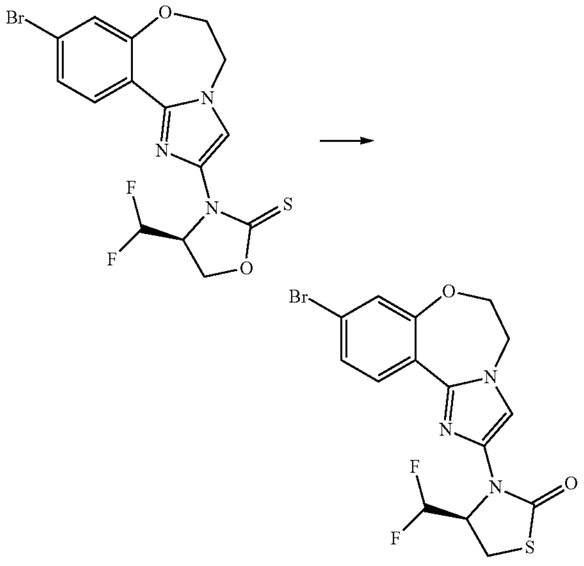

Dichloro(p-cymene)ruthenium(II) dimer (14.7 mg, 0.024 mmol) and 2-bicyclohexylphosphino-2',6'-dimethoxybiphenyl (9.7 mg, 0.024 mmol) were added to a solution of (S)-3-(10-bromo-6,7-dihydro-5H-benzo[b]imidazo[2,1-d][1,5]oxazepin-2-yl)-4-(difluor omethyl)oxazolidine-2-thione (33 mg, 0.079 mmol) in toluene (1 mL). The reaction solution was reacted under an air atmosphere at 110° C. for 12 hours. The reaction solution was cooled to room temperature, and diluted with EtOAc. The organic phase was washed with saturated aqueous sodium chloride solution, dried over anhydrous sodium sulfate, and concentrated under reduced pressure. The residue was subjected to column chromatography to obtain the title compound (R)-3-(9-bromo-5,6-dihydrobenzo[f]imidazo[1,2-d][1,4]oxazepin-2-yl)-4-(difluorometh yl)thiazolidin-2-one (26 mg, 79%).

$^1$H NMR (400 MHz, $CDCl_3$) δ 3.57-3.72 (m, 2H), 4.28-4.41 (m, 2H), 4.44-4.47 (m, 2H) 5.14-5.24 (m, 1H), 6.29-6.67 (m, 1H), 7.14-7.25 (m, 2H), 7.42 (s, 1H), 8.21 (d, J=8.8 Hz, 1H);

MS m/z (ESI): 416.1 $[M+H]^+$.

Step 3: Preparation of (S)-2-((2-((R)-4-(difluoromethyl)-2-oxothiazolidin-3-yl)-5,6-dihydrobenzo[f]imidazo[1,2-d][1,4]oxazepin-9-yl)amino)propanamide

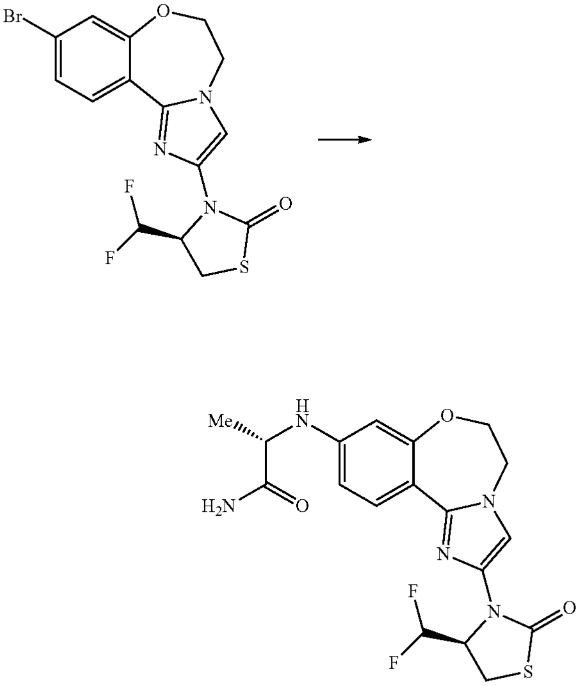

(R)-3-(9-Bromo-5,6-dihydrobenzo[f]imidazo[1,2-d][1,4]oxazepin-2-yl)-4-(difluoro methyl)thiazolidin-2-one (26 mg, 0.062 mmol), L-alanine (19.5 mg, 0.22 mmol), cuprous iodide (6 mg, 0.03 mmol) and potassium phosphate (40 mg, 0.19 mmol) were mixed in dimethyl sulfoxide (3 mL). The reaction system was purged with nitrogen three times, and reacted at 100° C. for 12 hours. The reaction solution was cooled to room temperature, ammonium chloride (20 mg, 0.37 mmol) and triethylamine (95 mg, 0.94 mmol) were added and the reaction solution was stirred for 5 minutes. O-(7-azabenzotriazol-1-yl)-N,N,N',N'-tetramethylurea hexafluorophosphate (212 mg, 0.56 mmol) was added, and the reaction solution was stirred at room temperature for 2 hours. The reaction solution was filtered, saturated aqueous sodium bicarbonate solution was added to the filtrate, which was then extracted with ethyl acetate three times. The organic phases were combined, dried over anhydrous sodium sulfate, and concentrated under reduced pressure. The residue was subjected to column chromatography to obtain the title compound (S)-2-((2-((R)-4-(difluoromethyl)-2-oxothiazolidin-3-yl)-5,6-dihydrobenzo[f]imidazo[1,2-d][1,4]oxazepin-9-yl)amino)propanamide (15 mg, 56%).

$^1$H NMR (400 MHz, $CD_3OD$) δ 1.37 (d, J=7.2 Hz, 3H), 3.57-3.61 (m, 1H), 3.83-3.87 (m, 2H), 4.33-4.41 (m, 4H), 5.12-5.19 (m, 1H), 6.15-6.17 (m, 1H), 6.47-6.52 (m, 2H), 7.28 (s, 1H), 8.10 (d, J=8.8 Hz, 1H);

MS m/z (ESI): 424.1 $[M+H]^+$.

Example 52

Preparation of (S)-2-((2-((S)-5-(difluoromethyl)-2-oxoimidazolidin-1-yl)-5,6-dihydrobenzo[f]imidazo[1,2-d][1,4]oxazepin-9-yl)amino)propanamide

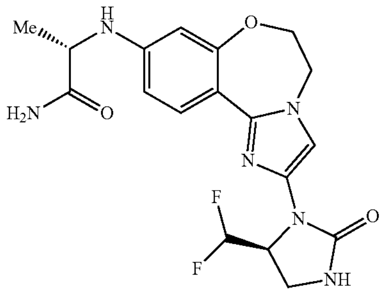 [SMILES: C[C@H](Nc1ccc2c(c1)OCCn1cc(N3C(=O)NC[C@H]3C(F)F)nc1-2)C(N)=O]

(S)-2-((2-((S)-5-(Difluoromethyl)-2-oxoimidazolidin-1-yl)-5,6-dihydrobenzo[f]imi dazo[1,2-d][1,4]oxazepin-9-yl) amino)propanamide was prepared by referring to the method of Example 51.

MS m/z (ESI): 407.2 $[M+H]^+$.

Example 53

Preparation of (S)-2-((2-((S)-5-(difluoromethyl)-3-methyl-2-oxoimidazolidin-1-yl)-5,6-dihydrobenzo[f]imidazo[1,2-d][1,4]oxazepin-9-yl)amino)propanamide

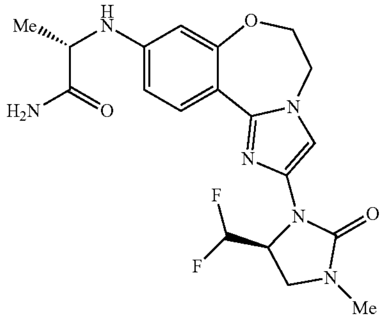 [SMILES: C[C@H](Nc1ccc2c(c1)OCCn1cc(N3C(=O)N(C)C[C@H]3C(F)F)nc1-2)C(N)=O]

(S)-2-((2-((S)-5-(Difluoromethyl)-3-methyl-2-oxoimidazolidin-1-yl)-5,6-dihydrobe nzo[f]imidazo[1,2-d][1,4]oxazepin-9-yl)amino)propanamide was prepared by referring to the method of Example 51.

$^1$H NMR (400 MHz, $CD_3OD$) δ 1.46 (d, J=7.0 Hz, 3H), 2.85 (s, 3H), 3.62-3.68 (m, 2H), 3.79-3.85 (m, 1H), 4.27-4.30 (m, 2H), 4.35-4.37 (m, 2H), 4.63-4.69 (m, 1H), 6.17 (d, J=2.0 Hz, 1H), 6.34-6.62 (m, 2H), 7.05 (s, 1H), 8.01 (d, J=8.8 Hz, 1H);

MS m/z (ESI): 421.2 $[M+H]^+$.

Example 54

Preparation of (S)-2-((2-((4S,5R)-4-(difluoromethyl)-5-methyl-2-oxooxazolidin-3-yl)-5,6-dihydrobenz o[f]imidazo[1,2-d][1,4]oxazepin-9-yl)amino)propanamide

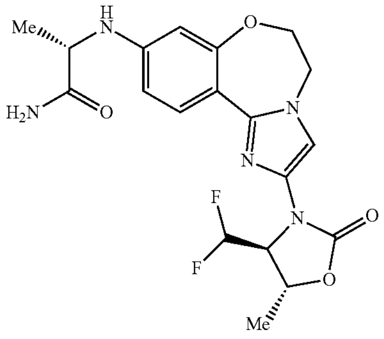 [SMILES: C[C@H](Nc1ccc2c(c1)OCCn1cc(N3C(=O)O[C@H](C)[C@H]3C(F)F)nc1-2)C(N)=O]

Step 1: Preparation of methyl (4S,5R)-5-methyl-2-oxooxazolidine-4-carboxylate

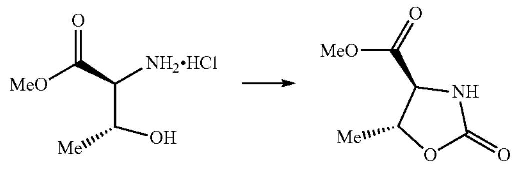

Methyl L-threoninate hydrochloride (500 mg, 2.95 mmol) was dissolved in dichloromethane (15 mL), and the resulting solution was cooled to 0° C. in an ice water bath. Triphosgene (289 mg, 0.97 mmol) was added, then a solution of triethylamine (895 mg, 8.84 mmol) in dichloromethane (2 mL) was added dropwise. After completion of the addition, the reaction solution was reacted at 0° C. for 1 hour. Water was added, and the reaction solution was extracted with dichloromethane. The organic phase was dried over anhydrous sodium sulfate, and concentrated under reduced pressure to remove the organic solvent. The resulting crude product was purified by column compound methyl chromatography to obtain the title (4S,5R)-5-methyl-2-oxooxazolidine-4-carboxylate (251 mg, 53%).

MS m/z (ESI): 160.1 $[M+H]^+$.

Step 2: Preparation of methyl (4S,5R)-3-benzyl-5-methyl-2-oxooxazolidine-4-carboxylate

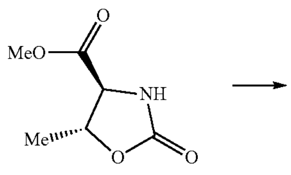

-continued

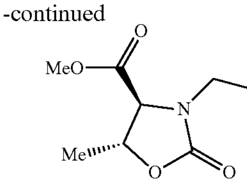

Methyl (4S,5R)-5-methyl-2-oxooxazolidine-4-carboxylate (200 mg, 1.26 mmol) was dissolved in DMF (5 mL), and the resulting solution was cooled to −15° C. NaH (60% in kerosene, 50 mg, 1.26 mmol) was added, and the reaction solution was stirred at −15° C. for 1 hour. Benzyl bromide (322 mg, 1.89 mmol) was added, and the reaction solution was stirred for 2 hours. Water was added to quench the reaction, and the reaction solution was extracted with dichloromethane. The organic phase was dried over anhydrous sodium sulfate, and concentrated under reduced pressure to remove the organic solvent. The resulting crude product was purified by column chromatography to obtain the title compound methyl (4S,5R)-3-benzyl-5-methyl-2-oxooxazolidine-4-carboxylate (260 mg, 83%).

MS m/z (ESI): 250.1 [M+H]$^+$.

Step 3: Preparation of (4R,5R)-3-benzyl-4-(hydroxymethyl)-5-methyloxazolidin-2-one

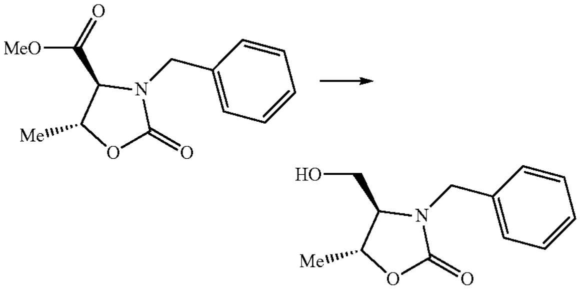

Methyl (4S,5R)-3-benzyl-5-methyl-2-oxooxazolidine-4-carboxylate (260 mg, 1.0 mmol) was dissolved in methanol (5 mL), and the resulting solution was cooled to 0° C. in an ice water bath. Sodium borohydride (11 mg, 3.1 mmol) was added in batches, the reaction solution was gradually warmed up to room temperature and reacted for 2 hours. The reaction solution was concentrated, and the resulting crude product was purified by column chromatography to obtain the title compound (4R,5R)-3-benzyl-4-(hydroxymethyl)-5-methyloxazolidin-2-one (180 mg, 78%).

MS m/z (ESI): 222.1 [M+H]$^+$.

Step 4: Preparation of (4S,5R)-3-benzyl-5-methyl-2-oxooxazolidine-4-carbaldehyde

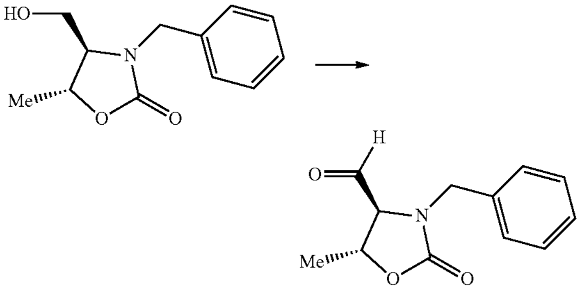

(4R,5R)-3-Benzyl-4-(hydroxymethyl)-5-methyloxazolidin-2-one (180 mg, 0.81 mmol) and IBX (683 mg, 2.44 mmol) were mixed in ethyl acetate (10 mL). Under a nitrogen atmosphere, the reaction solution was reacted at 85° C. for 3 hours. The reaction solution was cooled and filtered. The filtrate was concentrated under reduced pressure to obtain the crude product (4S,5R)-3-benzyl-5-methyl-2-oxooxazolidine-4-carbaldehyde (178 mg), which was used directly in the next step.

MS m/z (ESI): 220.2 [M+H]$^+$.

Step 5: Preparation of (4S,5R)-3-benzyl-4-(difluoromethyl)-5-methyloxazolidin-2-one

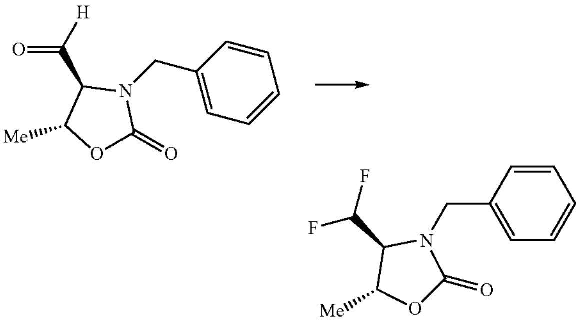

(4S,5R)-3-Benzyl-5-methyl-2-oxooxazolidine-4-carbaldehyde (178 mg, 0.81 mmol) was dissolved in dichloromethane (10 mL). Under a nitrogen atmosphere, the solution was cooled to 0° C. in an ice water bath, and DAST (262 mg, 1.62 mmol) was added dropwise. The reaction solution was naturally warmed up to room temperature and reacted for 3 hours. The reaction solution was slowly added dropwise to the pre-cooled saturated aqueous sodium bicarbonate solution, and extract with dichloromethane (20 mL×2). The organic phases were combined, dried over anhydrous sodium sulfate, and concentrated under reduced pressure to remove the organic solvent. The residue was subjected to column chromatography to obtain the title compound (4S,5R)-3-benzyl-4-(difluoromethyl)-5-methyloxazolidin-2-one (110 mg, two-step yield: 56%).

$^1$H NMR (400 MHz, $CDCl_3$) δ 1.33 (d, J=6.4 Hz, 3H), 3.27-3.33 (m, 1H), 4.16-4.20 (m, 1H), 4.41-4.64 (m, 1H), 4.91 (d, J=15.0 Hz, 1H), 5.56-5.88 (m, 1H), 7.27-7.44 (m, 5H);

MS m/z (ESI): 242.1 [M+H]$^+$.

Step 6: Preparation of (4S,5R)-4-(difluoromethyl)-5-methyloxazolidin-2-one

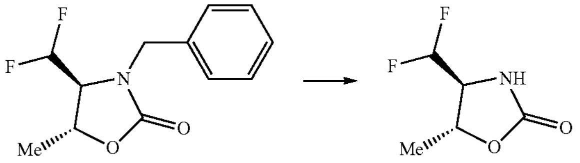 [SMILES: C[C@H]1OC(=O)N(Cc2ccccc2)[C@@H]1C(F)F ; C[C@H]1OC(=O)N[C@@H]1C(F)F]

(4S,5R)-3-Benzyl-4-(difluoromethyl)-5-methyloxazolidin-2-one (110 mg, 0.46 mmol) was dissolved in mesitylene (2 mL), followed by the addition of methanesulfonic acid (438 mg, 4.56 mmol). The reaction solution was heated to 135° C. and reacted for 5 hours. After cooling to room temperature, the reaction solution was slowly added dropwise to the pre-cooled saturated aqueous sodium bicarbonate solution, and extract with dichloromethane (20 mL×2). The organic phases were combined, dried over anhydrous sodium sulfate, and concentrated under reduced pressure to remove the organic solvent. The residue was subjected to column chromatography to obtain the crude title compound (4S,5R)-4-(difluoromethyl)-5-methyloxazolidin-2-one (68 mg), which was used directly in the next step.

MS m/z (ESI): 152.1 $[M+H]^+$.

Step 7: Preparation of (4S,5R)-3-(9-bromo-5,6-dihydrobenzo[f]imidazo[1,2-d][1,4]oxazepin-2-yl)-4-(difluoro methyl)-5-methyloxazolidin-2-one

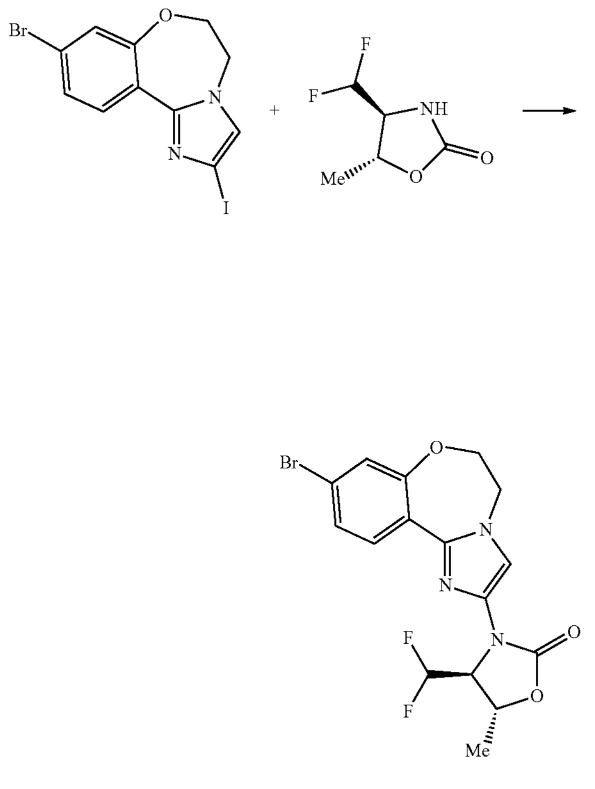

9-Bromo-2-iodo-5,6-dihydrobenzo[f]imidazo[1,2-d][1,4] oxazepine (100 mg, 0.25 mmol), (4S,5R)-4-(difluoromethyl)-5-methyloxazolidin-2-one (38.5 mg, 0.25 mmol), (1R,2R)-$N^1$,$N^2$-dimethylcyclohexane-1,2-diamine (22 mg, 0.15 mmol), cuprous iodide (14 mg, 0.08 mmol) and potassium phosphate (108 mg, 0.51 mmol) were mixed in dimethyl sulfoxide (3 mL), and the reaction solution was reacted at 130° C. for 3 hours. The reaction solution was cooled to room temperature, and 15% ammonia (5 mL) was added. The reaction solution was stirred for 5 minutes and extracted with ethyl acetate three times. The organic phases were combined, washed with saturated sodium chloride solution, dried over anhydrous sodium sulfate, and concentrated under reduced pressure to remove the organic solvent. The residue was subjected to column chromatography to obtain the title compound (S)-3-(9-bromo-3-fluoro-5,6-dihydrobenzo[f]imidazo[1,2-d][1,4]oxazepin-2-yl)-4-(diflu oromethyl)oxazolidin-2-one (61 mg, 57%).

MS m/z (ESI): 414.2 $[M+H]^+$.

Step 8: Preparation of (S)-2-((2-((4S,5R)-4-(difluoromethyl)-5-methyl-2-oxooxazolidin-3-yl)-5,6-dihydrobenz o[f]imidazo[1,2-d][1,4]oxazepin-9-yl)amino)propanamide

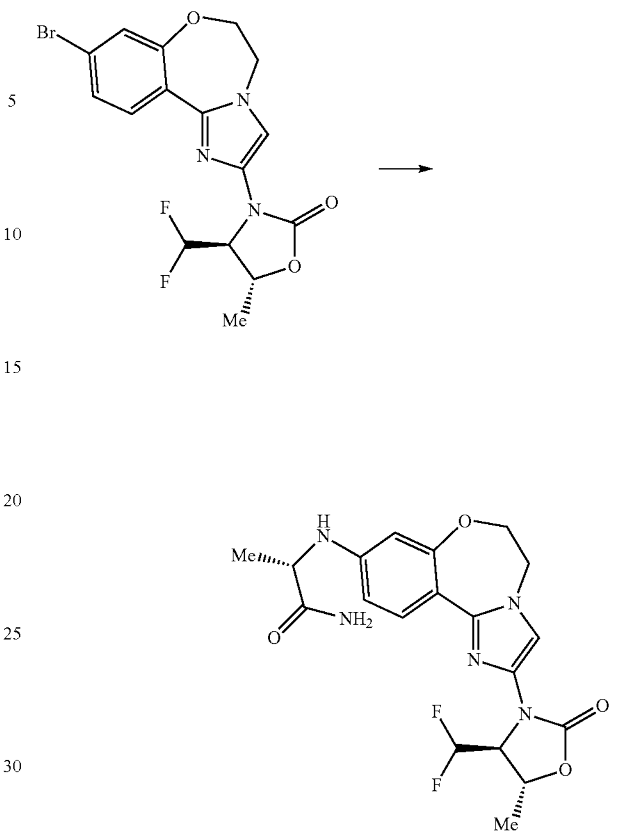

(4S,5R)-3-(9-Bromo-5,6-dihydrobenzo[f]imidazo[1,2-d][1,4]oxazepin-2-yl)-4-(difl uoromethyl)-5-methyloxazolidin-2-one (61 mg, 0.15 mmol), L-alanine (39 mg, 0.44 mmol), cuprous iodide (14 mg, 0.07 mmol) and potassium phosphate (94 mg, 0.44 mmol) were mixed in dimethyl sulfoxide (5 mL). The reaction system was purged with nitrogen three times, and reacted at 100° C. for 5 hours. The reaction solution was cooled to room temperature, ammonium chloride (47 mg, 0.88 mmol) and triethylamine (223 mg, 2.21 mmol) were added, and the reaction solution was stirred for 5 minutes. O-(7-azabenzotriazol-1-yl)-N,N,N',N'-tetramethylurea hexafluorophosphate (505 mg, 1.33 mmol) was added, and the reaction solution was stirred at room temperature for 2 hours. The reaction solution was filtered, saturated aqueous sodium bicarbonate solution was added to the filtrate, which was then extracted with ethyl acetate three times. The organic phases were combined, dried over anhydrous sodium sulfate, and concentrated under reduced pressure to remove the organic solvent. The residue was subjected to column chromatography to obtain the title compound (S)-2-((2-((S)-4-(difluoromethyl)-2-oxooxazolidin-3-yl)-6,7-dihydro-5H-benzo[b]imida zo[2,1-d][1,5]oxazocin-10-yl)amino)propanamide (33 mg, 53%).

$^1$H NMR (400 MHz, $CD_3OD$) δ 1.46 (d, J=6.8 Hz, 3H), 1.53 (d, J=6.2 Hz, 3H), 3.79-3.85 (m, 1H), 4.32-4.39 (m, 4H), 4.46-4.55 (m, 1H), 4.93-4.95 (m, 1H), 6.17 (s, 1H), 6.39-6.72 (m, 2H), 7.14 (s, 1H), 8.03 (d, J=8.6 Hz, 1H);

MS m/z (ESI): 422.1 $[M+H]^+$.

Example 55

Preparation of (R)-2-((2-((4S,5R)-4-(difluoromethyl)-5-methyl-2-oxooxazolidin-3-yl)-5,6-dihydrobenz o[f]imidazo[1,2-d][1,4]oxazepin-9-yl)amino)propanamide

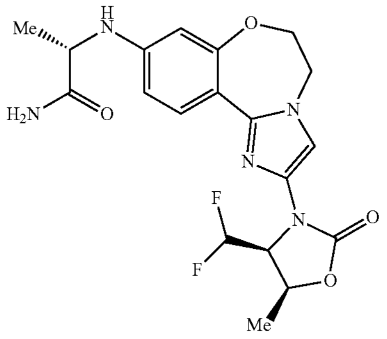 [SMILES: C[C@H](Nc1ccc2c(c1)OCCn1cc(N3C(=O)O[C@@H](C)[C@H]3C(F)F)nc1-2)C(N)=O]

(R)-2-((2-((4S,5R)-4-(Difluoromethyl)-5-methyl-2-oxooxazolidin-3-yl)-5,6-dihydr obenzo[f]imidazo[1,2-d][1,4]oxazepin-9-yl)amino)propanamide was prepared by referring to the method of Example 54.

MS m/z (ESI): 422.2 [M+H]$^+$.

Example 56

Preparation of (S)-2-((2-((S)-4-(difluoromethyl)-5,5-dimethyl-2-oxooxazolidin-3-yl)-5,6-dihydrobenzo[f]imidazo[1,2-d][1,4]oxazepin-9-yl)amino)propanamide

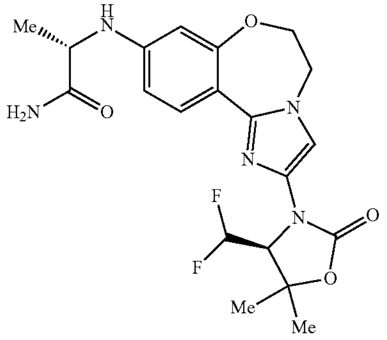 [SMILES: C[C@H](Nc1ccc2c(c1)OCCn1cc(N3C(=O)OC(C)(C)[C@H]3C(F)F)nc1-2)C(N)=O]

(S)-2-((2-((S)-4-(Difluoromethyl)-5,5-dimethyl-2-oxooxazolidin-3-yl)-5,6-dihydro benzo[f]imidazo[1,2-d][1,4]oxazepin-9-yl)amino)propanamide was prepared by referring to the method of Example 54.

MS m/z (ESI): 436.2 [M+H]$^+$.

Example 57

Preparation of (S)-2-((2-((S)-7-(difluoromethyl)-5-oxo-4-oxa-6-azaspiro[2.4]heptan-6-yl)-5,6-dihydrob enzo[f]imidazo[1,2-d][1,4]oxazepin-9-yl)amino)propanamide

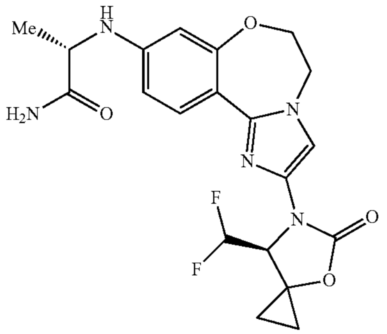 [SMILES: C[C@H](Nc1ccc2c(c1)OCCn1cc(N3C(=O)OC4(CC4)[C@H]3C(F)F)nc1-2)C(N)=O]

(S)-2-((2-((S)-7-(Difluoromethyl)-5-oxo-4-oxa-6-azaspiro[2.4]heptan-6-yl)-5,6-dih ydrobenzo[f]imidazo[1,2-d][1,4]oxazepin-9-yl)amino)propanamide was prepared by referring to the method of Example 54.

MS m/z (ESI): 434.2 [M+H]$^+$.

Example 58

Preparation of (S)-2-((2-((S)-8-(difluoromethyl)-6-oxo-2,5-dioxa-7-azaspiro[3.4]octan-7-yl)-5,6-dihyd robenzo[f]imidazo[1,2-d][1,4]oxazepin-9-yl)amino)propanamide

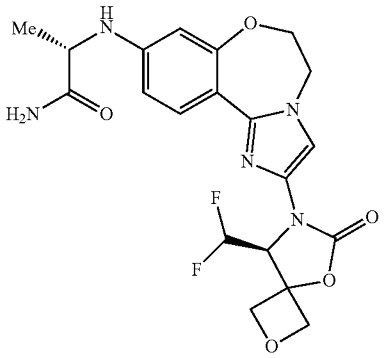 [SMILES: C[C@H](Nc1ccc2c(c1)OCCn1cc(N3C(=O)OC4(COC4)[C@H]3C(F)F)nc1-2)C(N)=O]

(S)-2-((2-((S)-8-(Difluoromethyl)-6-oxo-2,5-dioxa-7-azaspiro[3.4]octan-7-yl)-5,6-dihydrobenzo[f]imidazo[1,2-d][1,4]oxazepin-9-yl)amino)propanamide was prepared by referring to the method of Example 54.

MS m/z (ESI): 450.2 [M+H]$^+$.

Example 59

Preparation of (S)-2-((2-(6-oxo-2,7-dioxa-5-azaspiro[3.4]octan-5-yl)-5,6-dihydrobenzo[f]imidazo[1,2-d][1,4]oxazepin-9-yl)amino)propanamide

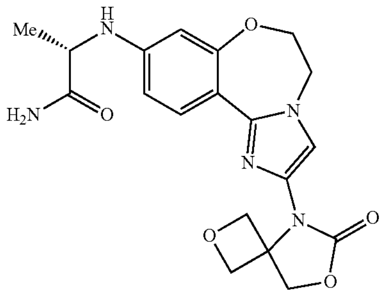 [SMILES: C[C@H](Nc1ccc2c(c1)OCCn1cc(N3C(=O)OCC34COC4)nc1-2)C(N)=O]

(S)-2-((2-(6-Oxo-2,7-dioxa-5-azaspiro[3.4]octan-5-yl)-5,6-dihydrobenzo[f]imidazo[1,2-d][1,4]oxazepin-9-yl)amino)propanamide was prepared by referring to the method of Example 1.

$^1$H NMR (400 MHz, $CD_3OD$) δ 1.37 (d, J=7.0 Hz, 3H), 3.69-3.77 (m, 1H), 4.27-4.38 (m, 4H), 4.62 (d, J=7.4 Hz, 2H), 4.70 (s, 2H), 5.12 (d, J=7.4 Hz, 2H), 6.10 (d, J=2.3 Hz, 1H), 6.33-6.38 (m, 1H), 7.18 (s, 1H), 7.96 (d, J=8.8 Hz, 1H);

MS m/z (ESI): 400.2 $[M+H]^+$.

Example 60

Preparation of (S)-2-((2-((R)-4-(methoxymethyl)-2-oxooxazolidin-3-yl)-5,6-dihydrobenzo[f]imidazo[1,2-d][1,4]oxazepin-9-yl)amino)propanamide

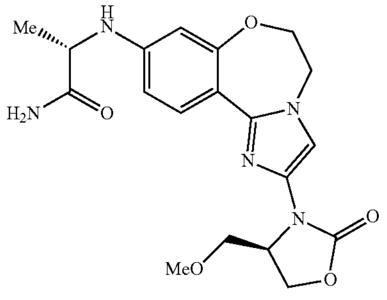 [SMILES: COC[C@@H]1COC(=O)N1c1cn2c(n1)-c1ccc(N[C@@H](C)C(N)=O)cc1OCC2]

(S)-2-((2-((R)-4-(Methoxymethyl)-2-oxooxazolidin-3-yl)-5,6-dihydrobenzo[f]imid azo[1,2-d][1,4]oxazepin-9-yl)amino)propanamide was prepared by referring to the method of Example 1.

$^1$H NMR (400 MHz, $CD_3OD$) δ 1.46 (d, J=7.0 Hz, 3H), 3.34 (s, 3H), 3.57-3.62 (m, 1H), 3.77-3.85 (m, 2H), 4.31-4.35 (m, 2H), 4.37-4.41 (m, 2H), 4.42-4.45 (m, 1H), 4.53-4.55 (m, 1H), 4.63-4.69 (m, 1H), 6.16-6.19 (m, 1H), 6.40-6.45 (m, 1H), 7.12 (s, 1H), 8.01 (d, J=8.8 Hz, 1H);

MS m/z (ESI): 402.2 $[M+H]^+$.

Example 61

Preparation of (2S)-2-((2-((5S)-5-(difluoromethyl)-3-oxo-2-oxa-4-azabicyclo[3.1.0]hexan-4-yl)-5,6-di hydrobenzo[f]imidazo[1,2-d][1,4]oxazepin-9-yl) amino)propanamide

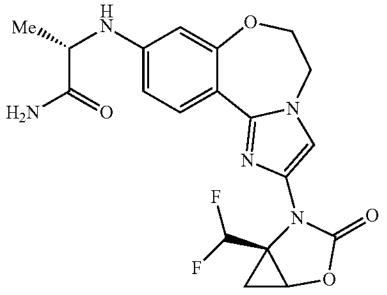 [SMILES: C[C@H](Nc1ccc2c(c1)OCCn1cc(N3C(=O)OC4C[C@@]43C(F)F)nc1-2)C(N)=O]

(2S)-2-((2-((5S)-5-(Difluoromethyl)-3-oxo-2-oxa-4-azabicyclo[3.1.0]hexan-4-yl)-5,6-dihydrobenzo[f]imidazo[1,2-d][1,4]oxazepin-9-yl)amino)propanamide was prepared by referring to the method of Example 1.

MS m/z (ESI): 420.1 $[M+H]^+$.

Example 62

Preparation of (S)-2-((2-((1R,5S)-6,6-difluoro-3-oxo-2-oxa-4-azabicyclo[3.1.0]hexan-4-yl)-5,6-dihydr obenzo[f]imidazo[1,2-d][1,4]oxazepin-9-yl) amino)propanamide

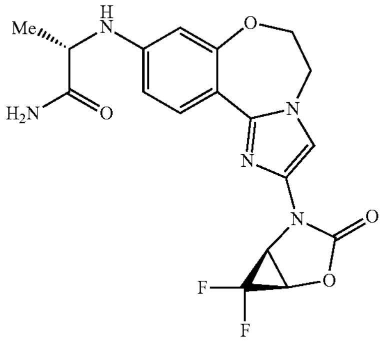 [SMILES: C[C@H](Nc1ccc2c(c1)OCCn1cc(N3C(=O)O[C@@H]4[C@H]3C4(F)F)nc1-2)C(N)=O]

(S)-2-((2-((1R,5S)-6,6-Difluoro-3-oxo-2-oxa-4-azabicyclo[3.1.0]hexan-4-yl)-5,6-d ihydrobenzo[f]imidazo[1,2-d][1,4]oxazepin-9-yl)amino)propanamide was prepared by referring to the method of Example 1.

MS m/z (ESI): 406.1 $[M+H]^+$.

Example 63

Preparation of (S)-2-((2-((S)-1,1-difluoro-5-oxo-6-oxa-4-azaspiro[2.4]heptan-4-yl)-5,6-dihydrobenzo[f]imidazo[1,2-d][1,4]oxazepin-9-yl)amino)propanamide

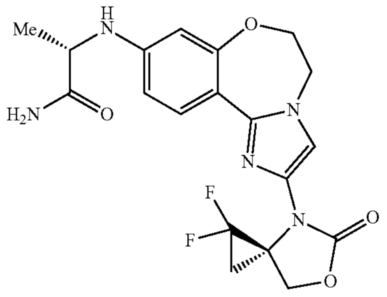 [SMILES: C[C@H](Nc1ccc2c(c1)OCCn1cc(N3C(=O)OC[C@]34CC4(F)F)nc1-2)C(N)=O]

(S)-2-((2-((S)-1,1-Difluoro-5-oxo-6-oxa-4-azaspiro[2.4]heptan-4-yl)-5,6-dihydrobe nzo[f]imidazo[1,2-d][1,4]oxazepin-9-yl)amino)propanamide was prepared by referring to the method of Example 1.

MS m/z (ESI): 420.1 $[M+H]^+$.

Example 64

Preparation of (S)-2-((2-((S)-5-(difluoromethyl)-3-methyl-2,4-dioxoimidazolidin-1-yl)-5,6-dihydroben zo[f]imidazo[1,2-d][1,4]oxazepin-9-yl)amino)propanamide

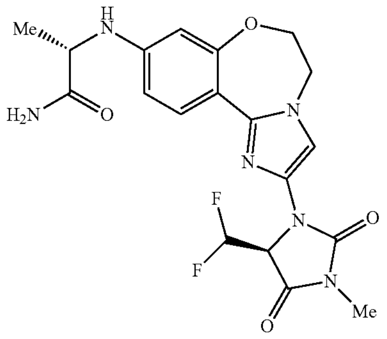 [SMILES: C[C@H](Nc1ccc2c(c1)OCCn1cc(N3C(=O)N(C)C(=O)[C@H]3C(F)F)nc1-2)C(N)=O]

(S)-2-((2-((S)-5-(Difluoromethyl)-3-methyl-2,4-dioxoimidazolidin-1-yl)-5,6-dihyd robenzo[f]imidazo[1,2-d][1,4]oxazepin-9-yl)amino)propanamide was prepared by referring to the method of Example 1.

MS m/z (ESI): 435.2 $[M+H]^+$.

Example 65

Preparation of methyl (9-(((S)-1-amino-1-oxopropan-2-yl)amino)-5,6-dihydrobenzo[f]imidazo[1,2-d][1,4]oxa zepin-2-yl)((S)-2,2-difluorocyclopropyl) carbamate

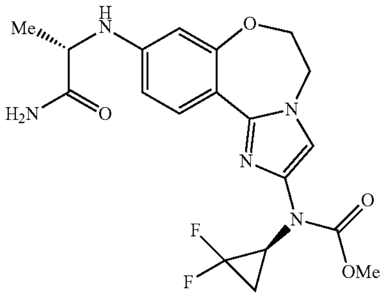 [SMILES: COC(=O)N(c1cn2c(n1)-c1ccc(N[C@@H](C)C(N)=O)cc1OCC2)[C@H]1CC1(F)F]

Methyl (9-(((S)-1-amino-1-oxopropan-2-yl)amino)-5,6-dihydrobenzo[f]imidazo[1,2-d][1,4]oxa zepin-2-yl)((S)-2,2-difluorocyclopropyl) carbamate was prepared by referring to the method of Example 1.

MS m/z (ESI): 422.2 [M+H]+.

Example 66

Preparation of (S)-2-((2-(5,5-difluoro-2-oxo-1,3-oxazinan-3-yl)-5,6-dihydrobenzo[f]imidazo[1,2-d][1,4]oxazepin-9-yl)amino)propanamide

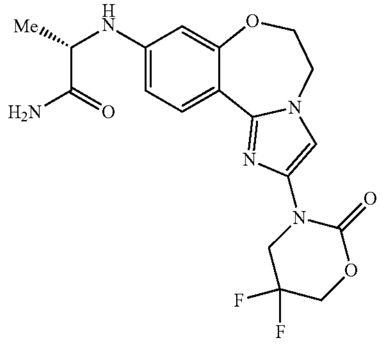 [SMILES: C[C@H](Nc1ccc2c(c1)OCCn1cc(N3CC(F)(F)COC3=O)nc1-2)C(N)=O]

(S)-2-((2-(5,5-Difluoro-2-oxo-1,3-oxazinan-3-yl)-5,6-dihydrobenzo[f]imidazo[1,2-d][1,4]oxazepin-9-yl)amino)propanamide was prepared by referring to the method of Example 1.

$^1H$ NMR (400 MHz, $CD_3OD$) δ 1.37 (d, J=7.0 Hz, 3H), 3.70-3.75 (m, 1H), 4.21-4.25 (m, 2H), 4.26-4.32 (m, 3H), 4.44-4.52 (m, 3H), 6.08 (d, J=2.2 Hz, 1H), 6.36-6.33 (m, 1H), 7.13 (s, 1H), 7.96 (d, J=8.8 Hz, 1H);

MS m/z (ESI): 408.1 $[M+H]^+$.

Example 67

Preparation of (S)-2-((2-((S)-4-(difluoromethyl)-2-oxo-1,3-oxazinan-3-yl)-5,6-dihydrobenzo[f]imidazo[1,2-d][1,4]oxazepin-9-yl)amino)propanamide

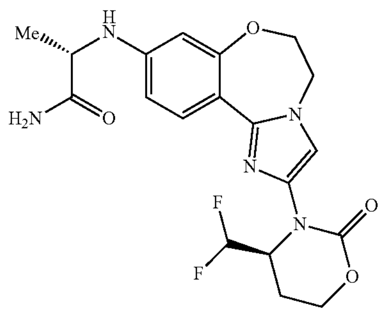

Step 1: Preparation of methyl ((benzyloxy)carbonyl)-L-homoserinate

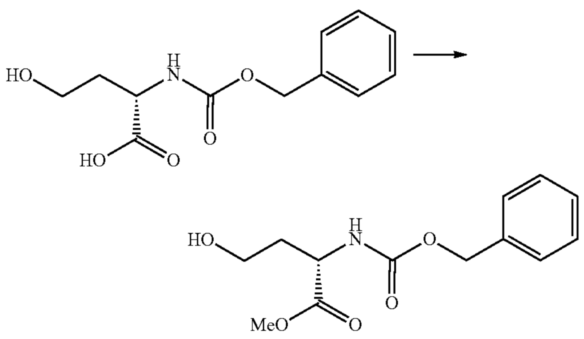

Potassium carbonate (545 mg, 3.95 mmol) and methyl iodide (617 mg, 4.35 mmol) were successively added to a solution of ((benzyloxy)carbonyl)-L-homoserine (1.0 g, 3.95 mmol) in N,N-dimethylformamide (6 mL), and the reaction solution was stirred at room temperature overnight. Saturated sodium bicarbonate solution was added to quench the reaction, and the reaction solution was extract with EtOAc. The organic phases were collected, dried over anhydrous sodium sulfate and concentrated under reduced pressure. The residue was subjected to column chromatography to obtain the title compound methyl ((benzyloxy) carbonyl)-L-homoserinate (920 mg, 87%).

MS m/z (ESI): 268.1 $[M+H]^+$.

Step 2: Preparation of methyl L-homoserinate

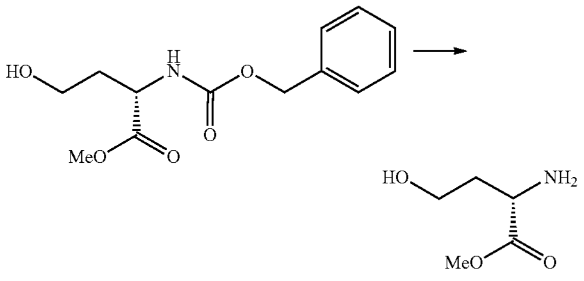

Methyl ((benzyloxy)carbonyl)-L-homoserinate (920 mg, 3.4 mmol) was dissolved in methanol (10 mL), followed by the addition of Pd/C (50 mg). Under a hydrogen atmosphere, the reaction solution was stirred at room temperature overnight. The reaction solution was filtered, and concentrated under reduced pressure obtain the crude title compound methyl L-homoserinate (288 mg, 64%).

MS m/z (ESI): 134.1 $[M+H]^+$.

Step 3: Preparation of methyl(S)-2-oxo-1,3-oxazinane-4-carboxylate

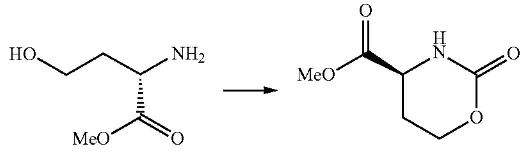 [SMILES: COC(=O)[C@@H](N)CCO ; COC(=O)[C@@H]1CCOC(=O)N1]

Methyl L-homoserinate (288 mg, 2.2 mmol) was dissolved in dichloromethane (15 mL), and the resulting solution was cooled in an ice bath. Triphosgene (258 mg, 0.87 mmol) was added, then a solution of triethylamine (658 mg, 6.51 mmol) in dichloromethane (2 mL) was added dropwise. After completion of the addition, the reaction solution was reacted in an ice bath for 1 hour. Water was added, and the reaction solution was extracted with dichloromethane. The organic phase was dried over anhydrous sodium sulfate, and concentrated under reduced pressure. The resulting crude product was purified by column chromatography to obtain the pure product methyl (S)-2-oxo-1,3-oxazinane-4-carboxylate (110 mg, 32%).

MS m/z (ESI): 160.1 $[M+H]^+$.

Step 4: Preparation of methyl(S)-3-benzyl-2-oxo-1,3-oxazinane-4-carboxylate

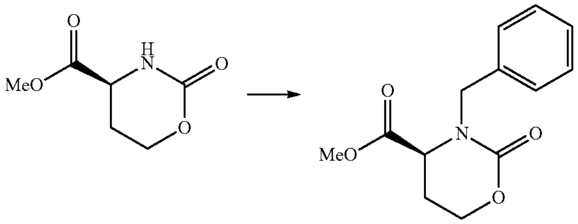 [SMILES: COC(=O)[C@@H]1CCOC(=O)N1 ; COC(=O)[C@@H]1CCOC(=O)N1Cc1ccccc1]

Methyl(S)-2-oxo-1,3-oxazinane-4-carboxylate (110 mg, 0.7 mmol) was dissolved in tetrahydrofuran (12 mL), and the resulting solution was cooled in an ice bath. Sodium hydride (42 mg, 1.06 mmol) was added, and the reaction solution was stirred for 10 minutes, then a solution of benzyl bromide (142 mg, 0.84 mmol) in tetrahydrofuran (2 mL) was added dropwise. After completion of the addition, the reaction solution was gradually warmed up to room temperature and reacted for 2 hours. Saturated ammonium chloride solution was added, and the reaction solution was extracted with ethyl acetate. The organic phase was dried over anhydrous sodium sulfate, and concentrated under reduced pressure. The resulting crude product was purified by column chromatography to obtain the pure product methyl (S)-3-benzyl-2-oxo-1,3-oxazinane-4-carboxylate (100 mg, 57%).

MS m/z (ESI): 250.1 $[M+H]^+$.

Step 5: Preparation of (S)-3-benzyl-4-(hydroxymethyl)-1,3-oxazinan-2-one

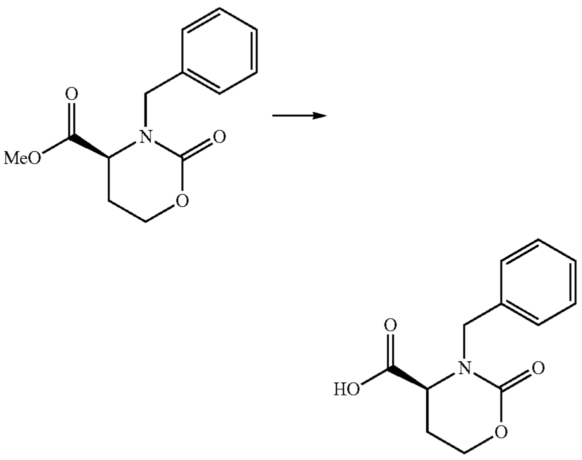

Methyl(S)-3-benzyl-2-oxo-1,3-oxazinane-4-carboxylate (100 mg, 0.4 mmol) was dissolved in methanol (5 mL), and the resulting solution was cooled in an ice bath. Sodium borohydride (30 mg, 0.8 mmol) was added in batches, and the reaction solution was gradually warmed up to room temperature and reacted for 2 hours. The reaction solution was concentrated, and the resulting crude product was purified by column chromatography to obtain the pure product (S)-3-benzyl-4-(hydroxymethyl)-1,3-oxazinan-2-one (70 mg, 79%).

MS m/z (ESI): 222.1 $[M+H]^+$.

Step 6: Preparation of (S)-3-benzyl-2-oxo-1,3-oxazinane-4-carbaldehyde

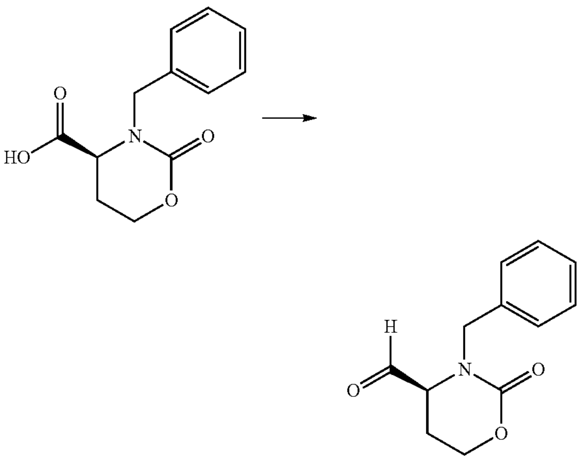

(S)-3-Benzyl-4-(hydroxymethyl)-1,3-oxazinan-2-one (70 mg, 0.32 mmol) and IBX (269 mg, 0.96 mmol) were mixed in ethyl acetate (5 mL). Under a nitrogen atmosphere, the reaction solution was stirred at 85° C. for 3 hours. The reaction solution was cooled and filtered. The filtrate was concentrated under reduced pressure to obtain the crude product(S)-3-benzyl-2-oxo-1,3-oxazinane-4-carbaldehyde (68 mg), which was used directly in the next step.

MS m/z (ESI): 220.1 $[M+H]^+$.

Step 7: Preparation of (S)-3-benzyl-4-(difluoromethyl)-1,3-oxazinan-2-one

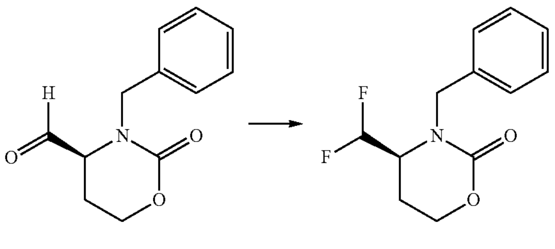 [SMILES: O=C[C@@H]1CCOC(=O)N1Cc1ccccc1 ; O=C1OCC[C@@H](C(F)F)N1Cc1ccccc1]

(S)-3-Benzyl-2-oxo-1,3-oxazinane-4-carbaldehyde (68 mg, 0.31 mmol) was dissolved in dichloromethane (5 mL). Under a nitrogen atmosphere, DAST (100 mg, 0.62 mmol) was added dropwise to the reaction solution in an ice bath. The reaction solution was naturally warmed up to room temperature and reacted for 3 hours. The reaction solution was slowly added dropwise to the pre-cooled saturated aqueous sodium bicarbonate solution, and extract with dichloromethane (10 mL×2). The organic phases were combined and concentrate under reduced pressure. The residue was subjected to column chromatography to obtain the title compound (S)-3-benzyl-4-(difluoromethyl)-1,3-oxazinan-2-one (55 mg, 73%).

MS m/z (ESI): 242.1 $[M+H]^+$.

Step 8: Preparation of (S)-4-(difluoromethyl)-1,3-oxazinan-2-one

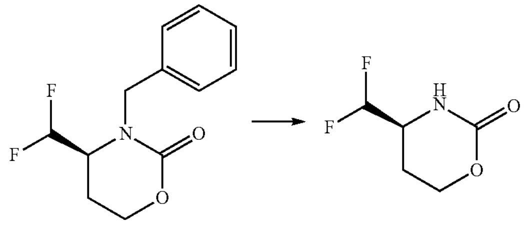 [SMILES: O=C1OCC[C@@H](C(F)F)N1Cc1ccccc1 ; O=C1N[C@H](C(F)F)CCO1]

(S)-3-Benzyl-4-(difluoromethyl)-1,3-oxazinan-2-one (55 mg, 0.23 mmol) was dissolved in ethanol (5 mL), followed by the addition of $Pd(OH)_2/C$ (10 mg). Under a hydrogen atmosphere, the reaction solution was stirred at 70° C. overnight. The reaction solution was cooled and filtered. The filtrate was concentrated under reduced pressure to obtain the title compound (S)-4-(difluoromethyl)-1,3-oxazinan-2-one (28 mg, 81%).

MS m/z (ESI): 152.1 $[M+H]^+$.

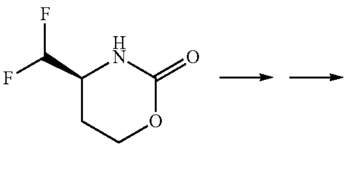

-continued

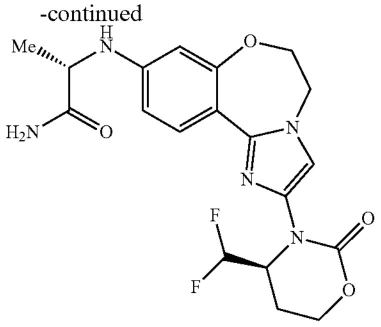

(S)-2-((2-((S)-4-(Difluoromethyl)-2-oxo-1,3-oxazinan-3-yl)-5,6-dihydrobenzo[f]im idazo[1,2-d][1,4]oxazepin-9-yl) amino)propanamide was prepared by referring to the method of Example 1.

MS m/z (ESI): 422.2 [M+H]$^+$.

Example 68

Preparation of (S)-2-((2-((S)-3-(difluoromethyl)-5-oxomorpholino)-5,6-dihydrobenzo[f]imidazo[1,2-d][1,4]oxazepin-9-yl)amino)propanamide

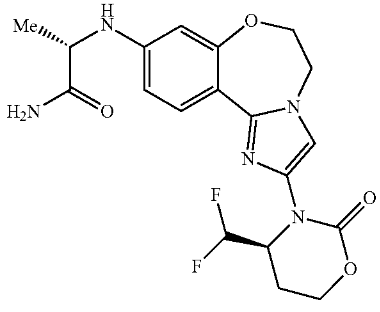 [SMILES: C[C@H](Nc1ccc2c(c1)OCCn1cc(N3C(=O)OCC[C@H]3C(F)F)nc1-2)C(N)=O]

Step 1: Preparation of (S)-2-(benzylamino)-3,3-difluoropropan-1-ol

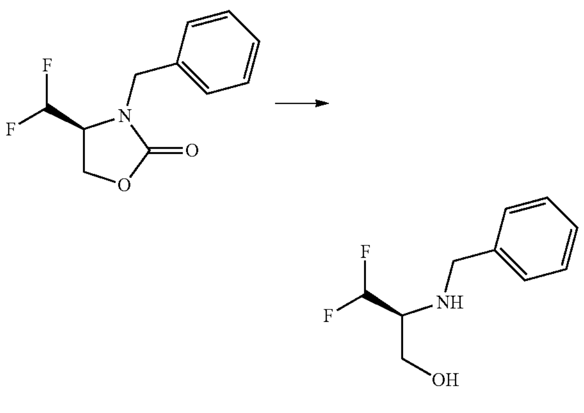

5 mol/L aqueous sodium hydroxide solution (1.5 mL, 7.5 mmol) was added to a solution of (S)-3-benzyl-4-(difluoromethyl)oxazolidin-2-one (340 mg, 1.5 mmol) in methanol (5 mL) at room temperature. After completion of the addition, the reaction solution was warmed up to 55° C., and stirred at this temperature for 3 hours. The reaction solution was cooled and concentrated under reduced pressure to remove the organic solvent. Water was added to the reaction flask, and the reaction solution was extracted with ethyl acetate three times. The organic phases were combined, dried over anhydrous sodium sulfate and concentrated under reduced pressure to remove the organic solvent and obtain the crude title compound (S)-2-(benzylamino)-3,3-difluoropropan-1-ol, which was used directly in the next step.

MS m/z (ESI): 202.1 [M+H]$^+$.

Step 2: Preparation of (S)-N-benzyl-2-chloro-N-(1,1-difluoro-3-hydroxypropan-2-yl)acetamide

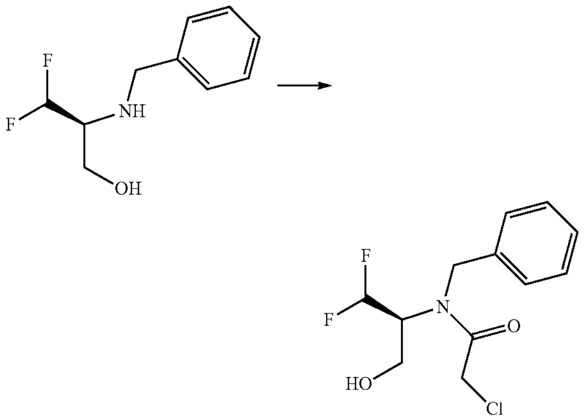

A solution of chloroacetyl chloride (186 mg, 1.65 mmol) in tetrahydrofuran (2 mL) was added dropwise to a solution of (S)-2-(benzylamino)-3,3-difluoropropan-1-ol (301 mg, 1.5 mmol) and triethylamine (379 mg, 3.75 mmol) in tetrahydrofuran (10 mL) in an ice bath. After completion of the addition, the reaction solution was stirred at this temperature for 2 hours. Water was added to the reaction flask to quench the reaction, and the reaction solution was extracted with ethyl acetate three times. The organic phases were combined, dried over anhydrous sodium sulfate and concentrated under reduced pressure to remove the organic solvent and obtain the crude title compound (S)-N-benzyl-2-chloro-N-(1,1-difluoro-3-hydroxypropan-2-yl)acetamide, which was used directly in the next step.

MS m/z (ESI): 278.1 [M+H]$^+$.

Step 3: Preparation of (S)-4-benzyl-5-(difluoromethyl)morpholin-3-one

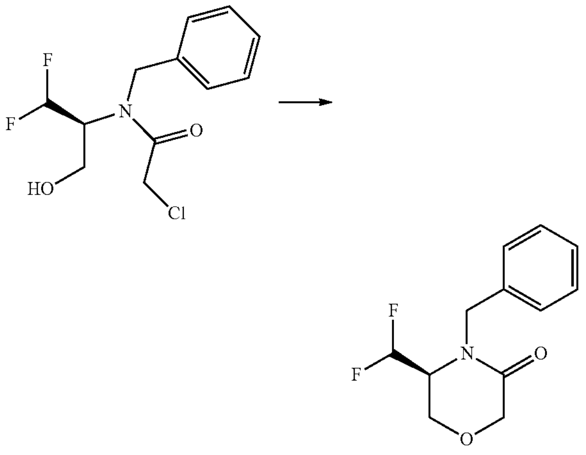

Sodium hydride (72 mg, 1.8 mmol) was added to a solution of (S)-N-benzyl-2-chloro-N-(1,1-difluoro-3-hydroxypropan-2-yl)acetamide (415 mg, 1.5 mmol) in tetrahydrofuran (8 mL) in an ice bath. After completion of the addition, the reaction solution was gradually warmed up to room temperature and stirred for 3 hours. Saturated ammonium chloride solution was added to the reaction flask to quench the reaction, and the reaction solution was extracted with ethyl acetate three times. The organic phases were combined, washed with saturated brine, dried over anhydrous sodium sulfate and concentrated under reduced pressure to remove the organic solvent. The residue was subjected to column chromatography to obtain the title compound (S)-4-benzyl-5-(difluoromethyl)morpholin-3-one (240 mg, 66%).

MS m/z (ESI): 242.1 $[M+H]^+$.

Step 4: Preparation of (S)-5-(difluoromethyl)morpholin-3-one

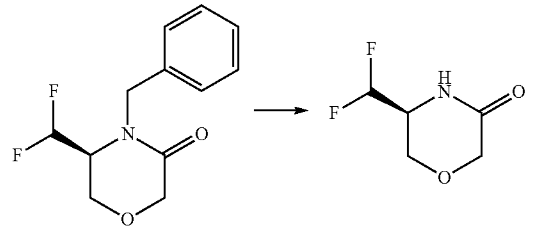 [SMILES: O=C1COC[C@@H](C(F)F)N1Cc1ccccc1 ; O=C1COC[C@@H](C(F)F)N1]

(S)-4-Benzyl-5-(difluoromethyl)morpholin-3-one (240 mg, 1.0 mmol) was dissolved in a solution of methanesulfonic acid (0.5 mL) and mesitylene (2.5 mL) at room temperature. The reaction solution was reacted under microwave at 135° C. for 1.5 hours. The reaction solution was concentrated, saturated aqueous sodium carbonate solution was added, and the reaction solution was extracted with ethyl acetate three times. The organic phases were combined, dried over anhydrous sodium sulfate and concentrated under reduced pressure to remove the organic solvent and obtain the crude title compound (S)-5-(difluoromethyl) morpholin-3-one.

MS m/z (ESI): 152.1 $[M+H]^+$.

Step 5: Preparation of (S)-4-(9-bromo-5,6-dihydrobenzo[f] imidazo[1,2-d][1,4]oxazepin-2-yl)-5-(difluorometh yl)morpholin-3-one

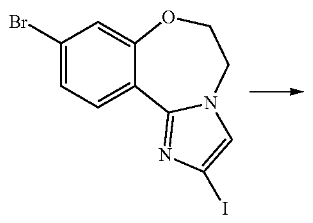

-continued

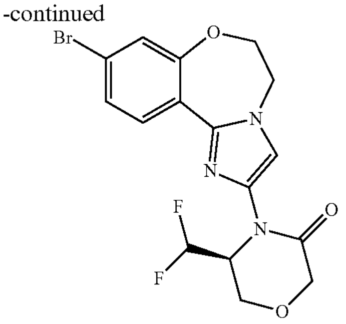

10-Bromo-2-iodo-6,7-dihydro-5H-benzo[b]imidazo[2,1-d][1,5]oxazocine (258 mg, 0.66 mmol), (S)-5-(difluoromethyl)morpholin-3-one (100 mg, 0.66 mmol), (1R,2R)-$N^1$, $N^2$-dimethylcyclohexane-1,2-diamine (38 mg, 0.27 mmol), cuprous iodide (25 mg, 0.13 mmol) and potassium carbonate (183 mg, 1.32 mmol) were mixed in 1,4-dioxane (4 mL). The reaction system was purged with nitrogen three times, and reacted at 125° C. for 5 hours. The reaction solution was cooled to room temperature, 15% ammonia (5 mL) was added, and the reaction solution was stirred for 5 minutes and extracted with EtOAc three times. The organic phases were combined, washed with saturated aqueous sodium chloride solution, dried over anhydrous sodium sulfate, and concentrated under reduced pressure to remove the organic solvent. The residue was subjected to column chromatography to obtain the title compound (S)-4-(9-bromo-5,6-dihydrobenzo[f]imidazo[1,2-d][1,4]oxazepin-2-yl)-5-(difluorometh yl)morpholin-3-one (110 mg, 40%).

MS m/z (ESI): 414.0 $[M+H]^+$.

Step 6: Preparation of (S)-2-((2-((S)-3-(difluoromethyl)-5-oxomorpholino)-5,6-dihydrobenzo[f]imidazo[1,2-d][1,4] oxazepin-9-yl)amino)propanamide

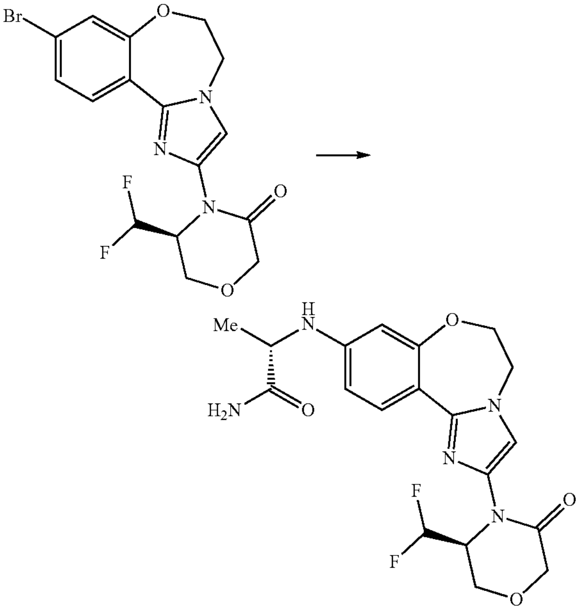

(S)-4-(9-Bromo-5,6-dihydrobenzo[f]imidazo[1,2-d][1,4] oxazepin-2-yl)-5-(difluoro methyl)morpholin-3-one (50 mg, 0.12 mmol), L-alanine (22 mg, 0.24 mmol), cuprous iodide (5 mg, 0.025 mmol) and potassium phosphate (51 mg, 0.24 mmol) were mixed in dimethyl sulfoxide (3 mL). The reaction system was purged with nitrogen three times, and reacted at 105° C. for 2.5 hours. The reaction solution was cooled to room temperature, ammonium chloride (39 mg, 0.73 mmol) and triethylamine (183 mg, 1.82 mmol) were added, and the reaction solution was stirred for 5 minutes. O-(7-azabenzotriazol-1-yl)-N,N,N',N'-tetramethylurea hexafluorophosphate (414 mg, 1.09 mmol) was added, and the reaction solution was stirred at room temperature for 2 hours. The reaction solution was filtered, saturated aqueous sodium bicarbonate solution was added to the filtrate, which was then extracted with ethyl acetate three times. The organic phases were combined, dried over anhydrous sodium sulfate, and concentrated under reduced pressure to remove the organic solvent. The residue was subjected to column chromatography obtain the title compound to (S)-2-((2-((S)-3-(difluoromethyl)-5-oxomorpholino)-5,6-dihydrobenzo[f]imidazo[1,2-d][1,4]oxazepin-9-yl)amino)propanamide (8.6 mg, 17%).

$^1$H NMR (400 MHz, $CD_3OD$) δ 1.37 (d, J=7.0 Hz, 3H), 3.75-3.77 (m, 1H), 3.92-3.97 (m, 1H), 4.19-4.21 (m, 1H), 4.22-4.25 (m, 2H), 4.28-4.33 (m, 3H), 4.45-4.53 (m, 2H), 6.06-6.10 (m, 1H), 6.22-6.37 (m, 2H), 7.26 (s, 1H), 7.95 (d, J=8.8 Hz, 1H);

MS m/z (ESI): 422.1 [M+H]$^+$.

Example 69

Preparation of (S)-2-((2-((S)-2-(difluoromethyl)-4-methyl-6-oxopiperazin-1-yl)-5,6-dihydrobenzo[f]imidazo[1,2-d][1,4]oxazepin-9-yl)amino)propanamide

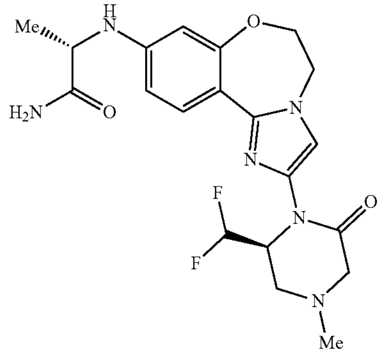 [SMILES: C[C@H](Nc1ccc2c(c1)OCCn1cc(N3C(=O)CN(C)C[C@H]3C(F)F)nc1-2)C(N)=O]

Step 1: Preparation of (S)-2-(benzylamino)-3,3-difluoropropan-1-ol

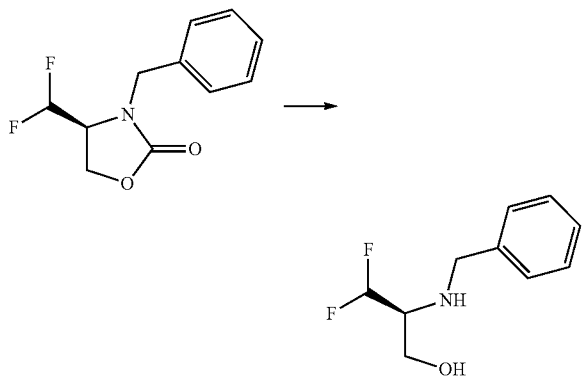

5 mol/L aqueous sodium hydroxide solution (8.8 mL, 44.0 mmol) was added to a solution of (S)-3-benzyl-4-(difluoromethyl)oxazolidin-2-one (2.0 g, 8.8 mmol) in methanol (30 mL) at room temperature. After completion of the addition, the reaction solution was warmed up to 55° C., and stirred at this temperature for 3 hours. The reaction solution was cooled and concentrated under reduced pressure to remove the organic solvent. Water was added to the reaction flask, and the reaction solution was extracted with ethyl acetate three times. The organic phases were combined, dried over anhydrous sodium sulfate and concentrated under reduced pressure to remove the organic solvent and obtain the crude title compound (S)-2-(benzylamino)-3,3-difluoropropan-1-ol, which was used directly in the next step.

MS m/z (ESI): 202.1 [M+H]$^+$.

Step 2: Preparation of (S)-N-benzyl-2-chloro-N-(1,1-difluoro-3-hydroxypropan-2-yl)acetamide

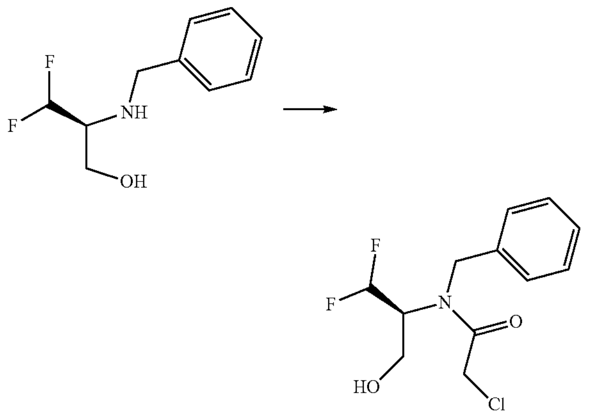

A solution of chloroacetyl chloride (1.2 g, 10.6 mmol) in tetrahydrofuran (5 mL) was added dropwise to a solution of (S)-2-(benzylamino)-3,3-difluoropropan-1-ol (1.8 g, 8.8 mmol) and triethylamine (1.8 g, 17.6 mmol) in tetrahydrofuran (30 mL) in an ice bath. After completion of the addition, the reaction solution was stirred at this temperature for 2 hours. Water was added to the reaction flask to quench the reaction, and the reaction solution was extracted with ethyl acetate three times. The organic phases were combined, dried over anhydrous sodium sulfate and concentrated under reduced pressure to remove the organic solvent and obtain the crude title compound (S)-N-benzyl-2-chloro-N-(1,1-difluoro-3-hydroxypropan-2-yl)acetamide, which was used directly in the next step.

MS m/z (ESI): 278.1 [M+H]$^+$.

Step 3: Preparation of (S)-N-benzyl-N-(1,1-difluoro-3-hydroxypropan-2-yl)-2-(methylamino)acetamide

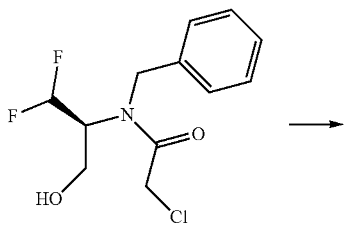

-continued

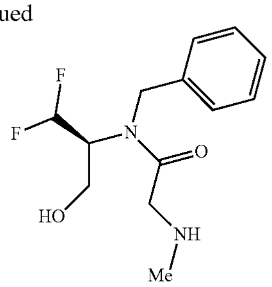

(S)-N-Benzyl-2-chloro-N-(1,1-difluoro-3-hydroxypropan-2-yl)acetamide (1.9 g, 6.9 mmol), methylamine hydrochloride (2.3 g, 34.5 mmol) and triethylamine (4.2 g, 41.4 mmol) were dissolved in tetrahydrofuran (25 mL). The reaction solution was reacted at room temperature for 1 hour, and warmed up to 60° C. and reacted for 2 hours. The reaction solution was concentrated, and the resulting residue was purified by column chromatography to obtain the pure product (S)-N-benzyl-N-(1,1-difluoro-3-hydroxypropan-2-yl)-2-(methylamino)acetamide (1.0 g, 53%).

MS m/z (ESI): 273.1 $[M+H]^+$.

Step 4: Preparation of (S)-1-benzyl-6-(difluoromethyl)-4-methylpiperazin-2-one

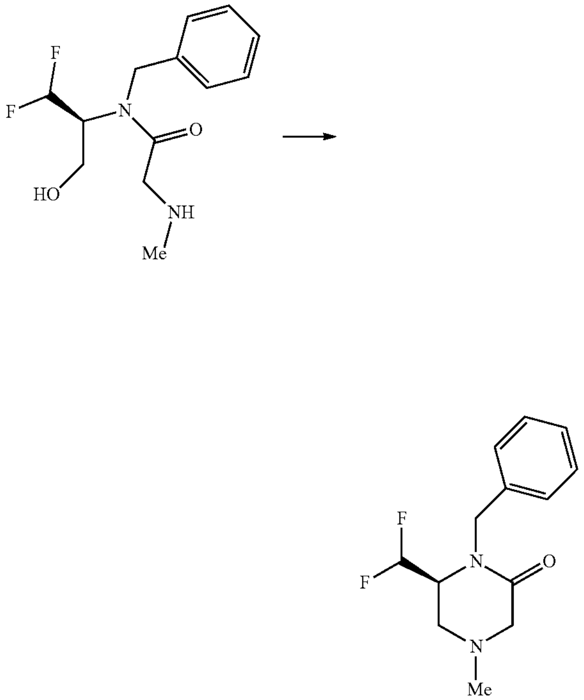

(S)-N-Benzyl-N-(1,1-difluoro-3-hydroxypropan-2-yl)-2-(methylamino)acetamide (272 mg, 1.0 mmol), triphenylphosphorus (341 mg, 1.3 mmol), diisopropyl azodicarboxylate (263 mg, 1.3 mmol) and N,N-diisopropylethylamine (194 mg, 1.5 mmol) were dissolved in tetrahydrofuran (12 mL), and reacted at room temperature overnight. The reaction solution was concentrated, and the resulting residue was purified by column chromatography to obtain the pure product (S)-1-benzyl-6-(difluoromethyl)-4-methylpiperazin-2-one (78 mg, 30%).

MS m/z (ESI): 255.1 $[M+H]^+$.

Step 5: Preparation of (S)-6-(difluoromethyl)-4-methylpiperazin-2-one

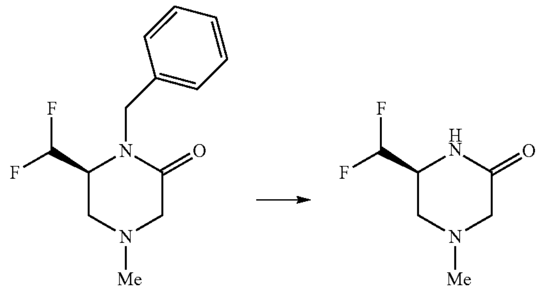 [SMILES: CN1CC(=O)N(Cc2ccccc2)[C@H](C(F)F)C1 ; CN1CC(=O)N[C@H](C(F)F)C1]

(S)-1-Benzyl-6-(difluoromethyl)-4-methylpiperazin-2-one (70 mg, 0.28 mmol) was dissolved in 0.5 mL of methanesulfonic acid at room temperature. The reaction solution was reacted under microwave at 150° C. for 1.5 hours. The reaction solution was concentrated, saturated aqueous sodium carbonate solution was added, and the reaction solution was extracted with ethyl acetate three times. The organic phases were combined, dried over anhydrous sodium sulfate and concentrated under reduced pressure to remove the organic solvent and obtain the crude title compound (S)-6-(difluoromethyl)-4-methylpiperazin-2-one.

MS m/z (ESI): 152.1 $[M+H]^+$.

Step 6: Preparation of (S)-1-(9-bromo-5,6-dihydrobenzo[f]imidazo[1,2-d][1,4]oxazepin-2-yl)-6-(difluorometh yl)-4-methylpiperazin-2-one

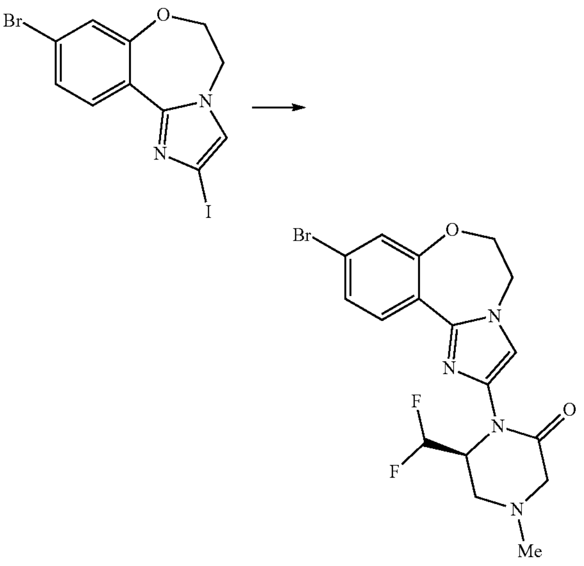

10-Bromo-2-iodo-6,7-dihydro-5H-benzo[b]imidazo[2,1-d][1,5]oxazocine (71 mg, 0.18 mmol), (S)-6-(difluoromethyl)-4-methylpiperazin-2-one (30 mg, 0.18 mmol), (1R, 2R)-$N^1$,$N^2$-dimethylcyclohexane-1,2-diamine (7 mg, 0.04 mmol), cuprous iodide (10 mg, 0.07 mmol) and potassium carbonate (51 mg, 0.37 mmol) were mixed in 1,4-dioxane (4 mL). The reaction system was purged with nitrogen three times, and reacted at 125° C. for 5 hours. The reaction solution was cooled to room temperature, and 15% ammonia was added. The reaction solution was stirred for 5 minutes and extracted with EtOAc three times. The organic phases were combined, washed with saturated aqueous sodium chloride solution, dried over anhydrous sodium sulfate, and concentrated under reduced pressure to remove the organic solvent. The residue was subjected to column chromatography to obtain the title compound (S)-1-(9-bromo-5,6-dihydrobenzo[f]imidazo[1,2-d][1,4]oxazepin-2-yl)-6-(difluorometh yl)-4-methylpiperazin-2-one (63 mg, 82%).

MS m/z (ESI): 427.1 [M+H]$^+$.

Step 7: Preparation of (S)-2-((2-((S)-2-(difluoromethyl)-4-methyl-6-oxopiperazin-1-yl)-5,6-dihydrobenzo[f]im idazo [1,2-d][1,4]oxazepin-9-yl)amino)propanamide

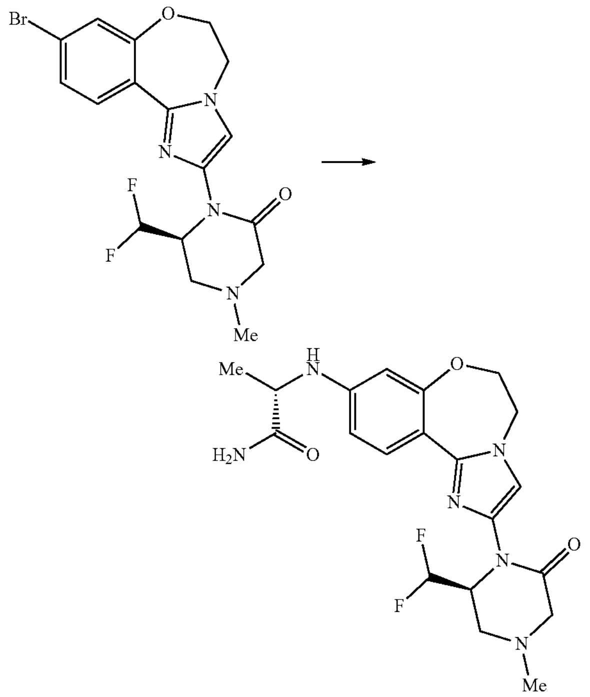

(S)-1-(9-Bromo-5,6-dihydrobenzo[f]imidazo[1,2-d][1,4] oxazepin-2-yl)-6-(difluoro methyl)-4-methylpiperazin-2-one (63 mg, 0.15 mmol), L-alanine (53 mg, 0.6 mmol), cuprous iodide (11 mg, 0.06 mmol) and potassium phosphate (191 mg, 0.9 mmol) were mixed in dimethyl sulfoxide (3 mL). The reaction system was purged with nitrogen three times, and reacted at 105° C. for 2 hours. The reaction solution was cooled to room temperature, ammonium chloride (49 mg, 0.9 mmol) and N,N-diisopropylethylamine (290 mg, 2.25 mmol) were added, and the reaction solution was stirred for 5 minutes. O-(7-azabenzotriazol-1-yl)-N,N,N',N'-tetramethylurea hexafluorophosphate (513 mg, 1.35 mmol) was added, and the reaction solution was stirred at room temperature for 1 hour. The reaction solution was filtered, saturated aqueous sodium bicarbonate solution was added to the filtrate, which was then extracted with ethyl acetate three times. The organic phases were combined, dried over anhydrous sodium sulfate, and concentrated under reduced pressure to remove the organic solvent. The residue was subjected to column chromatography the to obtain title compound (S)-2-((2-((S)-2-(difluoromethyl)-4-methyl-6-oxopiperazin-1-yl)-5,6-dihydrobenzo[f]im idazo [1,2-d][1,4]oxazepin-9-yl)amino)propanamide (4.6 mg, 7%).

$^1$H NMR (400 MHz, $CD_3OD$) δ=1.46 (d, J=7.0, 3H), 2.36 (s, 3H), 2.76-2.81 (m, 1H), 3.02 (s, 1H), 3.15-3.21 (m, 1H), 3.50-3.55 (m, 1H), 3.79-3.85 (m, 1H), 4.30-4.35 (m, 2H), 4.38-4.42 (m, 2H), 4.72-4.79 (m, 1H), 6.07-6.36 (m, 1H), 6.15-6.19 (m, 1H), 6.40-6.46 (m, 1H), 7.26 (s, 1H), 8.02 (d, J=8.8, 1H);

MS m/z (ESI): 435.1 [M+H]$^+$.

Example 70

Preparation of (S)-2-((2-((S)-2-(difluoromethyl)-6-oxopiperazin-1-yl)-5,6-dihydrobenzo[f]imidazo[1,2-d][1,4]oxazepin-9-yl)amino)propanamide

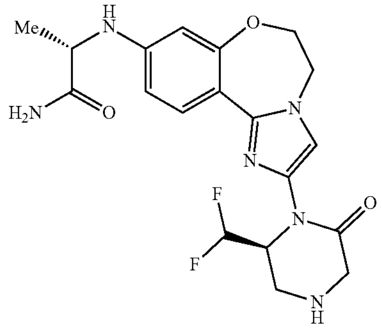 [SMILES: C[C@H](Nc1ccc2c(c1)OCCn1cc(N3C(=O)CNC[C@H]3C(F)F)nc1-2)C(N)=O]

(S)-2-((2-((S)-2-(Difluoromethyl)-6-oxopiperazin-1-yl)-5,6-dihydrobenzo[f]imidaz o[1,2-d][1,4]oxazepin-9-yl) amino)propanamide was prepared by referring to the method of Example 69.

MS m/z (ESI): 421.2 [M+H]$^+$.

Example 71

Preparation of (S)-2-((2-((S)-2-(difluoromethyl)-4-oxooxazolidin-3-yl)-5,6-dihydrobenzo[f]imidazo[1,2-d][1,4]oxazepin-9-yl)amino)propanamide

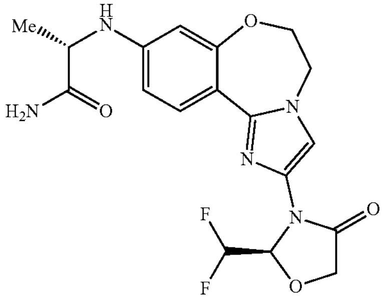 [SMILES: C[C@H](Nc1ccc2c(c1)OCCn1cc(N3C(=O)CO[C@H]3C(F)F)nc1-2)C(N)=O]

(S)-2-((2-((S)-2-(Difluoromethyl)-4-oxooxazolidin-3-yl)-5,6-dihydrobenzo[f]imida zo[1,2-d][1,4]oxazepin-9-yl) amino)propanamide was prepared by referring to the method of Example 1.

MS m/z (ESI): 408.1 [M+H]$^+$.

Example 72

Preparation of (S)-2-((2-((S)-4-(chlorodifluoromethyl)-2-oxooxazolidin-3-yl)-5,6-dihydrobenzo[f]imid azo[1,2-d][1,4]oxazepin-9-yl)amino)propanamide

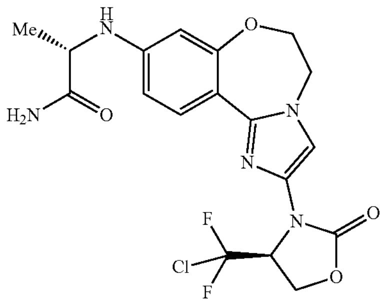 [SMILES: C[C@H](Nc1ccc2c(c1)OCCn1cc(N3C(=O)OC[C@H]3C(F)(F)Cl)nc1-2)C(N)=O]

(S)-2-((2-((S)-4-(Chlorodifluoromethyl)-2-oxooxazolidin-3-yl)-5,6-dihydrobenzo[f]imidazo[1,2-d][1,4]oxazepin-9-yl)amino)propanamide was prepared by referring to the method of Example 1.

MS m/z (ESI): 442.1 $[M+H]^+$.

Example 73

Preparation of (2S)-2-((2-((4S)-4-(difluoromethyl)-2-oxido-1,2,3-oxathiazolidin-3-yl)-5,6-dihydrobenz o[f]imidazo[1,2-d][1,4]oxazepin-9-yl)amino)propanamide

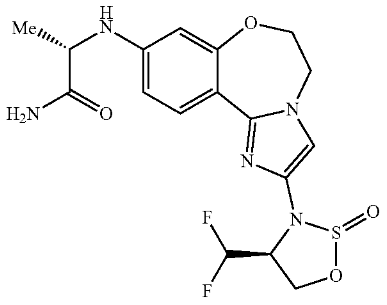 [SMILES: C[C@H](Nc1ccc2c(c1)OCCn1cc(N3[C@H](C(F)F)COS3=O)nc1-2)C(N)=O]

(2S)-2-((2-((4S)-4-(Difluoromethyl)-2-oxido-1,2,3-oxathiazolidin-3-yl)-5,6-dihydr obenzo[f]imidazo[1,2-d][1,4]oxazepin-9-yl)amino)propanamide was prepared by referring to the method of Example 1.

MS m/z (ESI): 428.1 $[M+H]^+$.

Example 74

Preparation of (S)-2-((2-((S)-4-(difluoromethyl)-2,2-dioxido-1,2,3-oxathiazolidin-3-yl)-5,6-dihydroben zo[f]imidazo[1,2-d][1,4]oxazepin-9-yl)amino)propanamide

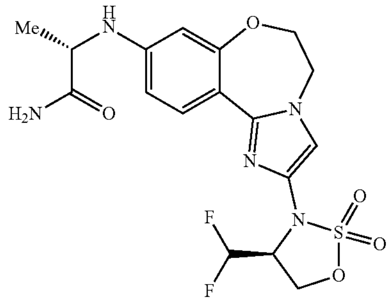 [SMILES: C[C@H](Nc1ccc2c(c1)OCCn1cc(N3[C@H](C(F)F)COS3(=O)=O)nc1-2)C(N)=O]

(S)-2-((2-((S)-4-(Difluoromethyl)-2,2-dioxido-1,2,3-oxathiazolidin-3-yl)-5,6-dihyd robenzo[f]imidazo[1,2-d][1,4]oxazepin-9-yl)amino)propanamide was prepared by referring to the method of Example 1.

MS m/z (ESI): 444.1 $[M+H]^+$.

Example 75

Preparation of (S)-2-((2-((S)-3-(difluoromethyl)-1,1-dioxidoisothiazolidin-2-yl)-5,6-dihydrobenzo[f]i midazo[1,2-d][1,4]oxazepin-9-yl)amino)propanamide

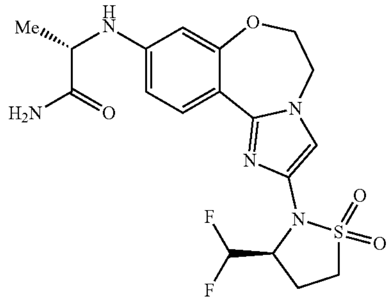 [SMILES: C[C@H](Nc1ccc2c(c1)OCCn1cc(N3[C@H](C(F)F)CCS3(=O)=O)nc1-2)C(N)=O]

(S)-2-((2-((S)-3-(Difluoromethyl)-1,1-dioxidoisothiazolidin-2-yl)-5,6-dihydrobenz o[f]imidazo[1,2-d][1,4]oxazepin-9-yl)amino)propanamide was prepared by referring to the method of Example 1.

MS m/z (ESI): 442.1 $[M+H]^+$.

Example 76

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-N-hydroxypropanamide

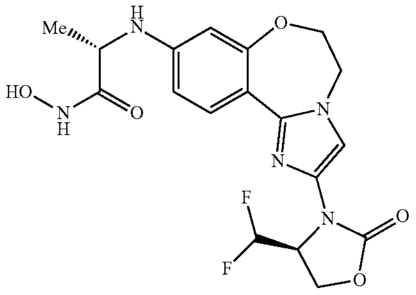 [SMILES: C[C@H](Nc1ccc2c(c1)OCCn1cc(N3C(=O)OC[C@H]3C(F)F)nc1-2)C(=O)NO]

(S)-2-((2-((S)-4-(Difluoromethyl)-2-oxooxazolidin-3-yl)-5,6-dihydrobenzo[f]imida zo[1,2-d][1,4]oxazepin-9-yl) amino)-N-hydroxypropanamide was prepared by referring to the method of Example 1.

$^1$H NMR (400 MHz, $CD_3OD$): δ 1.45 (d, J=6.9 Hz, 3H), 3.79-3.94 (m, 1H), 4.31-4.41 (m, 4H), 4.50-4.70 (m, 3H), 6.18-6.22 (m, 1H), 6.42-6.73 (m, 2H), 7.15 (s, 1H), 8.04 (d, J=8.8 Hz, 1H);

MS m/z (ESI): 424.1 $[M+H]^+$.

Example 77

Preparation of (S)-2-((2-((S)-4-(difluoromethyl)-2-oxooxazolidin-3-yl)-8-fluoro-5,6-dihydrobenzo[f]imidazo[1,2-d][1,4]oxazepin-9-yl)amino)propanamide

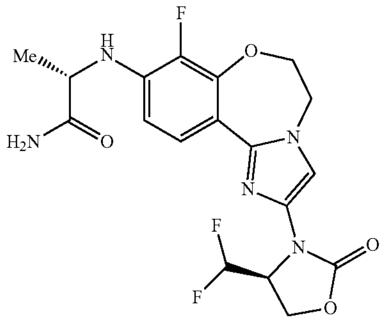 [SMILES: C[C@H](Nc1ccc2c(c1F)OCCn1cc(N3C(=O)OC[C@H]3C(F)F)nc1-2)C(N)=O]

Step 1: Preparation of 4-bromo-3-fluoro-2-methoxybenzaldehyde

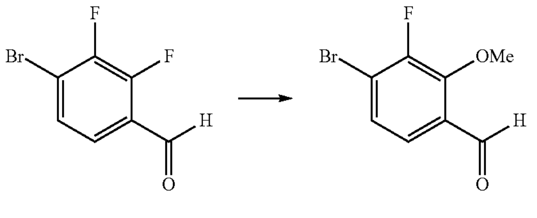 [SMILES: O=Cc1ccc(Br)c(F)c1F ; COc1c(C=O)ccc(Br)c1F]

Sodium methoxide (733 mg, 13.56 mmol) was added to a solution of 4-bromo-2,3-difluorobenzaldehyde (2.0 g, 9.05 mmol) in methanol (25 mL) at room temperature. The reaction solution was warmed up to 65° C. and reacted for 2 hours. The reaction solution was concentrated, and the resulting residue was purified by column chromatography to obtain 4-bromo-3-fluoro-2-methoxybenzaldehyde (1.78 g, 85%).

MS m/z (ESI): 233.0 $[M+H]^+$.

Step 2: Preparation of 4-bromo-3-fluoro-2-hydroxybenzaldehyde

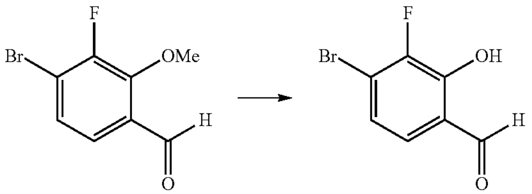 [SMILES: COc1c(C=O)ccc(Br)c1F ; O=Cc1ccc(Br)c(F)c1O]

Hydrobromic acid (8.7 mL, 48%) was added to a solution of 4-bromo-3-fluoro-2-methoxybenzaldehyde (1.78 g, 7.67 mmol) in acetic acid (15 mL) at room temperature. The reaction solution was warmed up to 120° C. and reacted for 16 hours. The reaction solution was cooled and concentrated under reduced pressure. Water and ethyl acetate were added to the reaction flask, and then two phases were separated. The organic phase was dried over anhydrous sodium sulfate, and concentrated under reduced pressure to remove the organic solvent. The resulting residue was purified by column chromatography to obtain 4-bromo-3-fluoro-2-hydroxybenzaldehyde (1.12 g, 67%).

MS m/z (ESI): 219.0 $[M+H]^+$.

Step 3: Preparation of 3-bromo-2-fluoro-6-(1H-imidazol-2-yl)phenol

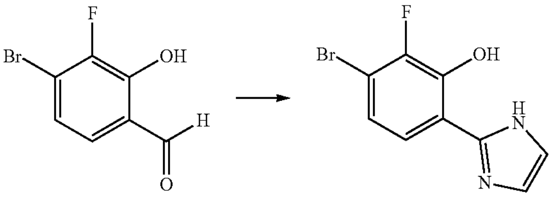 [SMILES: O=Cc1ccc(Br)c(F)c1O ; Oc1c(-c2ncc[nH]2)ccc(Br)c1F]

Aqueous glyoxal solution (40 wt. %, 3.73 g, 25.7 mmol) was added to a solution of 4-bromo-3-fluoro-2-hydroxybenzaldehyde (1.12 g, 5.14 mmol) in methanol (12 mL). In a water bath, ammonia (28 wt. %, 5.14 g, 51.4 mmol) was slowly added dropwise to the reaction solution under stirring, the addition process lasted for 30 minutes, and the temperature of the reaction solution was controlled not to exceed 40° C. The mixture was stirred at 35° C. for two days, cooled and concentrated under reduced pressure to remove the organic solvent. The resulting residue was purified by column chromatography to obtain 3-bromo-2-fluoro-6-(1H-imidazol-2-yl)phenol (1.31 g, 100%).

MS m/z (ESI): 257.0 $[M+H]^+$.

Step 4: Preparation of 9-bromo-8-fluoro-5,6-dihydrobenzo[f]imidazo[1,2-d][1,4]oxazepine

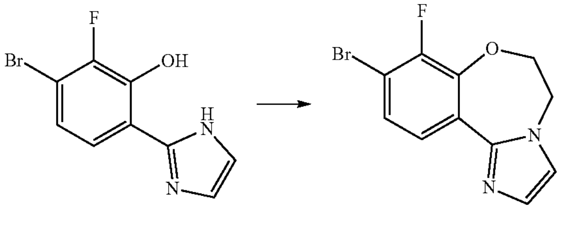 [SMILES: Oc1c(-c2ncc[nH]2)ccc(Br)c1F ; Fc1c(Br)ccc2c1OCCn1ccnc1-2]

3-Bromo-2-fluoro-6-(1H-imidazol-2-yl)phenol (1.31 g, 5.14 mmol), cesium carbonate (6.3 g, 19.53 mmol) and 1,2-dibromoethane (3.6 g, 19.12 mmol) were mixed in DMF (12 mL), and the reaction solution was stirred at 85° C. overnight. The reaction solution was cooled, and diluted with ethyl acetate. The organic phase was washed with saturated brine several times, dried over sodium sulfate, and concentrated under reduced pressure to remove the organic solvent. The resulting residue was purified by column chromatography to obtain the title compound 9-bromo-8-fluoro-5,6-dihydrobenzo[f]imidazo[1,2-d][1,4]oxazepine (995 mg, 69%).

MS m/z (ESI): 283.0 $[M+H]^+$.

Step 5: Preparation of 9-bromo-8-fluoro-2,3-diiodo-5,6-dihydrobenzo[f]imidazo[1,2-d][1,4]oxazepine

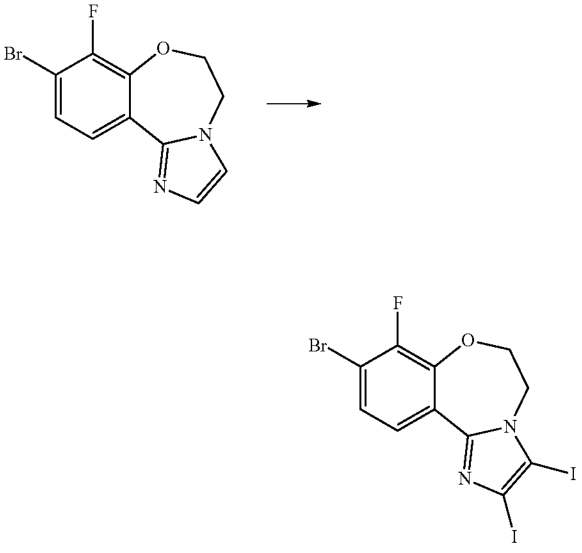

NIS (2.23 g, 9.88 mmol) was added to a solution of 9-bromo-8-fluoro-5,6-dihydrobenzo[f]imidazo[1,2-d][1,4]oxazepine (995 mg, 3.53 mmol) in DMF (8 mL) at room temperature, and the reaction solution was stirred at 60° C. overnight. The reaction solution was cooled, and water was added to precipitate a solid. After filtering, the solid was dissolved in ethyl acetate. The solution was washed with 1 M aqueous NaOH solution and saturated brine successively, dried over anhydrous sodium sulfate, and concentrated to obtain the title compound 9-bromo-8-fluoro-2,3-diiodo-5,6-dihydrobenzo[f]imidazo[1,2-d][1,4]oxazepine (1.79 g, 94%).

MS m/z (ESI): 534.7 $[M+H]^+$.

Step 6: Preparation of 9-bromo-8-fluoro-2-iodo-5,6-dihydrobenzo[f]imidazo[1,2-d][1,4]oxazepine

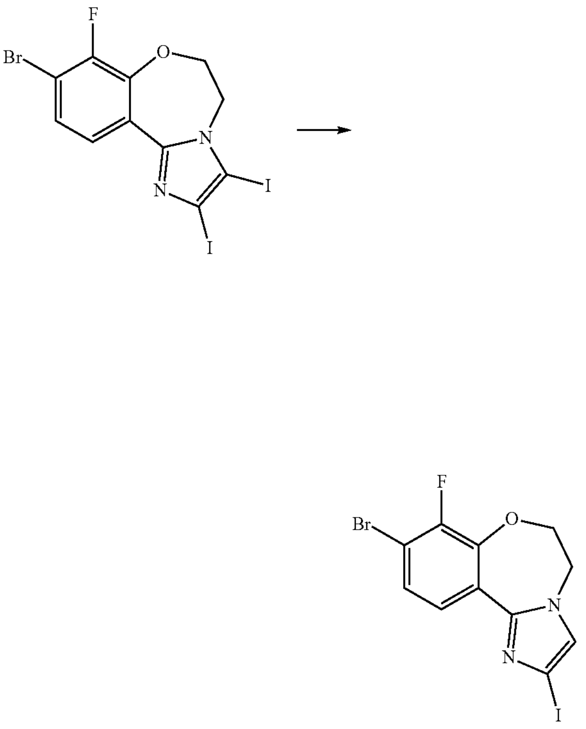

EtMgBr (1.0 M, THF solution, 1.23 mL, 3.69 mmol) was slowly added dropwise to a solution of 9-bromo-8-fluoro-2,3-diiodo-5,6-dihydrobenzo[f]imidazo[1,2-d][1,4]oxazepine (1.79 g, 3.35 mmol) in THF (10 mL) at −20° C. After completion of the addition, the reaction solution was stirred at −15° C. for 3 hours. The reaction solution was slowly warmed up to room temperature, saturated aqueous ammonium chloride solution was added dropwise, and the reaction solution was stirred for 15 minutes. The reaction solution was extracted with ethyl acetate several times. The organic phases were combined, washed with saturated brine, dried over sodium sulfate, and concentrated under reduced pressure to remove the organic solvent. The residue was subjected to column chromatography to obtain the title compound 9-bromo-8-fluoro-2-iodo-5,6-dihydrobenzo[f]imidazo[1,2-d][1,4]oxazepine (610 mg, 45%).

MS m/z (ESI): 408.9 $[M+H]^+$.

Step 7: Preparation of (S)-4-(difluoromethyl)-3-(8-fluoro-9-iodo-5,6-dihydrobenzo[f]imidazo[1,2-d][1,4]oxaze pin-2-yl)oxazolidin-2-one

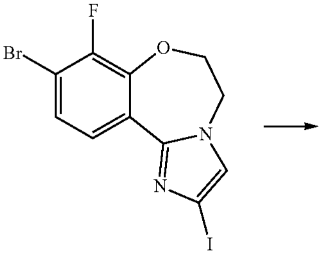

-continued

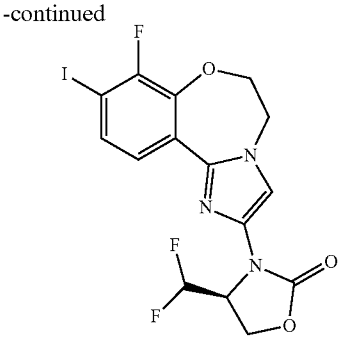

9-Bromo-8-fluoro-2-iodo-5,6-dihydrobenzo[f]imidazo[1,2-d][1,4]oxazepine (300 mg, 0.74 mmol), (S)-4-(difluoromethyl)oxazolidin-2-one (102 mg, 0.74 mmol), (1R,2R)-$N^1$,$N^2$-dimethylcyclohexane-1,2-diamine (42 mg, 0.30 mmol), cuprous iodide (28 mg, 0.15 mmol) and potassium carbonate (205 mg, 1.5 mmol) were mixed in 1,4-dioxane (6 mL). The reaction system was purged with nitrogen three times, and reacted at 105° C. for 5 hours. The reaction solution was cooled to room temperature, and 15% ammonia was added. The solution was stirred for 5 minutes and extracted with EtOAc three times. The organic phases were combined, washed with saturated aqueous sodium chloride solution, dried over anhydrous sodium sulfate, and concentrated under reduced pressure. The residue was subjected to column chromatography to obtain the title compound (S)-4-(difluoromethyl)-3-(8-fluoro-9-iodo-5,6-dihydrobenzo[f]imidazo[1,2-d][1,4]oxaze pin-2-yl)oxazolidin-2-one (225 mg, 65%).

MS m/z (ESI): 466.0 [M+H]+.

(S)-2-((2-((S)-4-(Difluoromethyl)-2-oxooxazolidin-3-yl)-8-fluoro-5,6-dihydrobenz o[f]imidazo[1,2-d][1,4]oxazepin-9-yl)amino)propanamide was prepared by referring to the method of Example 1.

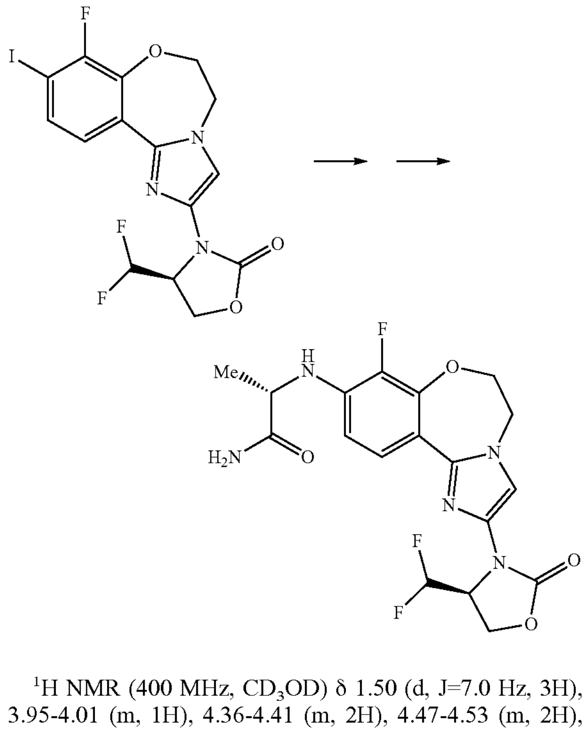

$^1$H NMR (400 MHz, $CD_3OD$) δ 1.50 (d, J=7.0 Hz, 3H), 3.95-4.01 (m, 1H), 4.36-4.41 (m, 2H), 4.47-4.53 (m, 2H), 4.57-4.67 (m, 2H), 4.93-4.98 (m, 1H), 6.37-6.42 (m, 1H), 6.44-6.73 (m, 1H), 7.20 (s, 1H), 7.87-7.91 (m, 1H);

MS m/z (ESI): 426.1 [M+H]+.

Example 78

Preparation of (S)-2-((2-((S)-4-(difluoromethyl)-2-oxooxazolidin-3-yl)-11-fluoro-5,6-dihydrobenzo[f]imidazo[1,2-d][1,4]oxazepin-9-yl)amino)propanamide

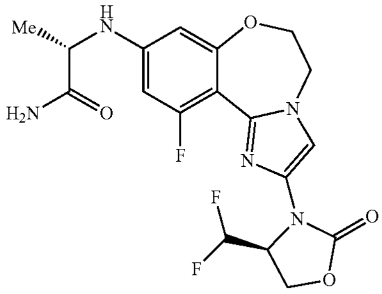 [SMILES: C[C@H](Nc1cc(F)c2c(c1)OCCn1cc(N3C(=O)OC[C@H]3C(F)F)nc1-2)C(N)=O]

(S)-2-((2-((S)-4-(Difluoromethyl)-2-oxooxazolidin-3-yl)-11-fluoro-5,6-dihydroben zo[f]imidazo[1,2-d][1,4]oxazepin-9-yl)amino)propanamide was prepared by referring to the method of Example 1.

$^1$H NMR (400 MHz, $CD_3OD$) δ 1.46 (d, J=4.0 Hz, 3H), 3.84 (m, 1H), 4.24 (m, 2H), 4.49 (m, 2H), 4.60 (m, 3H), 6.19 (s, 1H), 6.28 (d, J=8.0 Hz, 1H), 6.49 (t, J=56 Hz, 1H), 7.30 (s, 1H);

MS m/z (ESI): 426.1 [M+H]+.

Example 79

Preparation of (S)-2-((2-((S)-4-(difluoromethyl)-2-oxooxazolidin-3-yl)-10-fluoro-5,6-dihydrobenzo[f]imidazo[1,2-d][1,4]oxazepin-9-yl)amino)propanamide

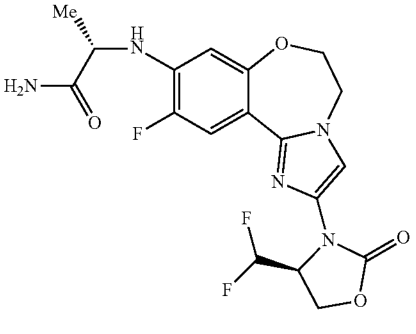 [SMILES: C[C@H](Nc1cc2c(cc1F)-c1nc(N3C(=O)OC[C@H]3C(F)F)cn1CCO2)C(N)=O]

(S)-2-((2-((S)-4-(Difluoromethyl)-2-oxooxazolidin-3-yl)-10-fluoro-5,6-dihydroben zo[f]imidazo[1,2-d][1,4]oxazepin-9-yl)amino)propanamide was prepared by referring to the method of Example 1.

$^1$H NMR (400 MHz, $CD_3OD$): δ 1.52 (d, J=6.8 Hz, 3H), 3.86-3.96 (m, 1H), 4.30-4.42 (m, 4H), 4.60-4.69 (m, 3H), 4.91-5.00 (m, 1H), 6.19-6.25 (m, 1H), 6.46-6.76 (m, 1H), 7.18 (s, 1H), 8.04 (d, J=13.4 Hz, 1H);

MS m/z (ESI): 426.1 [M+H]+.

Example 80

Preparation of (S)-3-(9-(4-amino-5-methyl-1H-imidazol-1-yl)-5,6-dihydrobenzo[f]imidazo[1,2-d][1,4]oxazenin-2-yl)-4-(difluoromethyl)oxazolidin-2-one

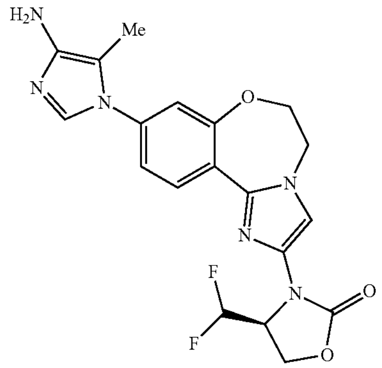 [SMILES: Cc1c(N)ncn1-c1ccc2c(c1)OCCn1cc(N3C(=O)OC[C@H]3C(F)F)nc1-2]

(S)-3-(9-(4-Amino-5-methyl-1H-imidazol-1-yl)-5,6-dihydrobenzo[f]imidazo[1,2-d][1,4]oxazepin-2-yl)-4-(difluoromethyl)oxazolidin-2-one was prepared by referring to the method of Example 1.

MS m/z (ESI): 417.1 [M+H]$^+$.

Example 81

Preparation of (S)-2-((2-((S)-4-(difluoromethyl)-2-oxooxazolidin-3-yl)-8-methyl-5,6-dihydrobenzo[f]imidazo[1,2-d][1,4]oxazepin-9-yl)amino)propanamide

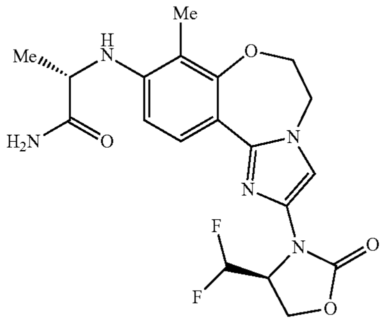 [SMILES: Cc1c(N[C@@H](C)C(N)=O)ccc2c1OCCn1cc(N3C(=O)OC[C@H]3C(F)F)nc1-2]

(S)-2-((2-((S)-4-(Difluoromethyl)-2-oxooxazolidin-3-yl)-8-methyl-5,6-dihydroben zo[f]imidazo[1,2-d][1,4]oxazepin-9-yl)amino)propanamide was prepared by referring to the method of Example 1.

$^1$H NMR (400 MHz, $CD_3OD$) δ 1.51 (d, J=6.9 Hz, 3H), 2.15 (s, 3H), 3.99-4.02 (m, 1H), 4.33-4.37 (m, 2H), 4.43-4.47 (m, 2H), 4.55-4.68 (m, 2H), 4.93-4.97 (m, 1H), 6.36 (d, J=8.9 Hz, 1H), 6.43-6.71 (m, 1H), 7.19 (s, 1H), 7.94 (d, J=8.8 Hz, 1H);

MS m/z (ESI): 422.1 [M+H]$^+$.

Example 82

Preparation of (S)-2-((2-((S)-4-(difluoromethyl)-2-oxooxazolidin-3-yl)-11-methyl-5,6-dihydrobenzo[f]imidazo[1,2-d][1,4]oxazepin-9-yl)amino)propanamide

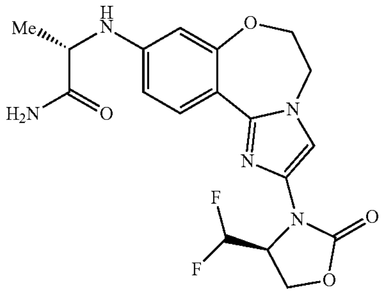 [SMILES: C[C@H](Nc1ccc2c(c1)OCCn1cc(N3C(=O)OC[C@H]3C(F)F)nc1-2)C(N)=O]

(S)-2-((2-((S)-4-(Difluoromethyl)-2-oxooxazolidin-3-yl)-11-methyl-5,6-dihydrobe nzo[f]imidazo[1,2-d][1,4]oxazepin-9-yl)amino)propanamide was prepared by referring to the method of Example 1.

MS m/z (ESI): 422.1 [M+H]$^+$.

Example 83

Preparation of (S)-2-((2-((S)-4-(difluoromethyl)-2-oxooxazolidin-3-yl)-10-methyl-5,6-dihydrobenzo[f]imidazo[1,2-d][1,4]oxazepin-9-yl)amino)propanamide

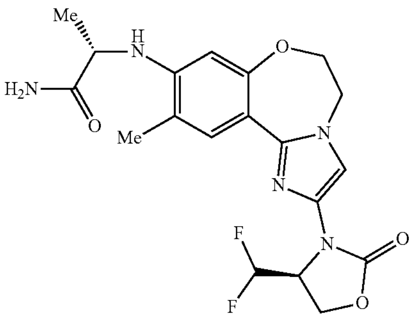 [SMILES: Cc1cc2c(cc1N[C@@H](C)C(N)=O)OCCn1cc(N3C(=O)OC[C@H]3C(F)F)nc1-2]

(S)-2-((2-((S)-4-(Difluoromethyl)-2-oxooxazolidin-3-yl)-10-methyl-5,6-dihydrobe nzo[f]imidazo[1,2-d][1,4]oxazepin-9-yl)amino)propanamide was prepared by referring to the method of Example 1.

$^1$H NMR (400 MHz, $CD_3OD$): δ 1.52 (d, J=6.9 Hz, 3H), 2.19 (s, 3H), 3.85-3.93 (m, 1H), 4.25-4.36 (m, 4H), 4.55-4.67 (m, 2H), 4.92-4.96 (m, 1H), 6.09 (s, 1H), 6.43-6.71 (m, 1H), 7.12 (s, 1H), 7.90 (s, 1H);

MS m/z (ESI): 422.1 [M+H]$^+$.

Example 84

Preparation of (S)-2-((2-((S)-4-(difluoromethyl)-2-oxooxazolidin-3-yl)-8-methoxy-5,6-dihydrobenzo[f]imidazo[1,2-d][1,4]oxazepin-9-yl)amino)propanamide

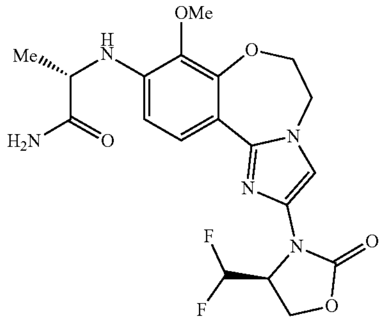 [SMILES: COc1c(N[C@@H](C)C(N)=O)ccc2c1OCCn1cc(N3C(=O)OC[C@H]3C(F)F)nc1-2]

(S)-2-((2-((S)-4-(Difluoromethyl)-2-oxooxazolidin-3-yl)-8-methoxy-5,6-dihydrobe nzo[f]imidazo[1,2-d][1,4]oxazepin-9-yl)amino)propanamide was prepared by referring to the method of Example 1.

MS m/z (ESI): 438.1 [M+H]$^+$.

Example 85

Preparation of (S)-2-((2-((S)-4-(difluoromethyl)-2-oxooxazolidin-3-yl)-11-methoxy-5,6-dihydrobenzo[f]imidazo[1,2-d][1,4]oxazepin-9-yl)amino)propanamide

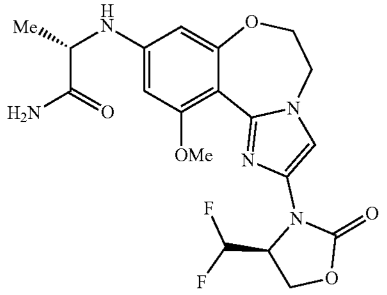 [SMILES: COc1cc(N[C@@H](C)C(N)=O)cc2c1-c1nc(N3C(=O)OC[C@H]3C(F)F)cn1CCO2]

(S)-2-((2-((S)-4-(Difluoromethyl)-2-oxooxazolidin-3-yl)-11-methoxy-5,6-dihydrob enzo[f]imidazo[1,2-d][1,4]oxazepin-9-yl)amino)propanamide was prepared by referring to the method of Example 1.

MS m/z (ESI): 438.1 [M+H]$^+$.

Example 86

Preparation of (S)-2-((2-((S)-4-(difluoromethyl)-2-oxooxazolidin-3-yl)-10-methoxy-5,6-dihydrobenzo[f]imidazo[1,2-d][1,4]oxazepin-9-yl)amino)propanamide

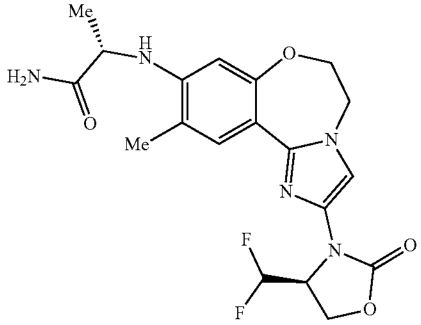 [SMILES: Cc1cc2c(cc1N[C@@H](C)C(N)=O)OCCn1cc(N3C(=O)OC[C@H]3C(F)F)nc1-2]

(S)-2-((2-((S)-4-(Difluoromethyl)-2-oxooxazolidin-3-yl)-10-methoxy-5,6-dihydrob enzo[f]imidazo[1,2-d][1,4]oxazepin-9-yl)amino)propanamide was prepared by referring to the method of Example 1.

MS m/z (ESI): 438.1 [M+H]$^+$.

Example 87

Preparation of (S)-2-((8-cyano-2-((S)-4-(difluoromethyl)-2-oxooxazolidin-3-yl)-5,6-dihydrobenzo[f]imidazo[1,2-d][1,4]oxazepin-9-yl)amino)propanamide

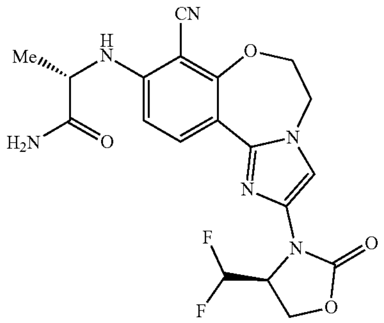 [SMILES: C[C@H](Nc1ccc2c(c1C#N)OCCn1cc(N3C(=O)OC[C@H]3C(F)F)nc1-2)C(N)=O]

(S)-2-((8-Cyano-2-((S)-4-(difluoromethyl)-2-oxooxazolidin-3-yl)-5,6-dihydrobenz o[f]imidazo[1,2-d][1,4]oxazepin-9-yl)amino)propanamide was prepared by referring to the method of Example 1.

MS m/z (ESI): 433.1 [M+H]$^+$.

Example 88

Preparation of (S)-2-((11-cyano-2-((S)-4-(difluoromethyl)-2-oxooxazolidin-3-yl)-5,6-dihydrobenzo[f]i midazo[1,2-d][1,4]oxazepin-9-yl)amino)propanamide

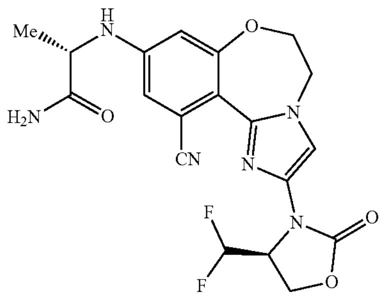 [SMILES: C[C@H](Nc1cc(C#N)c2c(c1)OCCn1cc(N3C(=O)OC[C@H]3C(F)F)nc1-2)C(N)=O]

(S)-2-((11-Cyano-2-((S)-4-(difluoromethyl)-2-oxooxazolidin-3-yl)-5,6-dihydroben zo[f]imidazo[1,2-d][1,4]oxazepin-9-yl)amino)propanamide was prepared by referring to the method of Example 1.

MS m/z (ESI): 433.1 [M+H]+.

Example 89

Preparation of (S)-2-((10-cyano-2-((S)-4-(difluoromethyl)-2-oxooxazolidin-3-yl)-5,6-dihydrobenzo[f]i midazo[1,2-d][1,4]oxazepin-9-yl)amino)propanamide

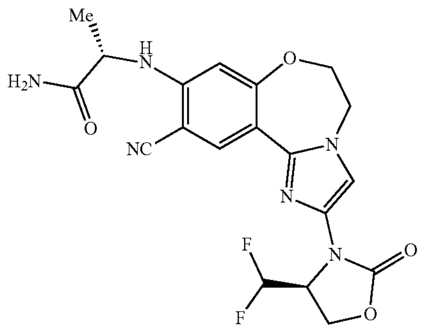 [SMILES: C[C@H](Nc1cc2c(cc1C#N)-c1nc(N3C(=O)OC[C@H]3C(F)F)cn1CCO2)C(N)=O]

(S)-2-((10-Cyano-2-((S)-4-(difluoromethyl)-2-oxooxazolidin-3-yl)-5,6-dihydroben zo[f]imidazo[1,2-d][1,4]oxazepin-9-yl)amino)propanamide was prepared by referring to the method of Example 1.

MS m/z (ESI): 433.1 [M+H]+.

Example 90

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-3-methoxypropanamide

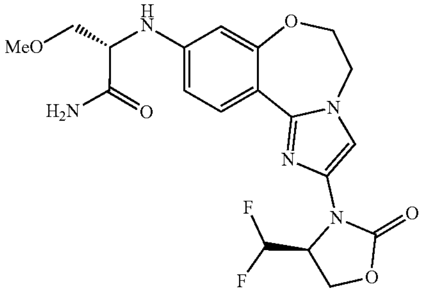 [SMILES: COC[C@H](Nc1ccc2c(c1)OCCn1cc(N3C(=O)OC[C@H]3C(F)F)nc1-2)C(N)=O]

(S)-2-((2-((S)-4-(Difluoromethyl)-2-oxooxazolidin-3-yl)-5,6-dihydrobenzo[f]imida zo[1,2-d][1,4]oxazepin-9-yl)amino)-3-methoxypropanamide was prepared by referring to the method of Example 1.

$^1$H NMR (400 MHz, $CD_3OD$) δ 3.39 (s, 3H), 3.67-3.76 (m, 2H), 3.94-3.98 (m, 1H), 4.30-4.34 (m, 2H), 4.37-4.41 (m, 2H), 4.57-4.66 (m, 2H), 4.91-4.96 (m, 1H), 6.21-6.25 (m, 1H), 6.43-6.46 (m, 1H), 6.48-6.73 (m, 1H), 7.15 (s, 1H), 8.06 (d, J=8.8 Hz, 1H);

MS m/z (ESI): 438.2 [M+H]+.

Example 91

Preparation of (2S,3R)-2-((2-((S)-4-(difluoromethyl)-2-oxooxazolidin-3-yl)-5,6-dihydrobenzo[f]imida zo[1,2-d][1,4]oxazepin-9-yl)amino)-3-methoxybutanamide

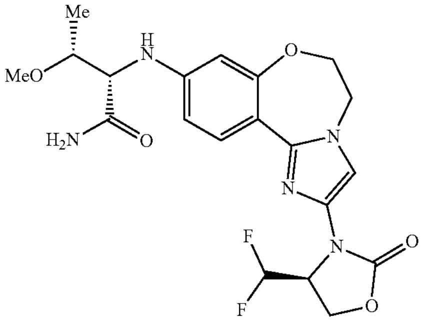 [SMILES: CO[C@H](C)[C@H](Nc1ccc2c(c1)OCCn1cc(N3C(=O)OC[C@H]3C(F)F)nc1-2)C(N)=O]

(2S,3R)-2-((2-((S)-4-(Difluoromethyl)-2-oxooxazolidin-3-yl)-5,6-dihydrobenzo[f]i midazo[1,2-d][1,4]oxazepin-9-yl)amino)-3-methoxybutanamide was prepared by referring to the method of Example 1.

$^1$H NMR (400 MHz, $CD_3OD$): δ 1.23-1.27 (d, J=6.9 Hz, 3H), 3.39 (s, 3H), 3.75-3.80 (m, 1H), 3.88-3.93 (m, 1H), 4.29-4.43 (m, 4H), 4.56-4.68 (m, 2H), 4.89-4.98 (m, 1H), 6.22-6.25 (m, 1H), 6.43-6.74 (m, 2H), 7.15 (s, 1H), 8.03-8.08 (d, J=8.8 Hz, 1H);

MS m/z (ESI): 452.2 [M+H]+.

Example 92

Preparation of (2S,3S)-2-((2-((S)-4-(difluoromethyl)-2-oxooxazolidin-3-yl)-5,6-dihydrobenzo[f] imidaz o[1,2-d][1,4]oxazepin-9-yl)amino)-3-methoxybutanamide

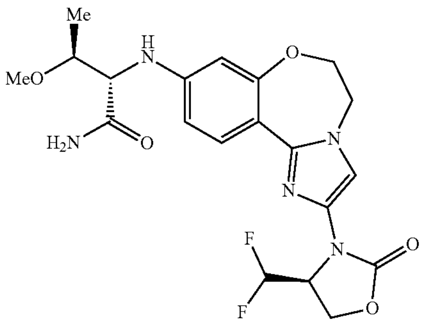 [SMILES: CO[C@@H](C)[C@H](Nc1ccc2c(c1)OCCn1cc(N3C(=O)OC[C@H]3C(F)F)nc1-2)C(N)=O]

(2S,3S)-2-((2-((S)-4-(Difluoromethyl)-2-oxooxazolidin-3-yl)-5,6-dihydrobenzo[f]i midazo[1,2-d][1,4]oxazepin-9-yl)amino)-3-methoxybutanamide was prepared by referring to the method of Example 1.

MS m/z (ESI): 452.2 [M+H]$^+$.

Example 93

Preparation of (S)-2-((2-((S)-4-(difluoromethyl)-2-oxooxazolidin-3-yl)-5,6-dihydroimidazo[1,2-d]pyri do[2,3-f][1,4]oxazepin-9-yl)amino)propanamide

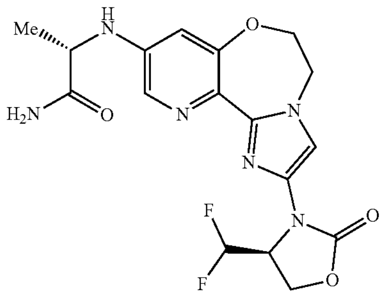

(S)-2-((2-((S)-4-(Difluoromethyl)-2-oxooxazolidin-3-yl)-5,6-dihydroimidazo[1,2-d]pyrido[2,3-f][1,4]oxazepin-9-yl) amino)propanamide was prepared by referring to the method of Example 1.

MS m/z (ESI): 409.2 [M+H]$^+$.

Example 94

Preparation of (S)-2-((2-((S)-4-(difluoromethyl)-2-oxooxazolidin-3-yl)-5,6-dihydroimidazo[1,2-d]pyri do[3,4-f][1,4]oxazepin-9-yl)amino)propanamide

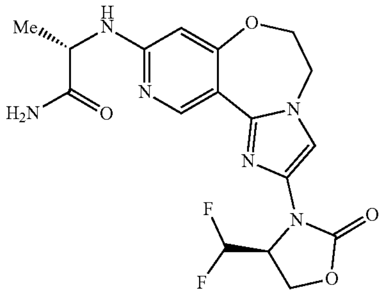

(S)-2-((2-((S)-4-(Difluoromethyl)-2-oxooxazolidin-3-yl)-5,6-dihydroimidazo[1,2-d]pyrido[3,4-f][1,4]oxazepin-9-yl) amino)propanamide was prepared by referring to the method of Example 1.

MS m/z (ESI): 409.2 [M+H]$^+$.

Example 95

Preparation of (S)-2-((2-((S)-4-(difluoromethyl)-2-oxooxazolidin-3-yl)-5,6-dihydroimidazo[1,2-d]pyri do[3,2-f][1,4]oxazepin-9-yl)amino)propanamide

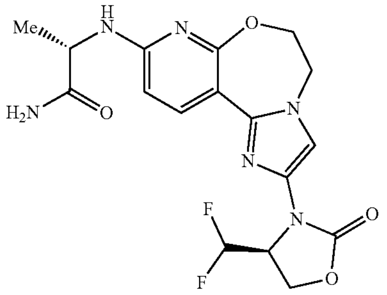

(S)-2-((2-((S)-4-(Difluoromethyl)-2-oxooxazolidin-3-yl)-5,6-dihydroimidazo[1,2-d]pyrido[3,2-f][1,4]oxazepin-9-yl) amino)propanamide was prepared by referring to the method of Example 1.

MS m/z (ESI): 409.2 [M+H]$^+$.

Example 96

Preparation of (S)-2-((2-((S)-4-(difluoromethyl)-2-oxooxazolidin-3-yl)-5,6-dihydrobenzo[f][1,2,4]triaz olo[1,5-d][1,4]oxazepin-9-yl)amino)propanamide

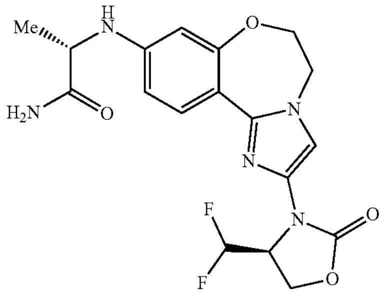

(S)-2-((2-((S)-4-(Difluoromethyl)-2-oxooxazolidin-3-yl)-5,6-dihydrobenzo[f][1,2,4]triazolo[1,5-d][1,4]oxazepin-9-yl)amino)propanamide was prepared by referring to the method of Example 1.

MS m/z (ESI): 409.2 [M+H]$^+$.

Example 97

Preparation of (S)-2-((2-((S)-2-(difluoromethyl)-5-oxopyrrolidin-1-yl)-5,6-dihydrobenzo[f]imidazo[1,2-d][1,4]oxazepin-9-yl)amino)propanamide

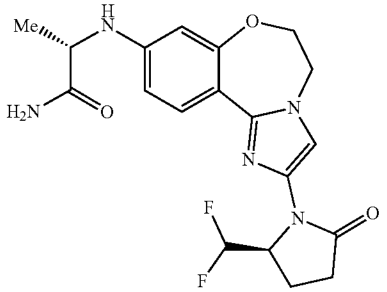

(S)-2-((2-((S)-2-(Difluoromethyl)-5-oxopyrrolidin-1-yl)-5,6-dihydrobenzo[f]imida zo[1,2-d][1,4]oxazepin-9-yl) amino)propanamide was prepared by referring to the method of Example 1.

$^1$H NMR (400 MHz, DMSO-$d_6$) δ 1.30 (d, J=8.0 Hz, 3H), 2.20-2.45 (m, 3H), 3.31 (d, J=8.0 Hz, 1H), 3.76 (t, J=7.6 Hz, 1H), 4.32-4.36 (m, 4H), 4.69-4.78 (m, 1H), 6.08 (s, 1H), 6.15 (d, J=8.0 Hz, 1H), 6.41 (d, J=8.0 Hz, 1H), 6.66 (t, J=56 Hz, 1H), 7.00 (s, 1H), 7.38 (d, J=8.0 Hz, 1H), 7.40 (s, 1H), 8.00 (d, J=8.0 Hz, 1H);

MS m/z (ESI): 406.2 [M+H]$^+$.

Example 98

Preparation of (S)-2-((2-((S)-7-(difluoromethyl)-2,5-dioxa-8-azaspiro[3.4]octan-8-yl)-5,6-dihydrobenz o[f]imidazo[1,2-d][1,4]oxazepin-9-yl)amino)propanamide

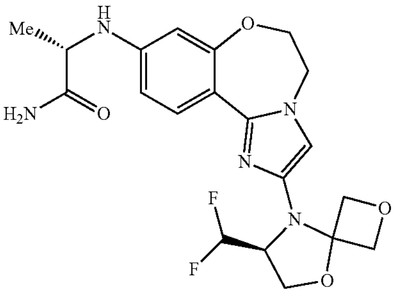 [SMILES: C[C@H](Nc1ccc2c(c1)OCCn1cc(N3[C@H](C(F)F)COC34COC4)nc1-2)C(N)=O]

(S)-2-((2-((S)-7-(Difluoromethyl)-2,5-dioxa-8-azaspiro [3.4]octan-8-yl)-5,6-dihydr obenzo[f]imidazo[1,2-d][1,4] oxazepin-9-yl)amino)propanamide was prepared by referring to the method of Example 1.

MS m/z (ESI): 436.2 [M+H]$^+$.

Example 99

Preparation of (S)-2-((2-(N-((S)-2,2-difluoro-1-(oxetan-3-yl)ethyl)acetamido)-5,6-dihydrobenzo[f] imid azo[1,2-d][1,4]oxazepin-9-yl)amino)propanamide

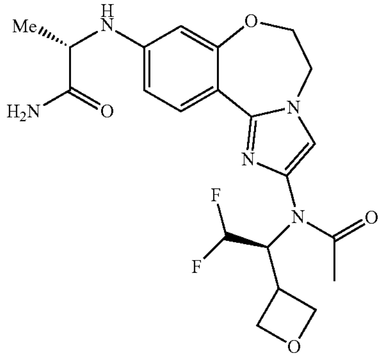 [SMILES: CC(=O)N(c1cn2c(n1)-c1ccc(N[C@@H](C)C(N)=O)cc1OCC2)[C@H](C(F)F)C1COC1]

(S)-2-((2-(N-((S)-2,2-Difluoro-1-(oxetan-3-yl)ethyl)acetamido)-5,6-dihydrobenzo[f]imidazo[1,2-d][1,4]oxazepin-9-yl)amino)propanamide was prepared by referring to the method of Example 1.

MS m/z (ESI): 450.2 [M+H]$^+$.

Example 100

Preparation of (S)-N-(9-((1-amino-1-oxopropan-2-yl)amino)-5,6-dihydrobenzo[f]imidazo[1,2-d][1,4]oxazepin-2-yl)-N-(2,2-difluoroethyl)oxetane-3-carboxamide

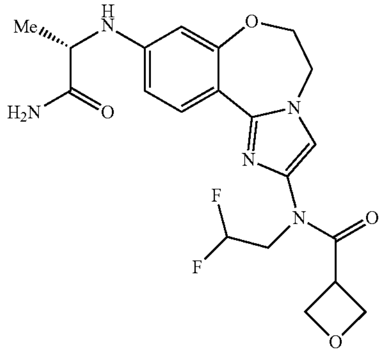 [SMILES: C[C@H](Nc1ccc2c(c1)OCCn1cc(N(CC(F)F)C(=O)C3COC3)nc1-2)C(N)=O]

(S)-N-(9-((1-Amino-1-oxopropan-2-yl)amino)-5,6-dihydrobenzo[f]imidazo[1,2-d][1,4]oxazepin-2-yl)-N-(2,2-difluoroethyl)oxetane-3-carboxamide was prepared by referring to the method of Example 1.

MS m/z (ESI): 436.2 $[M+H]^+$.

Example 101

Preparation of (S)-N-(9-(((S)-1-amino-1-oxopropan-2-yl)amino)-5,6-dihydrobenzo[f]imidazo[1,2-d][1,4]oxazepin-2-yl)-N-(2,2-difluoroethyl)oxetane-2-carboxamide

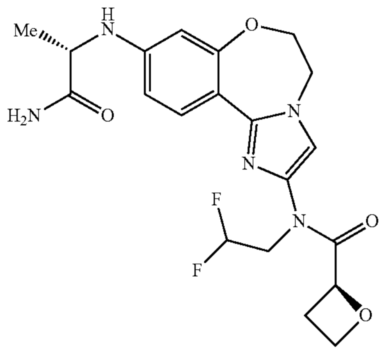 [SMILES: C[C@H](Nc1ccc2c(c1)OCCn1cc(N(CC(F)F)C(=O)[C@@H]3CCO3)nc1-2)C(N)=O]

(S)-N-(9-(((S)-1-Amino-1-oxopropan-2-yl)amino)-5,6-dihydrobenzo[f]imidazo[1,2-d][1,4]oxazepin-2-yl)-N-(2,2-difluoroethyl)oxetane-2-carboxamide was prepared by referring to the method of Example 1.

MS m/z (ESI): 436.2 $[M+H]^+$.

Example 102

Preparation of (R)-N-(9-(((S)-1-amino-1-oxopropan-2-yl)amino)-5,6-dihydrobenzo[f]imidazo[1,2-d][1,4]oxazepin-2-yl)-N-(2,2-difluoroethyl)oxetane-2-carboxamide

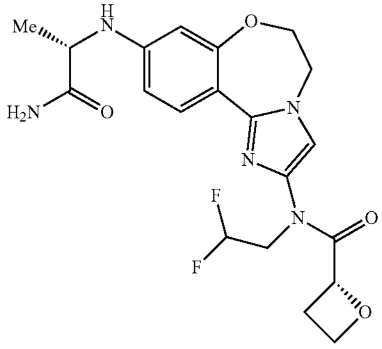 [SMILES: C[C@H](Nc1ccc2c(c1)OCCn1cc(N(CC(F)F)C(=O)[C@H]3CCO3)nc1-2)C(N)=O]

(R)-N-(9-(((S)-1-Amino-1-oxopropan-2-yl)amino)-5,6-dihydrobenzo[f]imidazo[1,2-d][1,4]oxazepin-2-yl)-N-(2,2-difluoroethyl)oxetane-2-carboxamide was prepared by referring to the method of Example 1.

MS m/z (ESI): 436.2 $[M+H]^+$.

Example 103

Preparation of (S)-2-((2-(N-(2,2-difluoroethyl)-2-methoxyacetamido)-5,6-dihydrobenzo[f]imidazo[1,2-d][1,4]oxazepin-9-yl)amino)propanamide

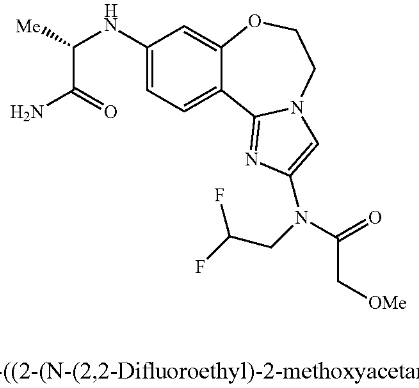

(S)-2-((2-(N-(2,2-Difluoroethyl)-2-methoxyacetamido)-5,6-dihydrobenzo[f]imidaz o[1,2-d][1,4]oxazepin-9-yl)amino)propanamide was prepared by referring to the method of Example 1.

MS m/z (ESI): 424.2 $[M+H]^+$.

Example 104

Preparation of (S)-2-((2-((3S,5S)-5-(difluoromethyl)-3-methoxy-2-oxopyrrolidin-1-yl)-5,6-dihydrobenzo[f]imidazo[1,2-d][1,4]oxazepin-9-yl)amino)propanamide

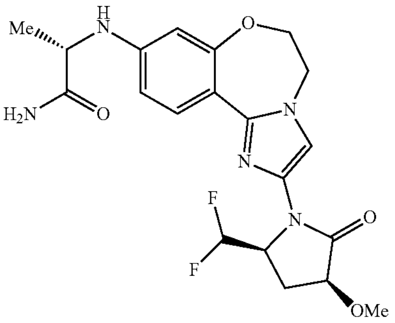 [SMILES: CO[C@H]1C[C@@H](C(F)F)N(c2cn3c(n2)-c2ccc(N[C@@H](C)C(N)=O)cc2OCC3)C1=O]

(S)-2-((2-((3S,5S)-5-(Difluoromethyl)-3-methoxy-2-oxopyrrolidin-1-yl)-5,6-dihydrobenzo[f]imidazo[1,2-d][1,4]oxazepin-9-yl)amino)propanamide was prepared by referring to the method of Example 1.

$^1$H NMR (400 MHz, $CD_3OD$) δ 1.46 (d, J=7.0 Hz, 3H), 2.10-2.20 (m, 1H), 2.74-2.84 (m, 1H), 3.57 (s, 3H), 3.81 (q, J=7.0 Hz, 1H), 4.25-4.40 (m, 5H), 4.71-4.84 (m, 1H), 6.13-6.18 (m, 1H), 6.37-6.70 (m, 2H), 7.38 (s, 1H), 8.04 (d, J=8.8 Hz, 1H);

MS m/z (ESI): 436.2 [M+H]$^+$.

Example 105

Preparation of (S)-2-((2-((3R,5S)-5-(difluoromethyl)-3-methoxy-2-oxopyrrolidin-1-yl)-5,6-dihydrobenzo[f]imidazo[1,2-d][1,4]oxazepin-9-yl)amino)propanamide

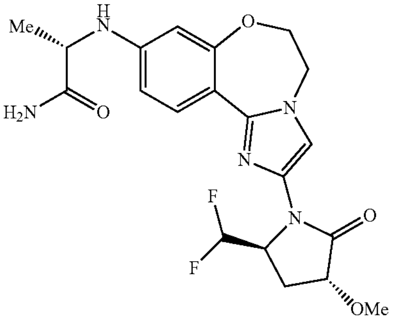 [SMILES: CO[C@@H]1C[C@@H](C(F)F)N(c2cn3c(n2)-c2ccc(N[C@@H](C)C(N)=O)cc2OCC3)C1=O]

(S)-2-((2-((3R,5S)-5-(Difluoromethyl)-3-methoxy-2-oxopyrrolidin-1-yl)-5,6-dihydrobenzo[f]imidazo[1,2-d][1,4]oxazepin-9-yl)amino)propanamide was prepared by referring to the method of Example 1.

MS m/z (ESI): 436.2 [M+H]$^+$.

Example 106

Preparation of (1S,5R)-2-(2-((S)-4-(difluoromethyl)-2-oxooxazolidin-3-yl)-5,6-dihydrobenzo[f]imidazo[1,2-d][1,4]oxazepin-9-yl)-2-azabicyclo[3.1.0]hexane-1-carboxamide

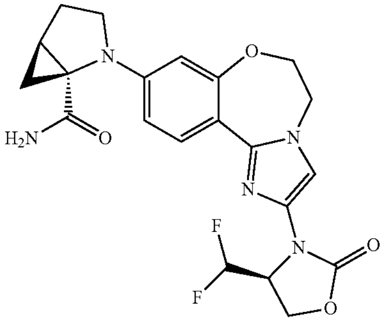 [SMILES: NC(=O)[C@]12C[C@H]1CCN2c1ccc2c(c1)OCCn1cc(N3C(=O)OC[C@H]3C(F)F)nc1-2]

(1S,5R)-2-(2-((S)-4-(Difluoromethyl)-2-oxooxazolidin-3-yl)-5,6-dihydrobenzo[f]imidazo[1,2-d][1,4]oxazepin-9-yl)-2-azabicyclo[3.1.0]hexane-1-carboxamide was prepared by referring to the method of Example 1.

MS m/z (ESI): 446.2 [M+H]$^+$.

Example 107

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-3-hydroxypropanamide

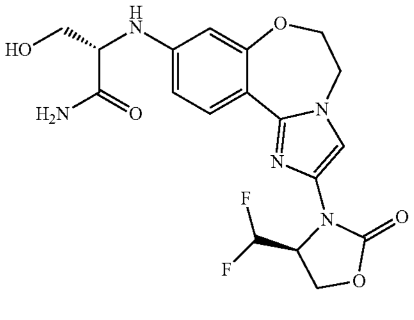 [SMILES: NC(=O)[C@H](CO)Nc1ccc2c(c1)OCCn1cc(N3C(=O)OC[C@H]3C(F)F)nc1-2]

(S)-2-((2-((S)-4-(Difluoromethyl)-2-oxooxazolidin-3-yl)-5,6-dihydrobenzo[f]imidazo[1,2-d][1,4]oxazepin-9-yl)amino)-3-hydroxypropanamide was prepared by referring to the method of Example 1.

$^1$H NMR (400 MHz, $CD_3OD$) δ 3.87 (s, 2H), 4.34 (d, J=4.3 Hz, 2H), 4.37-4.43 (m, 2H), 4.62 (m, 4H), 6.23 (d, J=2.6 Hz, 1H), 6.41-6.62 (m, 2H), 7.16 (s, 1H), 8.06 (d, J=8.8 Hz, 1H);

MS m/z (ESI): 424.1 [M+H]$^+$.

Example 108

Preparation of (S)-2-((2-((R)-4-(difluoromethyl)-2-oxothiazolidin-3-yl)-8-fluoro-5,6-dihydrobenzo[f]imidazo[1,2-d][1,4]oxazepin-9-yl)amino)propanamide

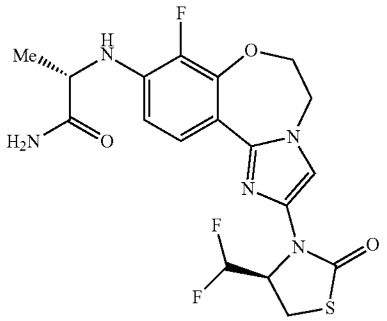 [SMILES: C[C@H](Nc1ccc2c(c1F)OCCn1cc(N3C(=O)SC[C@H]3C(F)F)nc1-2)C(N)=O]

Step 1: Preparation of 4-bromo-3-fluoro-2-methoxybenzaldehyde

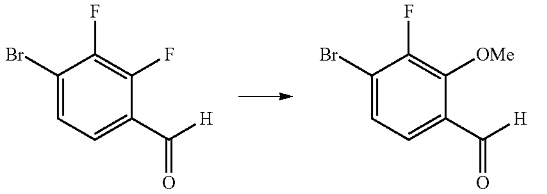 [SMILES: O=Cc1ccc(Br)c(F)c1F ; COc1c(C=O)ccc(Br)c1F]

Sodium methoxide (733 mg, 13.56 mmol) was added to a solution of 4-bromo-2,3-difluorobenzaldehyde (2.0 g, 9.05 mmol) in methanol (25 mL) at room temperature. The reaction solution was warmed up to 65° C. and reacted for 2 hours. The reaction solution was concentrated, and the resulting residue was purified by column chromatography to obtain 4-bromo-3-fluoro-2-methoxybenzaldehyde (1.78 g, 85%).

MS m/z (ESI): 233.0 $[M+H]^+$.

Step 2: Preparation of 4-bromo-3-fluoro-2-hydroxybenzaldehyde

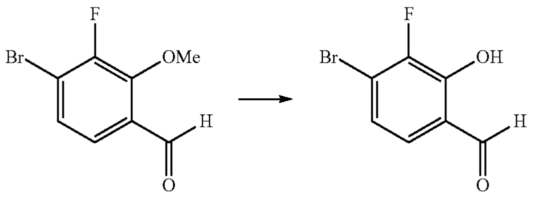 [SMILES: COc1c(C=O)ccc(Br)c1F ; O=Cc1ccc(Br)c(F)c1O]

Hydrobromic acid (8.7 mL, 48%) was added to a solution of 4-bromo-3-fluoro-2-methoxybenzaldehyde (1.78 g, 7.67 mmol) in acetic acid (15 mL) at room temperature. The reaction solution was warmed up to 120° C. and reacted for 16 hours. The reaction solution was cooled and concentrated under reduced pressure. Water and ethyl acetate were added to the reaction flask, and then two phases were separated. The organic phase was dried over anhydrous sodium sulfate, and concentrated under reduced pressure to remove the organic solvent. The residue was subjected to column chromatography to obtain 4-bromo-3-fluoro-2-hydroxybenzaldehyde (1.12 g, 67%).

MS m/z (ESI): 219.0 $[M+H]^+$.

Step 3: Preparation of 3-bromo-2-fluoro-6-(1H-imidazol-2-yl)phenol

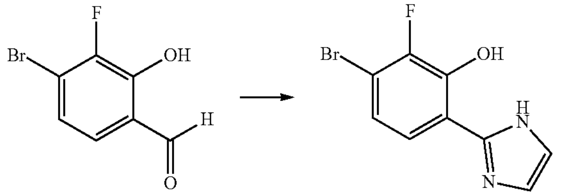 [SMILES: O=Cc1ccc(Br)c(F)c1O ; Oc1c(-c2ncc[nH]2)ccc(Br)c1F]

Aqueous glyoxal solution (40 wt. %, 3.73 g, 25.7 mmol) was added to a solution of 4-bromo-3-fluoro-2-hydroxybenzaldehyde (1.12 g, 5.14 mmol) in methanol (12 mL). In a water bath, ammonia (28 wt. %, 5.14 g, 51.4 mmol) was slowly added dropwise to the reaction solution under stirring, the addition process lasted for 30 minutes, and the temperature of the reaction solution was controlled not to exceed 40° C. The mixture was stirred at 35° C. for two days, cooled and concentrated under reduced pressure to remove the organic solvent. The resulting residue was purified by column chromatography to obtain 3-bromo-2-fluoro-6-(1H-imidazol-2-yl)phenol (1.31 g, 100%).

MS m/z (ESI): 257.0 $[M+H]^+$.

Step 4: Preparation of 9-bromo-8-fluoro-5,6-dihydrobenzo[f]imidazo[1,2-d][1,4]oxazepine

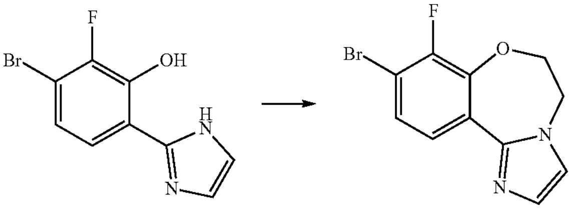 [SMILES: Oc1c(-c2ncc[nH]2)ccc(Br)c1F ; Fc1c(Br)ccc2c1OCCn1ccnc1-2]

3-Bromo-2-fluoro-6-(1H-imidazol-2-yl)phenol (1.31 g, 5.14 mmol), cesium carbonate (6.3 g, 19.53 mmol) and 1,2-dibromoethane (3.6 g, 19.12 mmol) were mixed in DMF (12 mL), and the reaction solution was stirred at 85° C. overnight. The reaction solution was cooled, and diluted with ethyl acetate. The organic phase was washed with saturated brine several times, dried over anhydrous sodium sulfate, and concentrated under reduced pressure to remove the organic solvent. The resulting residue was purified by column chromatography to obtain the title compound 9-bromo-8-fluoro-5,6-dihydrobenzo[f]imidazo[1,2-d][1,4]oxazepine (995 mg, 69%).

MS m/z (ESI): 283.0 $[M+H]^+$.

Step 5: Preparation of 9-bromo-8-fluoro-2,3-diiodo-5,6-dihydrobenzo[f]imidazo[1,2-d][1,4]oxazepine

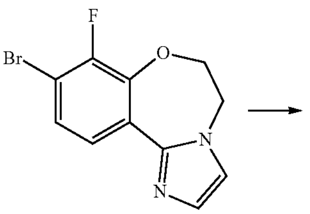

-continued

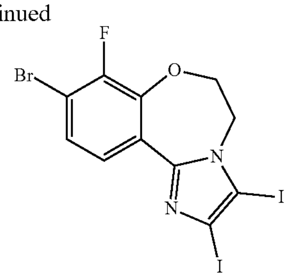

NIS (2.23 g, 9.88 mmol) was added to a solution of 9-bromo-8-fluoro-5,6-dihydrobenzo[f]imidazo[1,2-d][1,4] oxazepine (995 mg, 3.53 mmol) in DMF (8 mL) at room temperature, and the reaction solution was stirred at 60° C. overnight. The reaction solution was cooled, and water was added to precipitate a solid. After filtering, the solid was dissolved in ethyl acetate. The solution was washed with 1 M NaOH aqueous solution and saturated brine successively, dried over anhydrous sodium sulfate, and concentrated to obtain the title compound 9-bromo-8-fluoro-2,3-diiodo-5,6-dihydrobenzo[f]imidazo[1,2-d][1,4]oxazepine (1.79 g, 94%).

MS m/z (ESI): 534.7 $[M+H]^+$.

Step 6: Preparation of 9-bromo-8-fluoro-2-iodo-5,6-dihydrobenzo[f]imidazo[1,2-d][1,4]oxazepine

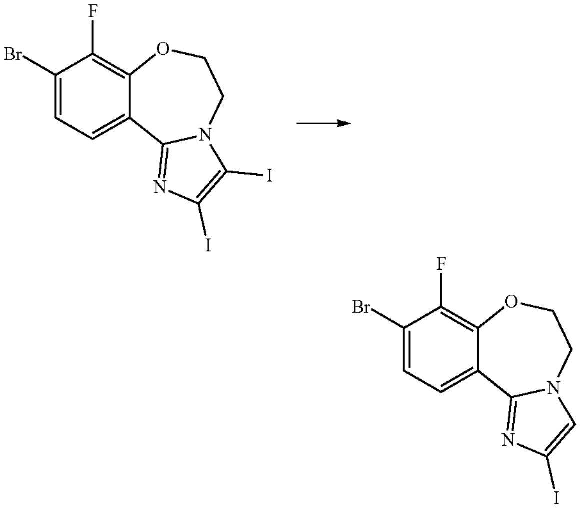

EtMgBr (1.0 M, THE solution, 1.23 mL, 3.69 mmol) was slowly added dropwise to a solution of 9-bromo-8-fluoro-2,3-diiodo-5,6-dihydrobenzo[f]imidazo[1,2-d][1,4] oxazepine (1.79 g, 3.35 mmol) in THF (10 mL) at −20° C. After completion of the addition, the reaction solution was stirred at −15° C. for 3 hours. The reaction solution was slowly warmed up to room temperature, and saturated aqueous ammonium chloride solution was added dropwise. The reaction solution was stirred for 15 minutes, and extracted with ethyl acetate several times. The organic phases were combined, washed with saturated brine, dried over anhydrous sodium sulfate, and concentrated under reduced pressure to remove the organic solvent. The residue was subjected to column chromatography to obtain the title compound 9-bromo-8-fluoro-2-iodo-5,6-dihydrobenzo[f] imidazo[1,2-d][1,4]oxazepine (610 mg, 45%).

MS m/z (ESI): 408.9 $[M+H]^+$.

Step 7: Preparation of (S)-4-(difluoromethyl)-3-(8-fluoro-9-iodo-5,6-dihydrobenzo[f]imidazo[1,2-d][1,4]oxaze pin-2-yl)oxazolidin-2-one

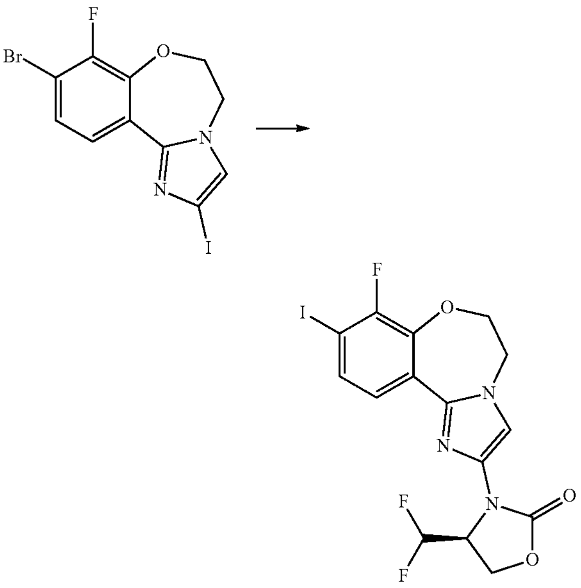 [SMILES: Fc1c(Br)ccc2c1OCCn1cc(I)nc1-2 ; O=C1OC[C@@H](C(F)F)N1c1cn2c(n1)-c1ccc(I)c(F)c1OCC2]

9-Bromo-8-fluoro-2-iodo-5,6-dihydrobenzo[f]imidazo[1,2-d][1,4]oxazepine (300 mg, 0.74 mmol), (S)-4-(difluoromethyl)oxazolidin-2-one (102 mg, 0.74 mmol), (1R,2R)-$N^1$,$N^2$-dimethylcyclohexane-1,2-diamine (42 mg, 0.30 mmol), cuprous iodide (28 mg, 0.15 mmol) and potassium carbonate (205 mg, 1.5 mmol) were mixed in 1,4-dioxane (6 mL). The reaction system was purged with nitrogen three times, and reacted at 105° C. for 5 hours. The reaction solution was cooled to room temperature, and 15% ammonia was added. The reaction solution was stirred for 5 minutes and extracted with EtOAc three times. The organic phases were combined, washed with saturated aqueous sodium chloride solution, dried over anhydrous sodium sulfate, and concentrated under reduced pressure. The residue was subjected to column chromatography to obtain the title compound (S)-4-(difluoromethyl)-3-(8-fluoro-9-iodo-5,6-dihydrobenzo[f] imidazo[1,2-d][1,4]oxaze pin-2-yl)oxazolidin-2-one (225 mg, 65%).

MS m/z (ESI): 466.0 $[M+H]^+$.

Step 8: Preparation of (S)-4-(difluoromethyl)-3-(8-fluoro-9-iodo-5,6-dihydrobenzo[f]imidazo[1,2-d][1,4]oxaze pin-2-yl)oxazolidine-2-thione

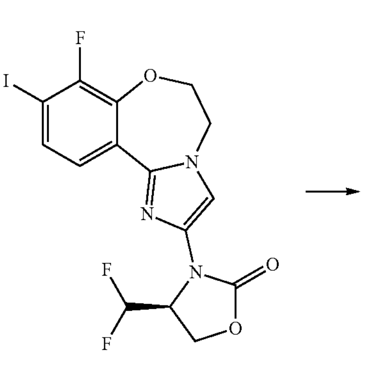

-continued

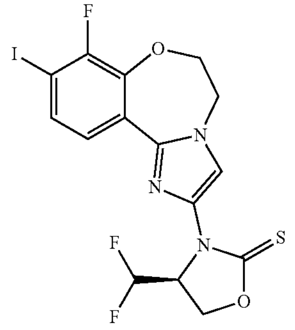

Lawesson's reagent (1.92 g, 4.73 mmol) was added to a solution of (S)-4-(difluoromethyl)-3-(8-fluoro-9-iodo-5,6-dihydrobenzo[f]imidazo[1,2-d][1,4]oxaze pin-2-yl)oxazolidin-2-one (220 mg, 0.47 mmol) in toluene (20 mL). The reaction solution was warmed up to 145° C. and reacted for 6 hours. The reaction solution was cooled to room temperature and filtered, and the filter cake was washed with EtOAc (20 mL). The filtrate was dried over anhydrous sodium sulfate, and concentrated under reduced pressure. The residue was subjected to column chromatography to obtain the title compound (S)-3-(9-bromo-8-fluoro-5,6-dihydrobenzo[f]imidazo[1,2-d][1,4]oxazepin-2-yl)-4-(diflu oromethyl)oxazolidine-2-thione (105 mg, 46%).

MS m/z (ESI): 482.1 $[M+H]^+$.

Step 9: Preparation of (R)-4-(difluoromethyl)-3-(8-fluoro-9-iodo-5,6-dihydrobenzo[f]imidazo[1,2-d][1,4]oxaz epin-2-yl)thiazolidin-2-one

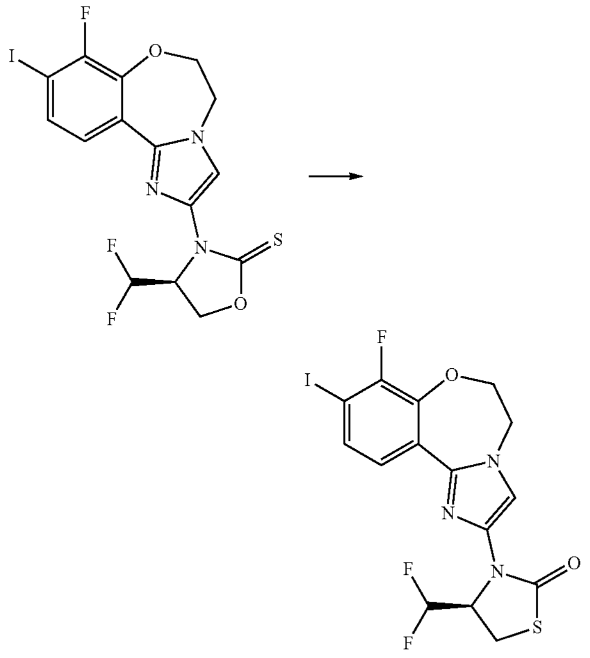

Dichloro(p-cymene)ruthenium(II) dimer (27 mg, 0.045 mmol) and 2-bicyclohexylphosphino-2',6'-dimethoxybiphenyl (27 mg, 0.065 mmol) were added to solution of a (S)-3-(9-bromo-8-fluoro-5,6-dihydrobenzo[f]imidazo[1,2-d][1,4]oxazepin-2-yl)-4-(diflu oromethyl)oxazolidine-2-thione (105 mg, 0.22 mmol) in toluene (3 mL). The reaction solution was reacted under air at 115° C. for 16 hours. The reaction solution was cooled to room temperature, and diluted with EtOAc. The organic phase was washed with saturated aqueous sodium chloride solution, dried over anhydrous sodium sulfate, and concentrated under reduced pressure. The residue was subjected to column chromatography to obtain the title compound (R)-4-(difluoromethyl)-3-(8-fluoro-9-iodo-5,6-dihydrobenzo[f]imidazo[1,2-d][1,4]oxaz epin-2-yl)thiazolidin-2-one (55 mg, 52%).

MS m/z (ESI): 482.1 $[M+H]^+$.

Step 10: Preparation of (S)-2-((2-((R)-4-(difluoromethyl)-2-oxothiazolidin-3-yl)-8-fluoro-5,6-dihydrobenzo[f]i midazo[1,2-d][1,4]oxazepin-9-yl)amino)propanamide

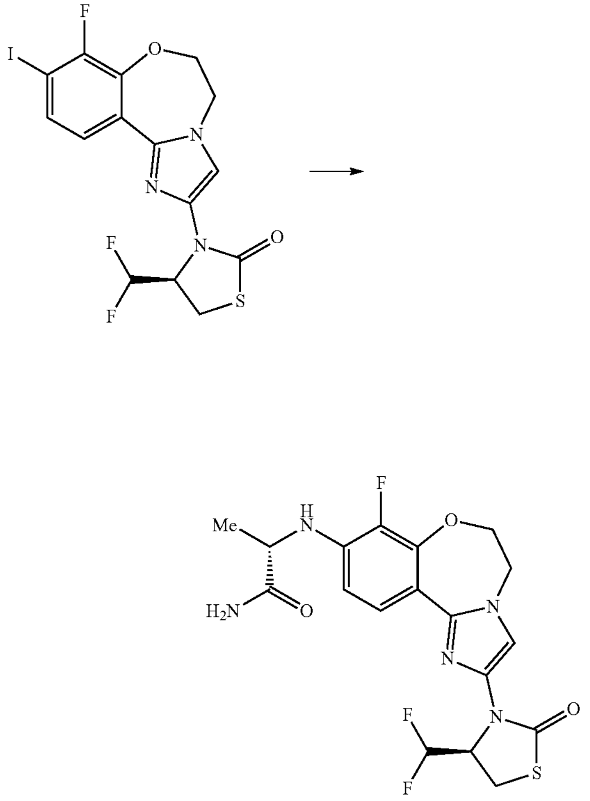

(R)-4-(Difluoromethyl)-3-(8-fluoro-9-iodo-5,6-dihydrobenzo[f]imidazo[1,2-d][1,4]oxazepin-2-yl)thiazolidin-2-one (40 mg, 0.083 mmol), L-alanine (15 mg, 0.17 mmol), cuprous iodide (6.3 mg, 0.033 mmol) and potassium phosphate (53 mg, 0.25 mmol) were mixed in dimethyl sulfoxide (3 mL). The reaction system was purged with nitrogen three times, and reacted at 125° C. for 1.5 hours. The reaction solution was cooled to room temperature, ammonium chloride (27 mg, 0.5 mmol) and DMAP (161 mg, 1.25 mmol) were added, and the reaction solution was stirred for 5 minutes. O-(7-azabenzotriazol-1-yl)-N,N,N',N'-tetramethylurea hexafluorophosphate (284 mg, 0.75 mmol) was added, and the reaction solution was stirred at room temperature for 2 hours. The reaction solution was filtered, saturated aqueous sodium bicarbonate solution was added to the filtrate, which was then extracted with ethyl acetate three times. The organic phases were combined, dried over anhydrous sodium sulfate, and concentrated under reduced pressure. The residue was subjected to column chromatography to obtain the title compound (S)-2-((2-((R)-4-(difluoromethyl)-2-oxothiazolidin-3-yl)-8-fluoro-5,6-dihydrobenzo[f]i midazo[1,2-d][1,4]oxazepin-9-yl)amino)propanamide (7.9 mg, 22%).

$^1$H NMR (400 MHz, $CD_3OD$) δ 1.49 (d, J=7.0 Hz, 3H), 3.54-3.60 (m, 1H), 3.76-3.93 (m, 1H), 3.95-4.00 (m, 1H), 4.36-4.40 (m, 2H), 4.47-4.52 (m, 2H), 5.10-5.20 (m, 1H), 6.32-6.62 (m, 2H), 7.32 (s, 1H), 7.85-7.91 (m, 1H);

MS m/z (ESI): 442.1 $[M+H]^+$.

Example 109

Preparation of (S)-2-((2-((R)-4-(difluoromethyl)-2-oxothiazolidin-3-yl)-8-fluoro-5,6-dihydrobenzo[f]imidazo[1,2-d][1,4]oxazepin-9-yl)amino)-3-methoxypropanamide

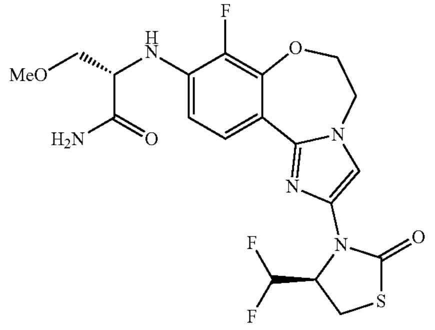 [SMILES: COC[C@H](Nc1ccc2c(c1F)OCCn1cc(N3C(=O)SC[C@H]3C(F)F)nc1-2)C(N)=O]

(S)-2-((2-((R)-4-(Difluoromethyl)-2-oxothiazolidin-3-yl)-8-fluoro-5,6-dihydrobenz o[f]imidazo[1,2-d][1,4]oxazepin-9-yl)amino)-3-methoxypropanamide was prepared by referring to Example 108.

$^1$H NMR (400 MHz, $CD_3OD$) δ 3.40 (s, 3H), 3.53-3.60 (m, 1H), 3.69-3.83 (m, 3H), 4.06-4.13 (m, 1H), 4.35-4.41 (m, 2H), 4.47-4.52 (m, 2H), 5.10-5.21 (m, 1H), 6.30-6.60 (m, 2H), 7.32 (s, 1H), 7.89 (d, J=8.5 Hz, 1H);

MS m/z (ESI): 472.1 $[M+H]^+$.

Example 110

Preparation of (S)-2-((2-((R)-4-(difluoromethyl)-2-oxothiazolidin-3-yl)-5,6-dihydrobenzo[f]imidazo[1,2-d][1,4]oxazepin-9-yl)amino)-3-methoxypropanamide

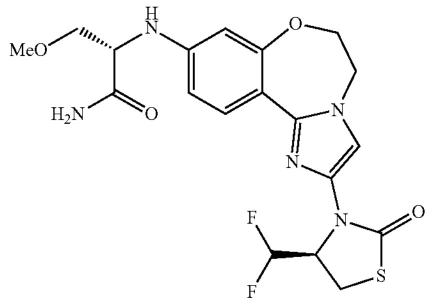 [SMILES: COC[C@H](Nc1ccc2c(c1)OCCn1cc(N3C(=O)SC[C@H]3C(F)F)nc1-2)C(N)=O]

Step 1: Preparation of (S)-2-((2-((R)-4-(difluoromethyl)-2-oxothiazolidin-3-yl)-5,6-dihydrobenzo[f]imidazo[1,2-d][1,4]oxazepin-9-yl)amino)-3-methoxypropanamide

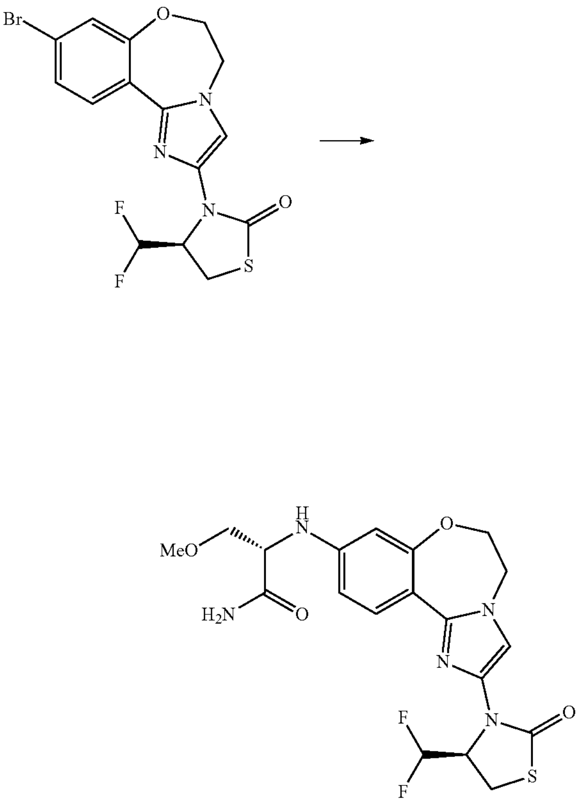

(R)-3-(9-Bromo-5,6-dihydrobenzo[f]imidazo[1,2-d][1,4]oxazepin-2-yl)-4-(difluoro methyl)thiazolidin-2-one (26 mg, 0.062 mmol), O-methyl-L-serine (22 mg, 0.18 mmol), cuprous iodide (6.0 mg, 0.03 mmol) and potassium phosphate (40 mg, 0.19 mmol) were mixed in dimethyl sulfoxide (3 mL). The reaction system was purged with nitrogen three times, and reacted at 100° C. for 12 hours. The reaction solution was cooled to room temperature, ammonium chloride (20 mg, 0.37 mmol) and triethylamine (95 mg, 0.94 mmol) were added, and the reaction solution was stirred for 5 minutes. O-(7-azabenzotriazol-1-yl)-N,N,N',N'-tetramethylurea hexafluorophosphate (212 mg, 0.56 mmol) was added, and the reaction solution was stirred at room temperature for 2 hours. The reaction solution was filtered, saturated aqueous sodium bicarbonate solution was added to the filtrate, which was then extracted with ethyl acetate three times. The organic phases were combined, dried over anhydrous sodium sulfate, and concentrated under reduced pressure to remove the organic solvent. The residue was subjected to column to the chromatography obtain title compound (S)-2-((2-((R)-4-(difluoromethyl)-2-oxothiazolidin-3-yl)-5,6-dihydrobenzo[f]imidazo[1,2-d][1,4]oxazepin-9-yl)amino)-3-methoxypropanamide (13 mg, 46%).

$^1$H NMR (400 MHz, $CD_3OD$) δ 3.39 (s, 3H), 3.53-3.57 (m, 1H), 3.62-3.76 (m, 3H), 3.93-3.98 (m, 1H), 4.16-4.30 (m, 4H), 5.06-5.16 (m, 1H), 6.21-6.23 (m, 1H), 6.28-6.52 (m, 2H), 7.23 (s, 1H), 8.02 (d, J=8.8 Hz, 1H);

MS m/z (ESI): 454.1 $[M+H]^+$.

Example 111

Preparation of (S)-1-(2-((R)-4-(difluoromethyl)-2-oxothiazolidin-3-yl)-5,6-dihydrobenzo[f]imidazo[1,2-d][1,4]oxazepin-9-yl)pyrrolidine-2-carboxamide

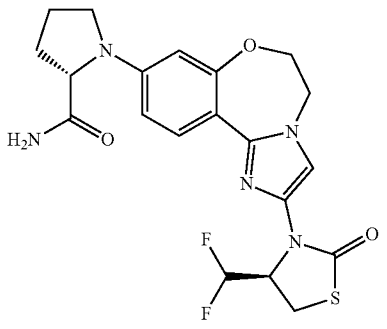 [SMILES: NC(=O)[C@@H]1CCCN1c1ccc2c(c1)OCCn1cc(N3C(=O)SC[C@H]3C(F)F)nc1-2]

(S)-1-(2-((R)-4-(Difluoromethyl)-2-oxothiazolidin-3-yl)-5,6-dihydrobenzo[f]imida zo[1,2-d][1,4]oxazepin-9-yl)pyrrolidine-2-carboxamide was prepared by referring to the method of Example 51.

$^1$H NMR (400 MHz, DMSO-$d_6$) δ 1.83-1.92 (m, 2H), 2.09-2.15 (m, 1H), 3.72-3.81 (m, 4H), 4.25-4.32 (m, 4H), 5.07-5.15 (m, 1H), 5.93-5.97 (m, 1H), 6.22-6.28 (m, 1H), 6.35-6.65 (s, 1H), 7.00 (s, 1H), 7.26 (s, 1H), 7.35 (s, 1H), 7.99 (d, J=8.6 Hz, 1H);

MS m/z (ESI): 450.1 $[M+H]^+$.

Example 112

Preparation of (S)-2-((2-((R)-4-(difluoromethyl)-2-oxothiazolidin-3-yl)-5,6-dihydrobenzo[f]imidazo[1,2-d][1,4]oxazepin-9-yl)(methyl)amino)propanamide

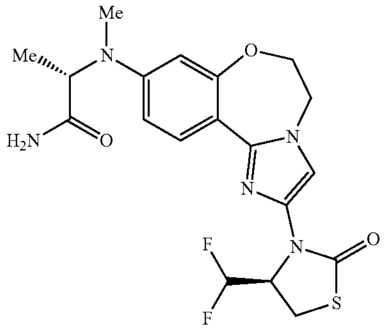 [SMILES: C[C@@H](C(N)=O)N(C)c1ccc2c(c1)OCCn1cc(N3C(=O)SC[C@H]3C(F)F)nc1-2]

(S)-2-((2-((R)-4-(Difluoromethyl)-2-oxothiazolidin-3-yl)-5,6-dihydrobenzo[f]imid azo[1,2-d][1,4]oxazepin-9-yl)(methyl)amino)propanamide was prepared by referring to the method of Example 51.

$^1$H NMR (400 MHz, $CD_3OD$) δ 1.40 (d, J=7.0 Hz, 3H), 2.90 (s, 3H), 3.53-3.58 (m, 1H), 3.75-3.80 (m, 1H), 4.30-4.44 (m, 4H), 4.46-4.51 (m, 1H), 5.08-5.18 (m, 1H), 6.22-6.41 (m, 2H), 6.51-6.73 (m, 1H), 7.28 (s, 1H), 8.11 (d, J=9.0 Hz, 1H);

MS m/z (ESI): 438.1 $[M+H]^+$.

Example 113

Preparation of (S)-2-((2-((R)-5-(methoxymethyl)-2-oxooxazolidin-3-yl)-5,6-dihydrobenzo[f]imidazo[1,2-d][1,4]oxazepin-9-yl)amino)propanamide

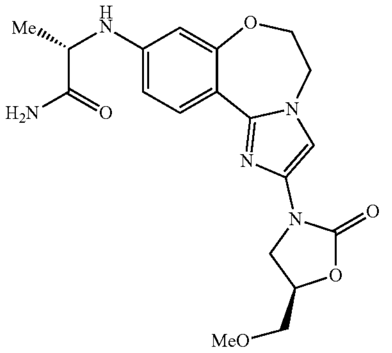 [SMILES: COC[C@H]1CN(c2cn3c(n2)-c2ccc(N[C@@H](C)C(N)=O)cc2OCC3)C(=O)O1]

(S)-2-((2-((R)-5-(Methoxymethyl)-2-oxooxazolidin-3-yl)-5,6-dihydrobenzo[f]imid azo[1,2-d][1,4]oxazepin-9-yl)amino)propanamide was prepared by referring to the method of Example 1.

$^1$H NMR (400 MHz, $CD_3OD$) δ 1.48 (d, J=7.0 Hz, 3H), 3.44 (s, 3H), 3.59-3.72 (m, 2H), 3.83 (q, J=7.0 Hz, 1H), 3.95-4.02 (m, 6.5 Hz, 1H), 4.20 (t, J=9.3 Hz, 1H), 4.28-4.33 (m, 2H), 4.35-4.42 (m, 2H), 4.81-4.86 (m, 1H), 6.17-6.21 (m, 1H), 6.43 (dd, J=8.8, 2.3 Hz, 1H), 7.12 (s, 1H), 8.01 (d, J=8.8 Hz, 1H);

MS m/z (ESI): 402.2 $[M+H]^+$.

Example 114

Preparation of (S)-2-((2-((R)-4-methoxy-2-oxopyrrolidin-1-yl)-5,6-dihydrobenzo[f]imidazo[1,2-d][1,4]oxazepin-9-yl)amino)propanamide

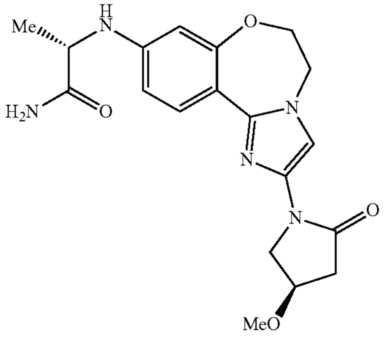 [SMILES: CO[C@@H]1CC(=O)N(c2cn3c(n2)-c2ccc(N[C@@H](C)C(N)=O)cc2OCC3)C1]

(S)-2-((2-((R)-4-Methoxy-2-oxopyrrolidin-1-yl)-5,6-dihydrobenzo[f]imidazo[1,2-d][1,4]oxazepin-9-yl)amino)propanamide was prepared by referring to the method of Example 1.

$^1$H NMR (400 MHz, $CDCl_3$) δ 1.52 (d, J=6.9 Hz, 3H), 2.57-2.67 (m, 1H), 2.78-2.88 (m, 1H), 3.40 (s, 3H), 3.79-3.88 (m, 1H), 4.10-4.43 (m, 7H), 6.19 (s, 1H), 6.42 (d, J=8.8 Hz, 1H), 7.32 (s, 1H), 8.16 (d, J=8.7 Hz, 1H);

MS m/z (ESI): 386.2 $[M+H]^+$.

Example 115

Preparation of (2S)-2-((2-(4-(cyanomethyl)-2-oxopyrrolidin-1-yl)-5,6-dihydrobenzo[f]imidazo[1,2-d][1,4]oxazepin-9-yl)amino)propanamide

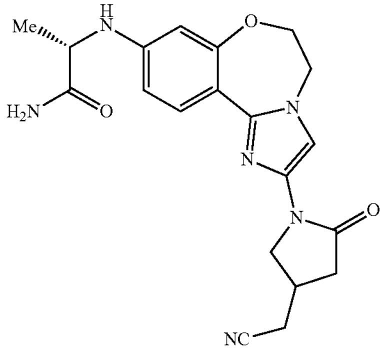 [SMILES: C[C@H](Nc1ccc2c(c1)OCCn1cc(N3CC(CC#N)CC3=O)nc1-2)C(N)=O]

(2S)-2-((2-(4-(Cyanomethyl)-2-oxopyrrolidin-1-yl)-5,6-dihydrobenzo[f]imidazo[1,2-d][1,4]oxazepin-9-yl)amino) propanamide was prepared by referring to the method of Example 1.

$^1$H NMR (400 MHz, DMSO-$d_6$) δ 1.30 (d, J=6.9 Hz, 3H), 2.29 (dd, J=16.9, 6.2 Hz, 1H), 2.70 (dd, J=16.5, 8.0 Hz, 1H), 2.77-2.88 (m, 3H), 3.64 (dd, J=10.8, 4.4 Hz, 1H), 3.76 (dt, J=13.7, 6.9 Hz, 1H), 4.13 (dd, J=10.6, 7.1 Hz, 1H), 4.33 (dd, J=8.5, 5.8 Hz, 4H), 6.08 (d, J=2.0 Hz, 1H), 6.12 (d, J=7.0 Hz, 1H), 6.40 (dd, J=8.8, 2.2 Hz, 1H), 6.99 (d, J=0.7 Hz, 1H), 7.37 (s, 2H), 7.99 (d, J=8.8 Hz, 1H);

MS m/z (ESI): 395.1 $[M+H]^+$.

Example 116

Preparation of (2S)-2-((2-(4-cyano-2-oxopyrrolidin-1-yl)-5,6-dihydrobenzo[f]imidazo[1,2-d][1,4]oxaz epin-9-yl)amino)propanamide

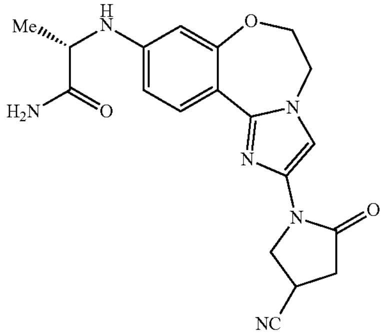 [SMILES: C[C@H](Nc1ccc2c(c1)OCCn1cc(N3CC(C#N)CC3=O)nc1-2)C(N)=O]

(2S)-2-((2-(4-Cyano-2-oxopyrrolidin-1-yl)-5,6-dihydrobenzo[f]imidazo[1,2-d][1,4]oxazepin-9-yl)amino)propanamide was prepared by referring to the method of Example 1.

$^1$H NMR (400 MHz, $CD_3OD$) δ 1.49 (d, J=7.0 Hz, 3H), 2.88 (dd, J=17.0, 6.7 Hz, 1H), 3.01 (dd, J=17.0, 9.3 Hz, 1H), 3.64-3.76 (m, 1H), 3.83 (q, J=7.1 Hz, 1H), 4.25 (dd, J=10.8, 5.9 Hz, 1H), 4.30-4.46 (m, 5H), 6.19 (d, J=1.8 Hz, 1H), 6.44 (dd, J=8.8, 2.3 Hz, 1H), 7.38 (s, 1H), 7.75 (s, 1H), 8.06 (d, J=8.8 Hz, 1H);

MS m/z (ESI): 381.1 $[M+H]^+$.

Example 117

Preparation of (S)-2-((2-((S)-2-(cyanomethyl)-5-oxopyrrolidin-1-yl)-5,6-dihydrobenzo[f]imidazo[1,2-d][1,4]oxazepin-9-yl)amino)propanamide

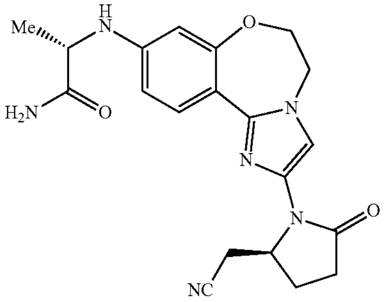 [SMILES: C[C@H](Nc1ccc2c(c1)OCCn1cc(N3C(=O)CC[C@H]3CC#N)nc1-2)C(N)=O]

(S)-2-((2-((S)-2-(Cyanomethyl)-5-oxopyrrolidin-1-yl)-5,6-dihydrobenzo[f]imidazo[1,2-d][1,4]oxazepin-9-yl)amino) propanamide was prepared by referring to the method of Example 1.

$^1$H NMR (400 MHz, DMSO-$d_6$) δ 1.30 (d, J=6.8 Hz, 3H), 1.99 (t, J=10.8 Hz, 1H), 2.42 (dd, J=22.2, 12.2 Hz, 3H), 2.62-2.71 (m, 1H), 3.13 (dd, J=16.8, 2.8 Hz, 1H), 3.69-3.80 (m, 1H), 4.17-4.48 (m, 4H), 4.53-4.66 (m, 1H), 6.08 (d, J=1.7 Hz, 1H), 6.15 (d, J=7.0 Hz, 1H), 6.40 (dd, J=8.8, 1.8 Hz, 1H), 7.01 (s, 1H), 7.38 (s, 1H), 7.41 (s, 1H), 7.98 (d, J=8.9 Hz, 1H);

MS m/z (ESI): 395.2 $[M+H]^+$.

Example 118

Preparation of (S)-2-((2-((R)-4-(cyanomethyl)-2-oxooxazolidin-3-yl)-5,6-dihydrobenzo[f]imidazo[1,2-d][1,4]oxazepin-9-yl)amino)propanamide

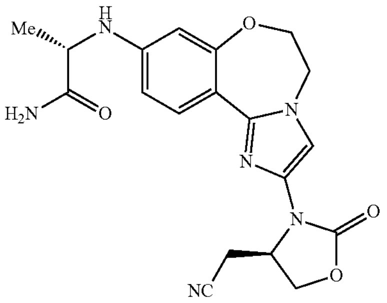 [SMILES: C[C@H](Nc1ccc2c(c1)OCCn1cc(N3C(=O)OC[C@H]3CC#N)nc1-2)C(N)=O]

(S)-2-((2-((R)-4-(Cyanomethyl)-2-oxooxazolidin-3-yl)-5,6-dihydrobenzo[f]imidaz o[1,2-d][1,4]oxazepin-9-yl) amino)propanamide was prepared by referring to the method of Example 1.

$^1$H NMR (400 MHz, DMSO-$d_6$) δ 1.30 (d, J=6.9 Hz, 3H), 3.14 (dd, J=17.1, 2.4 Hz, 1H), 3.45 (dd, J=17.1, 5.0 Hz, 1H), 3.72-3.80 (m, 1H), 4.33 (ddd, J=13.3, 8.4, 4.7 Hz, 5H), 4.66 (t, J=8.9 Hz, 1H), 4.77 (dt, J=8.4, 4.9 Hz, 1H), 6.08 (d, J=2.1 Hz, 1H), 6.17 (d, J=7.0 Hz, 1H), 6.40 (dd, J=8.8, 2.2 Hz, 1H), 7.02 (s, 1H), 7.20 (s, 1H), 7.39 (d, J=1.0 Hz, 1H), 7.98 (d, J=8.8 Hz, 1H);

MS m/z (ESI): 397.1 [M+H]$^+$.

Example 119

Preparation of (S)-2-((2-((R)-4-(cyanomethyl)-2-oxothiazolidin-3-yl)-5,6-dihydrobenzo[f]imidazo[1,2-d][1,4]oxazepin-9-yl)amino)propanamide

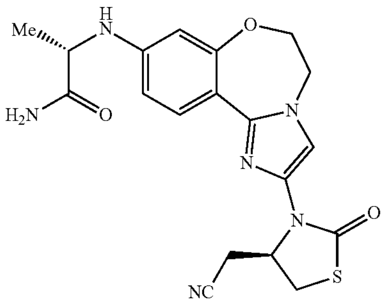 [SMILES: C[C@H](Nc1ccc2c(c1)OCCn1cc(N3C(=O)SC[C@H]3CC#N)nc1-2)C(N)=O]

(S)-2-((2-((R)-4-(Cyanomethyl)-2-oxothiazolidin-3-yl)-5,6-dihydrobenzo[f]imidaz o[1,2-d][1,4]oxazepin-9-yl) amino)propanamide was prepared by referring to the method of Example 1.

MS m/z (ESI): 436.2 [M+H]$^+$.

Example 120

Preparation of (S)-2-((2-((R)-4-(cyanomethyl)-2-oxooxazolidin-3-yl)-5,6-dihydrobenzo[f]imidazo[1,2-d][1,4]oxazepin-9-yl)amino)-3-methoxypropanamide

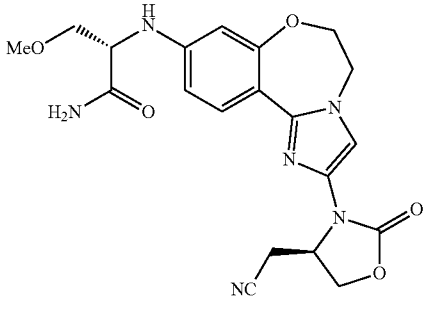 [SMILES: COC[C@H](Nc1ccc2c(c1)OCCn1cc(N3C(=O)OC[C@H]3CC#N)nc1-2)C(N)=O]

(S)-2-((2-((R)-4-(Cyanomethyl)-2-oxooxazolidin-3-yl)-5,6-dihydrobenzo[f]imidaz o[1,2-d][1,4]oxazepin-9-yl) amino)-3-methoxypropanamide was prepared by referring to the method of Example 1.

$^1$H NMR (400 MHz, DMSO-$d_6$) δ 3.14 (dd, J=17.6, 2.8 Hz, 1H), 3.28 (s, 3H), 3.46 (dd, J=17.3, 4.4 Hz, 1H), 3.56 (d, J=5.3 Hz, 2H), 3.92-4.01 (m, 1H), 4.24-4.48 (m, 5H), 4.66 (t, J=9.0 Hz, 1H), 4.74-4.81 (m, 1H), 6.09-6.21 (m, 2H), 6.46 (dd, J=8.7, 1.7 Hz, 1H), 7.16 (s, 1H), 7.20 (s, 1H), 7.46 (s, 1H), 7.99 (d, J=8.8 Hz, 1H);

MS m/z (ESI): 427.1 [M+H]$^+$.

Example 121

Preparation of (S)-2-((2-((R)-4-(2-methoxyethyl)-2-oxooxazolidin-3-yl)-5,6-dihydrobenzo[f]imidazo[1,2-d][1,4]oxazepin-9-yl)amino)propanamide

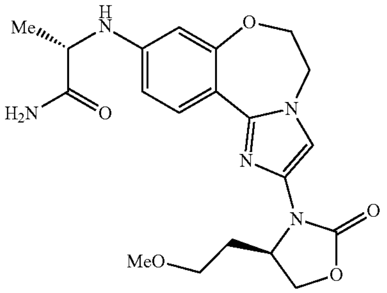 [SMILES: COCC[C@@H]1COC(=O)N1c1cn2c(n1)-c1ccc(N[C@@H](C)C(N)=O)cc1OCC2]

(S)-2-((2-((R)-4-(2-Methoxyethyl)-2-oxooxazolidin-3-yl)-5,6-dihydrobenzo[f]imid azo[1,2-d][1,4]oxazepin-9-yl) amino)propanamide was prepared by referring to Example 1.

MS m/z (ESI): 416.1 [M+H]$^+$.

Example 122

Preparation of (S)-2-((2-((S)-4-(difluoromethyl)-2-oxo-1,3-thiazinan-3-yl)-5,6-dihydrobenzo[f]imidazo[1,2-d][1,4]oxazepin-9-yl)amino)propanamide

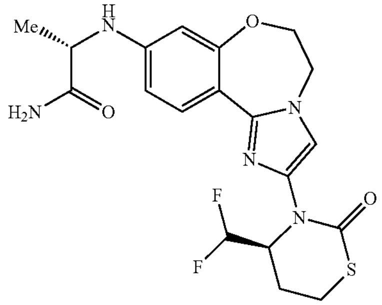 [SMILES: C[C@H](Nc1ccc2c(c1)OCCn1cc(N3C(=O)SCC[C@H]3C(F)F)nc1-2)C(N)=O]

(S)-2-((2-((S)-4-(Difluoromethyl)-2-oxo-1,3-thiazinan-3-yl)-5,6-dihydrobenzo[f]i midazo[1,2-d][1,4]oxazepin-9-yl) amino)propanamide was prepared by referring to Example 51.

MS m/z (ESI): 438.1 [M+H]$^+$.

Example 123

Preparation of (S)-2-((2-((S)-4-(difluoromethyl)-2-oxo-1,3-thiazinan-3-yl)-8-fluoro-5,6-dihydrobenzo[f]imidazo[1,2-d][1,4]oxazepin-9-yl)amino)propanamide

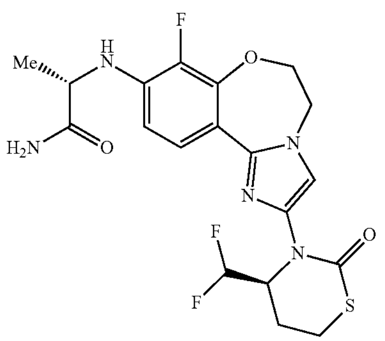 [SMILES: C[C@H](Nc1ccc2c(c1F)OCCn1cc(N3C(=O)SCC[C@H]3C(F)F)nc1-2)C(N)=O]

(S)-2-((2-((S)-4-(Difluoromethyl)-2-oxo-1,3-thiazinan-3-yl)-8-fluoro-5,6-dihydrob enzo[f]imidazo[1,2-d][1,4]oxazepin-9-yl)amino)propanamide was prepared by referring to Example 51.

MS m/z (ESI): 456.1 [M+H]$^+$.

Example 124

Preparation of (S)-2-((2-((S)-4-(difluoromethyl)-2-oxo-1,3-thiazinan-3-yl)-5,6-dihydrobenzo[f]imidazo[1,2-d][1,4]oxazepin-9-yl)amino)-3-methoxypropanamide

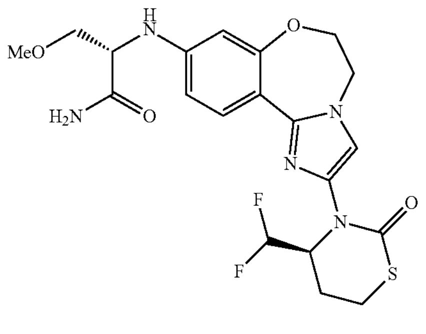 [SMILES: COC[C@H](Nc1ccc2c(c1)OCCn1cc(N3C(=O)SCC[C@H]3C(F)F)nc1-2)C(N)=O]

(S)-2-((2-((S)-4-(Difluoromethyl)-2-oxo-1,3-thiazinan-3-yl)-5,6-dihydrobenzo[f]i midazo[1,2-d][1,4]oxazepin-9-yl)amino)-3-methoxypropanamide was prepared by referring to Example 51.

MS m/z (ESI): 468.1 [M+H]$^+$.

Example 125

Preparation of (S)-2-((2-((S)-3-(difluoromethyl)-5-oxomorpholino)-8-fluoro-5,6-dihydrobenzo[f]imidazo[1,2-d][1,4]oxazepin-9-yl)amino)propanamide

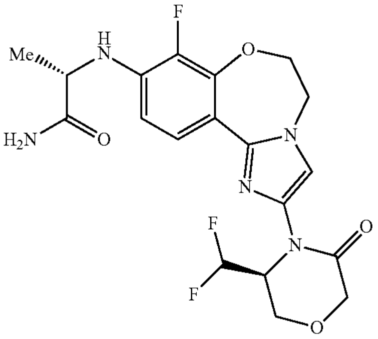 [SMILES: C[C@H](Nc1ccc2c(c1F)OCCn1cc(N3C(=O)COC[C@H]3C(F)F)nc1-2)C(N)=O]

(S)-2-((2-((S)-3-(Difluoromethyl)-5-oxomorpholino)-8-fluoro-5,6-dihydrobenzo[f]imidazo[1,2-d][1,4]oxazepin-9-yl)amino)propanamide was prepared by referring to Example 68.

MS m/z (ESI): 440.1 [M+H]$^+$.

Example 126

Preparation of (S)-2-((2-((S)-3-(difluoromethyl)-5-oxomorpholino)-5,6-dihydrobenzo[f]imidazo[1,2-d][1,4]oxazepin-9-yl)amino)-3-methoxypropanamide

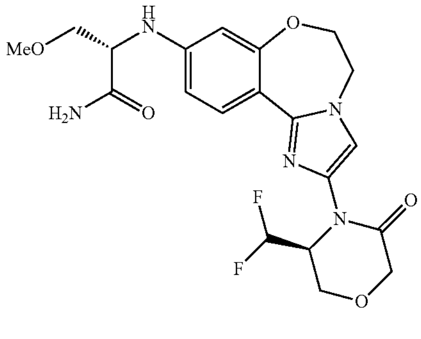 [SMILES: COC[C@H](Nc1ccc2c(c1)OCCn1cc(N3C(=O)COC[C@H]3C(F)F)nc1-2)C(N)=O]

(S)-2-((2-((S)-3-(Difluoromethyl)-5-oxomorpholino)-5,6-dihydrobenzo[f]imidazo[1,2-d][1,4]oxazepin-9-yl)amino)-3-methoxypropanamide was prepared by referring to Example 68.

MS m/z (ESI): 452.1 [M+H]$^+$.

Example 127

Preparation of (S)-2-((2-((S)-2-(difluoromethyl)-4-methyl-6-oxopiperazin-1-yl)-8-fluoro-5,6-dihydrobenzo[f]imidazo[1,2-d][1,4]oxazepin-9-yl)amino)propanamide

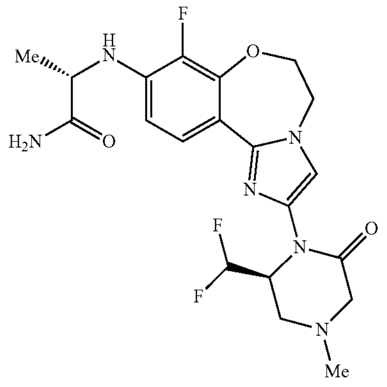 [SMILES: C[C@H](Nc1ccc2c(c1F)OCCn1cc(N3C(=O)CN(C)C[C@H]3C(F)F)nc1-2)C(N)=O]

(S)-2-((2-((S)-2-(Difluoromethyl)-4-methyl-6-oxopiperazin-1-yl)-8-fluoro-5,6-dihydrobenzo[f]imidazo[1,2-d][1,4]oxazepin-9-yl)amino)propanamide was prepared by referring to Example 69.

MS m/z (ESI): 453.1 $[M+H]^+$.

Example 128

Preparation of (S)-2-((2-((S)-2-(difluoromethyl)-4-methyl-6-oxopiperazin-1-yl)-5,6-dihydrobenzo[f]imidazo[1,2-d][1,4]oxazepin-9-yl)amino)-3-methoxypropanamide

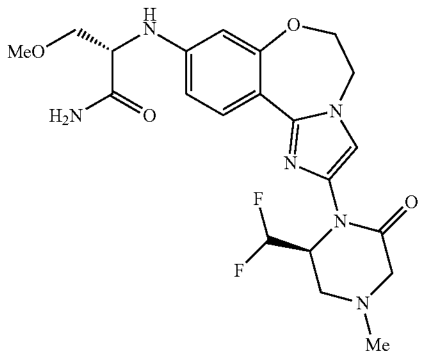 [SMILES: COC[C@H](Nc1ccc2c(c1)OCCn1cc(N3C(=O)CN(C)C[C@H]3C(F)F)nc1-2)C(N)=O]

(S)-2-((2-((S)-2-(Difluoromethyl)-4-methyl-6-oxopiperazin-1-yl)-5,6-dihydrobenzo[f]imidazo[1,2-d][1,4]oxazepin-9-yl)amino)-3-methoxypropanamide was prepared by referring to Example 69.

MS m/z (ESI): 465.1 $[M+H]^+$.

Example 129

Preparation of (2S,3R)-1-(2-((S)-4-(difluoromethyl)-2-oxooxazolidin-3-yl)-5,6-dihydrobenzo[f]imidazo[1,2-d][1,4]oxazepin-9-yl)-3-methylpyrrolidine-2-carboxamide

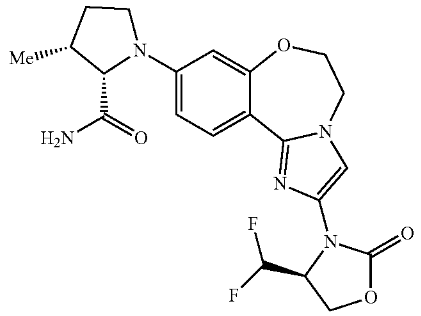 [SMILES: C[C@@H]1CCN(c2ccc3c(c2)OCCn2cc(N4C(=O)OC[C@H]4C(F)F)nc2-3)[C@@H]1C(N)=O]

(2S,3R)-1-(2-((S)-4-(Difluoromethyl)-2-oxooxazolidin-3-yl)-5,6-dihydrobenzo[f]imidazo[1,2-d][1,4]oxazepin-9-yl)-3-methylpyrrolidine-2-carboxamide was prepared by referring to Example 1.

MS m/z (ESI): 448.1 $[M+H]^+$.

Biological Assay and Evaluation

The present invention is further described below in combination with the following test examples, which are not intended to limit the scope of the present invention.

Test Example 1. Determination of the Inhibitory Effect of the Compounds of the Examples of the Present Invention on PI3Kα/β/γ/δ Kinase Activity Experimental objective: The objective of this test example is to determine the inhibitory effect of the compounds of the examples on PI3Kα/β/γ/δ kinase activity.

Experimental instruments: Centrifuge (5810R, purchased from Eppendorf), pipette (purchased from Eppendorf or Rainin), and microplate reader (Model: SynergyH1 full-function microplate reader, purchased from BioTek, USA).

Experimental method: Promega's ADP-Glo lipid kinase assay method (Promega #V9102) was applied in this experiment. Lipid kinase PI3Kα/β/γ/δ catalyzed the generation of ADP from ATP in the presence of the substrate PIP2: 3PS and ATP. The lipid kinase activity was characterized by measuring the ADP content in the reaction, and the half inhibitory concentration $IC_{50}$ of the compound on inhibiting PI3Kα/β/γ/δ kinase activity was thus obtained.

The specific experimental process is as follows:

The kinase reaction was carried out in a white 384-well plate (Perkin Elmer #6007299). 2 μL of the compound solution of different concentrations diluted with $ddH_2O$ containing 1% DMSO was added to each well. 2 μL of $ddH_2O$ containing 1% DMSO was added to the positive control well. 2 μL of 0.1~2 nM PI3K kinase solution diluted with 5× kinase buffer (HEPES 250 mM, $MgCl_2$ 15 mM, NaCl 250 mM, BSA 0.05%) was added to each well. 2 μL of 5× kinase buffer was added to the negative control well. 4 μL of 50 μM substrate PIP2: 3PS (Promega #V1701) formulated with 10×Dilution buffer and $ddH_2O$ was added to all wells. Finally, 2 μL of 50~100 μM ATP solution diluted with water was added to start the reaction. After the reaction was carried out at room temperature for 90 to 120 minutes, 10 μL of ADP-Glo Reagent (containing 10 mM $MgCl_2$) was added to each well, and reacted at room temperature for 60 minutes to remove excess ATP in the reaction. 20 μL of Kinase Detection Reagent was added to each well, and reacted at room temperature in the dark for 20 minutes. The chemiluminescence value was measured by the BioTek Synergy H1 microplate reader.

| Enzyme Name | Article number | Enzyme reaction concentration | Enzyme reaction time | ATP concentration |
|---|---|---|---|---|
| PI3Kα | Promega#V1721 | 0.1 nM | 120 min | 50 μM |
| PI3Kβ | Carna#11-102 | 0.4 nM | 90 min | 100 μM |
| PI3Kγ | Thermofisher#PV4786 | 0.4 nM | 120 min | 50 μM |
| PI3Kδ | Carna#11-103 | 0.1 nM | 90 min | 100 μM |

Experimental Data Processing Method:

The percentage inhibition data of the compound-treated well was calculated through the positive control well (DMSO control well) and negative control well (no kinase added) on the plate {% inhibition rate=100−[(test compound value−negative control value)]/(positive control value−negative control value)×100}. The $IC_{50}$ value was calculated by fitting the data of different concentrations and corresponding percentage inhibition rates to a four-parameter nonlinear logic formula with GraphPad prism.

Experimental Results:

According to the above scheme, the compounds of the examples of the present invention showed the following biological activities in Table 1 in the PI3Kα/β/γ/δ kinase activity test.

TABLE 1

| Example | PI3Kα, $IC_{50}$ (nM) | PI3Kβ, $IC_{50}$ (nM) | PI3Kγ, $IC_{50}$ (nM) | PI3Kδ, $IC_{50}$ (nM) | Selectivity of PI3Kα vs PI3Kβ | Selectivity of PI3Kα vs PI3Kγ | Selectivity of PI3Kα vs PI3Kδ |
|---|---|---|---|---|---|---|---|
| Example 10 | 7.9 | >10000 | 1788 | 1398 | >1266 | 226 | 177 |
| Example 38 | 4 | 1432 | 447 | 410 | 358 | 112 | 103 |
| Example 43 | 0.86 | 283 | 557 | 25 | 329 | 648 | 29 |
| Example 51 | 0.2 | 168 | 90 | 49 | 840 | 450 | 245 |
| Example 53 | 5 | 6190 | 402 | 373 | 1238 | 80 | 75 |
| Example 54 | 1.2 | 1799 | 481 | 336 | 1499 | 401 | 280 |
| Example 55 | 1.7 | 1872 | 363 | 213 | 1101 | 214 | 125 |
| Example 66 | 9.3 | 4574 | 2076 | 653 | 492 | 223 | 70 |
| Example 68 | 0.38 | 198 | 79 | 24 | 521 | 208 | 63 |
| Example 69 | 2.1 | 3179 | 332 | 142 | 1514 | 158 | 68 |
| Example 77 | 5.2 | 924 | 450 | 306 | 178 | 87 | 59 |
| Example 78 | 5.2 | 2786 | 510 | 459 | 536 | 98 | 88 |
| Example 97 | 2.1 | 1649 | 510 | 190 | 785 | 243 | 90 |
| Example 108 | 2.4 | 472 | 247 | 194 | 197 | 103 | 81 |
| Example 109 | 6.8 | 1069 | 1154 | 348 | 157 | 170 | 51 |
| Example 110 | 1 | 754 | 376 | 139 | 754 | 376 | 139 |
| Example 111 | 2.9 | 1227 | 736 | 125 | 423 | 254 | 43 |
| Example 112 | 2.2 | 523 | 478 | 69 | 238 | 217 | 31 |
| Example 117 | 2.5 | 1948 | 505 | 280 | 779 | 202 | 112 |
| Example 118 | 1.3 | 190 | 74 | 50 | 146 | 57 | 38 |
| Example 119 | 2.4 | 407 | 116 | 71 | 170 | 48 | 30 |
| Example 120 | 4.7 | 988 | 530 | 200 | 210 | 113 | 43 |

The above data show that the compounds of the examples of the present invention have a good activity and selectivity in inhibiting PI3Kα/β/γ/δ kinase activity.

Test Example 2. Determination of the Proliferation Inhibitory Effect of the Compounds of the Examples of the Present Invention on PI3Kα Mutant Cancer Cells Experimental objective: The objective of this test example is to determine the proliferation inhibitory activity of the compounds of the examples on PI3Kα mutant 10 cancer cells HCC1954 (H1047R), HGC-27 (E542K) and MKN1 (E545K).

Experimental instruments: Centrifuge (5702R, purchased from Eppendorf), carbon dioxide incubator (purchased from Thermo), biological safety cabinet (purchased from Shanghai Boxun Company), pipette (purchased from Eppendorf or Rainin), and microplate reader (Model: SynergyH1 full-function microplate reader, purchased from Bio Tek, USA).

Experimental method: The proliferation inhibitory effect of the compounds of the examples on PI3Kα mutant cancer cell lines HCC1954, HGC-27 and MKN1 was determined by Cell Titer-Glo method. The cell lines were cultured in RPMI 1640 medium (Gibco #22400089) containing 10% FBS (Gibco #10091148) and 1% P/S (Hyclone #SV30010) at 37° C. and 5% $CO_2$. Before the experiment, the cells were collected and counted, and then the cell density was adjusted. The cells were inoculated in a white 96-well plate (Corning #3610) at a density of 1000 to 10000 cells/well, and incubated in an incubator at 37° C., 5% $CO_2$ overnight. The compound solution of different concentrations was added, and corresponding vehicle control was set at the same time. The cell plate was further incubated in an incubator at 37° C., 5% $CO_2$ for 48 to 96 hours. The cell plate and its content were equilibrated to room temperature. 20 to 100 μL of Cell Titer-Glo solution (Promega #G7573) was added to each well, and the plate was shaked well and incubated at room temperature in the dark for 5 to 30 minutes. The chemiluminescence value was measured by the BioTek SynergyH1 microplate reader.

Experimental Data Processing Method:

The percentage inhibition data of the well treated by the compounds of the examples was calculated through the vehicle control well on the plate {% inhibition rate=100−(test compound value/vehicle control value)×100}. The $IC_{50}$ value was calculated by fitting the data of different concentrations and corresponding percentage inhibition rates to a four-parameter nonlinear logic formula with GraphPad prism.

Experimental Results:

According to the above scheme, the compounds of the examples of the present invention showed the following biological activities in Table 2 in the PI3Kα mutant cancer cells HCC1954 (H1047R), HGC-27 (E542K) and MKN1 (E545K) proliferation inhibition test.

TABLE 2

| Example | HCC1954 (H1047R) $IC_{50}$ (nM) | MKN1 (E545K) $IC_{50}$ (nM) | HGC-27(E542K) $IC_{50}$ (nM) |
|---|---|---|---|
| Example 38 | 204 | 615 | 417 |
| Example 43 | 112 | 214 | 169 |
| Example 48 | 205 | 399 | 396 |
| Example 51 | 21 | 60 | 40 |
| Example 54 | 79 | 84 | 93 |
| Example 55 | 160 | 508 | 325 |
| Example 68 | 70 | 113 | 111 |
| Example 69 | 601 | 584 | 433 |
| Example 77 | 226 | 653 | 499 |
| Example 90 | 222 | 368 | 531 |
| Example 97 | 184 | 268 | 186 |
| Example 108 | 98 | 118 | 233 |
| Example 109 | 243 | 426 | 455 |
| Example 110 | 57 | 109 | 137 |
| Example 111 | 40 | 66 | 77 |
| Example 112 | 29 | 42 | 32 |
| Example 118 | 140 | 398 | 371 |
| Example 119 | 134 | 304 | 358 |

The above data show that the compounds of the examples of the present invention have a good activity in inhibiting PI3Kα mutant cancer cells HCC1954 (H1047R), HGC-27 (E542K) and MKN1 (E545K) proliferation.

Test Example 3. Toxicity Test of a 7-Day Repeatedly Intragastric Administration in SD Rats 3.1 Experimental Objective The objective of this study is to investigate the possible toxicity of GDC-0077 and the compound of Example 51 in SD rats after a 7-day repeatedly intragastric administration, and to compare the toxicity differences between GDC-0077 and the compound of Example 51.

3.2 Experimental Materials and Instruments 3.2.1 Test Compound

Test compound 1: GDC-0077

Test compound 2: the compound of Example 51

3.2.2 Vehicle

Name: 20% aqueous SBE-B-CD (Captisol) solution 3.2.3 Animal Information

Species & strains: Sprague-Dawley (SD) rats

Animal grade: SPF grade

Number and sex of animals: 112 rats, half male and half female 3.2.4 Instruments ADVIA®2120 automatic blood analyzer, which was used for blood cell counting;

SYSMEX CA-500 blood coagulometer, which was used for the determination of coagulation function indicators;

TBA-120FR automatic biochemical analyzer, which was used for the determination of blood biochemical indicators;

Easylyte electrolyte analyzer, which was used for the determination of electrolyte; and Liquid chromatography—mass spectrometry (detector: API4000, electrospray source (ESI) positive ion mode, column: Agilent ZORBAX XDB-C18 (3.5 μm, 2.1×50 mm)), which was used for the biological analysis of plasma sample.

3.3 Experimental Method

1) In the experiment, 112 rats (56 rats/sex) were divided into 14 groups by sex and body weight, wherein 70 rats were used for toxicology study (groups 1 to 7, 5 rats/sex/group) and 42 rats were used for toxicokinetics study (groups 8 to 14, 3 rats/sex/group).

2) As the vehicle control group, the animals in groups 1 and 8 were intragastrically administered 20% aqueous SBE-B-CD (Captisol) solution.

3) The animals in groups 2 and 9, groups 3 and 10, and groups 4 and 11 were intragastrically administered GDC-0077 at 10, 30 and 60 mg/kg, respectively.

4) The animals in groups 5 and 12, groups 6 and 13, and groups 7 and 14 were intragastrically administered the compound of Example 51 at 10, 30 and 60 mg/kg, respectively.

5) The animals were administered once a day for 7 consecutive days (the animals in groups 7 and 14 were administered for 6 consecutive days).

6) The administration volume was 10 mL/kg.

7) During the experiment, items such as clinical observation, body weight, food intake, clinicopathological indicators (blood cell count, coagulation function, blood biochemistry), toxicokinetics and the like were studied.

8) All animals were euthanized on Day 8 (the animals in groups 7 and 14 were euthanized after administration on Day 6).

9) During the experiment, gross anatomy observation was carried out on animals in groups 1 to 7, animals in group 14 and dead animals (including animals in toxicokinetics study), and histopathological examination was carried out on abnormal tissues, gastrointestinal tissues (such as colon and cecum) and immune tissues (such as thymus).

3.4 Test Data List 3.4.1 Near-Death/Death

Regarding to GDC-0077 or the compound of Example 51 at the dose of 60 mg/kg, near-dead/dead animals were found. Regarding to other doses, no dead/near-dead animals were found.

3.4.2 Toxicokinetics

At the dose of 30 mg/kg, the average system exposure AUC of the compound of Example 51 after the last administration (male: 11400 h*ng/mL, female: 15900 h*ng/mL) was about 2.4 to 3.8 times that of GDC-0077 at the same dose (male: 3000 h*ng/mL, female: 6510 h*ng/mL), and similar to that of GDC-0077 at the dose of 60 mg/kg after the first administration (male: 15400 h*ng/mL, female: 22800 h*ng/mL).

At the dose of 10 mg/kg, the average system exposure AUC of the compound of Example 51 after the last administration (male: 2110 h*ng/mL, female: 3170 h*ng/mL) was about 1.4 to 2.5 times that of GDC-0077 (male: 845 h*ng/mL, female: 2250 h*ng/mL).

Therefore, the system exposure of the compound of Example 51 was significantly higher than that of GDC-0077 at the same dose.

3.4.3 Clinical Observation

GDC-0077: In the high-dose group, abnormal symptoms such as arched back, loose stools, perianal contamination and fluffy coat were observed.

The compound of Example 51: In the middle-dose and high-dose groups, abnormal symptoms such as arched back, loose stools, perianal contamination and fluffy coat were observed.

3.4.4 Body Weight and Food Intake

GDC-0077: In the middle-dose and high-dose groups, the final body weight of all animals declined, and their food intake also declined during the same period.

The compound of Example 51: In the low-dose, middle-dose and high-dose groups, the final body weight declined, and the corresponding food intake also declined.

3.4.5 Blood Cell Counting and Coagulation Function

GDC-0077: In each dose group, Retic decreased in both male and female animals.

The compound of Example 51: In each dose group, Retic decreased in both male and female animals; and in 30 mg/kg group and 60 mg/kg group, Neut increased and PLT decreased in both male and female animals.

3.4.6 Blood Biochemistry

GDC-0077: In each dose group, Glu and CHO increased in male animals: in 60 mg/kg group, AST and UREA increased in both male and female animals, A/G decreased in both male and female animals, and ALT increased in male animals; and in 30 mg/kg group, AST and UREA increased in both male and female animals, and ALT increased in female animals.

The compound of Example 51: In 60 mg/kg group, AST, Glu and UREA increased in both male and female animals: in 30 mg/kg group, AST and UREA increased in both male and female animals, and Glu increased in male animals; and in 10 mg/kg group, AST increased in both male and female animals.

3.4.7 Pathology

GDC-0077: The pathological changes under the microscope mainly included atrophy of goblet cells in the cecal mucosa, increase in thymic tingible body macrophages, and erosion, bleeding and edema of gastric mucosal.

The compound of Example 51: The pathological changes under the microscope mainly included bleeding and atrophy of glandular gastric mucosa: bleeding of cecal mucosa, atrophy of goblet cell, atrophy of colonic mucosa goblet cell: atrophy of splenic white pulp; and atrophy of thymic cortex or cortex and medulla, increase in tingible body macrophages and the like.

The main target organs of the toxicity of GDC-0077 and the compound of Example 51 are gastrointestinal tissues (such as stomach and cecum) and immune tissues (such as thymus).

3.5 Experimental Conclusion

During this experiment, the test compound GDC-0077 and the compound of Example 51 were administered intragastrically to SD rats for 7 days at a dose of 10, 30 and 60 mg/kg (once/day). The lethal dose of GDC-0077 and the compound of Example 51 is 60 mg/kg, and the maximum tolerated dose (MTD) is 30 mg/kg. At the dose of 30 mg/kg, the $C_{max}$ and $AUC_{(0-24h)}$ of the compound of Example 51 are significantly higher than those of GDC-0077. The tolerance of the compound of Example 51 is thus better than that of GDC-0077.

Test Example 4. In Vivo Efficacy Test of the Compounds of the Examples of the Present Invention 4.1 Experimental Objective The objective is to screen out compounds with significant efficacy and less toxic and side effects through in vivo efficacy test.

4.2 Main Experimental Instruments and Materials 4.2.1 Instruments:

1. Biological safety cabinet (BSC-1300II A2, Shanghai Boxun Medical Biological Instrument Corp.)
2. Ultra-clean workbench (CJ-2F, Suzhou Fengshi Laboratory Animal Equipment Co., Ltd.)
3. $CO_2$ incubator (Thermo-311)
4. Centrifuge (Centrifuge 5702R, Eppendorf)
5. Automatic cell counter (Countess II, Life)
6. Pipette (10-20 μL, Eppendorf)
7. Microscope (TS2, Nikon)
8. Vernier caliper (CD-6"AX, Mitutoyo, Japan)
9. Cell culture flask (T75/T225, Corning)
10. Electronic balance (CPA2202S, Sartorius)

4.2.2 Reagents:

1. RPMI-1640 medium (22400-089, Gibco)
2. Fetal Bovine Serum (FBS) (10091-148, Gibco)
3. 0.25% Trypsin (25200-056, Gibco)
4. Penicillin-streptomycin double antibiotics (15140-122, Gibco)
5. Phosphate buffered saline (PBS) (10010-023, Gibco)
6. Matrigel Matrix (356234, Corning)

4.2.3 Animal:

BALB/c nude mice, 6 to 8 weeks old, ♀, purchased from Shanghai Sippr-BK laboratory animal Co. Ltd.

4.3 Experimental Process 4.3.1 Cell Culture and Preparation of Cell Suspension a. HCC1954 cells were taken from the cell bank, and resuscitated in RPMI-1640 medium (RPMI-1640+10% FBS+1% SP). The resuscitated cells were placed in a cell culture flask (the cell type, date, operator's name and the like were marked on the wall of the flask), and cultured in a $CO_2$ incubator (the temperature of the incubator was 37° C., and the $CO_2$ concentration was 5%).

b. Passage was carried out after the cells covered 80 to 90% of the bottom of the culture flask. After passage, the cells continued to be cultured in the $CO_2$ incubator. This process was repeated until the number of cells met the requirement for in vivo efficacy test.

c. The cultured cells were collected and counted with the automatic cell counter. The cells were resuspended with PBS and matrigel according to the counting results to prepare a cell suspension (density: $5\times10^7$/mL), which was placed in an ice box for later use.

4.3.2 Cell Inoculation a. Before the inoculation, the nude mice were marked with disposable universal ear tags for rats and mice.

b. During the inoculation, the cell suspension was mixed well. 0.1 to 1 mL of cell suspension was sucked with a 1 ml syringe, the air bubbles were removed, and the syringe was placed on an ice bag for later use.

c. The nude mouse was bound with the left hand. The position of the right back near the right shoulder of the nude mouse (inoculation site) was disinfected with 75% alcohol, and inoculation was carried out after 30 seconds.

d. The test nude mice were subjected to inoculation successively (0.1 mL of cell suspension was inoculated to each mouse).

4.3.3 Tumor Volume Measurement, Grouping and Administration of the Tumor-Bearing Mouse a. According to the tumor growth, the tumor was measured on 14 to 18 days after the inoculation, and the tumor size was calculated.

Tumor volume calculation: tumor volume ($mm^3$)=length (mm)×width (mm)×width (mm)/2 b. According to the body weight and tumor size of the tumor-bearing mouse, grouping was carried out by a random grouping method.

c. According to the grouping results, the test compounds were administered (administration mode: oral administration; administration dose: 10 mg/kg; administration volume: 10 mL/kg: administration frequency: once/day: administration cycle: 21 days; vehicle: 0.5% CMC/1% Tween 80).

d. Tumor volume and body weight were measured twice a week after the administration of test compounds began.

e. After the end of the experiment, the animals were euthanized.

f. The data was processed with softwares such as Excel. Calculation of the tumor growth inhibition rate TGI (%) of a compound: when the tumor did not regress, TGI (%)=[(1−(average tumor volume of the treatment group at the end of the administration−average tumor volume of the treatment group at the beginning of the administration))/(average tumor volume of the vehicle control group at the end of the treatment−average tumor volume of the vehicle control group at the beginning of the treatment)]×100%. When the tumor regressed, TGI (%)=[1−(average tumor volume of the treatment group at the end of the administration−average tumor volume of the treatment group at the beginning of the administration)/average tumor volume of the treatment group at the beginning of the administration]×100%.

4.4 the Test Data is as Follows in Table 3;

TABLE 3

| Groups | Number of animals | Administration days (days) | Tumor growth inhibition rate |
|---|---|---|---|
| Control | 5 | 21 | — |
| Example 51 | 5 | 19 | 132% |
| Example 54 | 5 | 21 | 120% |
| Example 68 | 5 | 21 | 78% |
| Example 108 | 5 | 21 | 96% |
| Example 110 | 5 | 21 | 98% |

4.5 Experimental Results

It can be seen from the above results that the above compounds of the present application showed a good tumor growth inhibition rate.

Test Example 5. Pharmacokinetic (PK) Assay of the Compounds of the Examples of the Present Invention in Mice The pharmacokinetic assay of the preferred compounds of the examples of the present invention in mice was carried out in Balb/c male mice (Shanghai Jiesijie Laboratory Animal Co., LTD).

Administration mode: single intragastric administration.

Administration dose: 5 mg/10 ml/kg (body weight).

Formulation: the compound was dissolved in 0.5% CMC-Na by ultrasound to obtain a clear solution or homogeneous suspension.

Sampling points: 0.5, 1, 2, 4, 6, 8 and 24 hours after administration.

Sample Process:

1) 0.1 mL of blood was taken from the orbit, placed in a $K_2$-EDTA tube, and centrifuged for 5 to 20 minutes at room temperature at 1000 to 3000×g to separate the plasma, which was then stored at −80° C.

2) 160 μL of acetonitrile was added to 40 μL of plasma sample for precipitation, and then the mixture was centrifuged for 5 to 20 minutes at 500 to 2000×g.

3) 100 μL of processed supernatant was taken and analyzed by LC/MS/MS assay to determine the concentration of the test compound.

LC-MS/MS Assay:

Liquid chromatography condition: Shimadzu LC-20AD pump

Mass spectrometry condition: AB Sciex API 4000 mass spectrometer

Chromatographic column: phenomenex Gemiu 5 μm C18 50×4.6 mm

Mobile phase: solution A was 0.1% aqueous formic acid solution, and solution B was acetonitrile Flow rate: 0.8 mL/min Elution time: 0-4 minutes gradient elution Pharmacokinetics:

The main parameters were calculated using WinNonlin 6.1. The experimental results of the pharmacokinetic assay in mice are shown in Table 4 below:

TABLE 4

| | Pharmacokinetic assay (5 mg/kg) | | | | | |
|---|---|---|---|---|---|---|
| Example No. | Peak time $t_{max}$(h) | Plasma concentration $C_{max}$(ng/mL) | Area under curve $AUC_{0-t}$(ng/mL × h) | Area under curve $AUC_{0-\infty}$(ng/mL × h) | Half-life $t_{1/2}$(h) | Mean residence time MRT(h) |
| 43 | 0.5 | 2060 | 3442 | 3499 | 1.0 | 1.8 |
| 51 | 0.5 | 1057 | 2185 | 2274 | 1.6 | 2.2 |
| 53 | 0.5 | 1088 | 1283 | 1289 | 0.8 | 1.2 |
| 54 | 1.0 | 832 | 1560 | 1615 | 1.8 | 2.0 |

TABLE 4-continued

| | Pharmacokinetic assay (5 mg/kg) | | | | | |
|---|---|---|---|---|---|---|
| Example No. | Peak time $t_{max}$(h) | Plasma concentration $C_{max}$(ng/mL) | Area under curve $AUC_{0-t}$(ng/mL × h) | Area under curve $AUC_{0-\infty}$(ng/mL × h) | Half-life $t_{1/2}$(h) | Mean residence time MRT(h) |
| 68 | 0.5 | 641 | 1321 | 1339 | 1.6 | 1.8 |
| 77 | 0.5 | 2300 | 4089 | 4116 | 1.2 | 1.7 |
| 90 | 0.5 | 1287 | 2072 | 2086 | 1.0 | 1.6 |
| 108 | 0.5 | 1227 | 4238 | 4241 | 2.0 | 3.4 |
| 110 | 0.5 | 4020 | 13703 | 13712 | 2.8 | 3.7 |
| 111 | 0.5 | 466 | 1742 | 1744 | 2.8 | 3.9 |

It can be seen from the results of the pharmacokinetics assay in mice in the table that the compounds of the examples of the present invention showed good metabolic properties, and both the plasma exposure AUC and the maximum plasma concentration $C_{max}$ were good.

What is claimed is:

1. A compound of formula (V), a stereoisomer thereof, or a pharmaceutically acceptable salt thereof:

(V)

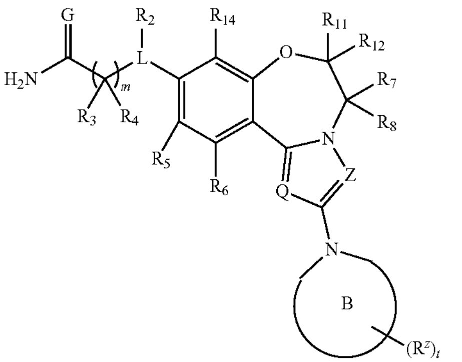

wherein:

G is selected from the group consisting of oxygen and sulfur;

L is nitrogen;

Q is N;

Z is —$CR_{aa}$;

ring B is selected from the group consisting of

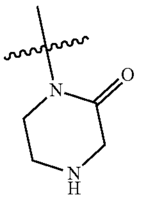
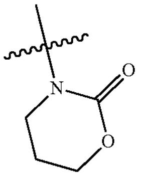
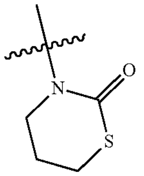
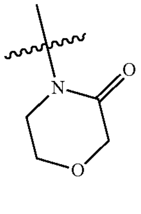
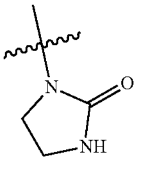
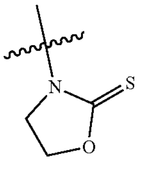

-continued

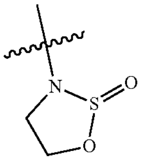
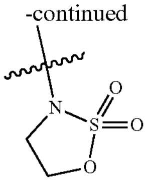
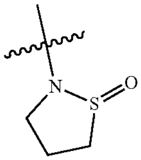
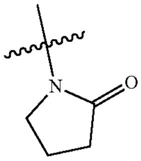
and
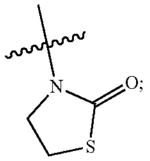
;

$R_5$, $R_6$ and $R_{14}$ are each independently selected from the group consisting of hydrogen, alkyl, haloalkyl, alkoxy, haloalkoxy, halogen and cyano;

$R_7$, $R_8$, $R_{11}$ and $R_{12}$ are each independently selected from the group consisting of hydrogen and alkyl;

$R^z$ is selected from the group consisting of hydrogen, alkyl, haloalkyl, alkoxy, haloalkoxy, halogen, and cyano, wherein the alkyl is optionally further substituted by one or more substituent(s) selected from the group consisting of cyano and alkoxy;

$R_2$ is selected from the group consisting of hydrogen and alkyl;

$R_3$ and $R_4$ are each independently selected from the group consisting of hydrogen, alkyl, haloalkyl, alkoxy, and hydroxyalkyl, wherein the alkyl is optionally further substituted by alkoxy;

or, any two groups of $R_2$, $R_3$, and $R_4$ are bonded to form a heterocyclyl, wherein the heterocyclyl is optionally further substituted by alkyl;

$R_{aa}$ is selected from the group consisting of hydrogen, alkyl, haloalkyl, alkoxy, hydroxyalkyl, haloalkoxy, halogen, cyano, and cycloalkyl;

m is 1; and t is 0, 1, or 2.

2. The compound, the stereoisomer thereof, or the pharmaceutically acceptable salt thereof according to claim 1, wherein:

ring B is selected from the group consisting of

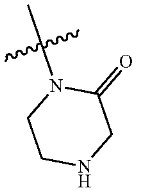
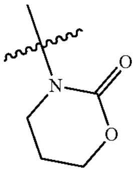
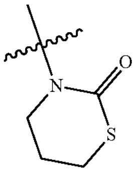

-continued

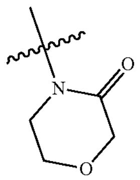 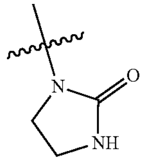 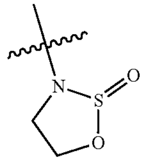

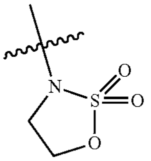 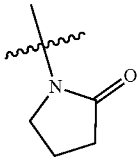 and

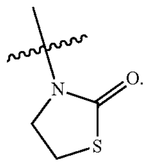

3. The compound of formula (VIII-A), the stereoisomer thereof, or the pharmaceutically acceptable salt thereof according to claim 1, wherein the compound is of formula (VIII-A):

(VII-A)

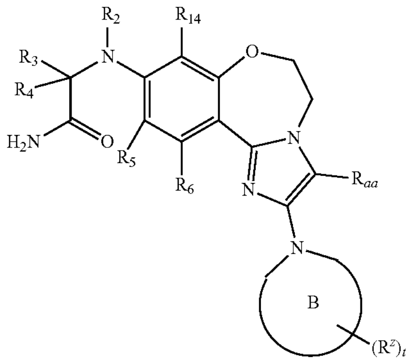

wherein:

ring B is selected from the group consisting of:

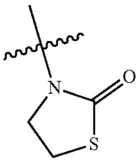 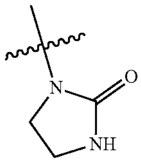 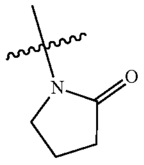

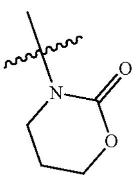 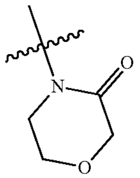 and

-continued

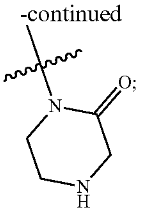

$R_2$ is selected from the group consisting of hydrogen and $C_{1-6}$ alkyl;

$R_3$ and $R_4$ are each independently selected from the group consisting of hydrogen, $C_{1-6}$ alkyl, $C_{1-6}$ haloalkyl and $C_{1-6}$ alkoxy;

or, $R_3$ and $R_4$ are bonded to form a 3 to 8 membered heterocyclyl;

or, $R_2$ and $R_3$ or $R_2$ and $R_4$ are bonded to form a 3 to 8 membered heterocyclyl;

$R_5$, $R_6$ and $R_{14}$ are each independently selected from the group consisting of hydrogen, halogen, cyano, $C_{1-6}$ alkyl, $C_{1-6}$ alkoxy and $C_{1-6}$ haloalkyl;

$R_{aa}$ is selected from the group consisting of hydrogen, $C_{1-6}$ alkyl, halogen and cyano;

$R^z$ is selected from the group consisting of hydrogen, $C_{1-6}$ alkyl optionally further substituted by one or more substituent(s) selected from the group consisting of cyano and alkoxy, cyano, and, $C_{1-6}$ haloalkyl; and t is 0, 1, or 2.

4. The compound of formula (VIII-A), the stereoisomer thereof, or the pharmaceutically acceptable salt thereof according to claim 3, wherein $R_2$ is selected from the group consisting of hydrogen and $C_{1-3}$ alkyl;

$R_3$ and $R_4$ are each independently selected from the group consisting of hydrogen, $C_{1-3}$ alkyl, and $C_{1-3}$ alkoxy;

or, $R_3$ and $R_4$ are bonded to form a 4 to 6 membered heterocyclyl;

or, $R_2$ and $R_3$ or $R_2$ and $R_4$ are bonded to form a 4 to 6 membered heterocyclyl;

$R_5$ and $R_6$ are each independently selected from the group consisting of hydrogen, halogen, cyano, $C_{1-3}$ alkyl, $C_{1-3}$ alkoxy and $C_{1-3}$ haloalkyl;

$R_{14}$ is selected from the group consisting of hydrogen and halogen;

$R^z$ is selected from the group consisting of hydrogen, $C_{1-3}$ haloalkyl, $C_{1-3}$ alkyl optionally further substituted by one or more substituent(s) selected from the group consisting of cyano and alkoxy, cyano; and $R_{aa}$ is selected from the group consisting of hydrogen and halogen.

5. The compound, the stereoisomer thereof, or the pharmaceutically acceptable salt thereof according to claim 1, wherein ring B is selected from the group consisting of

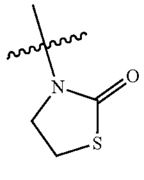 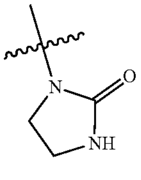 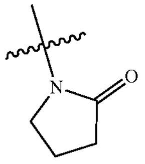

-continued

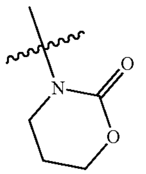

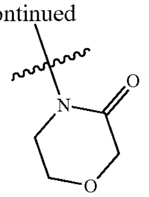

and

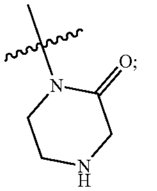

$R_2$ is selected from the group consisting of hydrogen and $C_{1-6}$ alkyl;

$R_3$ is selected from the group consisting of $C_{1-6}$ alkyl and $C_{1-6}$ alkoxy;

$R_5$ and $R_6$ are each independently selected from the group consisting of hydrogen and halogen;

$R_{14}$ is selected from the group consisting of hydrogen and halogen; and $R^z$ is selected from the group consisting of hydrogen, halogen, cyano, $C_{1-6}$ alkyl optionally further substituted by one or more substituent(s) selected from the group consisting of cyano and alkoxy, and $C_{1-6}$ alkyl substituted by halogen.

6. The compound, the stereoisomer thereof, or the pharmaceutically acceptable salt thereof according to claim 3, wherein the compound is of formula (X):

(X)

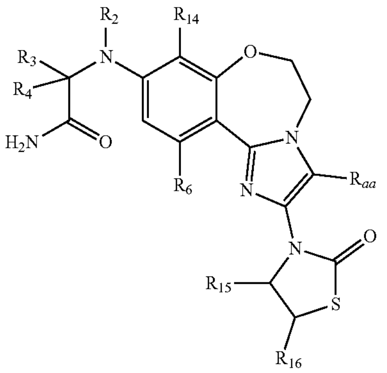

wherein:

$R_{15}$ and $R_{16}$ are each independently selected from the group consisting of hydrogen, $C_{1-6}$ alkyl optionally further substituted by one or more substituent(s) selected from the group consisting of cyano and alkoxy, cyano, and, $C_{1-6}$ haloalkyl; and $R_2$ to $R_4$, $R_6$, $R_{14}$, and $R_{aa}$ are as defined in claim 3.

7. The compound, the stereoisomer thereof, or the pharmaceutically acceptable salt thereof according to claim 1, wherein $R_2$ is selected from the group consisting of hydrogen and $C_{1-6}$ alkyl;

or, $R_2$ and $R_3$ or $R_2$ and $R_4$ are bonded to form pyrrolidinyl or azetidinyl;

$R_3$ and $R_4$ are each independently selected from the group consisting of hydrogen, $C_{1-6}$ alkyl, $C_{1-6}$ haloalkyl, and $C_{1-6}$ alkoxy;

or, $R_3$ and $R_4$ are bonded to form oxetanyl;

$R_5$ and $R_6$ are each independently selected from the group consisting of hydrogen, halogen, cyano, $C_{1-6}$ alkyl, $C_{1-6}$ alkoxy and $C_{1-6}$ haloalkyl;

$R_{14}$ is selected from the group consisting of hydrogen and halogen; and $R_{aa}$ is selected from the group consisting of hydrogen, halogen, cyano, $C_{1-6}$ alkyl, $C_{1-6}$ haloalkyl, $C_{1-6}$ alkoxy and $C_{3-8}$ cycloalkyl.

8. The compound, the stereoisomer thereof, or the pharmaceutically acceptable salt thereof according to claim 1, wherein $R_2$ is selected from the group consisting of hydrogen and $C_{1-3}$ alkyl;

$R_3$ is independently selected from the group consisting of $C_{1-3}$ alkyl, $C_{1-3}$ hydroxyalkyl, $C_{1-3}$ haloalkyl and $C_{1-3}$ alkoxy;

$R_5$ and $R_6$ are each independently selected from the group consisting of hydrogen, $C_{1-3}$ alkyl, $C_{1-3}$ alkoxy and $C_{1-3}$ haloalkyl;

$R_{14}$ is selected from the group consisting of hydrogen, $C_{1-3}$ alkyl, $C_{1-3}$ alkoxy and $C_{1-3}$ haloalkyl; and $R_{aa}$ is selected from the group consisting of halogen, cyano, $C_{1-3}$ alkyl, $C_{1-3}$ alkoxy and $C_{1-3}$ haloalkyl.

9. A compound, a stereoisomer thereof, or a pharmaceutically acceptable salt thereof, wherein the compound is one of the following structures:

1

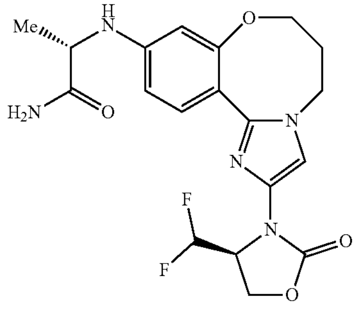

2

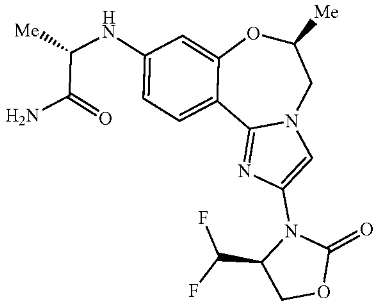

3

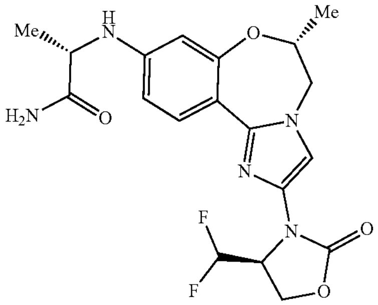

-continued
4
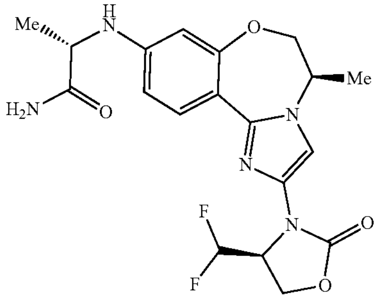
5
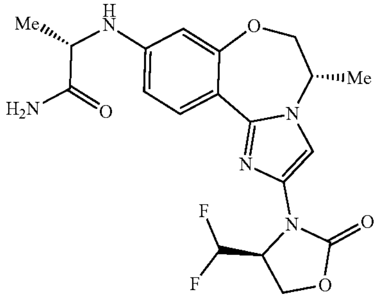
6
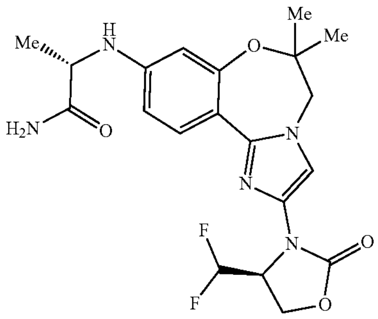
7
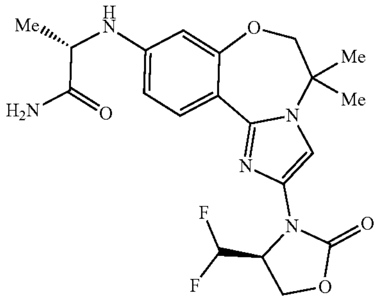
8
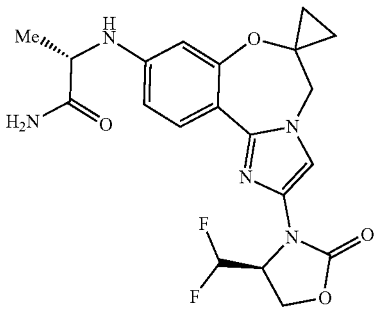
-continued
9
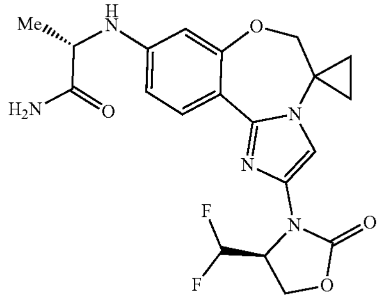
10
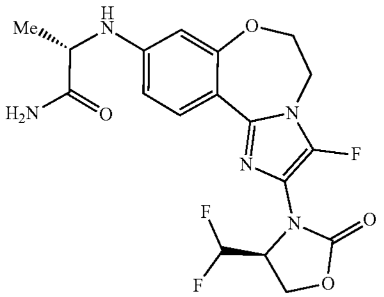
11
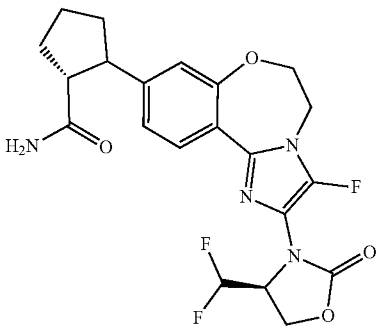
12
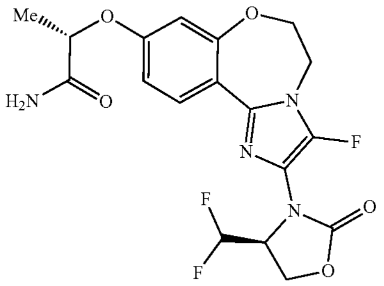
13
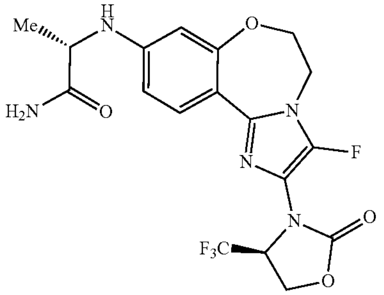

-continued
14
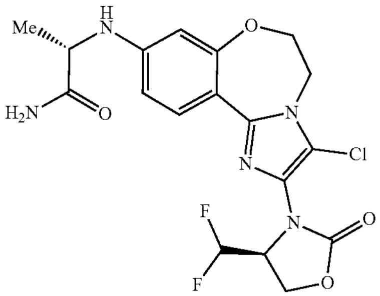
15
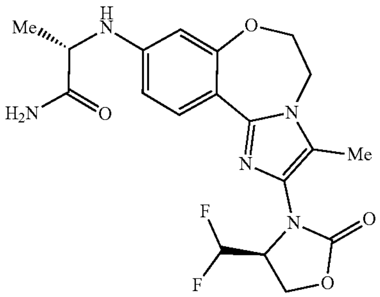
16
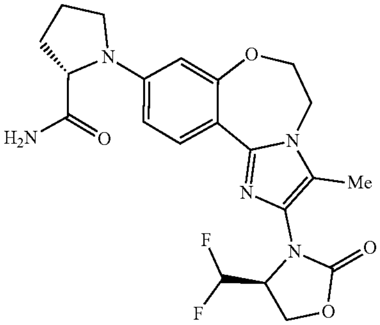
17
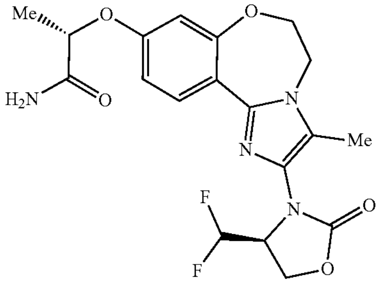
18
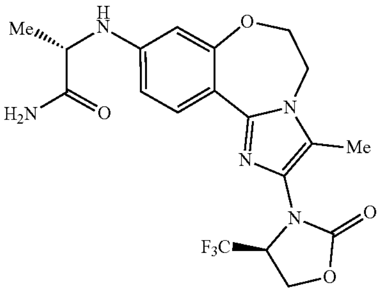
-continued
19
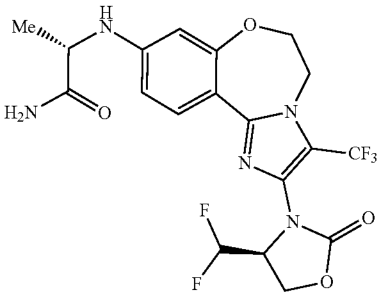
20
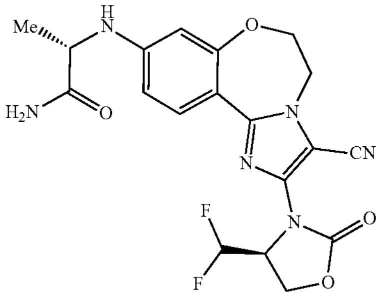
21
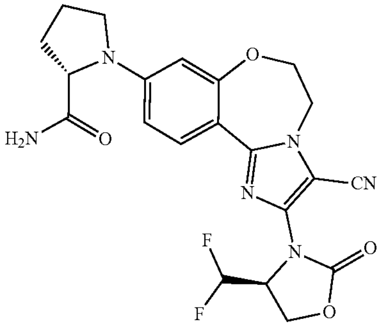
22
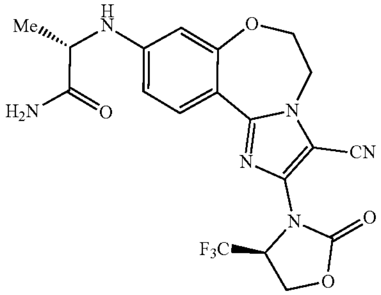
23
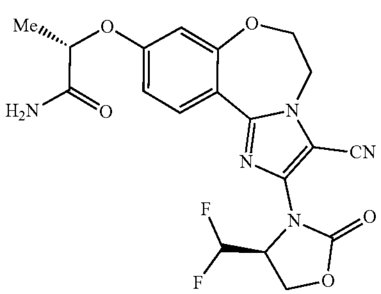

-continued
24
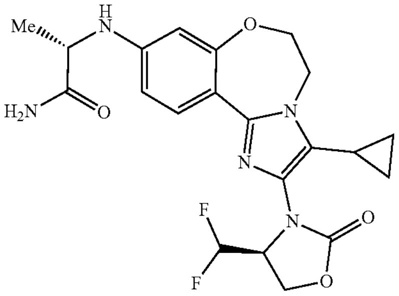
25
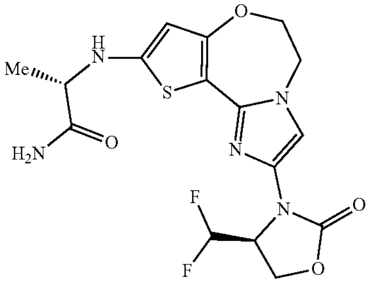
26
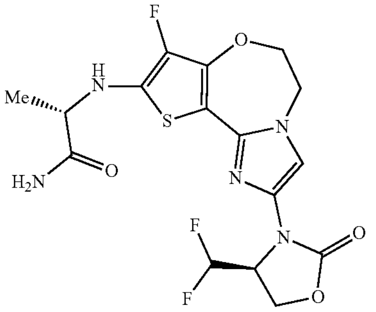
27
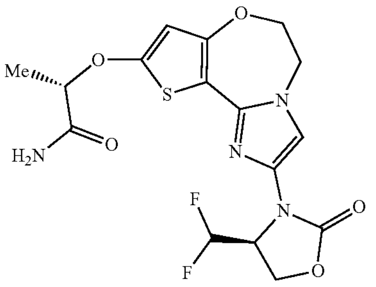
28
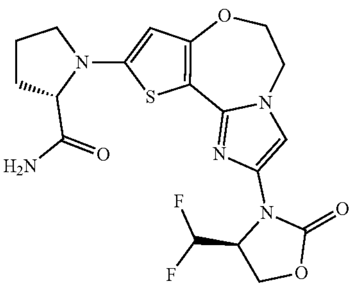
-continued
29
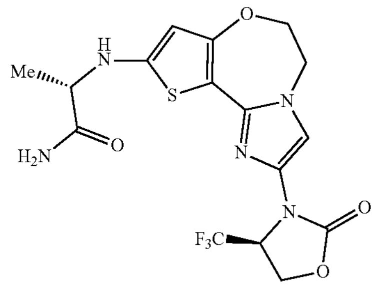
30
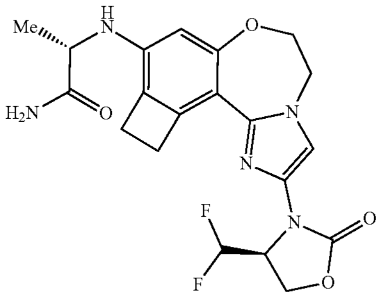
31
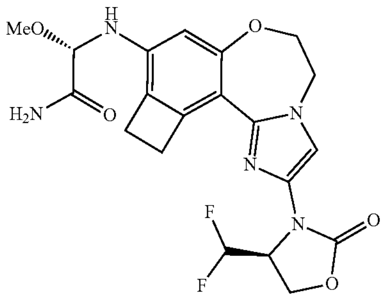
32
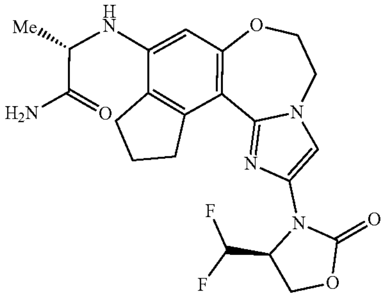
33
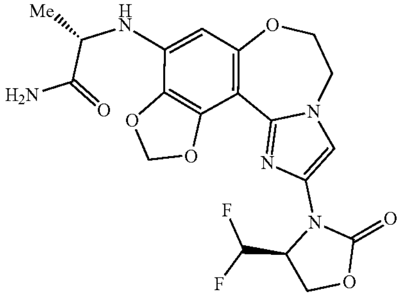

34
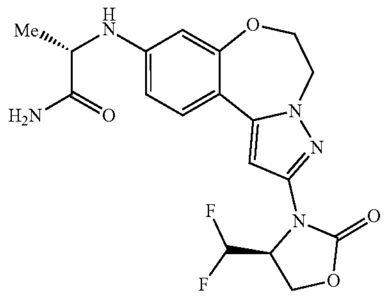
35
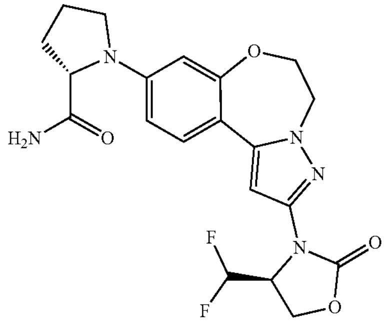
36
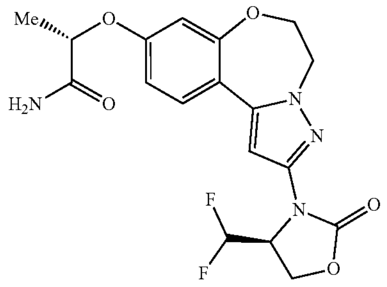
37
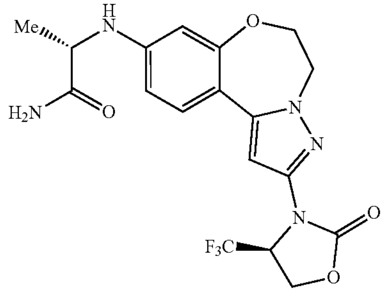
38
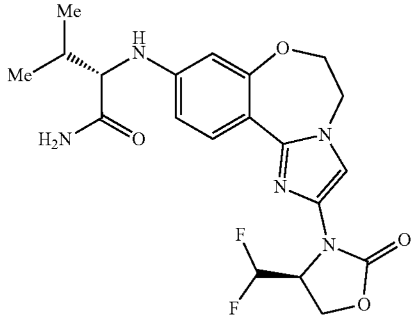
39
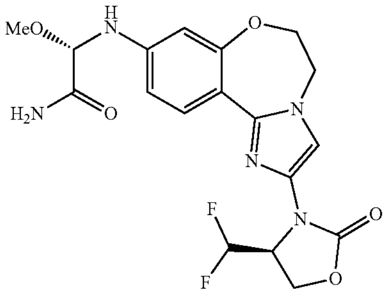
40
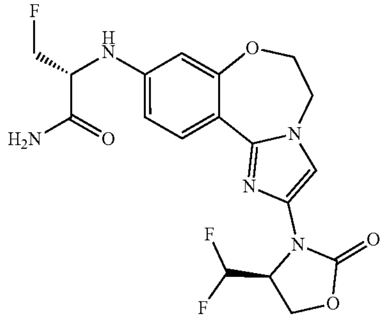
41
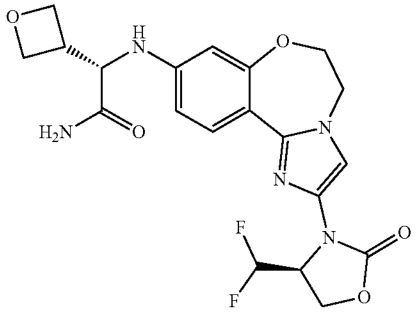
42
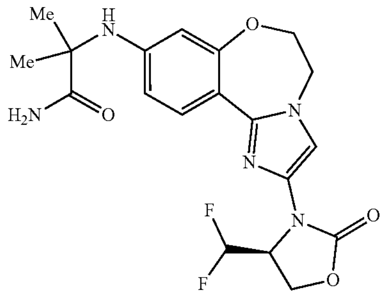
43
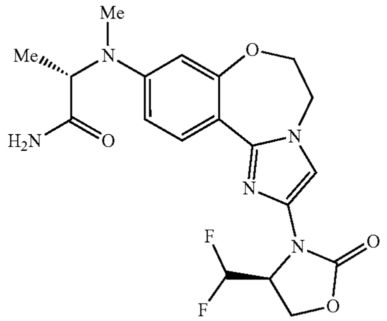

-continued
44
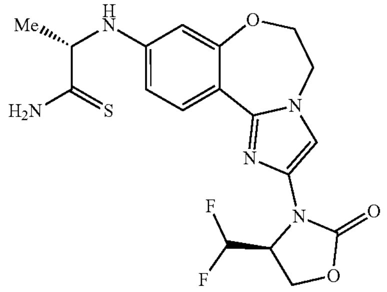
45
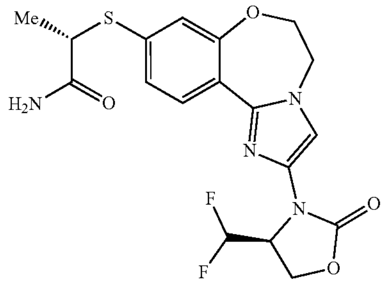
46
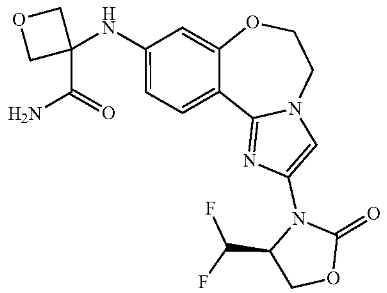
47
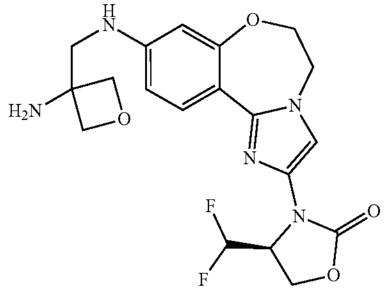
48
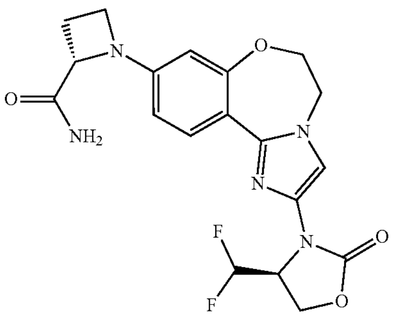
-continued
49
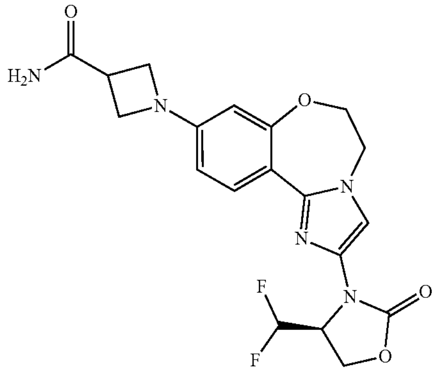
50
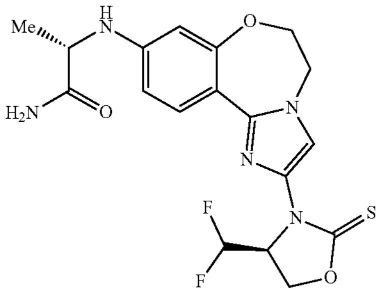
51
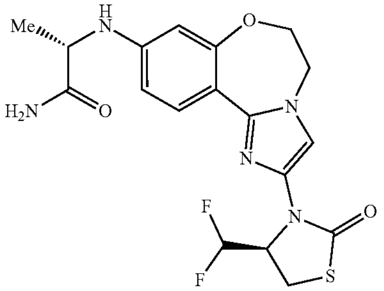
52
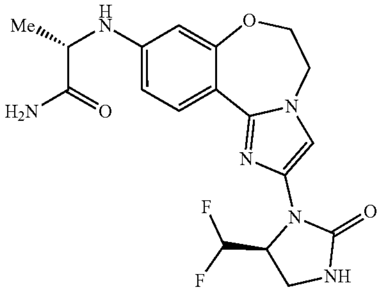
53
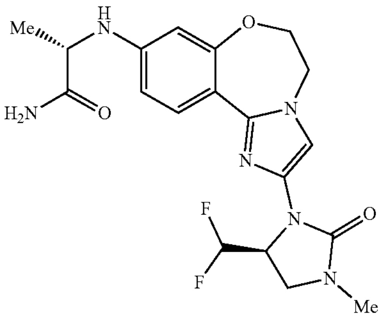

-continued
54
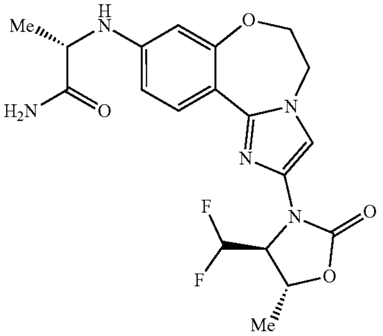
55
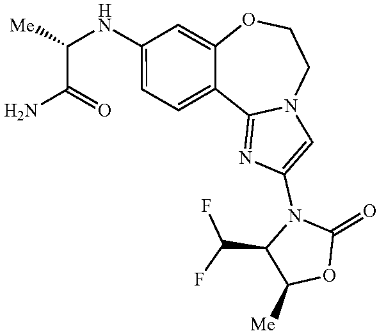
56
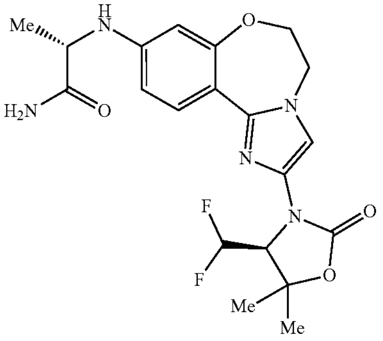
57
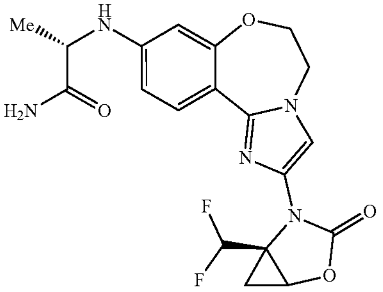
-continued
62
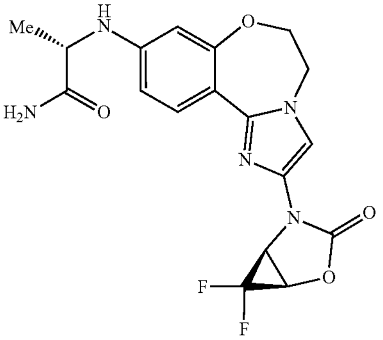
63
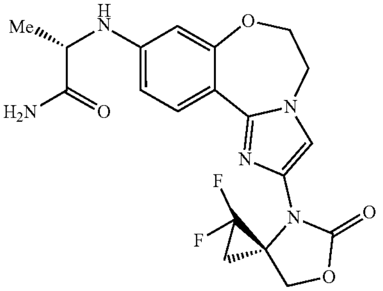
64
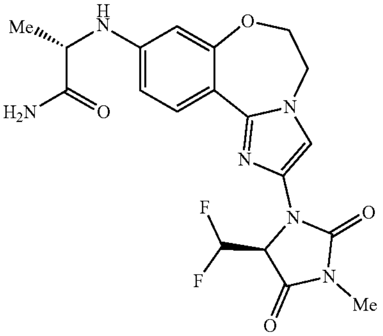
65
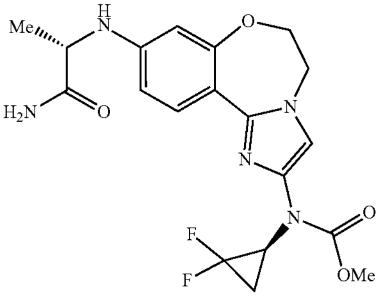
66
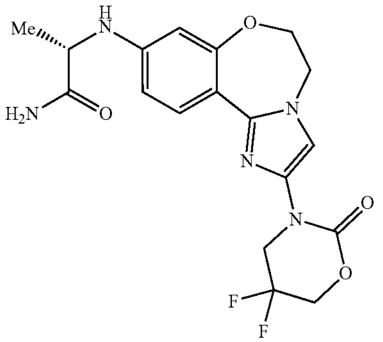

-continued
67
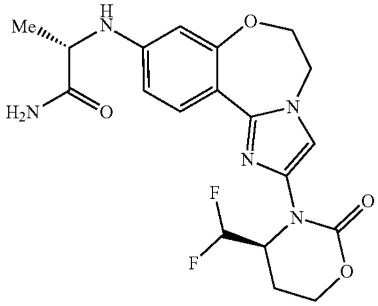
68
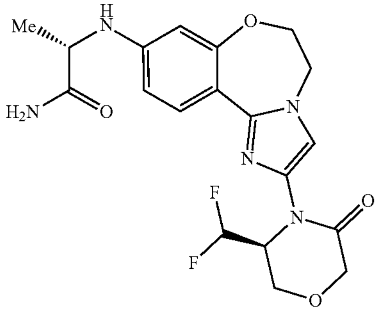
69
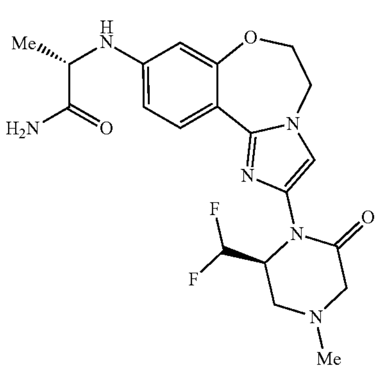
70
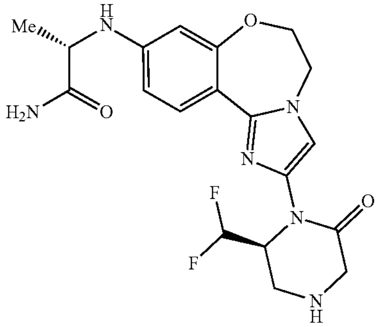
71
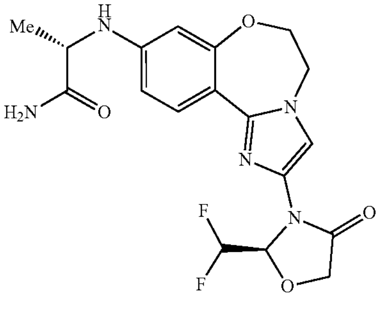
-continued
72
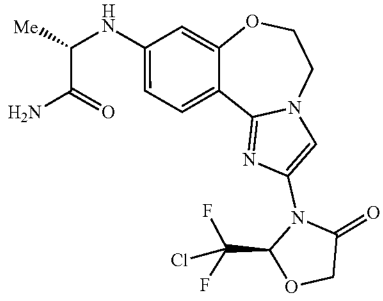
73
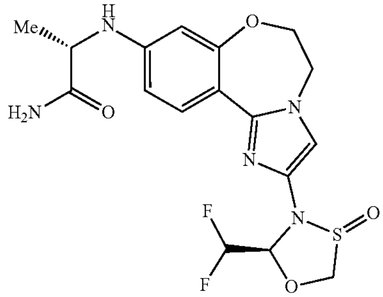
74
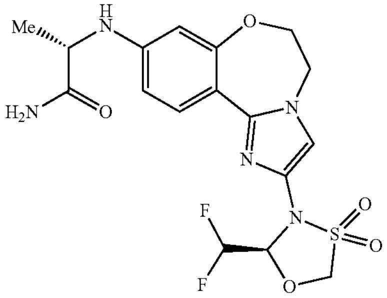
75
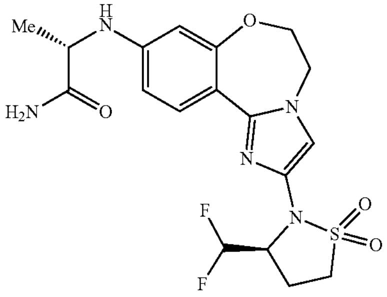
76
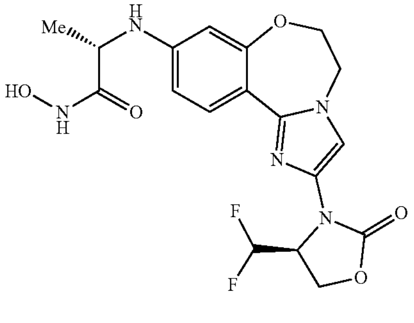

-continued
77
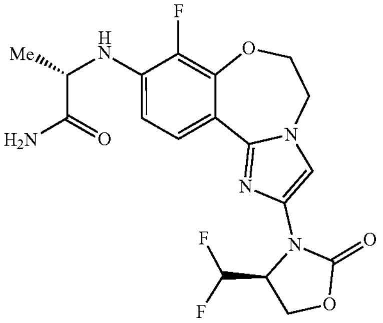
78
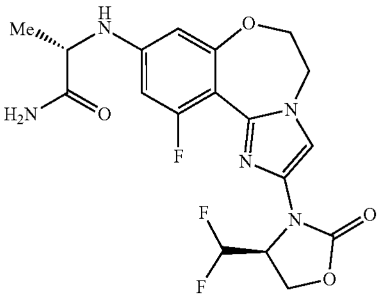
79
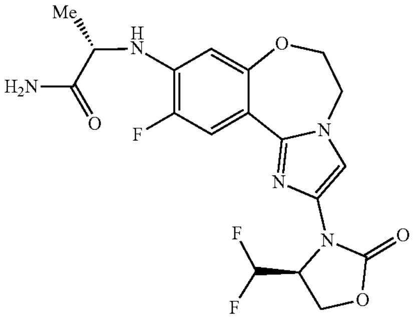
80
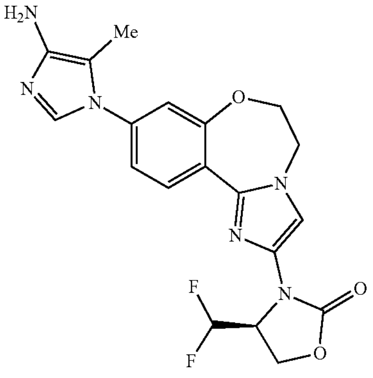
-continued
81
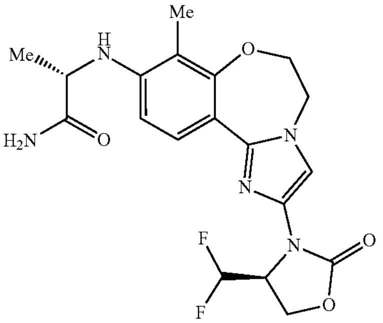
82
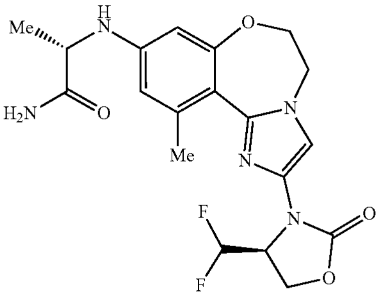
83
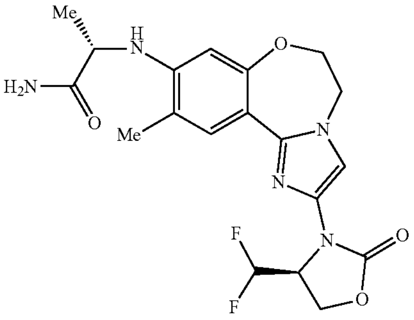
84
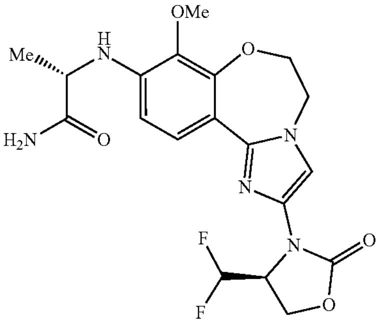
85
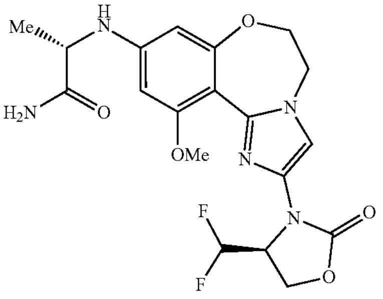

86
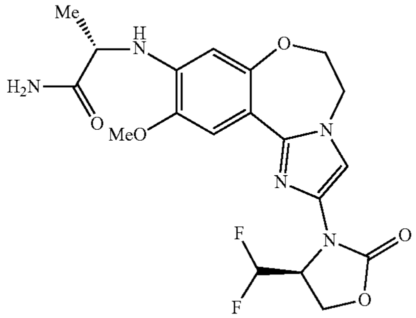
87
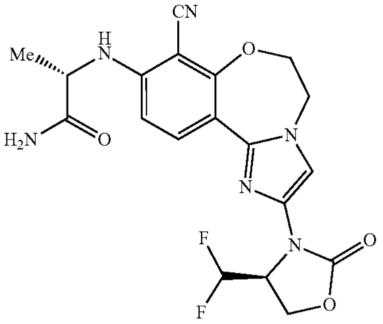
88
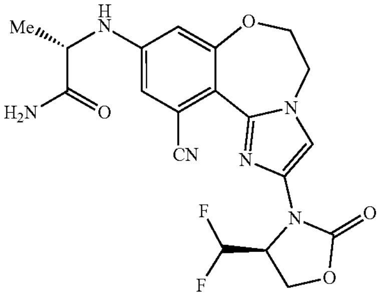
89
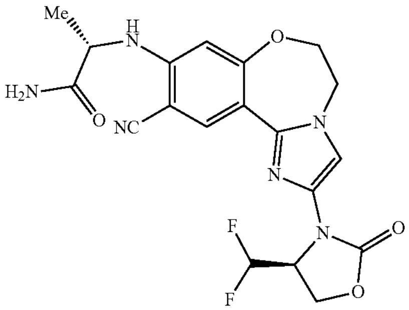
90
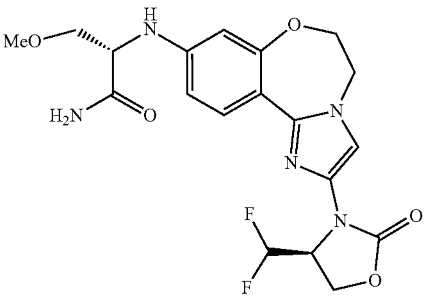
91
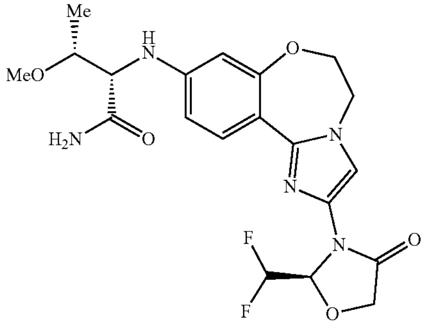
92
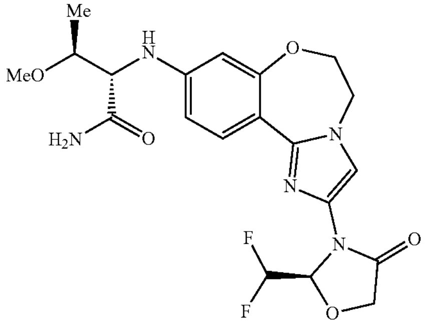
93
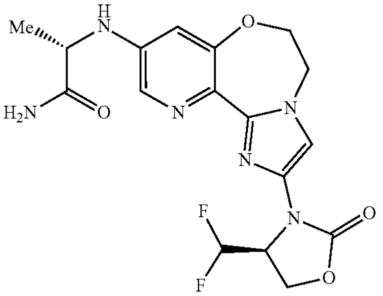
94
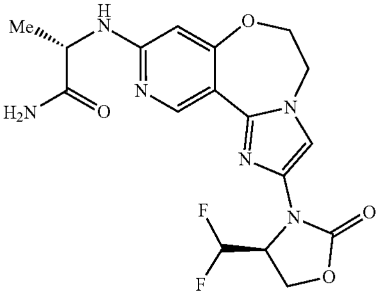
95
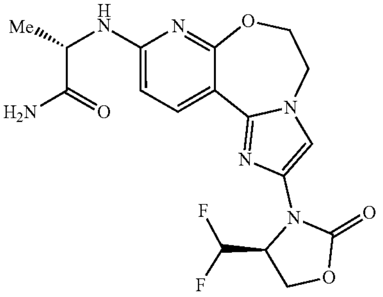

-continued
96
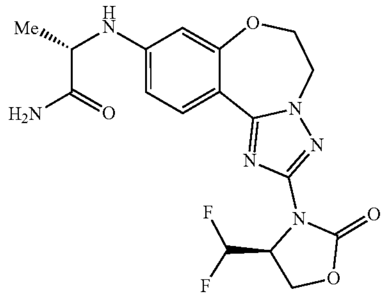
97
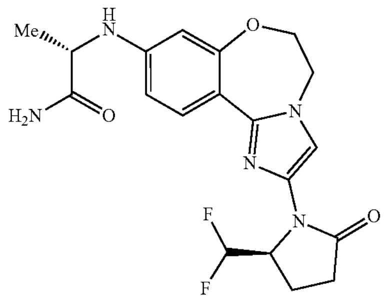
98
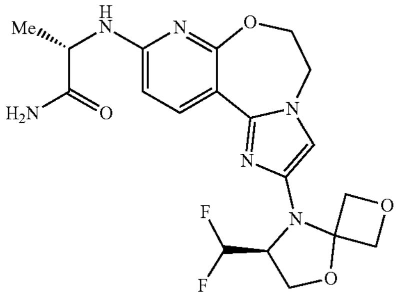
99
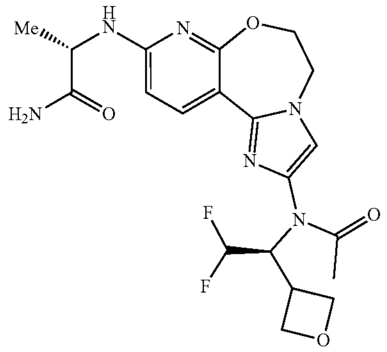
100
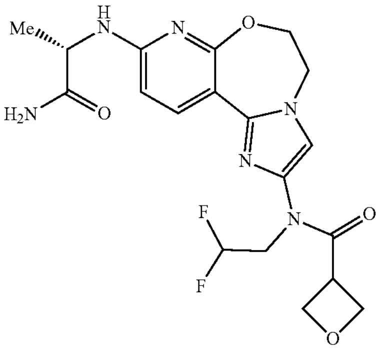
-continued
101
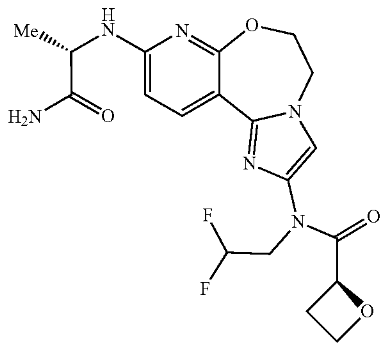
102
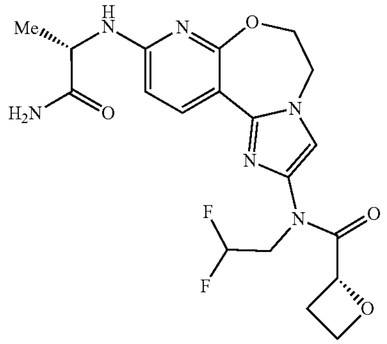
103
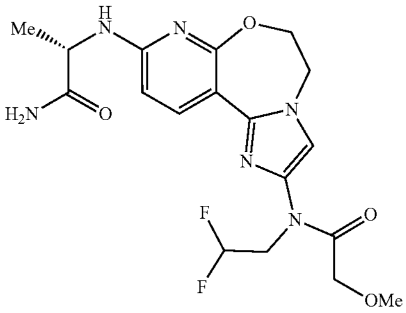
104
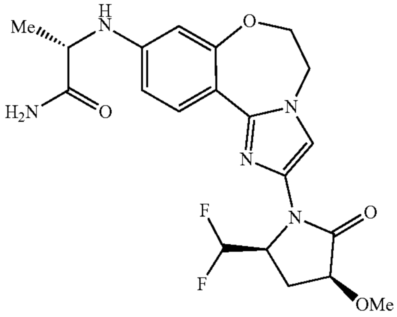
105
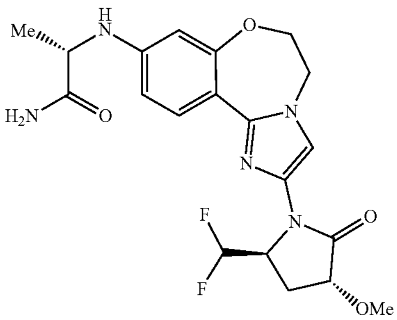

-continued
106
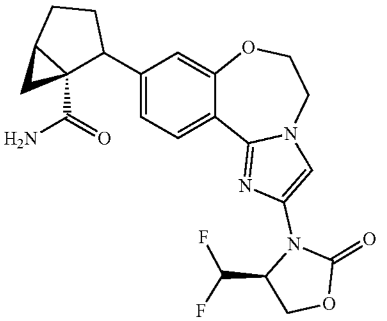
107
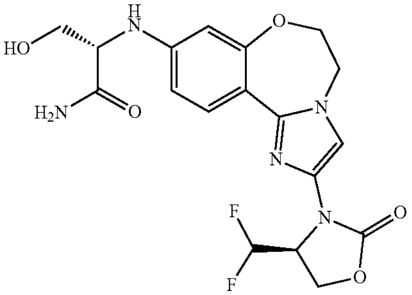
108
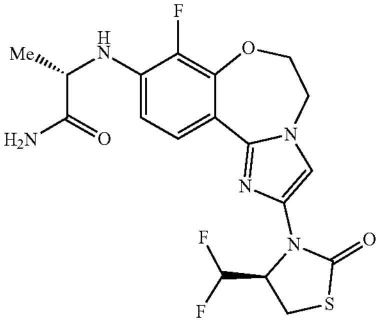
109
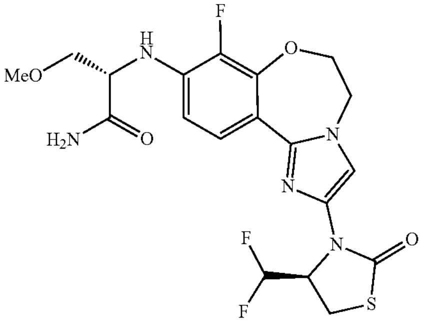
110
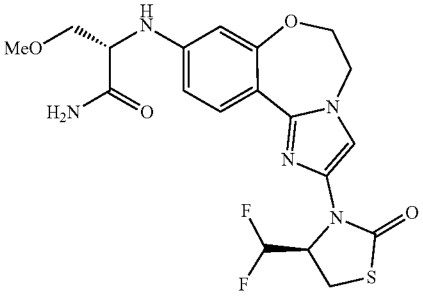
-continued
111
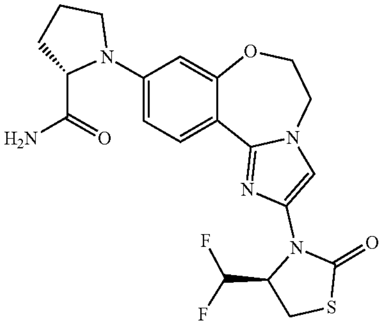
112
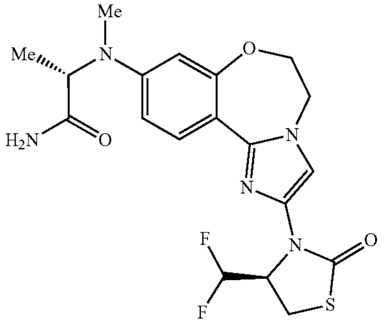
113
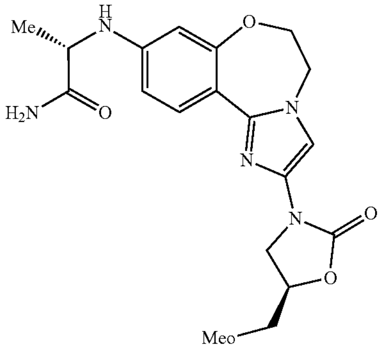
114
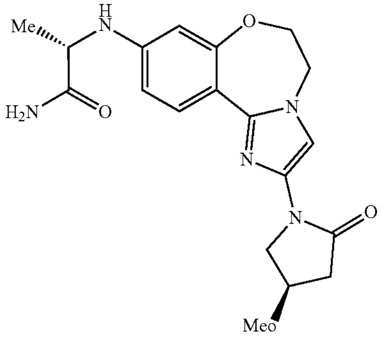

-continued
115
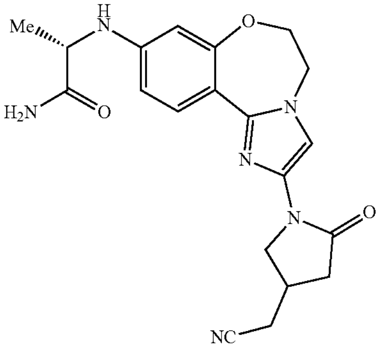
116
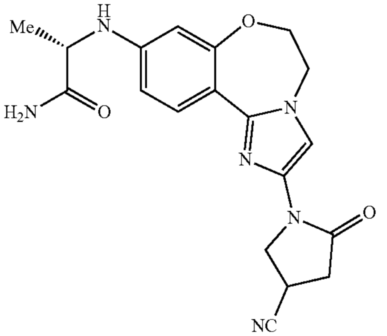
117
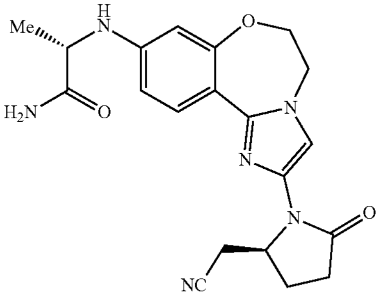
118
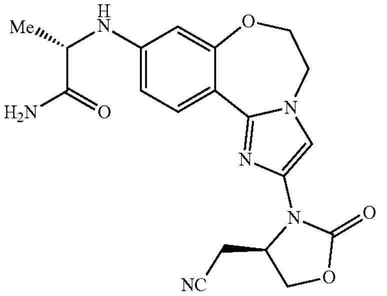
119
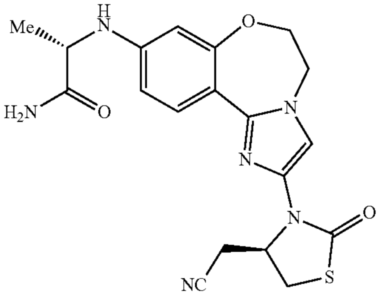
-continued
120
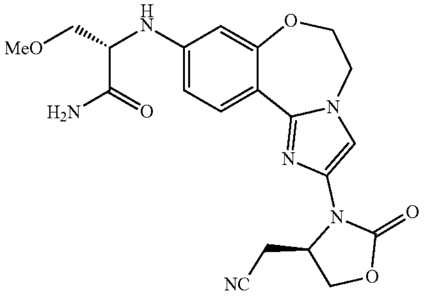
121
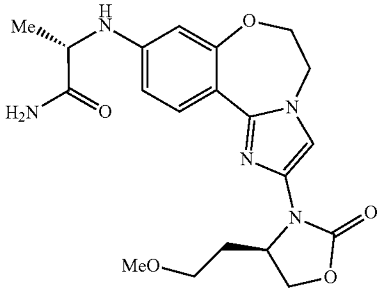
122
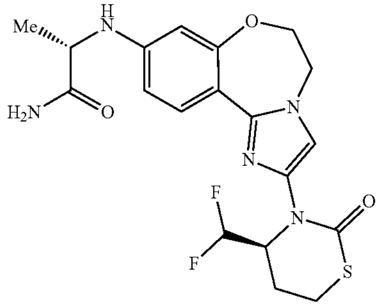
123
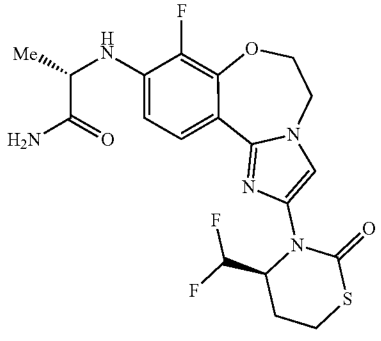
124
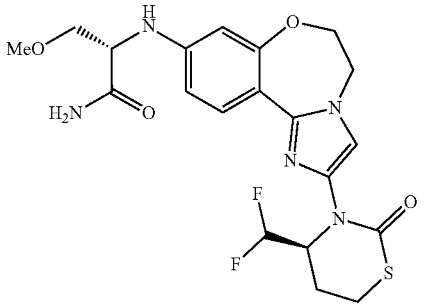

-continued

125

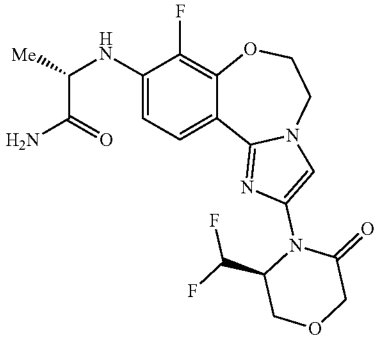

126

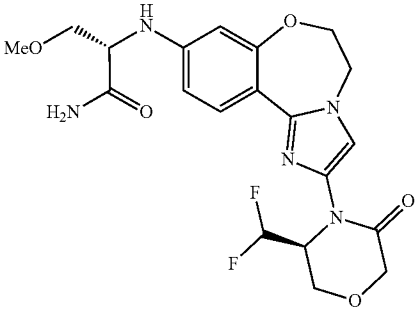

127

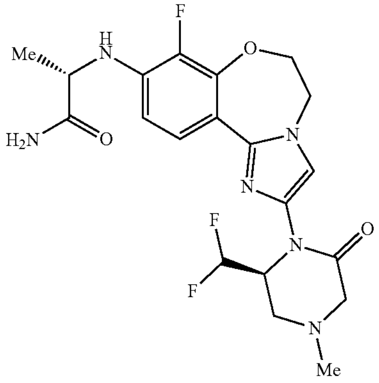

128

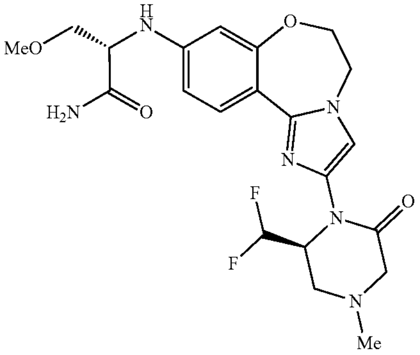

-continued

129

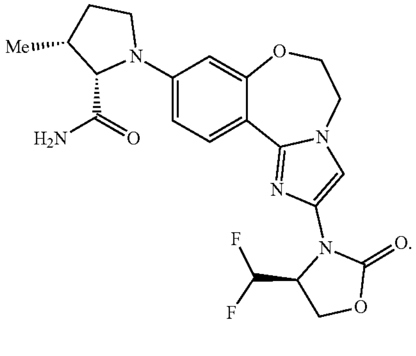

10. A pharmaceutical composition, comprising a therapeutically effective amount of the compound, the stereoisomer thereof, or the pharmaceutically acceptable salt thereof according to claim 1, and one or more pharmaceutically acceptable carrier(s), diluent(s) or excipient(s).

11. The compound of formula (VIII-A), the stereoisomer thereof, or the pharmaceutically acceptable salt thereof according to claim 3, wherein $R_2$ is selected from the group consisting of hydrogen, methyl, ethyl, and propyl;

$R_3$ and $R_4$ are each independently selected from the group consisting of hydrogen, methyl, ethyl, propyl, methoxy, and ethoxy;

or, $R_3$ and $R_4$ are bonded to form oxetanyl;

or, $R_2$ and $R_3$ or $R_2$ and $R_4$ are bonded to form pyrrolidinyl, tetrahydrofuranyl, piperidinyl or azetidinyl;

$R_5$ and $R_6$ are each independently hydrogen;

$R_{14}$ is selected from the group consisting of hydrogen, fluorine, and chlorine;

$R^z$ is selected from the group consisting of hydrogen, cyano, acetonitrilyl, propionitrilyl, and $C_{1-3}$ alkyl substituted by fluorine;

$R_{aa}$ is hydrogen.

12. The compound of formula (VIII-A), the stereoisomer thereof, or the pharmaceutically acceptable salt thereof according to claim 3, wherein $R^z$ is selected from the group consisting of methyl, acetonitrilyl, $—CHF_2$, $—CF_2CH_3$, and $CHF_2CH_2—$.

13. A pharmaceutical composition, comprising a therapeutically effective amount of the compound, the stereoisomer thereof, or the pharmaceutically acceptable salt thereof according to claim 6, and one or more pharmaceutically acceptable carrier(s), diluent(s) or excipient(s).

* * * * *